(12) United States Patent
Jenkins et al.

(10) Patent No.: US 9,139,612 B2
(45) Date of Patent: *Sep. 22, 2015

(54) ACTIVE AGENT PRODRUGS WITH HETEROCYCLIC LINKERS

(75) Inventors: Thomas E. Jenkins, Half Moon Bay, CA (US); Craig O. Husfeld, San Mateo, CA (US)

(73) Assignee: Signature Therapeutics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/000,594

(22) PCT Filed: Mar. 8, 2012

(86) PCT No.: PCT/US2012/028367
§ 371 (c)(1),
(2), (4) Date: Dec. 27, 2013

(87) PCT Pub. No.: WO2012/122422
PCT Pub. Date: Sep. 13, 2012

(65) Prior Publication Data
US 2014/0121152 A1    May 1, 2014

Related U.S. Application Data

(60) Provisional application No. 61/451,019, filed on Mar. 9, 2011, provisional application No. 61/583,523, filed on Jan. 5, 2012.

(51) Int. Cl.
| *A61K 38/00* | (2006.01) |
| *A61K 47/00* | (2006.01) |
| *C07K 5/06*  | (2006.01) |
| *C07K 5/062* | (2006.01) |
| *A61K 38/05* | (2006.01) |
| *A61K 38/06* | (2006.01) |
| *A61K 45/06* | (2006.01) |
| *C07K 5/08*  | (2006.01) |

(52) U.S. Cl.
CPC . *C07K 5/06* (2013.01); *A61K 38/05* (2013.01); *A61K 38/06* (2013.01); *A61K 45/06* (2013.01); *C07K 5/06026* (2013.01); *C07K 5/08* (2013.01); *A61K 38/00* (2013.01)

(58) Field of Classification Search
None
See application file for complete search history.

(56) References Cited

U.S. PATENT DOCUMENTS

| 4,454,338 | A | 6/1984 | Fujii et al. |
| 4,532,255 | A | 7/1985 | Fujii et al. |
| 5,109,118 | A | 4/1992 | Mizushima et al. |
| 5,217,987 | A | 6/1993 | Berger |
| 5,352,704 | A | 10/1994 | Okuyama et al. |
| 6,245,802 | B1 | 6/2001 | Iyengar et al. |
| 6,388,122 | B1 | 5/2002 | Kido et al. |
| 6,586,196 | B1 | 7/2003 | Bronstein et al. |
| 7,060,290 | B1 | 6/2006 | Morimoto et al. |
| 7,189,414 | B2 | 3/2007 | Rubinstein et al. |
| 7,893,105 | B2 | 2/2011 | Xiang et al. |
| 8,217,005 | B2 | 7/2012 | Jenkins et al. |
| 8,497,237 | B2 | 7/2013 | Jenkins et al. |
| 8,685,916 | B2 * | 4/2014 | Jenkins et al. ............... 514/1.1 |
| 8,802,681 | B2 | 8/2014 | Jenkins et al. |
| 8,921,418 | B2 | 12/2014 | Jenkins et al. |
| 8,962,547 | B2 | 2/2015 | Jenkins et al. |
| 2003/0035831 | A1 | 2/2003 | Modi |
| 2003/0180352 | A1 | 9/2003 | Patel et al. |
| 2004/0063628 | A1 | 4/2004 | Piccariello et al. |
| 2005/0080012 | A1 | 4/2005 | Mickle et al. |
| 2005/0176644 | A1 | 8/2005 | Mickle et al. |
| 2007/0082929 | A1 | 4/2007 | Gant et al. |
| 2007/0123468 | A1 | 5/2007 | Jenkins |
| 2007/0203055 | A1 | 8/2007 | Mickle et al. |
| 2009/0136980 | A1 | 5/2009 | Bebbington et al. |
| 2009/0137618 | A1 | 5/2009 | Jenkins |
| 2009/0192093 | A1 | 7/2009 | Mickle et al. |
| 2009/0209569 | A1 | 8/2009 | Arnelle et al. |
| 2010/0022792 | A1 | 1/2010 | Shen |
| 2010/0035826 | A1 | 2/2010 | Jenkins et al. |
| 2010/0080797 | A1 | 4/2010 | Yeomans et al. |
| 2010/0092562 | A1 | 4/2010 | Hollenbeck et al. |

(Continued)

FOREIGN PATENT DOCUMENTS

| EP | 1782834 | 5/2007 |
| WO | WO 0243767 | 6/2002 |

(Continued)

OTHER PUBLICATIONS

Prater et al, Successful Pain Management for the Recovering Addicted Patient (Primary Care Companion J elin Psychiatry 2002;4(4)).*
Pain Doctor (downloaded on Nov. 21, 2014 from URL: < http://paindoctor.com/conditions/common/phantom-limb-pain/>).*
Hyams (downloaded on Nov. 21, 2014 from URL: < http://www.pediatricweb.com/webpost/iframe/MedicalConditions_465.asp?tArticleId=94>).*
Opiois911 (downloaded on Nov. 21, 2014 from URL: < http://opioids911.org/safety.php>).*

(Continued)

*Primary Examiner* — Karlheinz R Skowronek
*Assistant Examiner* — Sergio Coffa
(74) *Attorney, Agent, or Firm* — Carol L. Francis; Khin K. Chin; Bozicevic, Field & Francis LLP

(57) ABSTRACT

The embodiments provide prodrug compounds of Formulae I-XVII. The present disclosure also provides compositions, and their methods of use, where the compositions comprise a prodrug compound of Formulae I-XVII that provides controlled release of an active agent. Such compositions can optionally provide a trypsin inhibitor that interacts with the enzyme that mediates the controlled release of an active agent from the prodrug so as to attenuate enzymatic cleavage of the prodrug.

29 Claims, 26 Drawing Sheets

(56) References Cited

U.S. PATENT DOCUMENTS

| | | |
|---|---|---|
| 2010/0227921 A1 | 9/2010 | Franklin et al. |
| 2010/0267614 A1 | 10/2010 | Jenkins |
| 2010/0286186 A1 | 11/2010 | Franklin et al. |
| 2011/0262355 A1 | 10/2011 | Jenkins et al. |
| 2011/0262359 A1 | 10/2011 | Jenkins et al. |
| 2011/0262360 A1 | 10/2011 | Jenkins et al. |
| 2012/0178772 A1 | 7/2012 | Jenkins et al. |
| 2012/0178773 A1 | 7/2012 | Jenkins et al. |
| 2012/0230916 A1 | 9/2012 | Jenkins et al. |
| 2013/0059914 A1 | 3/2013 | Jenkins et al. |
| 2013/0210700 A1 | 8/2013 | Jenkins et al. |
| 2013/0210854 A1 | 8/2013 | Jenkins et al. |
| 2014/0121152 A1 | 5/2014 | Jenkins et al. |
| 2014/0206597 A1 | 7/2014 | Jenkins et al. |
| 2015/0031635 A1 | 1/2015 | Jenkins et al. |

FOREIGN PATENT DOCUMENTS

| | | |
|---|---|---|
| WO | WO 2004082620 | 9/2004 |
| WO | WO 2005032474 | 4/2005 |
| WO | WO 2007120864 | 10/2007 |
| WO | WO 2007140272 | 12/2007 |
| WO | WO 2008012046 | 1/2008 |
| WO | WO 2007120648 | 7/2008 |
| WO | WO 2008101187 | 8/2008 |
| WO | WO 2008101202 | 8/2008 |
| WO | WO 2009067703 | 5/2009 |
| WO | WO 2010045599 | 4/2010 |
| WO | WO 2010100477 | 9/2010 |
| WO | WO 2011031350 | 3/2011 |
| WO | WO 2011133346 | 4/2011 |
| WO | WO 2011133178 | 10/2011 |

OTHER PUBLICATIONS

Bernkop-Schnurch, "The use of inhibitory agents to overcome the enzymatic barrier to perorally administered therapeutic peptides and proteins" J. Control. Release (1998), vol. 50, No. 1-2, pp. 1-16.

Birk et al., "Trypsin and chymotrypsin inhibitors from soybeans" Methods in Enzymology (1976) vol. 45, pp. 700-707.

Geratz et al., "Novel bis(benzamidine) compounds with an aromatic central link. Inhibitors of thrombin, pancreatic kallikrein, trypsin, and complement" J. Med. Chem. (1976), vol. 19, pp. 634-639.

Göke et al., "Effect of a Specific Serine Protease Inhibitor on the Rat Pancreas: Systemic Administration of Camostate and Exocrine" Digestion (1984) vol. 30, pp. 171-178.

Gomes et al., "Cyclization-activated prodrugs" Molecules, (2007), vol. 12, pp. 2484-2506.

Hijikata-Okunomiya et al., "Selective Inhibition of Trypsin by (2R,4R)-4-Phenyl-1-[$N^{\alpha}$-(7-methoxy-2-naphthalenesulfonyl)-L-arginyl]-2-piperidinecarboxylic Acid" J. Biochem. (2000), vol. 275, pp. 18995-18999.

Kunze et al., "Effects of the serine protease inhibitors FOY and FOY 305 on phospholipase A I (EC 3.1.1.32) activity in rat—liver lysosomes" Pharm. Research Com. (1983), vol. 15, pp. 451-459.

Lin et al., "The 0.25-nm X-ray structure of the Bowman-Birk type inhibitor from mung bean in ternary complex with porcine trypsin" Eur. J. Biochem., (1993), vol. 212, pp. 549-555.

Markwardt et al., "Comparative studies on the inhibition of trypsin, plasmin, and thrombin by derivatives of benzylamine and benzylamidine" Eur. J. Biochem, (1968), vol. 6, pp. 502-506.

Ozawa et al., "The reactive site of trypsin inhibitors" J. Biol. Chem. (1966), vol. 241, pp. 3955-3961.

Ramjee et al., "The Kinetic and Structural Characterization of the Reaction of Nafamostat with Bovine Pancreatic Trypsin" Thrmb Res. (2000), vol. 98, No. 6, pp. 559-569.

Renatus et al. "Structural and Functional Analyses of Benzamidine-Based Inhibitors in Complex with Trypsin: Implications for the Inhibition of Factor Xa, tPA, and Urokinase" J. Med. Chem., (1998), vol. 41, No. 27 pp. 5445-5456.

Tanizawa et al. "Inverse Substrates for Tryspin and Tryspin-like Enzymes" Acc. Chem. Res., (1987), vol. 20, pp. 337-343.

Testa et al, "Hydrolysis in Drug and Prodrug Metabolism" Verlag Helvetica Chimica Acta, Postfach, CH-8042, Switzerland (2003) pp. 420-534.

Tirkkonen et al., "Drug interactions with the potential to prevent prodrug activation as a common source of irrational prescribing in hospital inpatients" Clinical Pharmacology and Therapeutics, (2004) vol. 76, No. 6, pp. 639-647.

Umezawa, "Structure and activities of protease inhibitors of microbial origin" Methods in Enzymology (1976) vol. 45, pp. 678-695.

U.S. Appl. No. 13/415,793, filed Mar. 8, 2012, Jenkins et al.
U.S. Appl. No. 13/686,710, filed Nov. 27, 2012, Jenkins et al.
U.S. Appl. No. 13/686,725, filed Nov. 27, 2012, Jenkins et al.
U.S. Appl. No. 14/551,731, filed Nov. 24, 2014, Jenkins et al.
U.S. Appl. No. 14/593,855, filed Jan. 9, 2015, Jenkins et al.

Bak et al. (1999) "Acyloxyalkoxy-Based Cyclic Prodrugs of Opioid Peptides: Evaluation of the Chemical and Enzymatic Stability as Well as Their Transport Properties Across Caco-2 Cell Monolayers" *Pharm Res* 16(1):24-29.

Bioavailability and Bioequivalence Studies for Orally Administered Drug Products—General Considerations, Guidance for Industry, Food and Drug Administration, published on Oct. 2000.

Camostat Medilate (http://www.scbt.com/datasheet-203867-camostat-mesylate.html (downloaded on Nov. 14, 2013).

Gotoh et al. (2005) "The advantages of the Ussing chamber in drug absorption studies" *Journal of Biomolecular Screening* 10(5):517-523.

Katragadda et al. (2006) "Simultaneous Modulation of Transport and Metabolism of Acyclovir Prodrugs across Rabbit Cornea: An approach Involving Enzyme Inhibitors" *Int J Pharm* 320(1-2):104-113.

Nafamostat (PubChem, National Center for Biotechnology Information dated Dec. 20, 2005).

Pauletti, Giovanni et al. (1997) "Esterase-Sensitive Cyclic Prodrugs of Peptides: Evaluation of a Phenylpropionic Acid Promoiety in a Model Hexapeptide" *Pharm Res* 14(1):11-17.

Schanker et al. (1958) "Absorption of drugs from the rat small intestine" *Journal of Pharmacology and Experimental Therapeutics* 123(1):81-88.

Song, Xiaoping et al. (2002) "Synthesis of a Novel Cyclic Prodrug of RGD Peptidomimetic to Improve Its Cell Membrane Permeation" *Bioorg Chem* 30(4):285-301.

Van Gelder et al. (2002) "Intestinal absorption enhancement of the ester prodrug tenofovir disoproxil fumarate through modulation of the biochemical barrier by defined ester mixtures" *Drug Metabolism and Disposition* 30(8):924-930.

Katz, Joel, (1993), "Preop analgesia for postop pain", The Lancet, 342:65-66.

Bach, et al., (1988), "Phantom limb pain in amputees during the first 12 months following limb amputation, after preoperative lumbar epidural blockade", Pain, 33: 297-301.

Buvanendran, et al., (2010), "Perioperative Oral Pregabalin Reduces Chronic Pain After Total Knee Arthroplasty: A Prospective, Randomized, Controlled Trial", Pain Medicine, 110(1):199-207.

Gottschalk, et al., (2001), "New Concepts in Acute Pain Therapy: Preemptive Analgesia", American Family Physician, 63(10):1979-1984.

* cited by examiner

ACTIVE AGENT PRODRUGS WITH HETEROCYCLIC LINKERS

CROSS REFERENCE TO RELATED APPLICATIONS

This application claims the benefit of U.S. Provisional Application No. 61/451,019 filed Mar. 9, 2011 and U.S. Provisional Application No. 61/583,523 filed Jan. 5, 2012, which are hereby incorporated by reference in their entireties.

INTRODUCTION

A number of drugs are susceptible to misuse, abuse, or overdose. Use of and access to these drugs therefore needs to be controlled. The control of access to the drugs is expensive to administer and can result in denial of treatment for patients that are not able to present themselves for dosing. For example, patients suffering from acute pain may be denied treatment with a drug unless they have been admitted to a hospital. Furthermore, control of use is often ineffective, leading to substantial morbidity and deleterious social consequences.

SUMMARY

This disclosure concerns a prodrug of an active agent that provides controlled release of the active agent. Such a prodrug comprises an active agent covalently attached to a promoiety. The promoiety comprises an enzyme-cleavable moiety and a cyclizable spacer leaving group such that the active agent prodrug provides controlled release of the active agent via enzyme cleavage followed by intramolecular cyclization. The enzyme-mediated release of the active agent can occur in the gastrointestinal tract upon oral administration of the corresponding prodrug. Thus, prodrugs of the disclosure provide efficient delivery of active agent when ingested.

The present disclosure also provides a composition, such as a pharmaceutical composition, that comprises an active agent prodrug of the embodiments. Such a composition can optionally provide an inhibitor that interacts with the enzyme that mediates the controlled release of active agent from the prodrug so as to attenuate enzymatic cleavage of the prodrug. The disclosure provides for the enzyme being a gastrointestinal (GI) enzyme, such as trypsin. Also provided are methods of use, such as a method of providing patients with controlled release of active agent using an active agent prodrug of the embodiments.

The embodiments include an active agent prodrug that is a compound of formula I

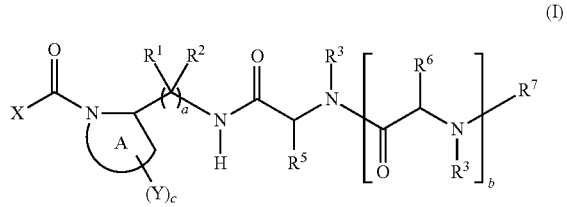

wherein
X is selected from a residue of a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; a residue of a phenolic active agent, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; and a residue of an amide-containing active agent, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include an opioid prodrug that is a compound of formula II:

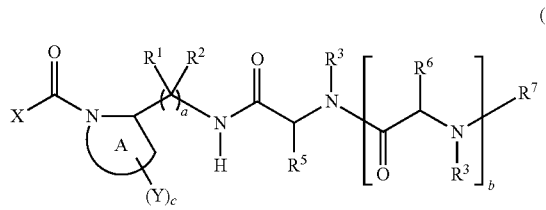

(II)

wherein

X is selected from a residue of a ketone-containing opioid, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; a residue of a phenolic opioid, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; and a residue of an amide-containing opioid, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Certain embodiments provide controlled release of ketone-containing active agent. More particularly, the embodiments relate to a prodrug of a ketone-containing active agent that provides controlled release of the active agent. Such a prodrug comprises a ketone-containing active agent covalently attached to a promoiety through the enolic oxygen atom of the ketone-containing active agent. The promoiety comprises an enzyme-cleavable moiety and a cyclizable spacer leaving group such that the ketone-modified active agent prodrug provides controlled release of active agent via enzyme cleavage followed by intramolecular cyclization. Ketone-modified active agent prodrugs of the disclosure provide efficient delivery of active agent when ingested. The present disclosure also provides a composition, such as a pharmaceutical composition, that comprises a ketone-modified active agent prodrug of the embodiments. Also provided are methods of use, such as a method of providing patients with controlled release of ketone-containing active agent using a ketone-modified active agent prodrug of the embodiments.

The embodiments include a ketone-modified active agent prodrug that is a compound of formula IIIa:

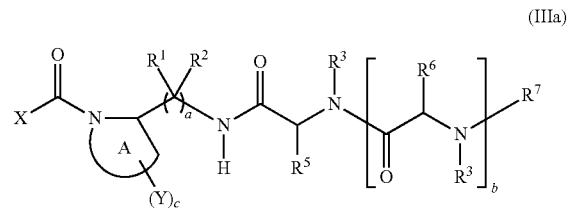

(IIIa)

wherein

X represents a residue of a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Certain embodiments provide controlled release of phenolic active agents. More particularly, the embodiments relate to a prodrug of a phenolic active agent that provides controlled release of the active agent. Such a prodrug comprises a phenolic active agent covalently attached to a promoiety through the phenolic oxygen atom of the phenolic active agent. The promoiety comprises an enzyme-cleavable moiety and a cyclizable spacer leaving group such that the phenolic active agent prodrug provides controlled release of active agent via enzyme cleavage followed by intramolecular cyclization. Phenolic active agent prodrugs of the disclosure provide efficient delivery of active agent when ingested. The present disclosure also provides a composition, such as a pharmaceutical composition, that comprises a phenolic active agent prodrug of the embodiments. Also provided are methods of use, such as a method of providing patients with controlled release of phenolic active agent using a phenolic active agent prodrug of the embodiments.

The embodiments include a phenolic active agent prodrug that is a compound of formula VIIa:

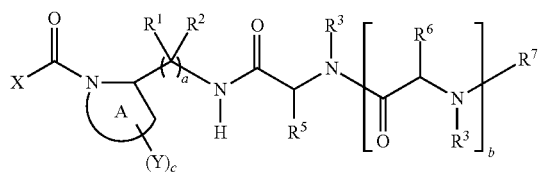

(VIIa)

wherein

X represents a residue of a phenolic active agent, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Certain embodiments provide controlled release of amide-containing active agents. More particularly, the embodiments relate to a prodrug of an amide-containing active agent that provides controlled release of the active agent. Such a prodrug comprises an amide-containing active agent covalently attached to a promoiety through the enolic oxygen atom of the amide enol moiety or through the oxygen of the imine tautomer of the amide-containing active agent. The promoiety comprises an enzyme-cleavable moiety and a cyclizable spacer leaving group such that the amide-modified active agent prodrug provides controlled release of active agent via enzyme cleavage followed by intramolecular cyclization. Amide-modified active agent prodrugs of the disclosure provide efficient delivery of active agent when ingested. The present disclosure also provides a composition, such as a pharmaceutical composition, that comprises an amide-modified active agent prodrug of the embodiments. Also provided are methods of use, such as a method of providing patients with controlled release of amide-containing active agent using an amide-modified active agent prodrug of the embodiments.

The embodiments include an amide containing active agent prodrug that is a compound of formula XIa:

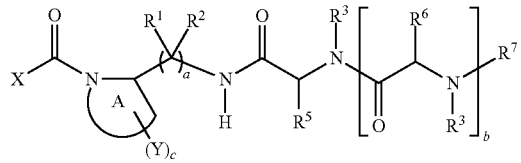

(XIa)

wherein

X represents a residue of an amide-containing active agent, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Certain embodiments provide controlled release of acetaminophen. More particularly, the embodiments relate to a prodrug of acetaminophen that provides controlled release of acetaminophen. Such a prodrug comprises acetaminophen covalently attached to a promoiety through the phenolic oxygen atom of acetaminophen or through the oxygen of the amide group of acetaminophen. The promoiety comprises an enzyme-cleavable moiety and a cyclizable spacer leaving group such that the acetaminophen prodrug provides controlled release of acetaminophen via enzyme cleavage followed by intramolecular cyclization. Acetaminophen prodrugs of the disclosure provide efficient delivery of acetaminophen when ingested. The present disclosure also provides a composition, such as a pharmaceutical composition, that comprises acetaminophen prodrug of the embodiments. Also provided are methods of use, such as a method of providing patients with controlled release of acetaminophen using acetaminophen prodrug of the embodiments.

The embodiments include an acetaminophen prodrug that is a compound of formula XIV:

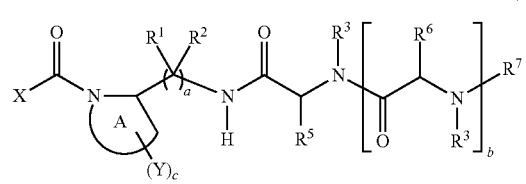

(XIV)

wherein

X represents acetaminophen, wherein the hydrogen atom of the phenolic hydroxyl group of acetaminophen is replaced by a covalent bond to —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$; or wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to acetaminophen through the oxygen of the amide group of acetaminophen, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

TERMS

Figure 1:
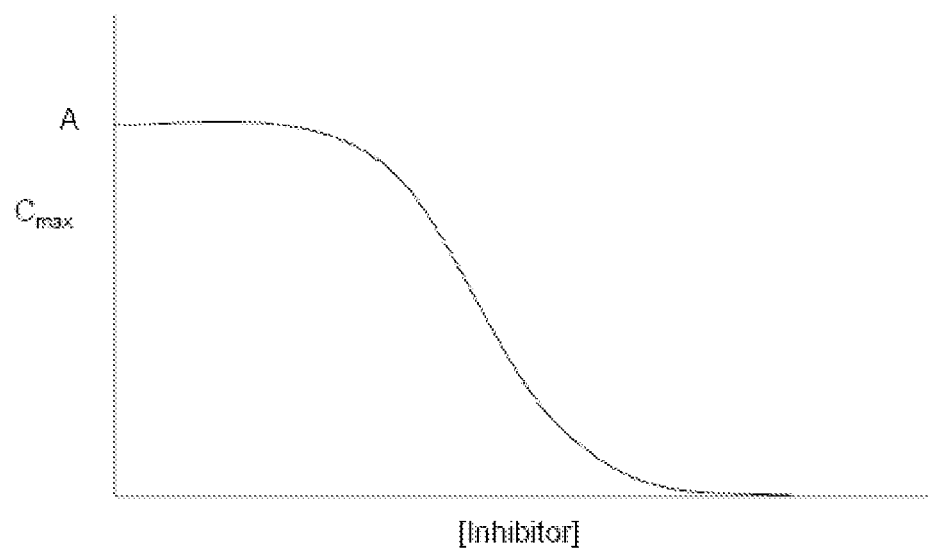
FIG. 1 is a schematic representing the effect of increasing the level of a GI enzyme inhibitor ("inhibitor", X axis) on a PK parameter (e.g., drug Cmax) (Y axis) for a fixed dose of prodrug. The effect of inhibitor upon a prodrug PK parameter can range from undetectable, to moderate, to complete inhibition (i.e., no detectable drug release).

The following terms have the following meaning unless otherwise indicated. Any undefined terms have their art recognized meanings.

"Alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

"Acylamino" refers to the groups —NR$^{20}$C(O)alkyl, —NR$^{20}$C(O) substituted alkyl, NR$^{20}$C(O)cycloalkyl, —NR$^{20}$C(O) substituted cycloalkyl, —NR$^{20}$C(O)cycloalkenyl, substituted cycloalkenyl, —NR$^{20}$C(O)alkenyl, —NR$^{20}$C(O) substituted alkenyl, —NR$^{20}$C(O)alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is $(C_7-C_{30})$ arylalkyl, e.g., the alkanyl, alkenyl or alkynyl moiety of the arylalkyl group is $(C_1-C_{10})$ and the aryl moiety is $(C_6-C_{20})$. In certain embodiments, an arylalkyl group is $(C_7-C_{20})$ arylalkyl, e.g., the alkanyl, alkenyl or alkynyl moiety of the arylalkyl group is $(C_1-C_8)$ and the aryl moiety is $(C_6-C_{12})$.

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group is specified, the numbers refer to the carbon atoms comprising each aromatic ring. For example, $(C_5-C_{14})$ arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a $(C_5-C_{14})$ aromatic. In certain embodiments, each aromatic ring system of an arylaryl group is independently a $(C_5-C_{10})$ aromatic. In certain embodiments, each aromatic ring system is identical, e.g., biphenyl, triphenyl, binaphthyl, trinaphthyl, etc.

"Carboxyl," "carboxy" or "carboxylate" refers to $-CO_2H$ or salts thereof.

"Cyano" or "nitrile" refers to the group $-CN$.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is $(C_3-C_{10})$ cycloalkyl. In certain embodiments, the cycloalkyl group is $(C_3-C_7)$ cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalk-enyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, $-O-$, $-S-$, $-S-S-$, $-O-S-$, $-NR^{37}R^{38}-$, $=N-N=$, $-N=N-$, $-N=N-NR^{39}R^{40}$, $-PR^{41}-$, $-P(O)_2-$, $-POR^{42}-$, $-O-P(O)_2$, $-S-O-$, $-S-(O)-$, $-SO_2-$, $-SnR^{43}R^{44}-$ and the like, where $R^{37}$, $R^{38}$, $R^{39}$, $R^{40}$, $R^{41}$, $R^{42}$, $R^{43}$ and $R^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heteroarylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These hetero atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$ O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

"Dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

"Gastrointestinal enzyme" or "GI enzyme" refers to an enzyme located in the gastrointestinal (GI) tract, which encompasses the anatomical sites from mouth to anus. Trypsin is an example of a GI enzyme.

"Gastrointestinal enzyme-cleavable moiety" or "GI enzyme-cleavable moiety" refers to a group comprising a site susceptible to cleavage by a GI enzyme. For example, a "trypsin-cleavable moiety" refers to a group comprising a site susceptible to cleavage by trypsin.

"Gastrointestinal enzyme inhibitor" or "GI enzyme inhibitor" refers to any agent capable of inhibiting the action of a gastrointestinal enzyme on a substrate. The term also encompasses salts of gastrointestinal enzyme inhibitors. For example, a "trypsin inhibitor" refers to any agent capable of inhibiting the action of trypsin on a substrate.

"Patient" includes humans, and also other mammals, such as livestock, zoo animals, and companion animals, such as a cat, dog, or horse.

"Pharmaceutical composition" refers to at least one compound and can further comprise a pharmaceutically acceptable carrier, with which the compound is administered to a patient.

"Pharmaceutically acceptable carrier" refers to a diluent, adjuvant, excipient or vehicle with, or in which a compound is administered.

"Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax) and side effects.

"PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"Preventing" or "prevention" or "prophylaxis" refers to a reduction in risk of occurrence of a condition, such as pain.

"Prodrug" refers to a derivative of an active agent that requires a transformation within the body to release the active agent. In certain embodiments, the transformation is an enzymatic transformation. In certain embodiments, the transformation is a cyclization transformation. In certain embodiments, the transformation is a combination of an enzymatic transformation and a cyclization transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Solvate" as used herein refers to a complex or aggregate formed by one or more molecules of a solute, e.g. a prodrug or a pharmaceutically acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Therapeutically effective amount" means the amount of a compound (e.g., prodrug) that, when administered to a patient for preventing or treating a condition such as pain, is sufficient to effect such treatment. The "therapeutically effective amount" will vary depending on the compound, the condition and its severity and the age, weight, etc., of the patient.

"Treating" or "treatment" of any condition, such as pain, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

DETAILED DESCRIPTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a compound refers to one or more compounds. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. In certain instances, this nomenclature has is derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed. E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds.

The compounds described also include isotopically labeled compounds where one or more atoms have an atomic mass different from the atomic mass conventionally found in nature. Examples of isotopes that can be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Representative Embodiments

Reference will now be made in detail to various embodiments. It will be understood that the invention is not limited to these embodiments. To the contrary, it is intended to cover alternatives, modifications, and equivalents as may be included within the spirit and scope of the allowed claims.

The disclosure provides a method of providing a patient with post administration-activated, controlled release of an active agent, which comprises administering to the patient a corresponding compound in which the active agent has a substituent which is a spacer leaving group bearing a nucleophilic nitrogen that is protected with an enzyme-cleavable moiety, the configuration of the spacer leaving group being such that, upon enzymatic cleavage of the cleavable moiety, the nucleophilic nitrogen is capable of forming a cyclic urea, liberating the compound from the spacer leaving group so as to provide the patient with controlled release of an active agent.

The corresponding compound (prodrug in accordance with the present disclosure) provides post administration-activated, controlled release of an active agent, because it requires enzymatic cleavage to initiate release of the compound, and because the rate of release of the active agent depends upon both the rate of enzymatic cleavage and the rate of cyclization. The prodrug is configured so that it will not provide excessively high plasma levels of the active agent if it is administered inappropriately, and cannot readily be decomposed to afford the active agent other than by enzymatic cleavage followed by controlled cyclization.

The enzyme capable of cleaving the enzyme-cleavable moiety can be a peptidase, also referred to as a protease—the enzyme-cleavable moiety being linked to the nucleophilic nitrogen through an amide (e.g. a peptide: —NHCO—) bond.

In some embodiments, the enzyme is a digestive enzyme, such as a digestive enzyme of a protein.

The enzyme-cleavable moiety linked to the nucleophilic nitrogen through an amide bond can be, for example, a residue of an amino acid or a peptide, a variant of a residue of an amino acid or a peptide, a derivative of a residue of an amino acid or a peptide, or a derivative of a residue of an amino acid variant or a peptide variant. As discussed below, an amino acid variant refers to an amino acid other than any of the 20 common naturally occurring L-amino acids that is hydrolyzable by a protease in a manner similar to the ability of a protease to hydrolyze a naturally occurring L-amino acid. A derivative refers to a substance that has been altered from another substance by modification, partial substitution, homologation, truncation, or a change in oxidation state. For example, an N-acyl derivative of an amino acid is an example of a derivative of an amino acid.

In some instances, the enzyme-cleavable moiety can be an (alpha) N-acyl derivative of an amino acid or peptide or an (alpha) N-acyl derivative of an amino acid variant or peptide variant.

The peptide can contain, for example, up to about 100 amino acid residues. Each amino acid can advantageously be a naturally occurring amino acid, such as an L-amino acid. Examples of naturally occurring amino acids are alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. Accordingly, examples of enzyme-cleavable moieties include residues of the L-amino acids listed herein and N-acyl derivatives thereof, and peptides formed from at least two of the L-amino acids listed herein and the N-acyl derivatives thereof. Additional examples include residues of amino acid variants and N-acyl derivatives thereof, and peptides formed from at least two of the L-amino acids listed above and/or variants thereof, and N-acyl derivatives thereof. Also included are derivatives of such amino acids or amino acid variants and peptides thereof.

The embodiments provide a prodrug with a substituent which is a spacer leaving group bearing a nucleophilic nitrogen that is protected with an enzyme-cleavable moiety. Upon enzymatic cleavage of the cleavable moiety, the nucleophilic nitrogen is capable of forming a cyclic urea. A representative scheme of a cyclization of a spacer group is shown below, wherein X is an active agent.

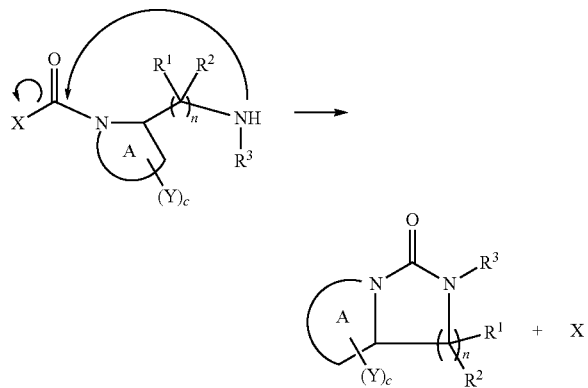

The rate of cyclization of the cyclic urea can be adjusted by incorporation of a heterocyclic ring within the spacer group. In certain embodiments, incorporation of a heterocyclic ring within the spacer group results in formation of a fused ring cyclic urea and in a faster cyclization reaction.

The cyclic group formed when the active agent is released is conveniently pharmaceutically acceptable, in particular a pharmaceutically acceptable cyclic urea. It will be appreciated that cyclic ureas are generally very stable and have low toxicity.

According to one aspect, the embodiments include pharmaceutical compositions, which comprise a GI enzyme-cleavable active agent prodrug and an optional GI enzyme inhibitor. Examples of active agent prodrugs and enzyme inhibitors are described below.

Active Agent Prodrugs

An "active agent" refers to a chemical substance that exerts a pharmacological action. Examples of active agents include, but are not limited to, active agents that are susceptible to misuse, abuse, or overdose. Certain examples of active agents include, but are not limited to, opioids, NSAIDs, other analgesics, GABA agonists, GABA antagonists, and psychostimulants.

The disclosure provides a prodrug which provides enzymatically-controlled release of an active agent. The disclosure provides a promoiety that is attached to an active agent through any suitable structural moiety on the drug, where the structural moiety has a reactive group. Examples of reactive groups on an active agent include, but are not limited to, ketone, phenol, and amide.

Formula I

Compounds of the present disclosure include compounds of formula I shown below. Compositions of the present disclosure also include compounds of formula I shown below. Pharmaceutical compositions and methods of the present disclosure also contemplate compounds of formula I.

The present embodiments provide a compound of formula I:

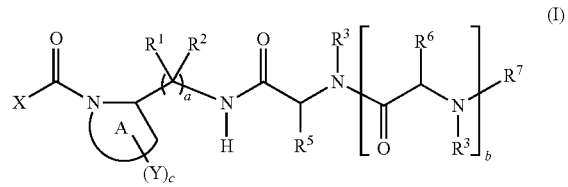

wherein

X is selected from a residue of a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; a residue of a phenolic active agent, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; and a residue of an amide-containing active agent, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl; or a salt, hydrate or solvate thereof.

Opioid Prodrugs

An "opioid" refers to a chemical substance that exerts its pharmacological action by interaction at an opioid receptor. An opioid can be a natural product, a synthetic compound or a semi-synthetic compound. In certain embodiments, an opioid is a compound with a pharmacophore that presents to the opioid receptor an aromatic group and an aliphatic amine group in an architecturally discrete way. See, for example, Foye's Principles of Medicinal Chemistry, Sixth Edition, ed. T. L. Lemke and D. A. Williams, Lippincott Williams & Wilkins, 2008, particularly Chapter 24, pages 653-678.

The disclosure provides an opioid prodrug that provides controlled release of an opioid. The disclosure provides a promoiety that is attached to an opioid through any structural moiety on the opioid, where the structural moiety has a reactive group. Examples of reactive groups on an opioid include, but are not limited to ketone, phenol, and amide.

It is contemplated that opioids bearing at least some of the functionalities described herein will be developed; such opioids are included as part of the scope of this disclosure.

Formula II

Compounds of the present disclosure include compounds of formula II shown below. Compositions of the present disclosure also include compounds of formula II shown below. Pharmaceutical compositions and methods of the present disclosure also contemplate compounds of formula II.

The present embodiments provide a compound of formula II:

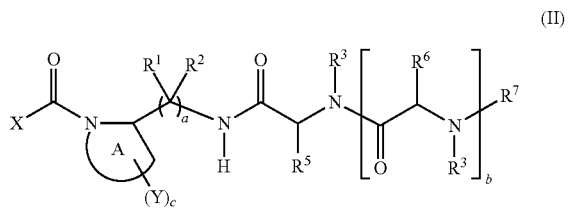

wherein

X is selected from a residue of a ketone-containing opioid, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; a residue of a phenolic opioid, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; and a residue of an amide-containing opioid, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In formula II, X can be selected from a residue of a ketone-containing opioid, wherein the hydrogen atom of the corresponding hydroxyl group of the enolic tautomer of the ketone is replaced by a covalent bond to —C(O)—N[(A ring)-Y$_c$]—(CR¹R²)$_a$—NH—C(O)—CH(R⁵)—N(R³)—[C(O)—CH(R⁶)—N(R³)]$_b$—R⁷; a residue of a phenolic opioid, wherein the hydrogen atom of the phenolic hydroxyl group is replaced by a covalent bond to —C(O)—N[(A ring)-Y$_c$]—(CR¹R²)$_a$—NH—C(O)—CH(R⁵)—N(R³)—[C(O)—CH(R⁶)—N(R³)]$_b$—R⁷; and a residue of an amide-containing opioid, wherein —C(O)—N[(A ring)-Y$_c$]—(CR¹R²)$_a$—NH—C(O)—CH(R⁵)—N(R³)—[C(O)—CH(R⁶)—N(R³)]$_b$—R⁷ is connected to the amide-containing opioid through the oxygen of the amide group, wherein the amide group is converted to an amide enol or an imine tautomer.

In certain instances, X is a ketone-containing opioid, wherein the hydrogen atom of the corresponding hydroxyl group of the enolic tautomer of the ketone is replaced by a covalent bond to —C(O)—N[(A ring)-Y$_c$]—(CR¹R²)$_a$—NH—C(O)—CH(R⁵)—N(R³)—[C(O)—CH(R⁶)—N(R³)]$_b$—R⁷.

In certain instances, X is a ketone-containing opioid, wherein the opioid is selected from acetylmorphone, hydrocodone, hydromorphone, ketobemidone, methadone, naloxone, naltrexone, N-methylnaloxone, N-methylnaltrexone, oxycodone, oxymorphone, and pentamorphone.

In certain instances, X is a residue of a phenolic opioid, wherein the hydrogen atom of the phenolic hydroxyl group is replaced by a covalent bond to —C(O)—N[(A ring)-Y$_c$]—(CR¹R²)$_a$—NH—C(O)—CH(R⁵)—N(R³)—[C(O)—CH(R⁶)—N(R³)]$_b$—R⁷.

In certain instances, X is a phenolic opioid, wherein the opioid is selected from buprenorphine, dihydroetorphine, diprenorphine, etorphine, hydromorphone, levorphanol, morphine, nalbuphine, nalmefene, nalorphine, naloxone, naltrexone, N-methyldiprenorphine, N-methylnaloxone, N-methylnaltrexone, oripavine, oxymorphone, butorphanol, dezocine, ketobemidone, meptazinol, o-desmethyltramadol, pentazocine, phenazocine, and tapentadol.

In certain instances, X is a residue of an amide-containing opioid, wherein —C(O)—N[(A ring)-Y$_c$]—(CR¹R²)$_a$—NH—C(O)—CH(R⁵)—N(R³)—[C(O)—CH(R⁶)—N(R³)]$_b$—R⁷ is connected to the amide-containing opioid through the oxygen of the amide group, wherein the amide group is converted to an amide enol or an imine tautomer.

In certain instances, X is an amide-containing opioid, wherein the opioid is selected from alfentanil, carfentanil, fentanyl, lofentanil, loperamide, olmefentanyl, remifentanil, and sufentanil.

Ketone-Modified Active Agent Prodrugs

The disclosure provides a ketone-modified active agent prodrug that provides controlled release of a ketone-containing active agent. In a ketone-modified active agent prodrug, a promoiety is attached to the ketone-containing active agent through the enolic oxygen atom of the ketone moiety. In a ketone-modified active agent prodrug, the hydrogen atom of the corresponding hydroxyl group of the enolic tautomer of the ketone-containing active agent is replaced by a covalent bond to a promoiety.

As disclosed herein, an enzyme-cleavable ketone-modified active agent prodrug is a ketone-modified active agent prodrug that comprises a promoiety comprising an enzyme-cleavable moiety, i.e., a moiety having a site susceptible to cleavage by an enzyme. In one embodiment, the cleavable moiety is a GI enzyme-cleavable moiety, such as a trypsin-cleavable moiety. Such a prodrug comprises a ketone-containing active agent covalently bound to a promoiety comprising an enzyme-cleavable moiety, wherein cleavage of the enzyme-cleavable moiety by an enzyme mediates release of the drug.

Formulae III-VI

Compounds of the present disclosure include compounds of formulae III-VI shown below. Compositions of the present disclosure also include compounds of formulae III-VI shown below. Pharmaceutical compositions and methods of the present disclosure also contemplate compounds of formulae III-VI. Reference to the formula number is meant to include compounds of both the "a" and "b" versions of the formula number.

The present embodiments provide a compound of formula IIIa:

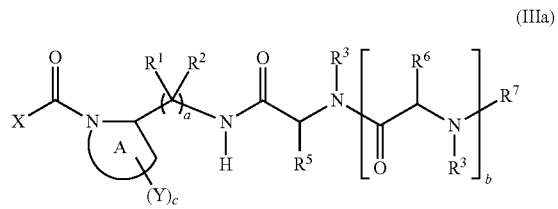

(IIIa)

wherein

X represents a residue of a ketone-containing active agent, wherein the hydrogen atom of the corresponding hydroxyl group of the enolic tautomer of the ketone is replaced by a covalent bond to —C(O)—N[(A ring)-Y$_c$]—(CR¹R²)$_a$—NH—C(O)—CH(R⁵)—N(R³)—[C(O)—CH(R⁶)—N(R³)]$_b$—R⁷;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R¹ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R² is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R¹ and R² together with the carbon to which they are attached can form a cycloalkyl or substituted cycloalkyl group, or two R¹ or R² groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula IIIb:

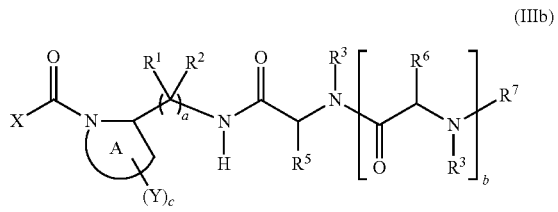

(IIIb)

wherein

X represents a residue of a ketone-containing opioid, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula IV:

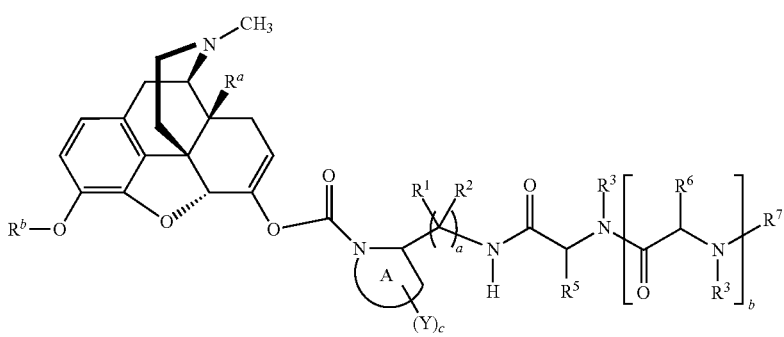

(IV)

wherein $R^a$ is hydrogen or hydroxyl;

$R^b$ is hydrogen or alkyl;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula Va:

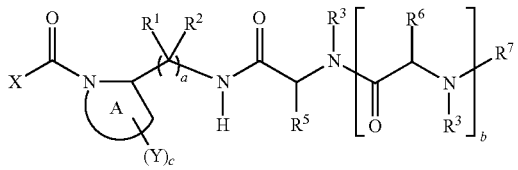

(Va)

wherein

X represents a residue of a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula Vb:

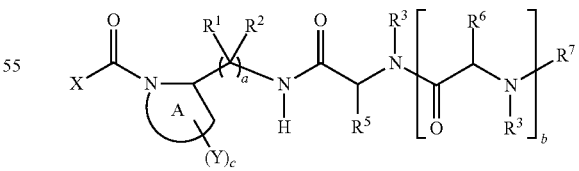

(Vb)

wherein

X represents a residue of a ketone-containing opioid, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula VIa:

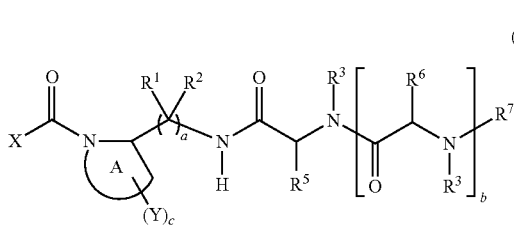

(VIa)

wherein

X represents a residue of a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula VIb:

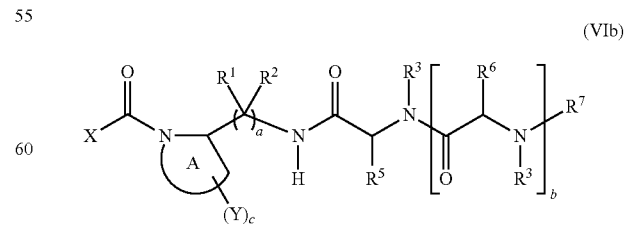

(VIb)

wherein

X represents a residue of a ketone-containing opioid, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In formula III and V-VI, X can be a residue of a ketone-containing active agent or a ketone-containing opioid.

In certain embodiments, the ketone-containing active agent is a ketone-containing opioid. A "ketone-containing opioid" refers to a subset of the opioids that contain a ketone group. As used herein, a ketone-containing opioid is an opioid containing an enolizable ketone group. A ketone-containing opioid is a compound with a pharmacophore that presents to the opioid receptor an aromatic group and an aliphatic amine group in an architecturally discrete way. See, for example, Foye's Principles of Medicinal Chemistry, Sixth Edition, ed. T. L. Lemke and D. A. Williams, Lippincott Williams & Wilkins, 2008, particularly Chapter 24, pages 653-678.

For example, ketone-containing opioids include, but are not limited to, acetylmorphone, hydrocodone, hydromorphone, ketobemidone, methadone, naloxone, naltrexone, N-methylnaloxone, N-methylnaltrexone, oxycodone, oxymorphone, and pentamorphone.

In certain embodiments, the ketone-containing opioid is hydrocodone, hydromorphone, oxycodone, or oxymorphone.

In certain embodiments, the ketone-containing opioid is naloxone, naltrexone, N-methylnaloxone, or N-methylnaltrexone.

In certain embodiments, the ketone-containing opioid is hydrocodone or oxycodone. In certain embodiments, the ketone-containing opioid is hydrocodone. In certain embodiments, the ketone-containing opioid is oxycodone.

It is contemplated that opioids bearing at least some of the functionalities described herein will be developed; such opioids are included as part of the scope of this disclosure.

In formula IV, $R^a$ can be hydrogen or hydroxyl. In certain instances, $R^a$ is hydrogen. In other instances, $R^a$ is hydroxyl.

In formula IV, $R^b$ is hydrogen or alkyl. In certain instances, $R^b$ is hydrogen. In other instances, $R^b$ is alkyl.

Particular compounds of interest, and salts or solvates or stereoisomers thereof, include:

N-(oxycodone-6-enol-carbonyl)-R-(piperidine-2-methylamine)-L-arginine-glycine-malonate (Compound KC-17):

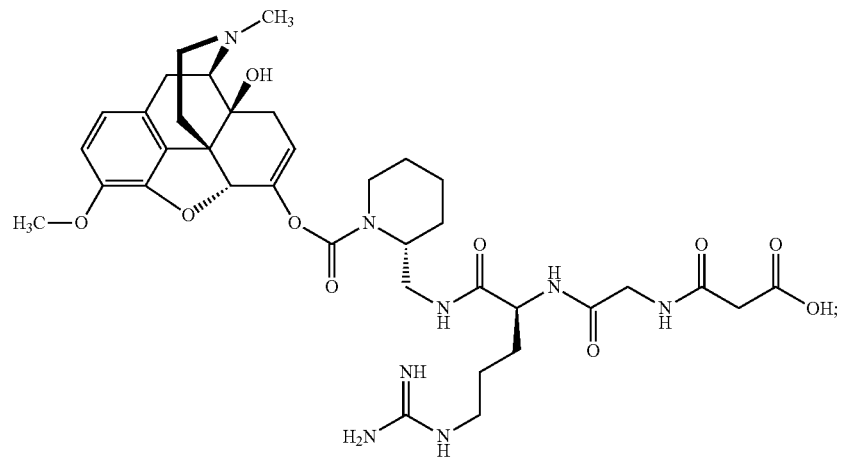

35

N-(oxycodone-6-enol-carbonyl)piperidine-2-methylamine-L-arginine-malonate (Compound KC-12):

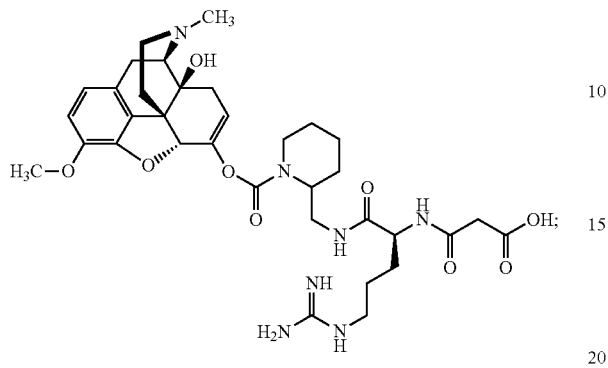

N-(oxycodone-6-enol-carbonyl)piperidine-2-methylamine-L-arginine-L-alanine-acetate (Compound KC-13):

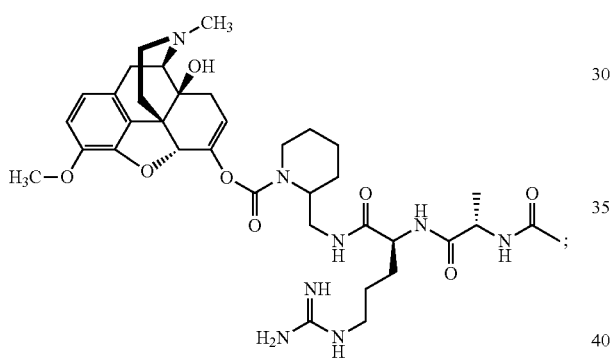

36

N-(oxycodone-6-enol-carbonyl)piperidine-2-methylamine-L-arginine-glycine-acetate (Compound KC-14):

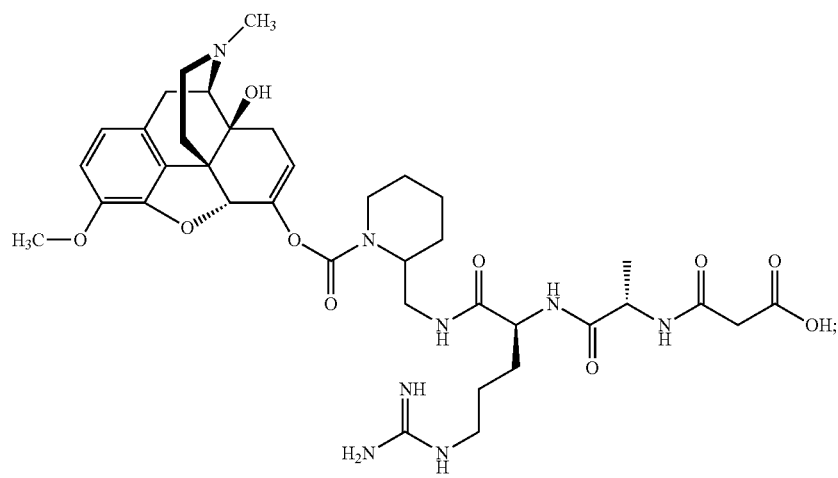

N-(oxycodone-6-enol-carbonyl)piperidine-2-methylamine-L-arginine-L-alanine-malonate (Compound KC-15):

N-(oxycodone-6-enol-carbonyl)piperidine-2-methy-lamine-L-arginine-glycine-malonate (Compound KC-16):
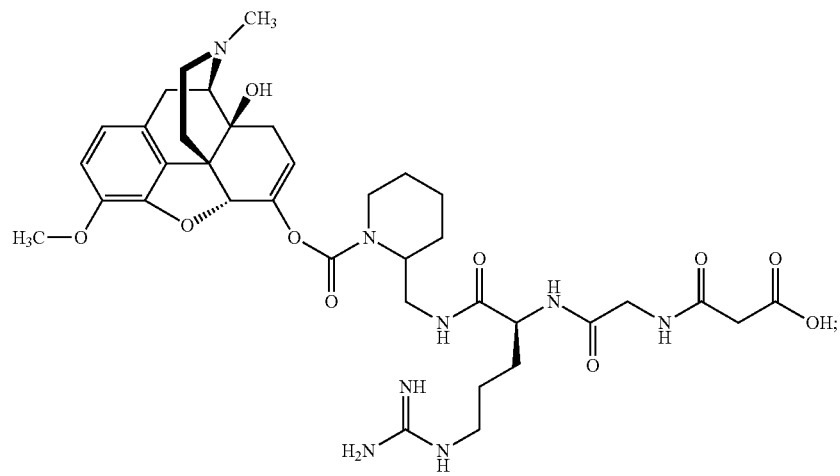
and
N-(hydrocodone-6-enol-carbonyl)-R-(piperidine-2-methylamine)-L-arginine-glycine-malonate (Compound KC-31):
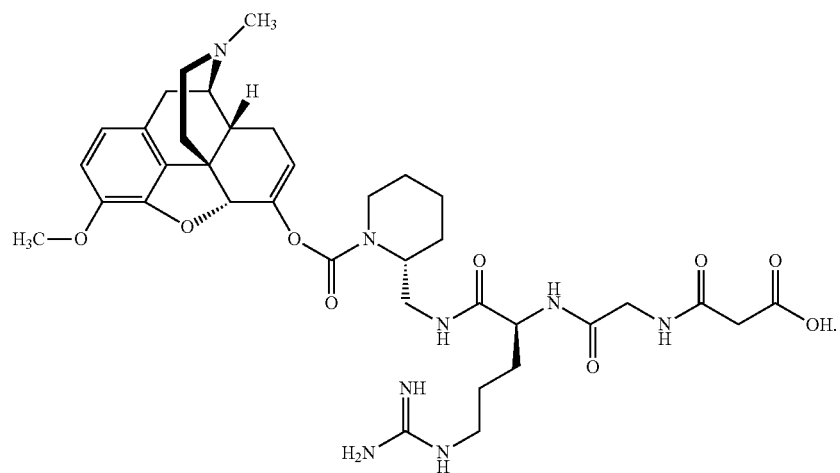

Particular compounds of interest, and salts or solvates or stereoisomers thereof, include:
Compound KC-32:
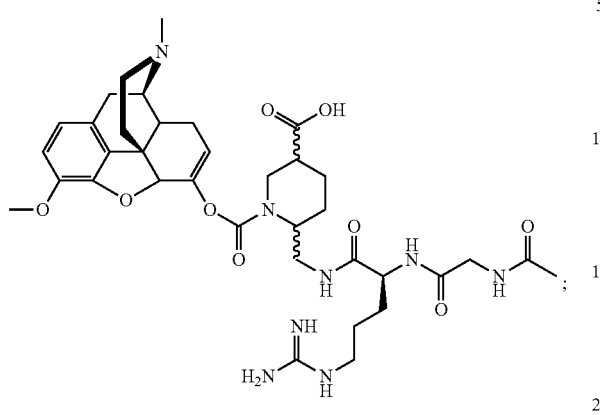
Compound KC-35:
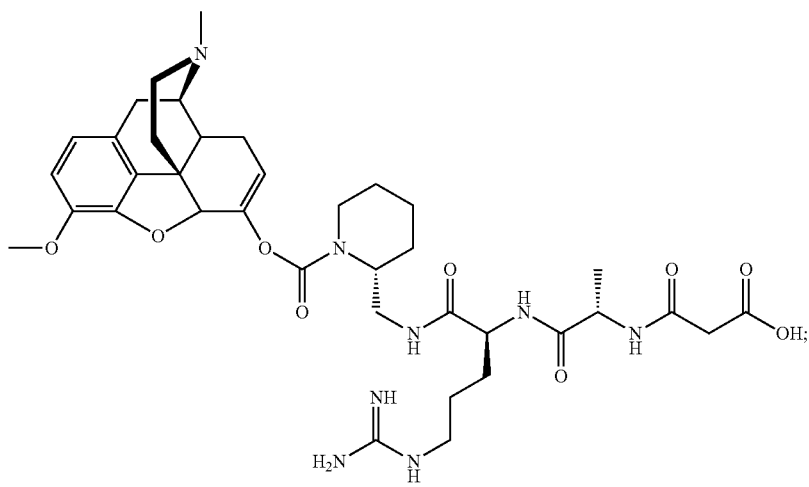
Compound KC-36:
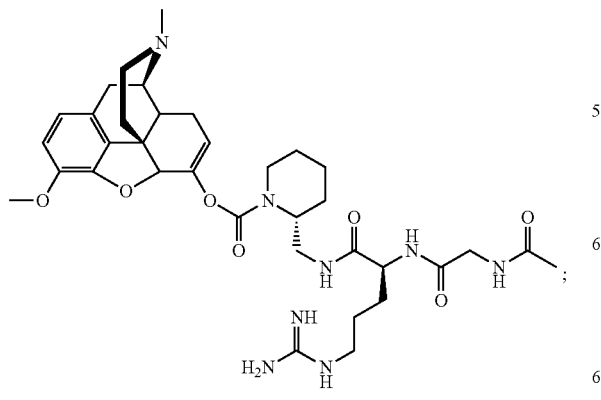
Compound KC-37:
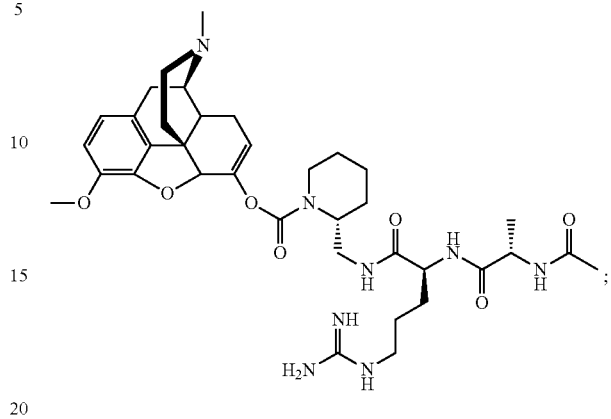
Compound KC-38:
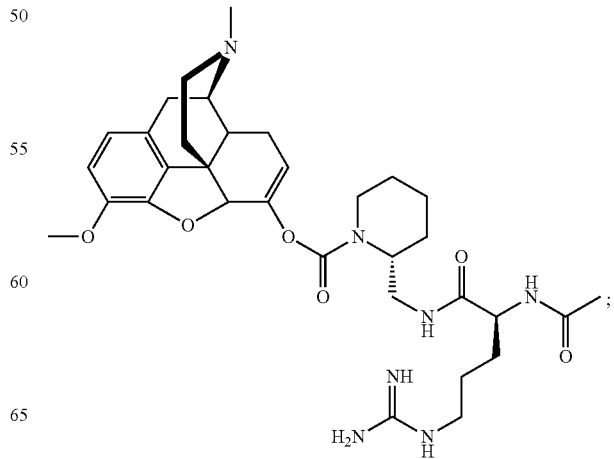

41
Compound KC-39:
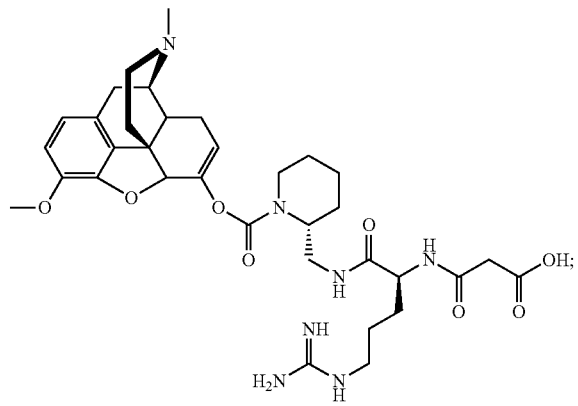
Compound KC-40:
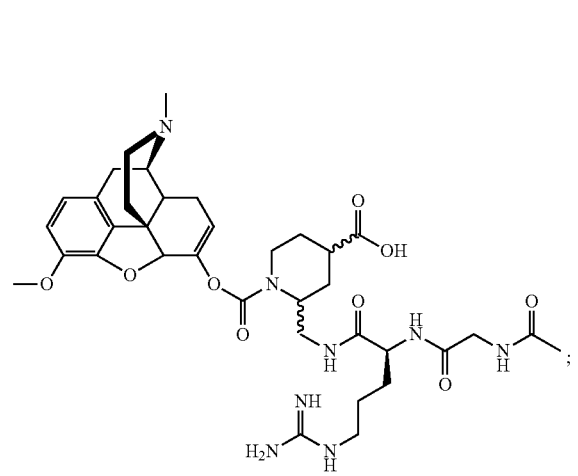
Compound KC-41:
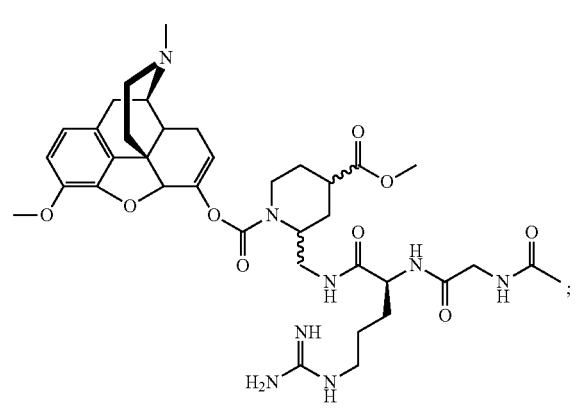
42
Compound KC-42:
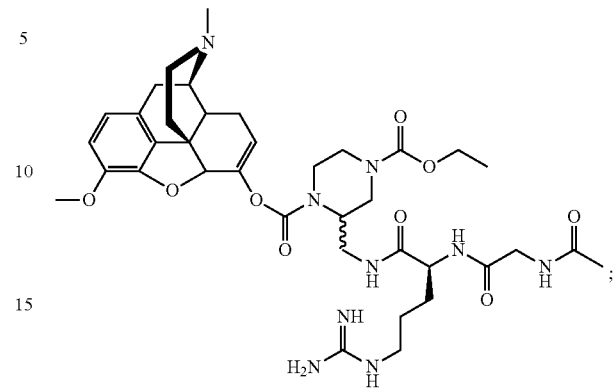
Compound KC-43:
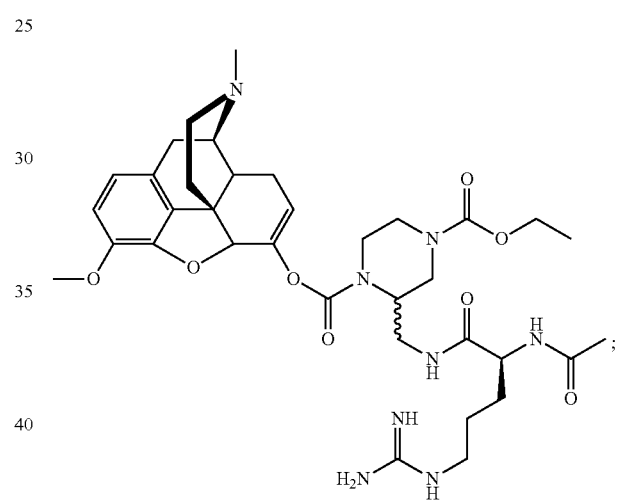
Compound KC-44:
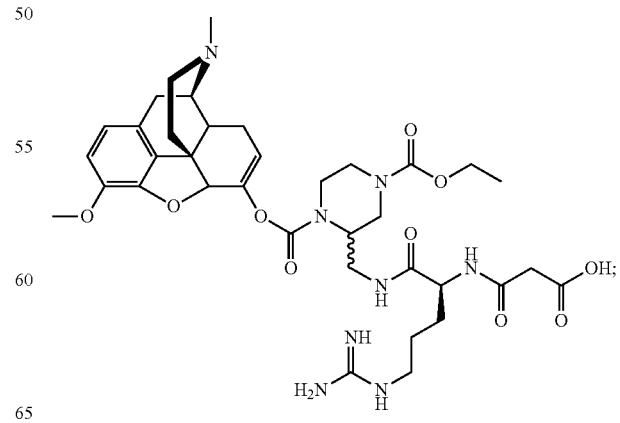

Compound KC-45:
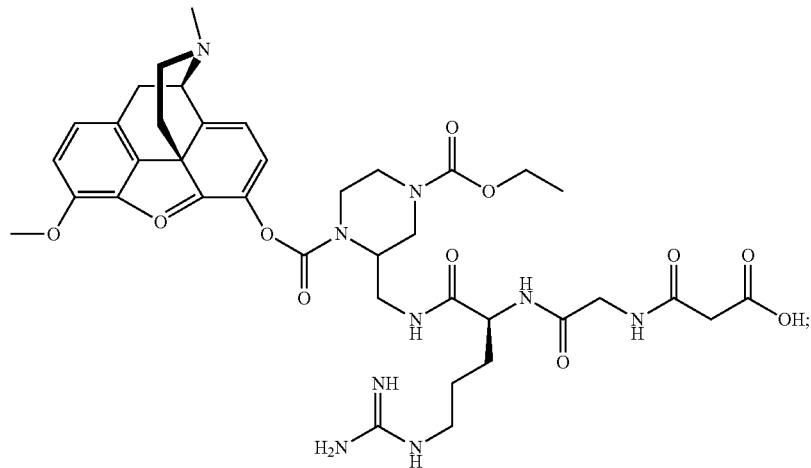
Compound KC-46:
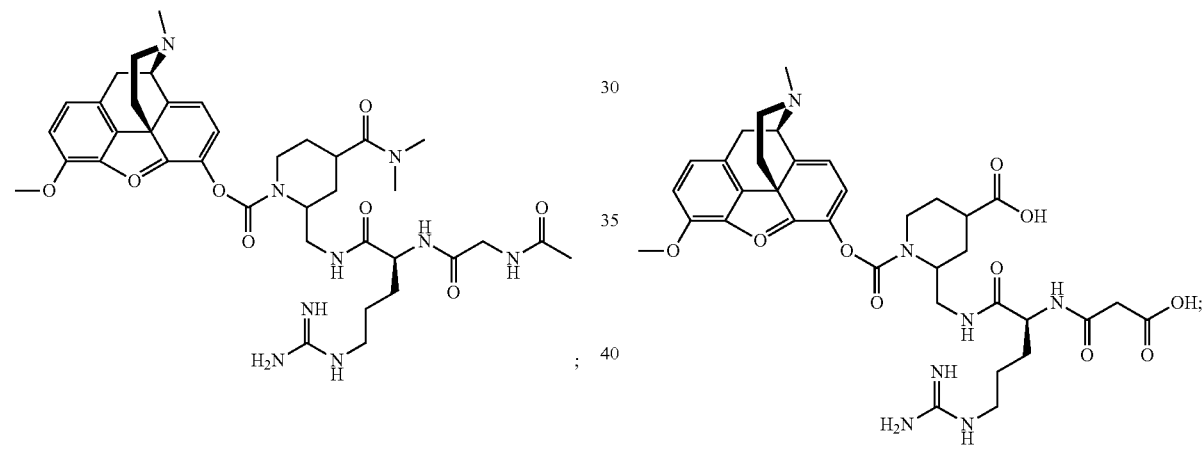
Compound KC-48:
Compound KC-47:
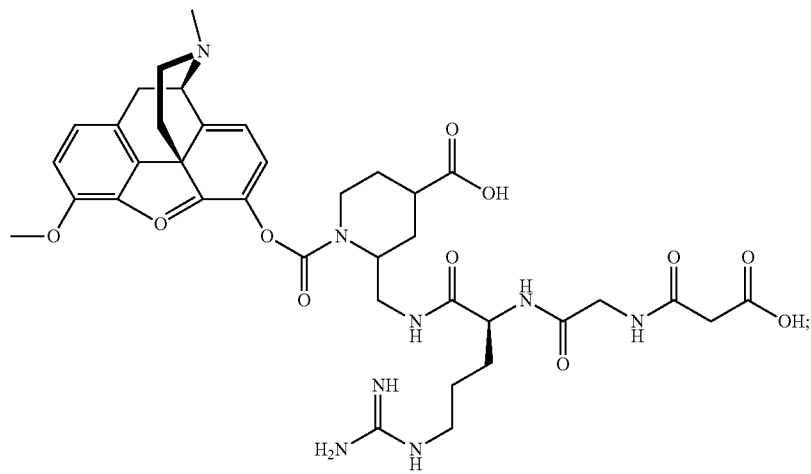

Compound KC-49:
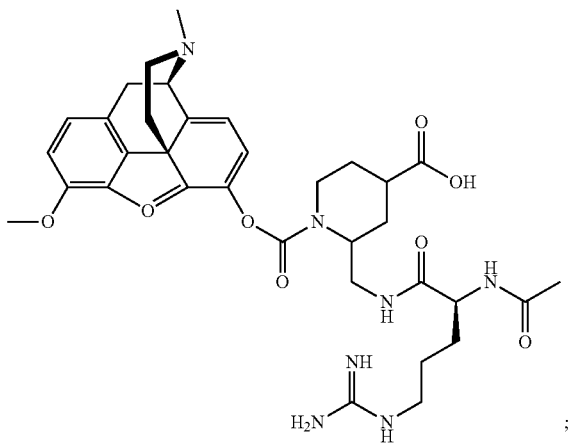
Compound KC-51:
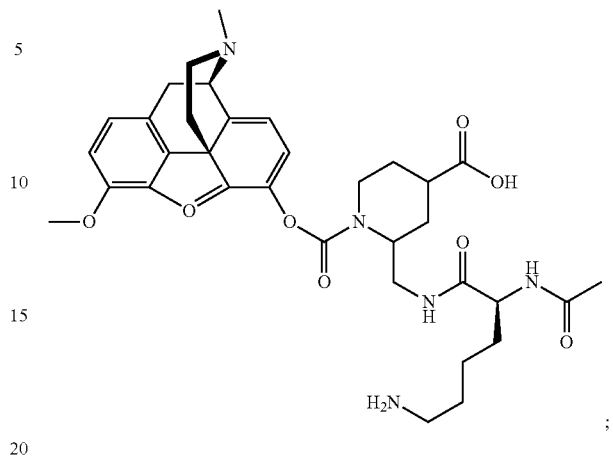
Compound KC-50:
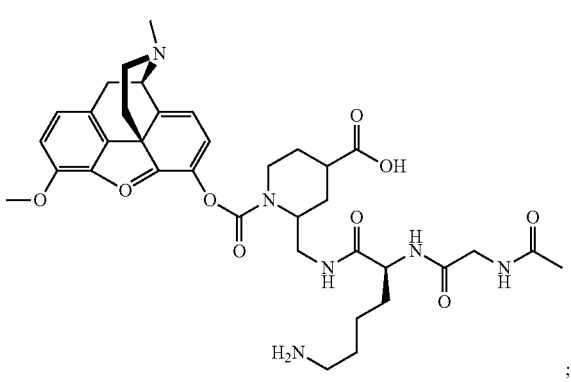
Compound KC-52:
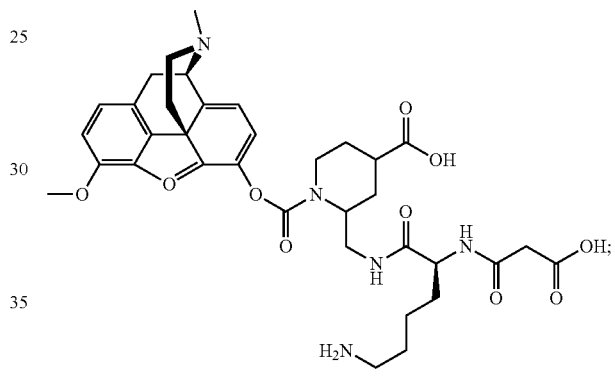
Compound KC-53:
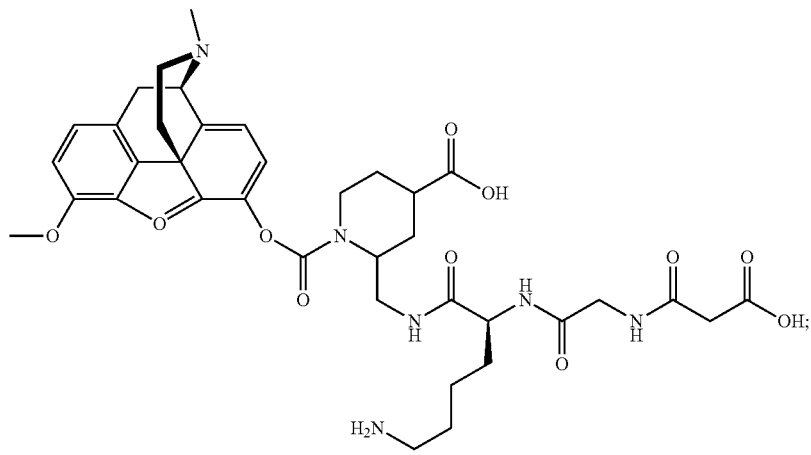

and
Compound KC-55:

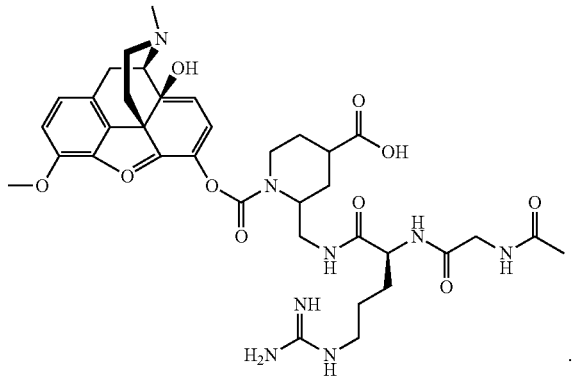

Phenolic Active Agent Prodrugs

The disclosure provides a phenolic active agent prodrug that provides controlled release of a phenolic active agent. In a phenolic active agent prodrug, a promoiety is attached to the phenolic active agent through the phenolic oxygen atom. In a phenolic active agent prodrug, the oxygen atom of the phenol group of the phenolic active agent is replaced by a covalent bond to a promoiety.

As disclosed herein, an enzyme-cleavable phenolic active agent prodrug is a phenolic active agent prodrug that comprises a promoiety comprising an enzyme-cleavable moiety, i.e., a moiety having a site susceptible to cleavage by an enzyme. In one embodiment, the cleavable moiety is a GI enzyme-cleavable moiety, such as a trypsin-cleavable moiety. Such a prodrug comprises a phenolic active agent covalently bound to a promoiety comprising an enzyme-cleavable moiety, wherein cleavage of the enzyme-cleavable moiety by an enzyme mediates release of the drug.

Formulae VII-X

Compounds of the present disclosure include compounds of formulae VII-X shown below. Compositions of the present disclosure also include compounds of formulae VII-X shown below. Pharmaceutical compositions and methods of the present disclosure also contemplate compounds of formulae VII-X. Reference to the formula number is meant to include compounds of both the "a" and "b" versions of the formula number.

The present embodiments provide a compound of formula VIIa:

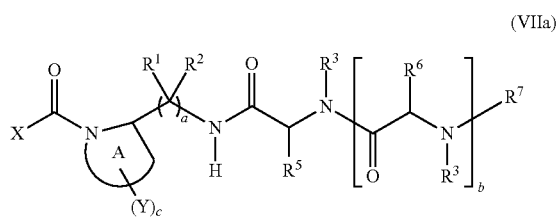

wherein

X represents a residue of a phenolic active agent, wherein the hydrogen atom of the phenolic hydroxyl group is replaced by a covalent bond to —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula VIIb:

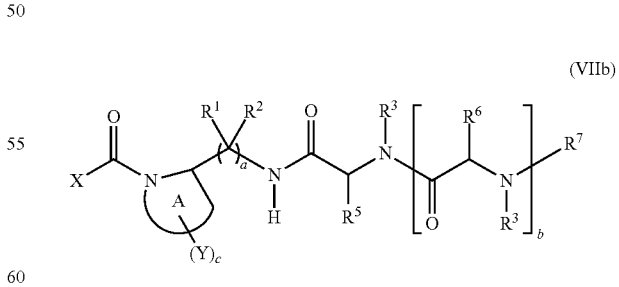

wherein

X represents a residue of a phenolic opioid, wherein the hydrogen atom of the phenolic hydroxyl group is replaced by a covalent bond to —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula VIII:

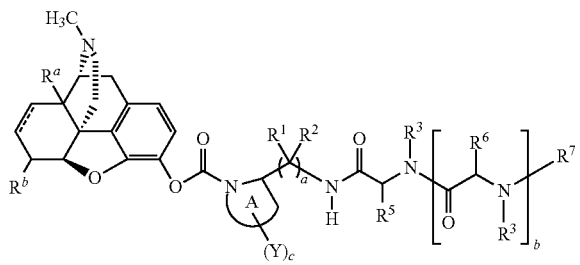

(VIII)

wherein $R^a$ is hydrogen or hydroxyl;

$R^b$ is hydrogen or alkyl;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, acylamino, substituted acylamino, substituted aminoacyl, amino, substituted amino, acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula IXa:

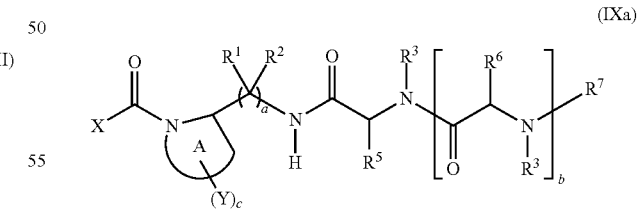

(IXa)

wherein

X represents a residue of a phenolic active agent, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula IXb:

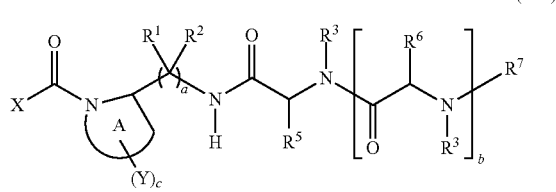

(IXb)

wherein

X represents a residue of a phenolic opioid, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula Xa:

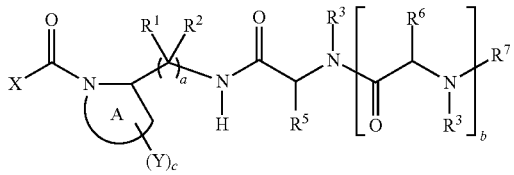

wherein

X represents a residue of a phenolic active agent, wherein the hydrogen atom of the phenolic hydroxyl group is replaced by a covalent bond to —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ represents a side chain of an amino acid, a side chain of an amino acid variant, a derivative of a side chain of an amino acid, or a derivative of a side chain of an amino acid variant that effects —C(O)—CH(R$^5$)—N(R$^3$)— to be a GI enzyme-cleavable moiety;

each R$^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula Xb:

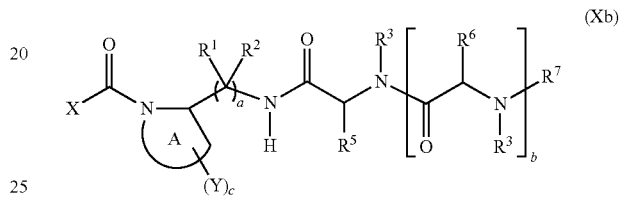

wherein

X represents a residue of a phenolic opioid, wherein the hydrogen atom of the phenolic hydroxyl group is replaced by a covalent bond to —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ represents a side chain of an amino acid, a side chain of an amino acid variant, a derivative of a side chain of an amino acid, or a derivative of a side chain of an amino acid variant that effects —C(O)—CH(R⁵)—N(R³)— to be a GI enzyme-cleavable moiety;

each R⁶ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In formula VII and IX-X, X can be a residue of a phenolic active agent or a phenolic opioid.

In certain embodiments, the phenolic active agent is a phenolic opioid. A "phenolic opioid" refers to a subset of the opioids that contain a phenol group. A phenolic opioid is a compound with a pharmacophore that presents to the opioid receptor an aromatic group and an aliphatic amine group in an architecturally discrete way. See, for example, Foye's Principles of Medicinal Chemistry, Sixth Edition, ed. T. L. Lemke and D. A. Williams, Lippincott Williams & Wilkins, 2008, particularly Chapter 24, pages 653-678.

For instance, the following opioids contain a phenol group that can be a point of attachment to a promoiety: buprenorphine, dihydroetorphine, diprenorphine, etorphine, hydromorphone, levorphanol, morphine, nalbuphine, nalmefene, nalorphine, naloxone, naltrexone, N-methyldiprenorphine, N-methylnaloxone, N-methylnaltrexone, oripavine, oxymorphone, butorphanol, dezocine, ketobemidone, meptazinol, o-desmethyltramadol, pentazocine, phenazocine, and tapentadol.

In certain embodiments, the phenolic opioid is hydromorphone, morphine, oxymorphone, or tapentadol.

In certain embodiments, the phenolic opioid is naloxone, naltrexone, N-methylnaloxone, or N-methylnaltrexone. In certain embodiments, the phenolic opioid is diprenorphine or N-methyldiprenorphine.

In certain embodiments, the phenolic opioid is hydromorphone. In certain embodiments, the phenolic opioid is morphine. In certain embodiments, the phenolic opioid is oxymorphone. In certain embodiments, the phenolic opioid is tapentadol.

It is contemplated that opioids bearing at least some of the functionalities described herein will be developed; such opioids are included as part of the scope of this disclosure.

In formula VIII, Rᵃ can be hydrogen or hydroxyl. In certain instances, Rᵃ is hydrogen. In other instances, Rᵃ is hydroxyl.

In formula VIII, Rᵇ is hydrogen or alkyl. In certain instances, Rᵇ is hydrogen. In other instances, Rᵇ is alkyl.

Particular compound of interest, and salts or solvates or stereoisomers thereof, includes:

N-(Tapentadol-carbonyl)piperidine-2-methylamine-L-arginine-malonate (Compound TP-5):

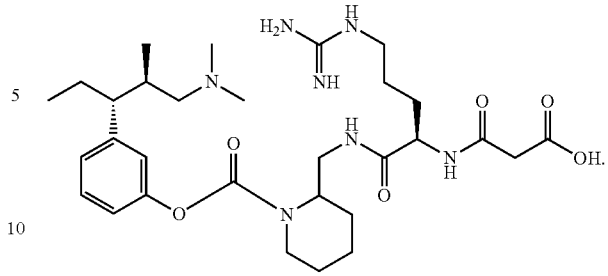

Amide-Modified Active Agent Prodrugs

The disclosure provides an amide-modified active agent prodrug that provides controlled release of an amide-containing active agent. As shown below, in an amide-modified active agent prodrug, a promoiety is attached to the amide-containing active agent through the enolic oxygen atom of the amide enol moiety or through the oxygen of the imine tautomer. In an amide-modified active agent prodrug, the hydrogen atom of the corresponding enolic group of the amide enol or of the imine tautomer of the amide-containing active agent is replaced by a covalent bond to a promoiety. In certain embodiments, the promoiety that replaces the hydrogen atom of the corresponding enolic group of the amide enol or the imine tautomer of the amide-containing active agent contains an acyl group as the point of connection.

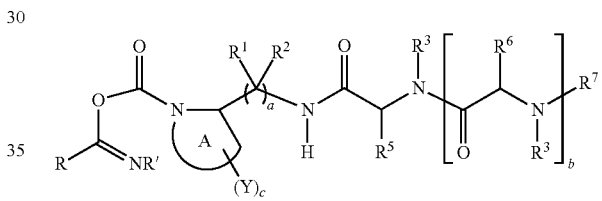

imine tautomer where R and R' are collectively the rest of the amide-containing opioid or one of the R and R' is hydrogen and the other is the rest is the amide-containing opioid

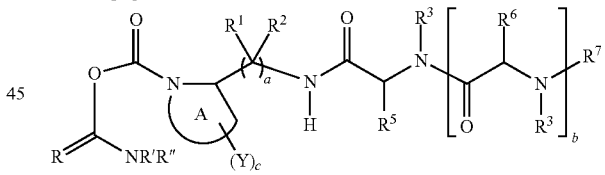

amide enol where R, R', and R" are collectively the rest of the amide-containing opioid or at least one of R, R', and R" is hydrogen and the rest of R, R', and R" are collectively the rest of the amide-containing opioid As disclosed herein, an enzyme-cleavable amide-modified active agent prodrug is an amide-modified active agent prodrug that comprises a promoiety comprising an enzyme-cleavable moiety, i.e., a moiety having a site susceptible to cleavage by an enzyme. Release of the active agent is mediated by enzymatic cleavage of the promoiety from the amide-containing active agent. In one embodiment, the cleavable moiety is a GI enzyme-cleavable moiety, such as a trypsin-cleavable moiety.

Formulae XI-XIII

Compounds of the present disclosure include compounds of formulae XI-XIII shown below. Compositions of the present disclosure also include compounds of formulae XI- XIII shown below. Pharmaceutical compositions and methods of the present disclosure also contemplate compounds of formulae XI-XIII. Reference to the formula number is meant to include compounds of both the "a" and "b" versions of the formula number.

The present embodiments provide a compound of formula XIa:

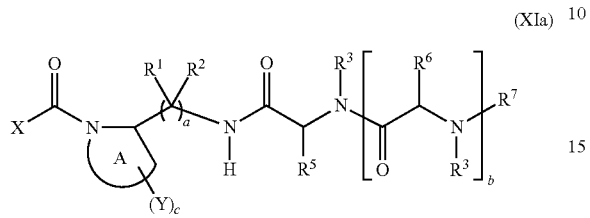

(XIa)

wherein

X represents a residue of an amide-containing active agent, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XIb:

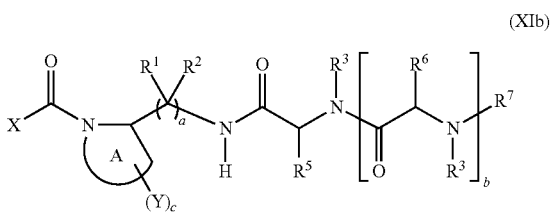

(XIb)

wherein

X represents a residue of an amide-containing opioid, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XIIa:

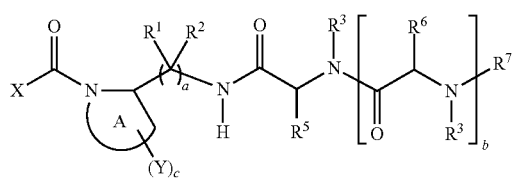

(XIIa)

wherein

X represents a residue of an amide-containing active agent, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each R$^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XIIb:

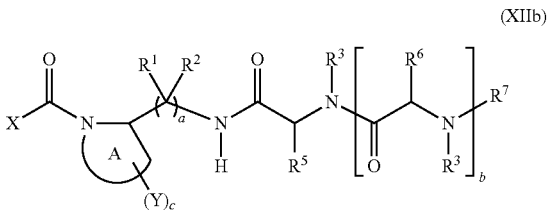

(XIIb)

wherein

X represents a residue of an amide-containing opioid, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XIIIa:

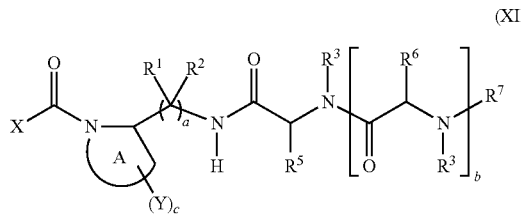

(XIIIa)

wherein

X represents a residue of an amide-containing active agent, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH(R$^5$)—N(R$^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XIIIb:

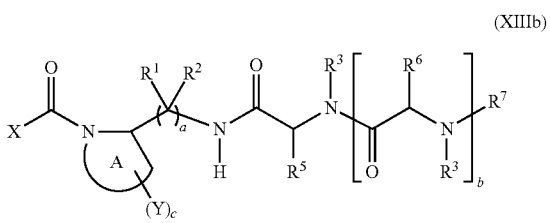

(XIIIb)

wherein

X represents a residue of an amide-containing opioid, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In formula XI-XIII, X can be a residue of an amide-containing active agent, where the amide-containing active agent is connected through the oxygen of the amide group, wherein the amide group is converted to an amide enol or an imine tautomer of an amide-containing opioid, where the amide-containing active agent is connected through the oxygen of the amide group, wherein the amide group is converted to an amide enol or an imine tautomer.

In certain embodiments, the amide-containing active agent is an amide-containing opioid. An "amide-containing opioid" refers to a subset of the opioids that contain an amide group. As used herein, an amide-containing opioid is an opioid containing an enolizable amide group. An amide-containing opioid is a compound with a pharmacophore that presents to the opioid receptor an aromatic group and an aliphatic amine group in an architecturally discrete way. See, for example, Foye's Principles of Medicinal Chemistry, Sixth Edition, ed. T. L. Lemke and D. A. Williams, Lippincott Williams & Wilkins, 2008, particularly Chapter 24, pages 653-678.

For instance, the following opioids contain an amide group that can be a point of attachment to a promoiety: alfentanil, carfentanil, fentanyl, lofentanil, loperamide, olmefentanyl, remifentanil, and sufentanil.

It is contemplated that opioids bearing at least some of the functionalities described herein will be developed; such opioids are included as part of the scope of this disclosure.

Acetaminophen Prodrugs

"Acetaminophen" (i.e., para-acetylaminophenol, paracetamol, or APAP) refers to a chemical substance that exerts its pharmacological action by inhibiting cyclooxygenase (COX), such as COX-2. Acetaminophen can be a synthetic compound or a semi-synthetic compound. In certain embodiments, acetaminophen is a compound with a pharmacophore that inhibits COX (e.g., COX-2) and has analgesic and antipyretic effects. See, for example, Foye's Principles of Medicinal Chemistry, Sixth Edition, ed. T. L. Lemke and D. A. Williams, Lippincott Williams & Wilkins, 2008, particularly Chapter 36, pages 959-965.

The disclosure provides for an acetaminophen prodrug, wherein the acetaminophen has an optionally substituted acetaminophen structure:

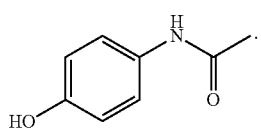

The disclosure provides an acetaminophen prodrug that provides controlled release of acetaminophen. In an acetaminophen prodrug, a promoiety is attached to acetaminophen through the phenolic oxygen atom wherein the hydrogen atom of the phenolic hydroxyl group of acetaminophen is replaced by a covalent bond to the promoiety or through the oxygen of the amide group of acetaminophen, wherein the amide group is converted to an amide enol or an imine tautomer.

It is contemplated that acetaminophens bearing at least some of the functionalities described herein will be developed; such acetaminophens are included as part of the scope of this disclosure.

Formula XIV

Compounds of the present disclosure include compounds of formula XIV shown below. Compositions of the present disclosure also include compounds of formula XIV shown below. Pharmaceutical compositions and methods of the present disclosure also contemplate compounds of formula XIV.

The present embodiments provide a compound of formula XIV:

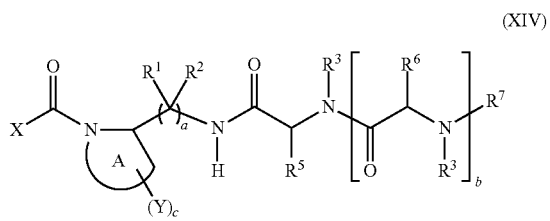

wherein

X represents acetaminophen, wherein the hydrogen atom of the phenolic hydroxyl group of acetaminophen is replaced by a covalent bond to —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$; or wherein —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$ is connected to acetaminophen through the oxygen of the amide group of acetaminophen, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In formula XIV, X represents acetaminophen, wherein the hydrogen atom of the phenolic hydroxyl group of acetaminophen is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; or wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to acetaminophen through the oxygen of the amide group of acetaminophen, wherein the amide group is converted to an amide enol or an imine tautomer.

In certain instances, X represents acetaminophen, wherein the hydrogen atom of the phenolic hydroxyl group of acetaminophen is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$.

In certain instances, X represents acetaminophen, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to acetaminophen through the oxygen of the amide group of acetaminophen, wherein the amide group is converted to an amide enol or an imine tautomer. In certain instances, X represents acetaminophen, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to acetaminophen through the oxygen of the amide group of acetaminophen, wherein the amide group is converted to an amide enol. In certain instances, X represents acetaminophen, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to acetaminophen through the oxygen of the amide group of acetaminophen, wherein the amide group is converted to an imine tautomer.

Compounds with Certain A Rings

Formulae XV-XVII

Compounds of the present disclosure include compounds of formulae XV-XVII shown below. Compositions of the present disclosure also include compounds of formulae XV-XVII shown below. Pharmaceutical compositions and methods of the present disclosure also contemplate compounds of formulae XV-XVII.

The present embodiments provide a compound of formula XVa:

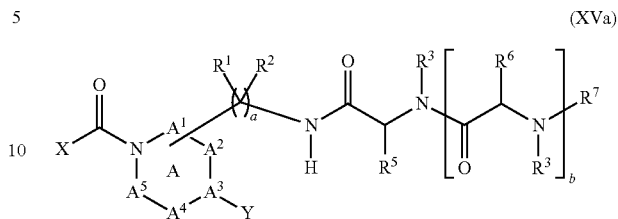

(XVa)

wherein

X is selected from a residue of a ketone-containing active agent, wherein the hydrogen atom of the corresponding hydroxyl group of the enolic tautomer of the ketone is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; a residue of a phenolic active agent, wherein the hydrogen atom of the phenolic hydroxyl group is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; and a residue of an amide-containing active agent, wherein —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

$A^1$, $A^2$, $A^4$, and $A^5$ are independently selected from carbon, nitrogen, oxygen, and sulfur;

$A^3$ is carbon or nitrogen;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XVb:

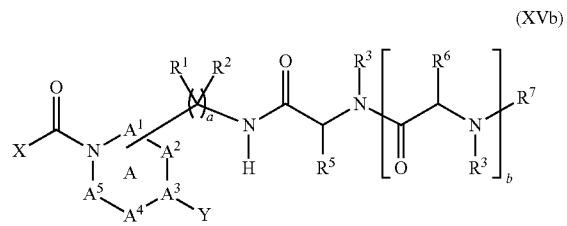

(XVb)

wherein

X is selected from a residue of a ketone-containing opioid, wherein the hydrogen atom of the corresponding hydroxyl group of the enolic tautomer of the ketone is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; a residue of a phenolic opioid, wherein the hydrogen atom of the phenolic hydroxyl group is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; and a residue of an amide-containing opioid, wherein —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

$A^1$, $A^2$, $A^4$, and $A^5$ are independently selected from carbon, nitrogen, oxygen, and sulfur;

$A^3$ is carbon or nitrogen;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XVIa:

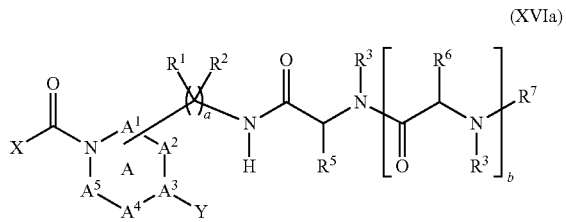

(XVIa)

wherein

X is selected from a residue of a ketone-containing active agent, wherein the hydrogen atom of the corresponding hydroxyl group of the enolic tautomer of the ketone is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; a residue of a phenolic active agent, wherein the hydrogen atom of the phenolic hydroxyl group is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; and a residue of an amide-containing active agent, wherein —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

$A^1$, $A^2$, $A^4$, and $A^5$ are independently selected from carbon, nitrogen, oxygen, and sulfur;

$A^3$ is carbon or nitrogen;

Y is selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two R¹ or R² groups on adjacent carbon atoms, together with the carbon atoms to which they are attached, can form a cycloalkyl or substituted cycloalkyl group;

a is an integer from one to 8;

each R³ is independently hydrogen, alkyl, substituted alkyl, aryl or substituted aryl;

R⁵ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each R⁶ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XVIb:

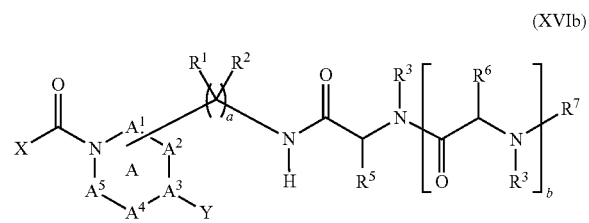

(XVIb)

wherein

X is selected from a residue of a ketone-containing opioid, wherein the hydrogen atom of the corresponding hydroxyl group of the enolic tautomer of the ketone is replaced by a covalent bond to —C(O)—N[(A ring)-Y]—(CR¹R²)ₐ—NH—C(O)—CH(R⁵)—N(R³)—[C(O)—CH(R⁶)—N(R³)]ᵦ—R⁷; a residue of a phenolic opioid, wherein the hydrogen atom of the phenolic hydroxyl group is replaced by a covalent bond to —C(O)—N[(A ring)-Y]—(CR¹R²)ₐ—NH—C(O)—CH(R⁵)—N(R³)—[C(O)—CH(R⁶)—N(R³)]ᵦ—R⁷; and a residue of an amide-containing opioid, wherein —C(O)—N[(A ring)-Y]—(CR¹R²)ₐ—NH—C(O)—CH(R⁵)—N(R³)—[C(O)—CH(R⁶)—N(R³)]ᵦ—R⁷ is connected to the amide-containing opioid through the oxygen of the amide group, wherein the amide group is converted to an amide enol or an imine tautomer;

A¹, A², A⁴, and A⁵ are independently selected from carbon, nitrogen, oxygen, and sulfur;

A³ is carbon or nitrogen;

Y is selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R¹ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R² is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R¹ and R² together with the carbon to which they are attached can form a cycloalkyl or substituted cycloalkyl group, or two R¹ or R² groups on adjacent carbon atoms, together with the carbon atoms to which they are attached, can form a cycloalkyl or substituted cycloalkyl group;

a is an integer from one to 8;

each R³ is independently hydrogen, alkyl, substituted alkyl, aryl or substituted aryl;

R⁵ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each R⁶ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XVIIa:

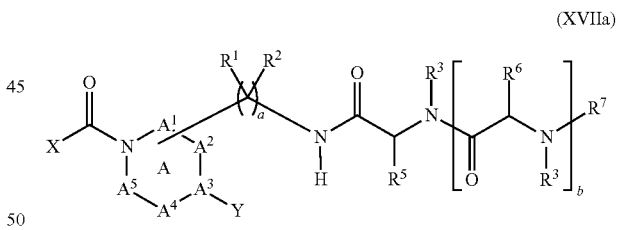

(XVIIa)

wherein

X is selected from a residue of a ketone-containing active agent, wherein the hydrogen atom of the corresponding hydroxyl group of the enolic tautomer of the ketone is replaced by a covalent bond to —C(O)—N[(A ring)-Y]—(CR¹R²)ₐ—NH—C(O)—CH(R⁵)—N(R³)—[C(O)—CH(R⁶)—N(R³)]ᵦ—R⁷; a residue of a phenolic active agent, wherein the hydrogen atom of the phenolic hydroxyl group is replaced by a covalent bond to —C(O)—N[(A ring)-Y]—(CR¹R²)ₐ—NH—C(O)—CH(R⁵)—N(R³)—[C(O)—CH(R⁶)—N(R³)]ᵦ—R⁷; and a residue of an amide-containing active agent, wherein —C(O)—N[(A ring)-Y]—(CR¹R²)ₐ—NH—C(O)—CH(R⁵)—N(R³)—[C(O)—CH(R⁶)—N(R³)]ᵦ—R⁷ is connected to the amide-containing opioid through the oxygen of the amide group, wherein the amide group is converted to an amide enol or an imine tautomer;

$A^1$, $A^2$, $A^4$, and $A^5$ are independently selected from carbon, nitrogen, oxygen, and sulfur;

$A^3$ is carbon or nitrogen;

Y is selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The present embodiments provide a compound of formula XVII:

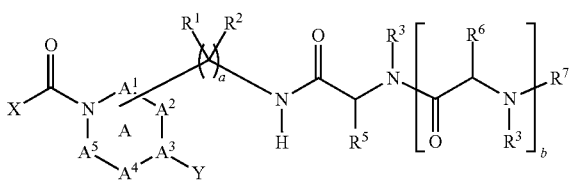

(XVII)

wherein

X is selected from a residue of a ketone-containing opioid, wherein the hydrogen atom of the corresponding hydroxyl group of the enolic tautomer of the ketone is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; a residue of a phenolic opioid, wherein the hydrogen atom of the phenolic hydroxyl group is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; and a residue of an amide-containing opioid, wherein —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

$A^1$, $A^2$, $A^4$, and $A^5$ are independently selected from carbon, nitrogen, oxygen, and sulfur;

$A^3$ is carbon or nitrogen;

Y is selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In formulae XV-XVII, X can be selected from a residue of a ketone-containing active agent or opioid, wherein the hydrogen atom of the corresponding hydroxyl group of the enolic tautomer of the ketone is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; a residue of a phenolic active agent or opioid, wherein the hydrogen atom of the phenolic hydroxyl group is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$; and a residue of an amide-containing active agent or opioid, wherein —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer.

In certain instances, X is a ketone-containing opioid, wherein the hydrogen atom of the corresponding hydroxyl group of the enolic tautomer of the ketone is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$.

In certain instances, X is a ketone-containing opioid, wherein the opioid is selected from acetylmorphone, hydrocodone, hydromorphone, ketobemidone, methadone, naloxone, naltrexone, N-methylnaloxone, N-methylnaltrexone, oxycodone, oxymorphone, and pentamorphone.

In certain instances, X is a residue of a phenolic opioid, wherein the hydrogen atom of the phenolic hydroxyl group is replaced by a covalent bond to —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$.

In certain instances, X is a phenolic opioid, wherein the opioid is selected from buprenorphine, dihydroetorphine, diprenorphine, etorphine, hydromorphone, levorphanol, morphine, nalbuphine, nalmefene, nalorphine, naloxone, naltrexone, N-methyldiprenorphine, N-methylnaloxone, N-methylnaltrexone, oripavine, oxymorphone, butorphanol, dezocine, ketobemidone, meptazinol, o-desmethyltramadol, pentazocine, phenazocine, and tapentadol.

In certain instances, X is a residue of an amide-containing opioid, wherein —C(O)—N[(A ring)-Y]—$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer.

In certain instances, X is an amide-containing opioid, wherein the opioid is selected from alfentanil, carfentanil, fentanyl, lofentanil, loperamide, olmefentanyl, remifentanil, and sufentanil.

In formulae XV-XVII, $A^1$, $A^2$, $A^4$, and $A^5$ are independently selected from carbon, nitrogen, oxygen, and sulfur. In certain instances, $A^1$, $A^2$, $A^4$, and $A^5$ are independently selected from carbon and nitrogen. In certain instances, $A^1$, $A^2$, $A^4$, and $A^5$ are independently selected from carbon and oxygen. In certain instances, $A^1$, $A^2$, $A^4$, and $A^5$ are independently selected from carbon and sulfur. In certain instances, $A^1$, $A^2$, $A^4$, and $A^5$ are carbon.

In formulae XV-XVII, $A^3$ is carbon or nitrogen. In certain instances, $A^3$ is carbon. In certain instances, $A^3$ is nitrogen.

In certain instances, —$(CR^1R^2)_a$—NH—C(O)—CH($R^5$)—N($R^3$)—[C(O)—CH($R^6$)—N($R^3$)]$_b$—$R^7$ is attached to $A^1$. In certain instances, —$(CR^1R^2)_a$—NH—C(O)—CH($R^5$)—N($R^3$)—[C(O)—CH($R^6$)—N($R^3$)]$_b$—$R^7$ is attached to $A^2$. In certain instances, —$(CR^1R^2)_a$—NH—C(O)—CH($R^5$)—N($R^3$)—[C(O)—CH($R^6$)—N($R^3$)]$_b$—$R^7$ is attached to $A^4$. In certain instances, —$(CR^1R^2)_a$—NH—C(O)—CH($R^5$)—N($R^3$)—[C(O)—CH($R^6$)—N($R^3$)]$_b$—$R^7$ is attached to $A^5$.

Certain Embodiments of Formulae I-XVII

In formulae I-XIV, the A ring can be a heterocyclic 5 to 12-membered ring.

In certain instances, the A ring is a heterocyclic 5 to 11-membered ring. In certain instances, the A ring is a heterocyclic 5 to 10-membered ring. In certain instances, the A ring is a heterocyclic 5 to 9-membered ring. In certain instances, the A ring is a heterocyclic 5 to 8-membered ring. In certain instances, the A ring is a heterocyclic 5 to 7-membered ring. In certain instances, the A ring is a heterocyclic 5 or 6-membered ring. In certain instances, the A ring is a heterocyclic 5-membered ring.

In certain instances, the A ring is a heterocyclic 6 to 12-membered ring. In certain instances, the A ring is a heterocyclic 6 to 11-membered ring. In certain instances, the A ring is a heterocyclic 6 to 10-membered ring. In certain instances, the A ring is a heterocyclic 6 to 9-membered ring. In certain instances, the A ring is a heterocyclic 6 to 8-membered ring. In certain instances, the A ring is a heterocyclic 6 or 7-membered ring. In certain instances, the A ring is a heterocyclic 6-membered ring. In certain instances, the A ring is a heterocyclic 7-membered ring. In certain instances, the A ring is a heterocyclic 8-membered ring.

In formulae I-XVII, c can be a number from zero to 3. In certain instances, c is zero. In certain instances, c is 1. In certain instances, c is 2. In certain instances, c is 3.

In formulae I-XVII, each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano.

In formulae I-XVII, Y can be carboxyl or amino. In certain instances, Y is carboxyl. In certain instances, Y is amino.

In certain instances, Y is alkyl or substituted alkyl. In certain instances, Y is alkyl. In certain instances, Y is substituted alkyl. In certain instances, Y is alkenyl or substituted alkenyl. In certain instances, Y is alkenyl. In certain instances, Y is substituted alkenyl. In certain instances, Y is alkynyl or substituted alkynyl. In certain instances, Y is alkynyl. In certain instances, Y is substituted alkynyl. In certain instances, Y is aryl or substituted aryl. In certain instances, Y is aryl. In certain instances, Y is substituted aryl.

In certain instances, Y is acyl or substituted acyl. In certain instances, Y is acyl. In certain instances, Y is substituted acyl. In certain instances, Y is carboxyl. In certain instances, Y is alkoxycarbonyl or substituted alkoxycarbonyl. In certain instances, Y is alkoxycarbonyl. In certain instances, Y is substituted alkoxycarbonyl. In certain instances, Y is aminoacyl or substituted aminoacyl. In certain instances, Y is aminoacyl. In certain instances, Y is substituted aminoacyl. In certain instances, Y is amino or substituted amino. In certain instances, Y is amino. In certain instances, Y is substituted amino. In certain instances, Y is acylamino or substituted acylamino. In certain instances, Y is acylamino. In certain instances, Y is substituted acylamino. In certain instances, Y is cyano.

In certain instances, Y is substituted alkyl. In certain instances, Y is an alkyl group substituted with a carboxylic group such as a carboxylic acid, alkoxycarbonyl or aminoacyl. In certain instances, Y is —$(CH_2)_q(C_6H_4)$—COOH, —$(CH_2)_q(C_6H_4)$—COOCH$_3$, or —$(CH_2)_q(C_6H_4)$—COOCH$_2$CH$_3$, where q is an integer from one to 10. In certain instances, Y is aminoacyl. In certain instances, Y is an alkyl group substituted with an amino group, substituted amino, or acylamino.

In certain instances, Y is aminoacyl or substituted aminoacyl.

In certain instances, Y is aminoacyl comprising phenylenediamine. In certain instances, Y is

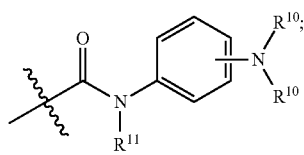

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, Y is

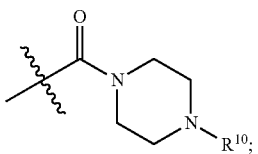

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, Y is

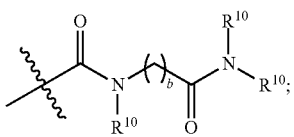

wherein each $R^{10}$ is independently hydrogen, alkyl, substituted alkyl, or acyl and b is a number from one to 5. In certain instances, Y is

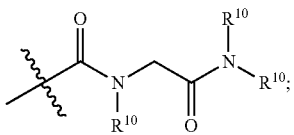

wherein each $R^{10}$ is independently hydrogen, alkyl, substituted alkyl, or acyl. In certain instances, Y is

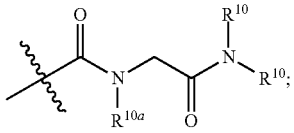

wherein $R^{10a}$ is alkyl and each $R^{10}$ is independently hydrogen, alkyl, substituted alkyl, or acyl.

In certain instances, Y is

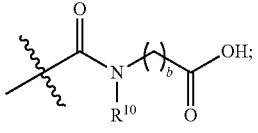

wherein $R^{10}$ is independently hydrogen, alkyl, substituted alkyl, or acyl and b is a number from one to 5. In certain instances, Y is

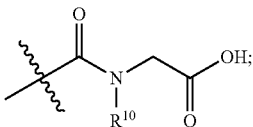

wherein $R^{10}$ is independently hydrogen, alkyl, substituted alkyl, or acyl.

In certain instances, Y is an aminoacyl group, such as —C(O)NR$^{10a}$R$^{10b}$, wherein each R$^{10a}$ and R$^{10b}$ is independently selected from hydrogen, alkyl, substituted alkyl, and acyl. In certain instances, Y is an aminoacyl group, such as —C(O)NR$^{10a}$R$^{10b}$, wherein R$^{10a}$ is an alkyl and R$^{10b}$ is substituted alkyl. In certain instances, Y is an aminoacyl group, such as —C(O)NR$^{10a}$R$^{10b}$, wherein R$^{10a}$ is an alkyl and R$^{10b}$ is alkyl substituted with a carboxylic acid or alkoxycarbonyl. In certain instances, Y is an aminoacyl group, such as —C(O)NR$^{10a}$R$^{10b}$ wherein R$^{10a}$ is methyl and R$^{10b}$ is alkyl substituted with a carboxylic acid or alkoxycarbonyl.

In certain instances, Y is carboxyl.
In certain instances, Y is acyl or substituted acyl.
In certain instances, Y is alkoxycarbonyl or substituted alkoxycarbonyl.
In certain instances, Y is amino or substituted amino.
In certain instances, Y is acylamino or substituted acylamino.

In formulae I-XVII, a can be an integer from one to 8. In certain instances, a is one. In certain instances, a is 2. In certain instances, a is 3. In certain instances, a is 4. In certain instances, a is 5. In certain instances, a is 6. In certain instances, a is 7. In certain instances, a is 8.

In formulae I-XVII, each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano.

In certain instances, $R^1$ is hydrogen. In certain instances, $R^1$ is alkyl or substituted alkyl. In certain instances, $R^1$ is alkyl. In certain instances, $R^1$ is substituted alkyl. In certain instances, $R^1$ is alkenyl or substituted alkenyl. In certain instances, $R^1$ is alkenyl. In certain instances, $R^1$ is substituted alkenyl. In certain instances, $R^1$ is alkynyl or substituted alkynyl. In certain instances, $R^1$ is alkynyl. In certain instances, $R^1$ is substituted alkynyl. In certain instances, $R^1$ is aryl or substituted aryl. In certain instances, $R^1$ is aryl. In certain instances, $R^1$ is substituted aryl. In certain instances, $R^1$ is acyl or substituted acyl. In certain instances, $R^1$ is acyl. In certain instances, $R^1$ is substituted acyl. In certain instances, $R^1$ is carboxyl. In certain instances, $R^1$ is alkoxycarbonyl or substituted alkoxycarbonyl. In certain instances, $R^1$ is alkoxycarbonyl. In certain instances, $R^1$ is substituted alkoxycarbonyl. In certain instances, $R^1$ is aminoacyl or substituted aminoacyl. In certain instances, $R^1$ is aminoacyl. In certain instances, $R^1$ is substituted aminoacyl. In certain instances, $R^1$ is amino or substituted amino. In certain instances, $R^1$ is amino. In certain instances, $R^1$ is substituted amino. In certain instances, $R^1$ is acylamino or substituted acylamino. In certain instances, $R^1$ is acylamino. In certain instances, $R^1$ is substituted acylamino. In certain instances, $R^1$ is cyano.

In formulae I-XVII, each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano.

In certain instances, $R^2$ is hydrogen. In certain instances, $R^2$ is alkyl or substituted alkyl. In certain instances, $R^2$ is alkyl. In certain instances, $R^2$ is substituted alkyl. In certain instances, $R^2$ is alkenyl or substituted alkenyl. In certain instances, $R^2$ is alkenyl. In certain instances, $R^2$ is substituted alkenyl. In certain instances, $R^2$ is alkynyl or substituted alkynyl. In certain instances, $R^2$ is alkynyl. In certain instances, $R^2$ is substituted alkynyl. In certain instances, $R^2$ is aryl or substituted aryl. In certain instances, $R^2$ is aryl. In certain instances, $R^2$ is substituted aryl. In certain instances, $R^2$ is acyl or substituted acyl. In certain instances, $R^2$ is acyl. In certain instances, $R^2$ is substituted acyl. In certain instances, $R^2$ is carboxyl. In certain instances, $R^2$ is alkoxycarbonyl or substituted alkoxycarbonyl. In certain instances, $R^2$ is alkoxycarbonyl. In certain instances, $R^2$ is substituted alkoxycarbonyl. In certain instances, $R^2$ is aminoacyl or substituted aminoacyl. In certain instances, $R^2$ is aminoacyl. In certain instances, $R^2$ is substituted aminoacyl. In certain instances, $R^2$ is amino or substituted amino. In certain instances, $R^2$ is amino. In certain instances, $R^2$ is substituted amino. In certain instances, $R^2$ is acylamino or substituted acylamino. In certain instances, $R^2$ is acylamino. In certain instances, $R^2$ is substituted acylamino. In certain instances, $R^2$ is cyano.

In certain instances, one of $R^1$ and $R^2$ is hydrogen. In certain instances, one of $R^1$ and $R^2$ is alkyl. In certain instances, one of $R^1$ and $R^2$ is substituted alkyl. In certain instances, one of $R^1$ and $R^2$ is alkenyl or substituted alkenyl. In certain instances, one of $R^1$ and $R^2$ is alkynyl or substituted alkynyl. In certain instances, one of $R^1$ and $R^2$ is aryl or substituted aryl. In certain instances, one of $R^1$ and $R^2$ is acyl or substituted acyl. In certain instances, one of $R^1$ and $R^2$ is carboxyl. In certain instances, one of $R^1$ and $R^2$ is alkoxycarbonyl or substituted alkoxycarbonyl. In certain instances, one of $R^1$ and $R^2$ is aminoacyl or substituted aminoacyl. In certain instances, one of $R^1$ and $R^2$ is amino or substituted amino. In certain instances, one of $R^1$ and $R^2$ is acylamino or substituted acylamino. In certain instances, one of $R^1$ and $R^2$ is cyano.

In certain instances, $R^1$ and $R^2$ are hydrogen. In certain instances, $R^1$ and $R^2$ on the same carbon are both alkyl. In certain instances, $R^1$ and $R^2$ on the same carbon are methyl. In certain instances, $R^1$ and $R^2$ on the same carbon are ethyl.

In certain instances, $R^1$ and $R^1$ which are vicinal are both alkyl and $R^2$ and $R^2$ which are vicinal are both hydrogen. In certain instances, $R^1$ and $R^1$ which are vicinal are both ethyl and $R^2$ and $R^2$ which are vicinal are both hydrogen. In certain instances, $R^1$ and $R^1$ which are vicinal are both methyl and $R^2$ and $R^2$ which are vicinal are both hydrogen.

In certain instances, in the chain of $-[C(R^1)(R^2)]_a-$, not every carbon is substituted. In certain instances, in the chain of $-[C(R^1)(R^2)]_a-$, there is a combination of different alkyl substituents, such as methyl or ethyl.

In certain instances, one or both of $R^1$ and $R^2$ is substituted alkyl. In certain instances, one or both of $R^1$ and $R^2$ is an alkyl group substituted with a carboxylic group such as a carboxylic acid, alkoxycarbonyl or aminoacyl. In certain instances, one or both of $R^1$ and $R^2$ is $-(CH_2)_q(C_6H_4)-COOH$, $-(CH_2)_q(C_6H_4)-COOCH_3$, or $-(CH_2)_q(C_6H_4)-COOCH_2CH_3$, where q is an integer from one to 10. In certain instances, one or both of $R^1$ and $R^2$ is aminoacyl.

In formulae I-XVII, $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group. In certain instances, $R^1$ and $R^2$ together with the carbon to which they are attached can form a cycloalkyl group. Thus, in certain instances, $R^1$ and $R^2$ on the same carbon form a spirocycle. In certain instances, $R^1$ and $R^2$ together with the carbon to which they are attached can form a substituted cycloalkyl group. In certain instances, two $R^1$ or $R^2$ groups on adjacent carbon atoms, together with the carbon atoms to which they are attached, can form a cycloalkyl group. In certain instances, two $R^1$ or $R^2$ groups on adjacent carbon atoms, together with the carbon atoms to which they are attached, can form a substituted cycloalkyl group.

In certain instances, one of $R^1$ and $R^2$ is aminoacyl.

In certain instances, one of $R^1$ and $R^2$ is aminoacyl comprising phenylenediamine. In certain instances, one or both of $R^1$ and $R^2$ is

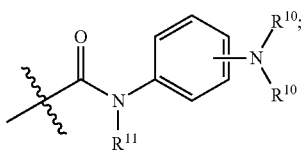

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^1$ and $R^2$ is

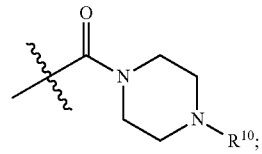

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^1$ and $R^2$ is

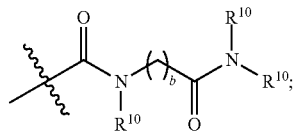

wherein each $R^{10}$ is independently hydrogen, alkyl, substituted alkyl, or acyl and b is a number from one to 5. In certain instances, one of $R^1$ and $R^2$ is

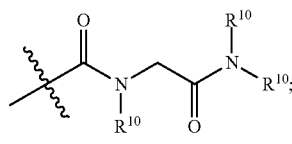

wherein each $R^{10}$ is independently hydrogen, alkyl, substituted alkyl, or acyl. In certain instances, one of $R^1$ and $R^2$ is

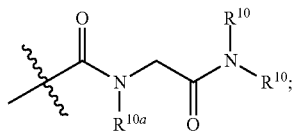

wherein $R^{10a}$ is alkyl and each $R^{10}$ is independently hydrogen, alkyl, substituted alkyl, or acyl.

In certain instances, one of $R^1$ and $R^2$ is

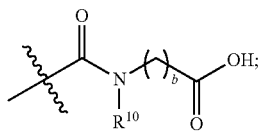

wherein $R^{10}$ is independently hydrogen, alkyl, substituted alkyl, or acyl and b is a number from one to 5. In certain instances, one of $R^1$ and $R^2$ is

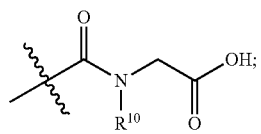

wherein $R^{10}$ is independently hydrogen, alkyl, substituted alkyl, or acyl.

In certain instances, one of $R^1$ and $R^2$ is an aminoacyl group, such as $-C(O)NR^{10a}R^{10b}$, wherein each $R^{10a}$ and $R^{10b}$ is independently selected from hydrogen, alkyl, substituted alkyl, and acyl. In certain instances, one of $R^1$ and $R^2$ is an aminoacyl group, such as $-C(O)NR^{10a}R^{10b}$, wherein $R^{10a}$ is an alkyl and $R^{10b}$ is substituted alkyl. In certain instances, one of $R^1$ and $R^2$ is an aminoacyl group, such as $-C(O)NR^{10a}R^{10b}$, wherein $R^{10a}$ is an alkyl and $R^{10b}$ is alkyl substituted with a carboxylic acid or alkoxycarbonyl. In certain instances, one of $R^1$ and $R^2$ is an aminoacyl group, such as $-C(O)NR^{10a}R^{10b}$, wherein $R^{10a}$ is methyl and $R^{10b}$ is alkyl substituted with a carboxylic acid or alkoxycarbonyl.

In certain instances, one of $R^1$ and $R^2$ are carboxyl.

In certain instances, one of $R^1$ and $R^2$ is acyl or substituted acyl.

In certain instances, one of $R^1$ and $R^2$ is alkoxycarbonyl or substituted alkoxycarbonyl.

In certain instances, one of $R^1$ and $R^2$ is amino or substituted amino.

In certain instances, one of $R^1$ and $R^2$ is acylamino or substituted acylamino.

In certain instances, $R^1$ or $R^2$ can modulate a rate of intramolecular cyclization. $R^1$ or $R^2$ can speed up a rate of intramolecular cyclization, when compared to the corresponding molecule where $R^1$ and $R^2$ are both hydrogen. In certain instances, $R^1$ or $R^2$ comprise an electron-withdrawing group or an electron-donating group. In certain instances, $R^1$ or $R^2$ comprise an electron-withdrawing group. In certain instances, $R^1$ or $R^2$ comprise an electron-donating group.

Atoms and groups capable of functioning as electron-withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, $-[C(R^1)(R^2)]_a-$ is selected from $-CH(CH_2F)CH(CH_2F)-$; $-CH(CHF_2)CH(CHF_2)-$; $-CH(CF_3)CH(CF_3)-$; $-CH_2CH(CF_3)-$; $-CH_2CH(CHF_2)-$; $-CH_2CH(CH_2F)-$; $-CH_2CH(F)CH_2-$; $-CH_2C(F_2)CH_2-$; $-CH_2CH(C(O)NR^{20}R^{21})-$; $-CH_2CH(C(O)OR^{22})-$; $-CH_2CH(C(O)OH)-$; $-CH(CH_2F)CH_2CH(CH_2F)-$; $-CH(CHF_2)CH_2CH(CHF_2)-$; $-CH(CF_3)CH_2CH(CF_3)-$; $-CH_2CH_2CH(CF_3)-$; $-CH_2CH_2CH(CHF_2)-$; $-CH_2CH_2CH(CH_2F)-$; $-CH_2CH_2CH(C(O)NR^{23}R^{24})-$; $-CH_2CH_2CH(C(O)OR^{25})-$; and $-CH_2CH_2CH(C(O)OH)-$, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formulae I-XIV, when a is one, the A ring is a heterocyclic 6 to 12-membered ring; and when the A ring is a heterocyclic 5-membered ring, then a is an integer from 2 to 8.

In certain instances, when a is one, the A ring is a heterocyclic 6 to 11-membered ring. In certain instances, when a is one, the A ring is a heterocyclic 6 to 10-membered ring. In certain instances, when a is one, the A ring is a heterocyclic 6 to 9-membered ring. In certain instances, when a is one, the A ring is a heterocyclic 6 to 8-membered ring. In certain instances, when a is one, the A ring is a heterocyclic 6 to 7-membered ring. In certain instances, when a is one, the A ring is a heterocyclic 6-membered ring.

In certain instances, when the A ring is a heterocyclic 5-membered ring, then a is an integer from 2 to 7. In certain instances, when the A ring is a heterocyclic 5-membered ring, then a is an integer from 2 to 6. In certain instances, when the A ring is a heterocyclic 5-membered ring, then a is an integer from 2 to 5. In certain instances, when the A ring is a heterocyclic 5-membered ring, then a is an integer from 2 to 4. In certain instances, when the A ring is a heterocyclic 5-membered ring, then a is an integer from 2 to 3. In certain instances, when the A ring is a heterocyclic 5-membered ring, then a is 2.

In certain instances, the A ring is a heterocyclic 7-membered or 8-membered ring and a is 1 or 2. In certain instances, the A ring is a heterocyclic 7-membered ring and a is 1. In certain instances, the A ring is a heterocyclic 7-membered ring and a is 2. In certain instances, the A ring is a heterocyclic 8-membered ring and a is 1. In certain instances, the A ring is a heterocyclic 8-membered ring and a is 2.

In certain instances, a certain group of compounds are compounds of formulae I-XIV, wherein A ring is a 5-membered ring and a is 2. A certain group of compounds are compounds of formulae I-XIV, wherein A ring is a 6-membered ring and a is one.

In formulae I-XVII, each $R^3$ can independently be hydrogen, alkyl, substituted alkyl, aryl or substituted aryl.

In certain instances, at least one $R^3$ is hydrogen. In certain instances, at least one $R^3$ is alkyl. In certain instances, at least one $R^3$ is substituted alkyl. In certain instances, at least one $R^3$ is aryl. In certain instances, at least one $R^3$ is substituted aryl.

In certain instances, each of the $R^3$ is hydrogen or alkyl. In certain instances, all $R^3$ are hydrogen. In certain instances, all $R^3$ are alkyl. In certain instances, the $R^3$ of N—$R^3$ that is adjacent to C—$R^5$ is hydrogen or alkyl. In certain instances, the $R^3$ of N—$R^3$ that is adjacent to C—$R^5$ is hydrogen. In certain instances, the $R^3$ of N—$R^3$ that is adjacent to C—$R^5$ is alkyl.

In formulae I-IV, VII-VIII, XI, XIV, and XV, $R^5$ can be selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl.

In certain instances, in formulae I-IV, VII-VIII, XI, XIV, and XV, $R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^5$ is selected from hydrogen, alkyl, substituted alkyl, arylalkyl, substituted arylalkyl, heteroarylalkyl, and substituted heteroarylalkyl. In certain instances, $R^5$ is hydrogen. In certain instances, $R^5$ is alkyl. In certain instances, $R^5$ is substituted alkyl. In certain instances, $R^5$ is arylalkyl or substituted arylalkyl. In certain instances, $R^5$ is heteroarylalkyl or substituted heteroarylalkyl.

In certain instances, in formulae I-IV, VII-VIII, XI, XIV, and XV, $R^5$ is a side chain of an amino acid, a side chain of an amino acid variant, a derivative of a side chain of an amino acid, or a derivative of a side chain of an amino acid variant.

In formulae V, IX, XII, and XVI, $R^5$ can be a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states.

In certain instances, $R^5$ can be a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In certain instances, $R^5$ is a side chain of an L-amino acid selected from L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, L-homoarginine, L-homolysine, L-ornithine, L-arginine mimic, L-arginine homologue, L-arginine truncate, L-arginine with varying oxidation states, L-lysine mimic, L-lysine homologue, L-lysine truncate, and L-lysine with varying oxidation states.

In certain instances, $R^5$ is a side chain of an L-amino acid selected from L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

In certain instances, $R^5$ is a side chain of an amino acid selected from arginine, lysine, homoarginine, homolysine, ornithine, arginine mimic, arginine homologue, arginine truncate, arginine with varying oxidation states, lysine mimic, lysine homologue, lysine truncate, and lysine with varying oxidation states. Examples of arginine and lysine mimics include arylguanidines, arylamidines (substituted benzamidines), benzylamines and (bicyclo[2.2.2]octan-1-yl) methanamine, citrulline, homocitrulline and derivatives thereof. In certain instances, $R^5$ is a side chain of an amino acid selected from arginine, lysine, homoarginine, homolysine, and ornithine. In certain instances, $R^5$ is a side chain of an amino acid selected from arginine or lysine. In certain instances, $R^5$ is a side chain of arginine. In certain instances, $R^5$ is a side chain of lysine.

In certain instances, $R^5$ is a side chain of an L-amino acid selected from L-arginine, L-lysine, L-homoarginine, L-homolysine, L-ornithine, L-arginine mimic, L-arginine homologue, L-arginine truncate, L-arginine with varying oxidation states, L-lysine mimic, L-lysine homologue, L-lysine truncate, and L-lysine with varying oxidation states. In certain instances, $R^5$ is a side chain of an L-amino acid selected from L-arginine, L-lysine, L-homoarginine, L-homolysine, and L-ornithine. In certain instances, $R^5$ is a side chain of an L-amino acid selected from L-arginine or L-lysine. In certain instances, $R^5$ is a side chain of L-arginine. In certain instances, $R^5$ is a side chain of L-lysine.

In certain instances, $R^5$ represents —$CH_2CH_2CH_2NH(C(=NH)(NH_2))$ or —$CH_2CH_2CH_2CH_2NH_2$, the configuration of the carbon atom to which $R^5$ is attached corresponding with that in an L-amino acid.

In formulae VI, X, XIII, and XVII, $R^5$ can be a side chain of an amino acid, a side chain of an amino acid variant, a derivative of a side chain of an amino acid, or a derivative of a side chain of an amino acid variant that effects —C(O)—C($R^5$)—N($R^3$)— to be a GI enzyme-cleavable moiety, such as a trypsin-cleavable moiety. A GI enzyme-cleavable moiety is a structural moiety that is capable of being cleaved by a GI enzyme. A trypsin-cleavable moiety is a structural moiety that is capable of being cleaved by trypsin. In certain instances, a GI enzyme-cleavable moiety comprises a charged moiety that can fit into an active site of a GI enzyme and is able to orient the prodrug for cleavage at a scissile bond. In certain instances, a trypsin-cleavable moiety comprises a charged moiety that can fit into an active site of trypsin and is able to orient the prodrug for cleavage at a scissile bond. For instance, the charged moiety of a GI enzyme-cleavable moiety, such as a trypsin-cleavable moiety, can be a basic moiety that exists as a charged moiety at physiological pH. A derivative of an amino acid or of an amino acid variant refers to a substance that has been altered from another substance by modification, partial substitution, homologation, truncation, or a change in oxidation state, while retaining the ability to be cleaved by a GI enzyme.

For example, to form a trypsin-cleavable moiety, $R^5$ can include, but is not limited to, a side chain of lysine (such as L-lysine), arginine (such as L-arginine), homolysine, homoarginine, and ornithine. Other values for $R^5$ include, but are not limited to, a side chain of an arginine mimic, arginine homologue, arginine truncate, arginine with varying oxidation states (for instance, metabolites), lysine mimic, lysine homologue, lysine truncate, and lysine with varying oxidation states (for instance, metabolites). Examples of arginine and lysine mimics include arylguanidines, arylamidines (substituted benzamidines), benzylamines, (bicyclo[2.2.2]octan-1-yl)methanamine, citrulline, homocitrulline and derivatives thereof.

In certain instances, $R^5$ is a side chain of an amino acid that effects —C(O)—C($R^5$)—N($R^3$)— to be a GI enzyme-cleavable moiety, such as a trypsin-cleavable moiety. In certain instances, $R^5$ is a side chain of an amino acid variant that effects —C(O)—C($R^5$)—N($R^3$)— to be a GI enzyme-cleavable moiety, such as a trypsin-cleavable moiety. In certain instances, $R^5$ is a derivative of a side chain of an amino acid that effects —C(O)—C($R^5$)—N($R^3$)— to be a GI enzyme-cleavable moiety, such as a trypsin-cleavable moiety. In certain instances, $R^5$ is a derivative of a side chain of an amino acid variant that effects —C(O)—C($R^5$)—N($R^3$)— to be a GI enzyme-cleavable moiety, such as a trypsin-cleavable moiety.

In certain instances, $R^5$ is a side chain of an amino acid selected from arginine, lysine, homoarginine, homolysine, ornithine, arginine mimic, arginine homologue, arginine truncate, arginine with varying oxidation states, lysine mimic, lysine homologue, lysine truncate, and lysine with varying oxidation states. In certain instances, $R^5$ is a side chain of an amino acid selected from arginine, lysine, homoarginine, homolysine, and ornithine. In certain instances, $R^5$ is a side chain of an amino acid selected from arginine or lysine. In certain instances, $R^5$ is a side chain of arginine. In certain instances, $R^5$ is a side chain of lysine.

In certain instances, $R^5$ is a side chain of an L-amino acid selected from L-arginine, L-lysine, L-homoarginine, L-homolysine, L-ornithine, L-arginine mimic, L-arginine homologue, L-arginine truncate, L-arginine with varying oxidation states, L-lysine mimic, L-lysine homologue, L-lysine truncate, and L-lysine with varying oxidation states. In certain instances, $R^5$ is a side chain of an L-amino acid selected from L-arginine, L-lysine, L-homoarginine, L-homolysine, and L-ornithine. In certain instances, $R^5$ is a side chain of an L-amino acid selected from L-arginine and L-lysine. In certain instances, $R^5$ is a side chain of L-arginine. In certain instances, $R^5$ is a side chain of L-lysine.

In certain instances, $R^5$ represents —CH$_2$CH$_2$CH$_2$NH(C(=NH)(NH$_2$)) or —CH$_2$CH$_2$CH$_2$CH$_2$NH$_2$, the configuration of the carbon atom to which $R^5$ is attached corresponding with that in an L-amino acid.

In formulae I-XVII, b is a number from zero to 100. In certain instances, b is zero to 50. In certain instances, b is zero to 90, 80, 70, 60, 50, 40, 30, 20, or 10. In certain instances, b is 100. In certain instances, b is 75. In certain instances, b is 50. In certain instances, b is 25. In certain instances, b is 20. In certain instances, b is 15. In certain instances, b is 10. In certain instances, b is 9. In certain instances, b is 8. In certain instances, b is 7. In certain instances, b is 6. In certain instances, b is 5. In certain instances, b is 4. In certain instances, b is 3. In certain instances, b is 2. In certain instances, b is one. In certain instances, b is zero. In certain instances, b is zero or one. In certain instances, b is zero or one or two.

In formulae I-IV, VII-VIII, XI, XIV, and XV, each $R^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl.

In certain instances, formulae I-IV, VII-VIII, XI, XIV, and XV, each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^6$ is hydrogen. In certain instances, $R^6$ is alkyl. In certain instances, $R^6$ is substituted alkyl. In certain instances, $R^6$ is arylalkyl or substituted arylalkyl. In certain instances, $R^6$ is heteroarylalkyl or substituted heteroarylalkyl.

In certain instances, formulae I-IV, VII-VIII, XI, XIV, and XV, $R^6$ is a side chain of an amino acid, a side chain of an amino acid variant, a derivative of a side chain of an amino acid, or a derivative of a side chain of an amino acid variant. In certain instances, $R^6$ is a side chain of an amino acid. In certain instances, $R^6$ is a side chain of an amino acid variant. In certain instances, $R^6$ is a derivative of a side chain of an amino acid. In certain instances, $R^6$ is a derivative of a side chain of an amino acid variant.

In formulae V, VI, IX, X, XII, XIII, XVI, and XVI, each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

In certain instances, $R^6$ is a side chain of an L-amino acid selected from L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

In certain instances, $R^6$ that is immediately adjacent to $R^5$ represents —H or —CH$_3$, the configuration of the carbon atom to which $R^6$ is attached corresponding with that in an L-amino acid. In certain instances, $R^6$ that is immediately adjacent to $R^5$ represents —H. In certain instances, $R^6$ that is immediately adjacent to $R^5$ represents —CH$_3$, the configuration of the carbon atom to which $R^6$ is attached corresponding with that in an L-amino acid.

In certain instances, $R^6$ that is immediately adjacent to $R^5$ is a side chain of an amino acid selected from L-alanine and glycine. In certain instances, $R^6$ that is immediately adjacent to $R^5$ is a side chain of L-alanine. In certain instances, $R^6$ that is immediately adjacent to $R^5$ is a side chain of glycine.

In formulae I-XVII, $R^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl.

In certain instances, $R^7$ is hydrogen, alkyl, acyl, or substituted acyl. In certain instances, $R^7$ is hydrogen, acyl, or substituted acyl. In certain instances, $R^7$ is hydrogen. In certain instances, $R^7$ is alkyl. In certain instances, $R^7$ is acyl or substituted acyl. In certain instances, $R^7$ is acyl. In certain instances, $R^7$ is substituted acyl. In certain instances, $R^7$ can be acetyl, benzoyl, malonyl, piperonyl or succinyl. In certain instances, $R^7$ can be acetyl. In certain instances, $R^7$ can be malonyl.

In certain instances, a certain group of compounds are compounds of formulae I-XVII, wherein $R^5$ is a side chain of an amino acid selected from arginine and lysine and b is one. In certain instances, a certain group of compounds are compounds of formulae I-XVII, wherein $R^5$ is a side chain of an amino acid selected from arginine and lysine; $R^6$ is a side chain of an amino acid selected from alanine and glycine; and b is one. In certain instances, a certain group of compounds are compounds of formulae I-XVII, wherein $R^5$ is a side chain of an amino acid selected from L-arginine and L-lysine and b is one. In certain instances, a certain group of compounds are compounds of formulae I-XVII, wherein $R^5$ is a side chain of an amino acid selected from L-arginine and L-lysine; $R^6$ is a side chain of an amino acid selected from L-alanine and glycine; and b is one. In certain instances, a certain group of compounds are compounds of formulae I-XVII, wherein $R^5$ is a side chain of L-arginine; $R^6$ is a side chain of an amino acid selected from L-alanine and glycine; and b is one. In certain instances, a certain group of compounds are compounds of formulae I-XVII, wherein $R^5$ is a side chain of L-lysine; $R^6$ is a side chain of an amino acid selected from L-alanine and glycine; and b is one.

In certain instances, a certain group of compounds are compounds of formulae I-XVII, wherein $R^6$ is a side chain of glycine and b is one. In certain instances, a certain group of compounds are compounds of formulae I-XVII, wherein $R^5$ is a side chain of an amino acid selected from arginine and lysine; $R^6$ is a side chain of glycine; and b is one. In certain instances, a certain group of compounds are compounds of formulae I-XVII, wherein $R^5$ is a side chain of an amino acid selected from L-arginine and L-lysine; $R^6$ is a side chain of glycine; and b is one.

In certain instances, a certain group of compounds are compounds of formulae I-XVII, wherein $R^6$ is a side chain of alanine and b is one. In certain instances, a certain group of compounds are compounds of formulae I-XVII, wherein $R^6$ is a side chain of L-alanine and b is one. In certain instances, a certain group of compounds are compounds of formulae I-XVII, wherein $R^5$ is a side chain of an amino acid selected from arginine and lysine; $R^6$ is a side chain of alanine; and b is one. In certain instances, a certain group of compounds are compounds of formulae I-XVII, wherein $R^5$ is a side chain of an amino acid selected from L-arginine and L-lysine; $R^6$ is a side chain of L-alanine; and b is one.

In certain instances, a certain group of compounds are compounds of formulae I-XVII, wherein $R^5$ is a side chain of L-arginine; $R^6$ is a side chain of L-alanine; and b is one. In certain instances, a certain group of compounds are compounds of formulae I-XVII, wherein $R^5$ is a side chain of L-arginine; $R^6$ is a side chain of glycine; and b is one. In certain instances, a certain group of compounds are compounds of formulae I-XVII, wherein $R^5$ is a side chain of L-lysine; $R^6$ is a side chain of L-alanine; and b is one. In certain instances, a certain group of compounds are compounds of formulae I-XVII, wherein $R^5$ is a side chain of L-lysine; $R^6$ is a side chain of glycine; and b is one.

Amino Acids Found in Prodrugs

"Amino acid" means a building block of a polypeptide. As used herein, "amino acid" includes the 20 common naturally occurring L-amino acids and all amino acids variants. In certain embodiments, an amino acid is a cleavable substrate for a gastrointestinal enzyme.

"Naturally occurring amino acids" means the 20 common naturally occurring L-amino acids, that is, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

"Amino acid variants" means an amino acid other than any of the 20 common naturally occurring L-amino acids that is hydrolyzable by a protease in a manner similar to the ability of a protease to hydrolyze a naturally occurring L-amino acid. Amino acid variants, thus, include amino acids or analogs of amino acids other than the 20 naturally-occurring amino acids. Amino acid variants include synthetic amino acids.

The embodiments also include derivatives of amino acids and of amino acid variants. A derivative of an amino acid or of an amino acid variant refers to a substance that has been altered from another substance by modification, partial substitution, homologation, truncation, or a change in oxidation state, while retaining the ability to be cleaved by a GI enzyme.

Certain examples of amino acid variants include, but are not limited to: 2-aminoindane-2-carboxylic acid, 2-aminoisobutyric acid, 4-amino-phenylalanine, 5-hydroxylysine, biphenylalanine, citrulline, cyclohexylalanine, cyclohexylglycine, diethylglycine, dipropylglycine, homoarginine, homocitrulline, homophenylalanine, homoproline, homoserine, homotyrosine, hydroxyproline, lanthionine, naphthylalanine, norleucine, ornithine, phenylalanine(4-fluoro), phenylalanine(4-nitro), phenylglycine, pipecolic acid, tert-butylalanine, tert-butylglycine, tert-leucine, tetrahydroisoquinoline-3-carboxylic acid, α-aminobutyric acid, γ-amino butyric acid, 2,3-diaminoproprionic acid, phenylalanine(2,3,4,5,6 pentafluoro), aminohexanoic acid and derivatives thereof.

Certain examples of amino acid variants include, but are not limited to, N-methyl amino acids. For example, N-methyl-alanine, N-methyl aspartic acid, N-methyl-glutamic acid, N-methyl-glycine (sarcosine) are N-methyl amino acids.

Certain examples of amino acid variants include, but are not limited to: dehydroalanine, ethionine, hypusine, lanthionine, pyrrolysine, α-aminoisobutyric acid, selenomethionine and derivatives thereof.

Certain examples of amino acid variants include, but are not limited to: (3,2-amino benzoic acid, 2-amino methyl benzoic acid, 2-amino-3-guanidinopropionic acid, 2-amino-3-methoxy benzoic acid, 2-amino-3-ureidopropionic acid, 3-amino benzoic acid, 4-amino benzoic acid, 4-amino methyl benzoic acid, 4-nitroanthranillic acid, 5-acetamido-2-aminobenzoic acid, butanoic acid (HMB), glutathione, homocysteine, statine, taurine, β-alanine, 2-hydroxy-4-(methylthio), (3,4)-diamino benzoic acid, (3,5)-diamino benzoic acid and derivatives thereof.

Certain examples of amino acid variants include, but are not limited to: (2 amino ethyl) cysteine, 2-amino-3-ethyoxybutanoic acid, buthionine, cystathion, cysteic acid, ethionine, ethoxytheorine, methylserine, N-ε-ε-dimethyl-lysine, N-ω-nitro-arginine, saccharopine, isoserine derivatives thereof, and combinations thereof.

Certain examples of amino acid variants include, but are not limited to: l-carnitine, selenocysteine, l-sarcosine, l-lysinol, benzoic acid, citric acid, choline, EDTA or succinic acid and derivatives thereof.

Certain examples of amino acid variants are amino alcohols. Examples of amino alcohols include, but are not limited to: alaminol, indano, norephedrine, asparaginol, aspartimol, glutamol, leucinol, methioninol, phenylalaminol, prolinol, tryptophanol, valinol, isoleucinol, argininol, serinol, tyrosinol, threoninol, cysteinol, lysinol, histidinol and derivatives thereof.

General Synthetic Procedures for Formulae I-XVII

Representative synthetic schemes for compounds disclosed herein are shown below. Compounds of Formulae I-XVII can be synthesized by using the disclosed methods.

Representative Synthetic Schemes

A representative synthesis for Compound S1-104 is shown in Scheme 1. In Scheme 1, X, A ring, Y, and c are defined herein. $PG^1$ is an amino protecting group.

Scheme 1

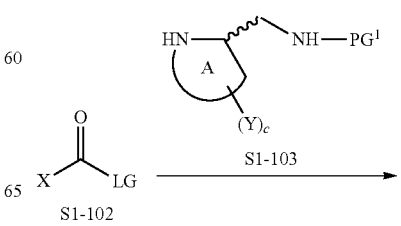

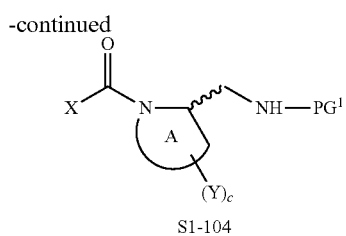

S1-104

In Scheme 1, Compound S1-102 is an active agent where the active agent comprises a functional group that is connected to —C(O)-LG. To form Compound S1-102, active agent X comprises a functional group, such as a ketone, an alcohol of a phenol, or an amide, that reacts with a reagent to form a connection to —C(O)-LG.

With continued reference to Scheme 1, LG of Compound S1-102 is a leaving group. In certain instances, when X is connected through an enolic oxygen, LG is a leaving group, such as 4-nitrophenolate.

With continued reference to Scheme 1, Compound S1-102 reacts with Compound S1-103 to form Compound S1-104. In Scheme 1, Compound S1-103 is a commercially available starting material. Alternatively, Compound S1-103 can be synthesized via a variety of different synthetic routes using commercially available starting materials and/or starting materials prepared by conventional synthetic methods.

A representative synthesis for Compound S1-203 is shown in Scheme 2. In Scheme 2, A ring, Y, c, and $R^5$ are defined herein. $PG^1$ and $PG^2$ are amino protecting groups.

Scheme 2

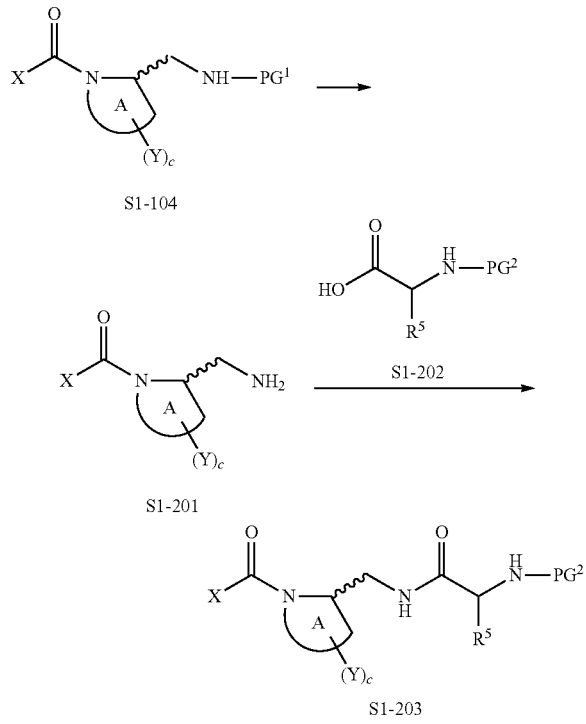

In Scheme 2, the protecting group $PG^1$ is removed from Compound S1-104 to form Compound S1-201. Conditions to remove amino groups can be found in Greene and Wuts. When $PG^1$ is a Boc group, the protecting group can be removed with acidic conditions, such as treatment with hydrochloric acid or trifluoroacetic acid.

With reference to Scheme 2, Compound S1-201 reacts with Compound S1-202 to form Compound S1-203 in a peptide coupling reaction. In certain embodiments, $R^5$ is a side chain of an amino acid and is optionally protected. Protecting groups for the side chain of amino acids are known to those skilled in art and can be found in Greene and Wuts. In certain instances, the protecting group for the side chain of arginine is a sulfonyl-type protecting group, such as 2,2,4,6,7-pentamethyldihydrobenzofurane (Pbf). Other protecting groups include 2,2,5,7,8-pentamethylchroman (Pmc) and 1,2-dimethylindole-3-sulfonyl (MIS).

A peptide coupling reaction typically employs a conventional peptide coupling reagent and is conducted under conventional coupling reaction conditions, typically in the presence of a trialkylamine, such as triethylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), O-(7-azabenzotriazol-1-yl)-N,N,N',N'-tetramethyluronium hexafluorophosphate (HATU) and the like. Optionally, well-known coupling promoters, such as N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound S1-201 reacts with Compound S1-202 to form Compound S1-203 in the presence of HATU.

A representative synthesis for Compound S1-303 is shown in Scheme 3. In Scheme 3, $R^a$, A ring, Y, c, $R^5$, $R^6$, and $R^7$ are defined herein. $PG^2$ is an amino protecting group.

Scheme 3

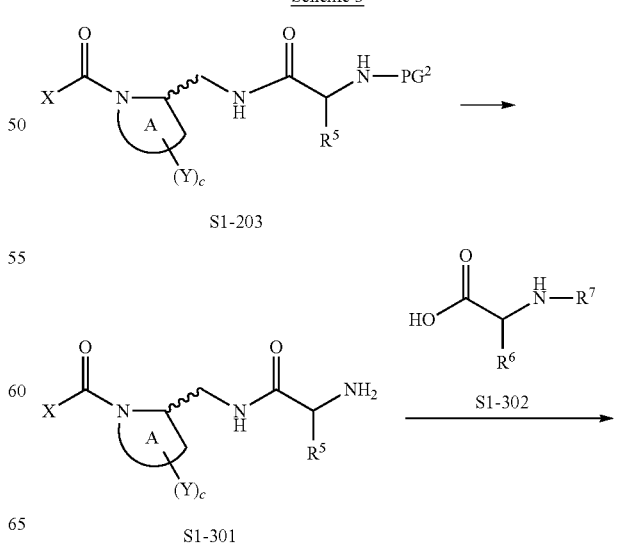

-continued

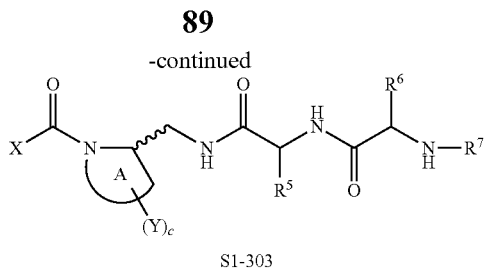

S1-303

In Scheme 3, the protecting group PG² is removed from Compound S1-203 to form Compound S1-301. Conditions to remove amino groups can be found in Greene and Wuts. When PG² is a Boc group, the protecting group can be removed with acidic conditions, such as treatment with hydrochloric acid or trifluoroacetic acid.

With reference to Scheme 3, Compound S1-301 reacts with Compound S1-302 to form Compound S1-303 in a peptide coupling reaction. A peptide coupling reaction typically employs a conventional peptide coupling reagent and is conducted under conventional coupling reaction conditions, typically in the presence of a trialkylamine, such as triethylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris (dimethylamino)phosphonium hexafluorophosphate (BOP), O-(7-azabenzotriazol-1-yl)-N,N,N,N',N'-tetramethyluronium hexafluorophosphate (HATU) and the like. Optionally, well-known coupling promoters, such as N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound S1-301 reacts with Compound S1-302 to form Compound S1-303 in the presence of HATU.

In certain instances in Scheme 3, Compound S1-301 is reacted with Compound S1-302 with R⁷ as a protecting group for an amino group. In these instances, the protecting group can be removed and the R⁷ group as an N-derivative group can be attached. Conditions for removal of other protecting groups depend on the identity of the protecting group and are known to those skilled in the art. The conditions can also be found in Greene and Wuts. For example, a malonyl group can be attached via a reaction with mono-tert-butyl malonate. Reaction using mono-tert-butyl malonate can be aided with use of activation reagents, such as symmetric anhydrides, O-(benzotriazol-1-yl)-N,N,N',N'-tetramethyluronium hexafluorophosphate (HBTU), dicyclohexylcarbodiimide (DCC) diisopropylcarbodiimide (DIC)/1-hydroxybenzotriazole (HOBt), and benzotriazole-1-yl-oxytris(dimethylamino)phosphonium hexafluorophosphate (BOP). In another example, an alkanoyl group, such as an acetyl group, can be attached via a reaction with alkanoyl anhydride or alkanoyl halide.

Additional amino acids can be added to the compound through standard peptide coupling reactions as discussed herein. Removal of other protecting groups can be performed if other protecting groups were used, such as protecting groups present on the R⁵ or R⁶ moiety. Conditions for removal of other protecting groups depend on the identity of the protecting group and are known to those skilled in the art. The conditions can also be found in Greene and Wuts.

Additional Representative Synthetic Schemes

A representative synthesis for Compound S2-104 is shown in Scheme 4. In Scheme 4, Rᵃ, A ring, Y, and c are defined herein. PG¹ is an amino protecting group. Although the schemes herein show a morphinan structure for X in Formulae I-XVII, the entire scope of X as an active agent as applicable to Formula I-XVII is contemplated.

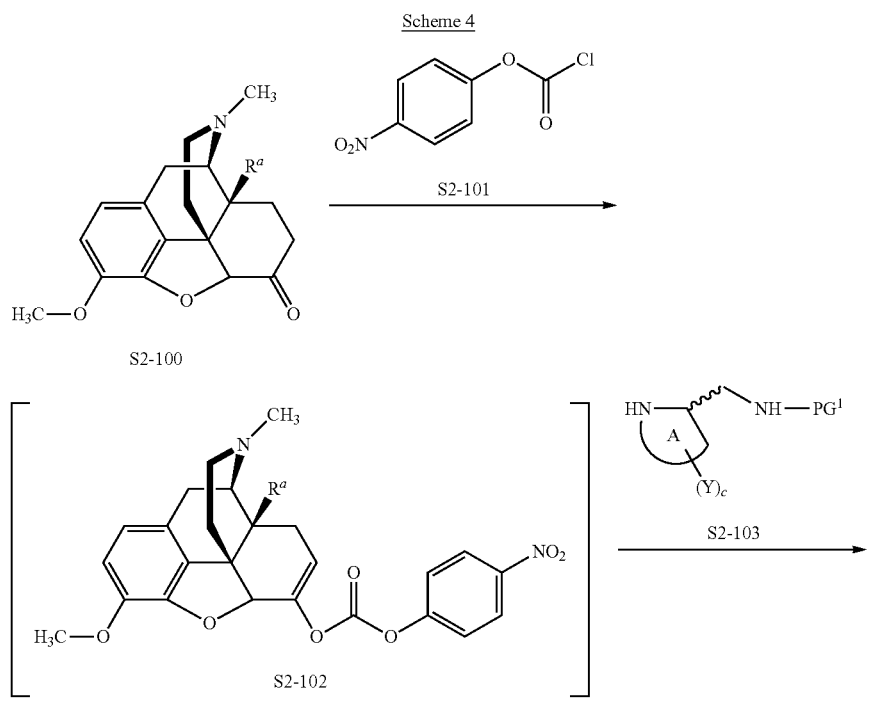

-continued

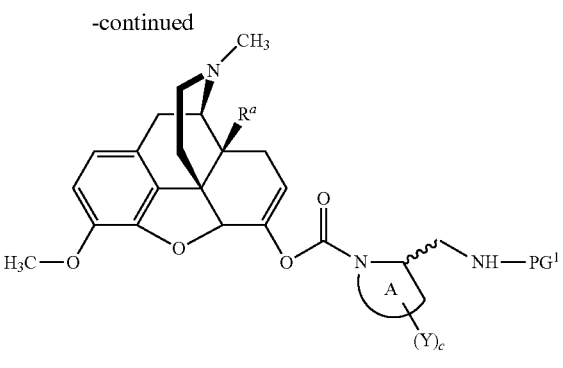

S2-104

In Scheme 1, Compound S2-100 is a commercially available starting material. Alternatively, Compound S2-100 can be semi-synthetically derived from natural materials or synthesized via a variety of different synthetic routes using commercially available starting materials and/or starting materials prepared by conventional synthetic methods.

With continued reference to Scheme 4, Compound S2-100 is enolized. Enolization of a ketone can be performed with reaction with a strong base, such as potassium hexamethyldisilazide (KHMDS). The enolate of Compound S2-100 is then reacted with an activation agent, such as Compound S2-101, to form intermediate Compound S2-102. Suitable activation agents include carbonate-forming reagents, such as chloroformates. In Scheme 4, the activation agent Compound S2-101 is 4-nitrophenyl chloroformate. Other suitable activation agents can be used prior to reaction with Compound S2-103.

With continued reference to Scheme 4, Compound S2-102 reacts with Compound S2-103 to form Compound S2-104. In Scheme 4, Compound S2-103 is a commercially available starting material. Alternatively, Compound S2-103 can be synthesized via a variety of different synthetic routes using commercially available starting materials and/or starting materials prepared by conventional synthetic methods.

A representative synthesis for Compound S2-203 is shown in Scheme 5. In Scheme 5, $R^a$, A ring, Y, c, and $R^5$ are defined herein. $PG^1$ and $PG^2$ are amino protecting groups.

Scheme 5

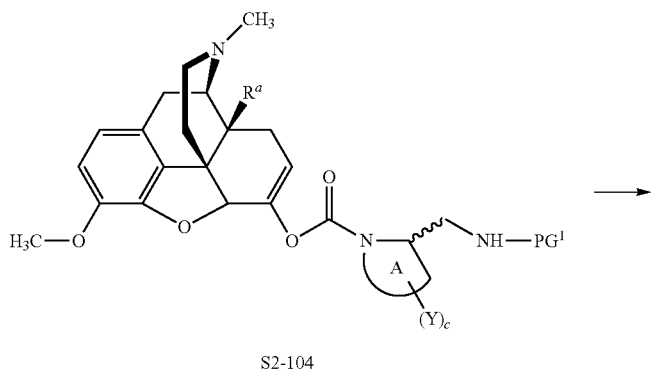

S2-104

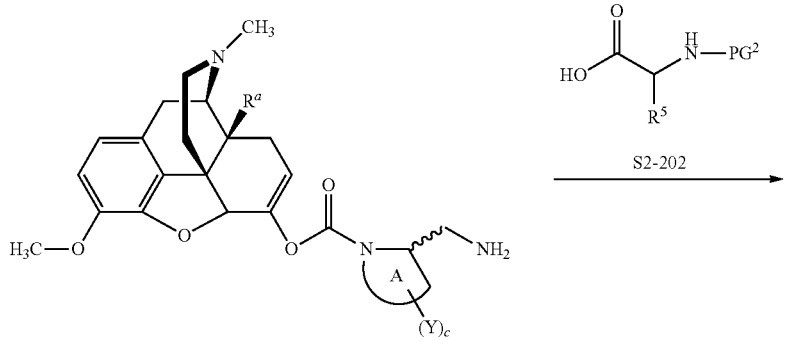

S2-201

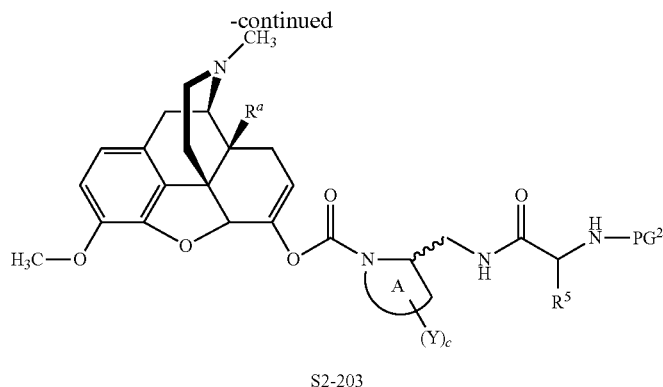

S2-203

In Scheme 5, the protecting group PG¹ is removed from Compound S2-104 to form Compound S2-201. Conditions to remove amino groups can be found in Greene and Wuts. When PG¹ is a Boc group, the protecting group can be removed with acidic conditions, such as treatment with hydrochloric acid or trifluoroacetic acid.

With reference to Scheme 5, Compound S2-201 reacts with Compound S2-202 to form Compound S2-203 in a peptide coupling reaction. In certain embodiments, $R^5$ is a side chain of an amino acid and is optionally protected. Protecting groups for the side chain of amino acids are known to those skilled in art and can be found in Greene and Wuts. In certain instances, the protecting group for the side chain of arginine is a sulfonyl-type protecting group, such as 2,2,4,6,7-pentamethyldihydrobenzofurane (Pbf). Other protecting groups include 2,2,5,7,8-pentamethylchroman (Pmc) and 1,2-dimethylindole-3-sulfonyl (MIS).

A peptide coupling reaction typically employs a conventional peptide coupling reagent and is conducted under conventional coupling reaction conditions, typically in the presence of a trialkylamine, such as triethylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris (dimethylamino)phosphonium hexafluorophosphate (BOP), O-(7-azabenzotriazol-1-yl)-N,N,N,N',N'-tetramethyluronium hexafluorophosphate (HATU) and the like. Optionally, well-known coupling promoters, such as N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound S2-201 reacts with Compound S2-202 to form Compound S2-203 in the presence of HATU.

A representative synthesis for Compound S2-303 is shown in Scheme 6. In Scheme 6, $R^a$, A ring, Y, c, $R^5$, $R^6$, and $R^7$ are defined herein. $PG^2$ is an amino protecting group.

Scheme 6

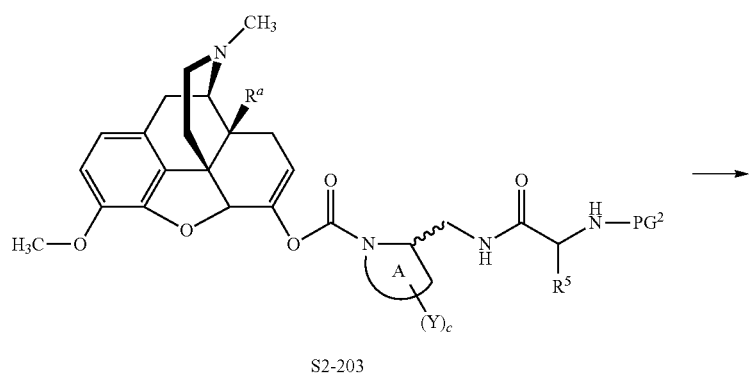

S2-203

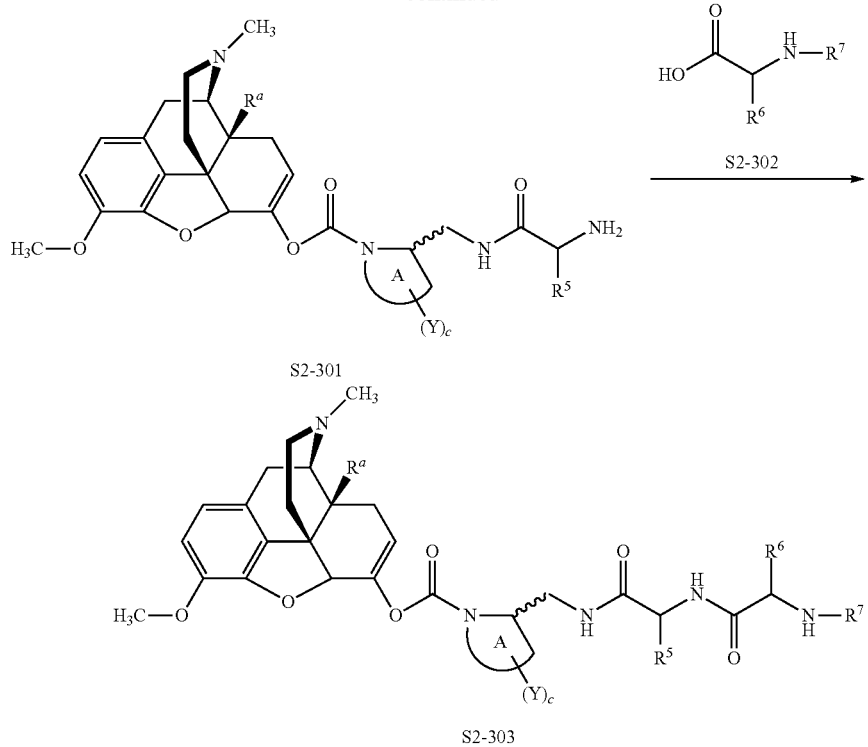

In Scheme 6, the protecting group $PG^2$ is removed from Compound S2-203 to form Compound S2-301. Conditions to remove amino groups can be found in Greene and Wuts. When $PG^2$ is a Boc group, the protecting group can be removed with acidic conditions, such as treatment with hydrochloric acid or trifluoroacetic acid.

With reference to Scheme 6, Compound S2-301 reacts with Compound S2-302 to form Compound S2-303 in a peptide coupling reaction. A peptide coupling reaction typically employs a conventional peptide coupling reagent and is conducted under conventional coupling reaction conditions, typically in the presence of a trialkylamine, such as triethylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), O-(7-azabenzotriazol-1-yl)-N,N,N,N',N'-tetramethyluronium hexafluorophosphate (HATU) and the like. Optionally, well-known coupling promoters, such as N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound S2-301 reacts with Compound S2-302 to form Compound S2-303 in the presence of HATU.

In certain instances in Scheme 6, Compound S2-301 is reacted with Compound S2-302 with $R^7$ as a protecting group for an amino group. In these instances, the protecting group can be removed and the $R^7$ group as an N-derivative group can be attached. Conditions for removal of other protecting groups depend on the identity of the protecting group and are known to those skilled in the art. The conditions can also be found in Greene and Wuts. For example, a malonyl group can be attached via a reaction with mono-tert-butyl malonate. Reaction using mono-tert-butyl malonate can be aided with use of activation reagents, such as symmetric anhydrides, O-(benzotriazol-1-yl)-N,N,N',N'-tetramethyluronium hexafluorophosphate (HBTU), dicyclohexylcarbodiimide (DCC) diisopropylcarbodiimide (DIC)/1-hydroxybenzotriazole (HOBt), and benzotriazole-1-yl-oxytris(dimethylamino)phosphonium hexafluorophosphate (BOP). In another example, an alkanoyl group, such as an acetyl group, can be attached via a reaction with alkanoyl anhydride or alkanoyl halide.

Additional amino acids can be added to the compound through standard peptide coupling reactions as discussed herein. Removal of other protecting groups can be performed if other protecting groups were used, such as protecting groups present on the $R^5$ or $R^6$ moiety. Conditions for removal of other protecting groups depend on the identity of the protecting group and are known to those skilled in the art. The conditions can also be found in Greene and Wuts.

Additional Representative Synthetic Schemes

Representative synthesis for Compound S-404 is shown in Scheme 7. In Scheme 7, A ring, Y, c, and $R^5$ are defined herein. $PG^1$ and $PG^2$ are amino protecting groups. Although the schemes herein show $R^1$ and $R^2$ as being hydrogen and a being one, the entire scope of $R^1$, $R^2$, and a as applicable to Formula I-XVII is contemplated.

Scheme 7

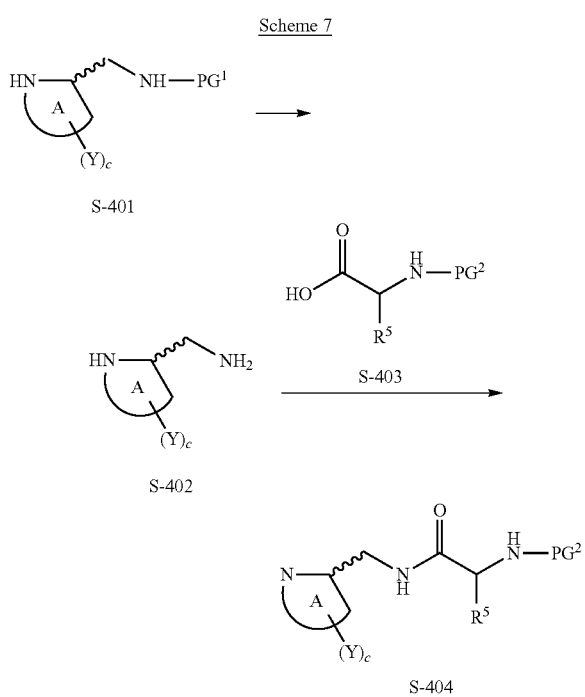

In Scheme 7, Compound S-401 is a commercially available starting material. Alternatively, Compound S-401 can be semi-synthetically derived from natural materials or synthesized via a variety of different synthetic routes using commercially available starting materials and/or starting materials prepared by conventional synthetic methods.

With continued reference to Scheme 7, the protecting group $PG^1$ is removed from Compound S-401 to form Compound S-402. Conditions to remove amino groups can be found in Greene and Wuts. When $PG^1$ is a Boc group, the protecting group can be removed with acidic conditions, such as treatment with hydrochloric acid or trifluoroacetic acid.

With continued reference to Scheme 7, Compound S-402 reacts with Compound S-403 to form Compound S-404 in a peptide coupling reaction. In certain embodiments, $R^5$ is a side chain of an amino acid and is optionally protected. Protecting groups for the side chain of amino acids are known to those skilled in art and can be found in Greene and Wuts. In certain instances, the protecting group for the side chain of arginine is a sulfonyl-type protecting group, such as 2,2,4,6,7-pentamethyldihydrobenzofurane (Pbf). Other protecting groups include 2,2,5,7,8-pentamethylchroman (Pmc) and 1,2-dimethylindole-3-sulfonyl (MIS).

A peptide coupling reaction typically employs a conventional peptide coupling reagent and is conducted under conventional coupling reaction conditions, typically in the presence of a trialkylamine, such as triethylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), O-(7-azabenzotriazol-1-yl)-N,N,N',N'-tetramethyluronium hexafluorophosphate (HATU) and the like. Optionally, well-known coupling promoters, such as N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound S-402 reacts with Compound S-403 to form Compound S-404 in the presence of HATU.

A representative synthesis for Compound S-503 is shown in Scheme 5. In Scheme 8, A ring, Y, c, and $R^5$ are defined herein. $PG^2$ is an amino protecting group.

Scheme 8

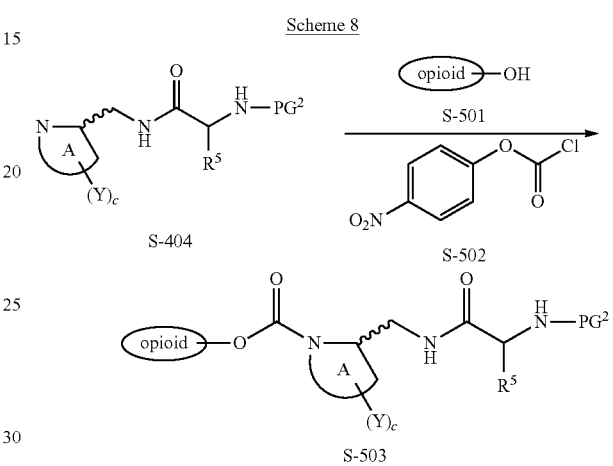

In Scheme 8, Compound S-501 is reacted with an activation agent, such as Compound S-502. Suitable activation agents include carbonate-forming reagents, such as chloroformates. In Scheme 8, the activation agent Compound S-502 is 4-nitrophenyl chloroformate. Other suitable activation agents can be used prior to reaction with Compound S-404.

With continued reference to Scheme 8, activated Compound S-501 reacts with Compound S-404 to form Compound S-503. In Scheme 8, Compound S-501 is a commercially available starting material. Alternatively, Compound S-501 can be synthesized via a variety of different synthetic routes using commercially available starting materials and/or starting materials prepared by conventional synthetic methods.

Scheme 9

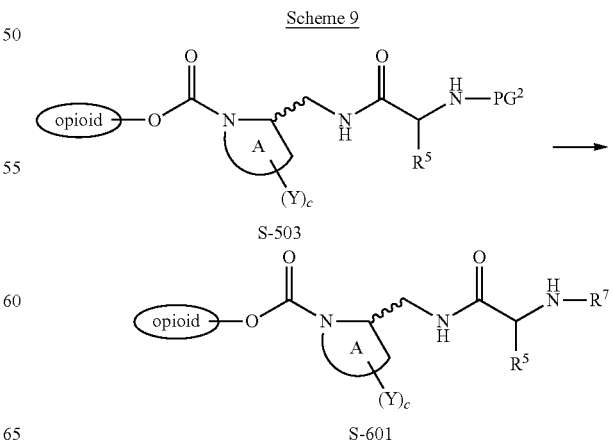

Additional amino acids can be added to the compound through standard peptide coupling reactions as discussed herein. For example, additional amino acids can be added to Compound S-503 with removal of protecting group $PG^2$ and addition of amino acids through standard peptide coupling reactions. Additional amino acids can be also added to Compound S-404 before reaction with Compound S-501 with removal of protecting group $PG^2$ and addition of amino acids through standard peptide coupling reactions.

In Scheme 9, Compound S-503 is converted to Compound S-601 with $R^7$ as an N-derivative group. Conditions for removal of protecting groups depend on the identity of the protecting group and are known to those skilled in the art. The conditions can also be found in Greene and Wuts. In certain instances, for example, a malonyl group can be attached via a reaction with mono-tert-butyl malonate. Reaction using mono-tert-butyl malonate can be aided with use of activation reagents, such as symmetric anhydrides, O-(benzotriazol-1-yl)-N,N,N',N'-tetramethyluronium hexafluorophosphate (HBTU), dicyclohexylcarbodiimide (DCC) diisopropylcarbodiimide (DIC)/1-hydroxybenzotriazole (HOBt), and benzotriazole-1-yl-oxytris(dimethylamino)phosphonium hexafluorophosphate (BOP). In another example, an alkanoyl group, such as an acetyl group, can be attached via a reaction with alkanoyl anhydride or alkanoyl halide.

Removal of other protecting groups can be performed if other protecting groups were used, such as protecting groups present on the $R^5$ or $R^6$ moiety. Conditions for removal of other protecting groups depend on the identity of the protecting group and are known to those skilled in the art. The conditions can also be found in Greene and Wuts.

Enzyme Inhibitors

The enzyme capable of cleaving the enzyme-cleavable moiety of an active agent prodrug can be a peptidase, also called a protease. In certain embodiments, the enzyme is an enzyme located in the gastrointestinal (GI) tract, i.e., a gastrointestinal enzyme, or a GI enzyme. The enzyme can be a digestive enzyme such as a gastric, intestinal, pancreatic or brush border enzyme or enzyme of GI microbial flora, such as those involved in peptide hydrolysis. Examples include a pepsin, such as pepsin A or pepsin B; a trypsin; a chymotrypsin; an elastase; a carboxypeptidase, such as carboxypeptidase A or carboxypeptidase B; an aminopeptidase (such as aminopeptidase N or aminopeptidase A; an endopeptidase; an exopeptidase; a dipeptidylaminopeptidase such as dipeptidylaminopeptidase IV; a dipeptidase; a tripeptidase; or an enteropeptidase. In certain embodiments, the enzyme is a cytoplasmic protease located on or in the GI brush border. In certain embodiments, the enzyme is trypsin. Accordingly, in certain embodiments, the corresponding composition is administered orally to the patient.

The disclosure provides for a composition comprising a GI enzyme inhibitor. Such an inhibitor can inhibit at least one of any of the GI enzymes disclosed herein. An example of a GI enzyme inhibitor is a protease inhibitor, such as a trypsin inhibitor.

As used herein, the term "GI enzyme inhibitor" refers to any agent capable of inhibiting the action of a GI enzyme on a substrate. The ability of an agent to inhibit a GI enzyme can be measured using assays well known in the art.

In certain embodiments, the GI enzyme capable of cleaving the enzyme-cleavable moiety may be a protease. The disclosure provides for inhibitors of proteases.

Proteases can be classified as exopeptidases or endopeptidases. Examples of exopeptidases include aminopeptidase and carboxypeptidase (A, B, or Y). Examples of endopeptidases include trypsin, chymotrypsin, elastase, pepsin, and papain. The disclosure provides for inhibitors of exopeptidase and endopeptidase.

In some embodiments, the enzyme is a digestive enzyme of a protein. The disclosure provides for inhibitors of digestive enzymes. A gastric phase involves stomach enzymes, such as pepsin. An intestinal phase involves enzymes in the small intestine duodenum, such as trypsin, chymotrypsin, elastase, carboxypeptidase A, and carboxypeptidase B. An intestinal brush border phase involves enzymes in the small intestinal brush border, such as aminopeptidase N, aminopeptidase A, endopeptidases, dipeptidases, dipeptidylaminopeptidase, and dipeptidylaminopeptidase IV. An intestinal intracellular phase involves intracellular peptidases, such as dipeptidases (i.e. iminopeptidase) and aminopeptidase.

In certain embodiments, the enzyme inhibitor in the disclosed compositions is a peptidase inhibitor or protease inhibitor. In certain embodiments, the enzyme is a digestive enzyme such as a gastric, pancreatic or brush border enzyme, such as those involved in peptide hydrolysis. Examples include pepsin, trypsin, chymotrypsin, colipase, elastase, aminopeptidase N, aminopeptidase A, dipeptidylaminopeptidase IV, tripeptidase or enteropeptidase.

Proteases can be inhibited by naturally occurring peptide or protein inhibitors, or by small molecule naturally occurring or synthetic inhibitors. Examples of protein or peptide inhibitors that are protease inhibitors include, but are not limited to, α1-antitrypsin from human plasma, aprotinin, trypsin inhibitor from soybean (SBTI), Bowman-Birk Inhibitor from soybean (BBSI), trypsin inhibitor from egg white (ovomucoid), chromostatin, and potato-derived carboxypeptidase inhibitor. Examples of small molecule irreversible inhibitors that are protease inhibitors include, but are not limited to, TPCK (1-chloro-3-tosylamido-4-phenyl-2-butanone), TLCK (1-chloro-3-tosylamido-7-amino-2-heptone), and PMSF (phenylmethyl sulfonyl fluoride). Examples of small molecule irreversible inhibitors that are protease inhibitors include, but are not limited to benzamidine, apixaban, camostat, 3,4-dichloroisocoumarin, ε-aminocaprionic acid, amastatin, lysianadioic acid, 1,10-phenanthroline, cysteamine, and bestatin. Other examples of small molecule inhibitors are Compound 101, Compound 102, Compound 103, Compound 104, Compound 105, Compound 106, Compound 107, Compound 108, Compound 109 and Compound 110.

The following table shows examples of gastrointestinal (GI) proteases, examples of their corresponding substrates, and examples of corresponding inhibitors.

Table of Examples of GI Proteases and Corresponding Substrates and Inhibitors

| GI Protease | Substrates | Inhibitors |
| --- | --- | --- |
| Trypsin | Arg, Lys, positively charged residues | TLCK, Benzamidine, Apixaban, Bowman Birk |
| Chymotrypsin | Phe, Tyr, Trp, bulky hydrophobic residues | ε-Aminocaprionic TPCK Bowman-Birk |
| Pepsin | Leu, Phe, Trp, Tyr | Pepstatin, PMSF |
| Carboxypeptidase B | Arg, Lys | Potato-derived inhibitor, Lysianadioic acid |
| Carboxypeptidase A | not Arg, Lys | Potato-derived inhibitor, 1,10-phenanthroline |
| Elastase | Ala, Gly, Ser, small neutral residues | α1-antitrypsin, 3,4-dichlorocoumarin |

-continued

Table of Examples of GI Proteases and Corresponding Substrates and Inhibitors

| GI Protease | Substrates | Inhibitors |
|---|---|---|
| Aminopeptidase | All free N-terminal AA | Bestatin, Amastatin |

Trypsin Inhibitors

As used herein, the term "trypsin inhibitor" refers to any agent capable of inhibiting the action of trypsin on a substrate. The term "trypsin inhibitor" also encompasses salts of trypsin inhibitors. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241, 3955 and Y. Birk, 1976, Meth. Enzymol. 45, 700. In certain instances, a trypsin inhibitor can interact with an active site of trypsin, such as the 51 pocket and the S3/4 pocket. The 51 pocket has an aspartate residue which has affinity for positively charged moiety. The S3/4 pocket is a hydrophobic pocket. The disclosure provides for specific trypsin inhibitors and non-specific serine protease inhibitors.

There are many trypsin inhibitors known in the art, both those specific to trypsin and those that inhibit trypsin and other proteases such as chymotrypsin. The disclosure provides for trypsin inhibitors that are proteins, peptides, and small molecules. The disclosure provides for trypsin inhibitors that are irreversible inhibitors or reversible inhibitors. The disclosure provides for trypsin inhibitors that are competitive inhibitors, non-competitive inhibitors, or uncompetitive inhibitors. The disclosure provides for natural, synthetic or semi-synthetic trypsin inhibitors.

Trypsin inhibitors can be derived from a variety of animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678.

In one embodiment, the trypsin inhibitor is derived from soybean. Trypsin inhibitors derived from soybean (*Glycine max*) are readily available and are considered to be safe for human consumption. They include, but are not limited to, SBTI, which inhibits trypsin, and Bowman-Birk inhibitor, which inhibits trypsin and chymotrypsin. Such trypsin inhibitors are available, for example from Sigma-Aldrich, St. Louis, Mo., USA.

A trypsin inhibitor can be an arginine mimic or lysine mimic, either natural or synthetic compound. In certain embodiments, the trypsin inhibitor is an arginine mimic or a lysine mimic, wherein the arginine mimic or lysine mimic is a synthetic compound. As used herein, an arginine mimic or lysine mimic can include a compound capable of binding to the $P^1$ pocket of trypsin and/or interfering with trypsin active site function. The arginine or lysine mimic can be a cleavable or non-cleavable moiety.

Examples of trypsin inhibitors, which are arginine mimics and/or lysine mimics, include, but are not limited to, arylguanidine, benzamidine, 3,4-dichloroisocoumarin, diisopropylfluorophosphate, gabexate mesylate, and phenylmethanesulfonyl fluoride, or substituted versions or analogs thereof. In certain embodiments, trypsin inhibitors comprise a covalently modifiable group, such as a chloroketone moiety, an aldehyde moiety, or an epoxide moiety. Other examples of trypsin inhibitors are aprotinin, camostat and pentamidine.

Other examples of trypsin inhibitors include compounds of formula:

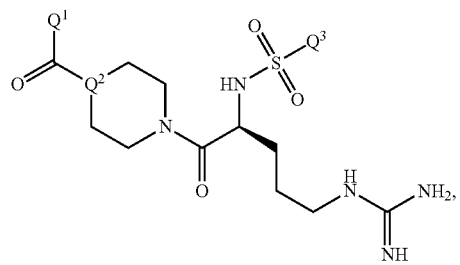

wherein:

$Q^1$ is selected from —O-$Q^4$ or -$Q^4$-COOH, where $Q^4$ is $C_1$-$C_4$ alkyl;

$Q^2$ is N or CH; and $Q^3$ is aryl or substituted aryl.

Certain trypsin inhibitors include compounds of formula:

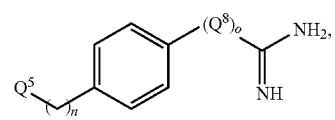

wherein:

$Q^5$ is —C(O)—COOH or —NH-$Q^6$-$Q^7$-$SO_2$—$C_6H_5$, where $Q^6$ is —$(CH_2)_p$—COOH;

$Q^7$ is —$(CH_2)_r$—$C_6H_5$;

$Q^8$ is NH;

n is a number from zero to two;

o is zero or one;

p is an integer from one to three; and r is an integer from one to three.

Other examples of trypsin inhibitors include compounds of formula:

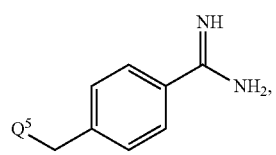

wherein:

$Q^5$ is —C(O)—COOH or —NH-$Q^6$-$Q^7$-$SO_2$—$C_6H_5$, where $Q^6$ is —$(CH_2)_p$—COOH;

$Q^7$ is —$(CH_2)_r$—$C_6H_5$; and p is an integer from one to three; and r is an integer from one to three.

Certain trypsin inhibitors include the following:

| Compound 101 | 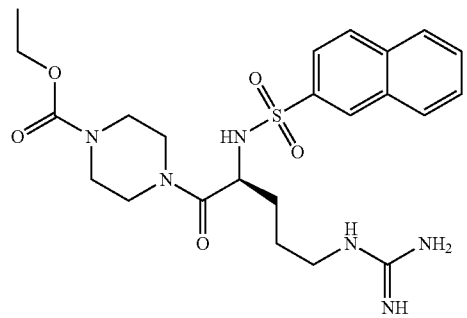 [SMILES: CCOC(=O)N1CCN(C(=O)[C@H](CCCNC(=N)N)NS(=O)(=O)c2ccc3ccccc3c2)CC1] | (S)-ethyl 4-(5-guanidino-2-(naphthalene-2-sulfonamido)pentanoyl)piperazine-1-carboxylate |
| Compound 102 | 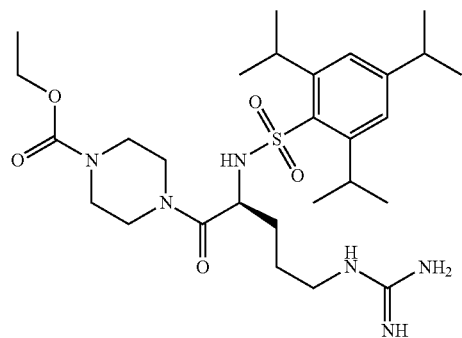 [SMILES: CCOC(=O)N1CCN(C(=O)[C@H](CCCNC(=N)N)NS(=O)(=O)c2c(C(C)C)cc(C(C)C)cc2C(C)C)CC1] | (S)-ethyl 4-(5-guanidino-2-(2,4,6-triisopropylphenylsulfonamido)pentanoyl)piperazine-1-carboxylate |
| Compound 103 | 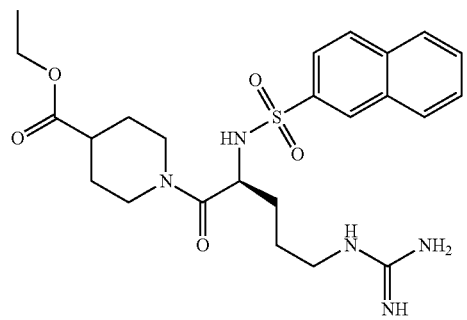 [SMILES: CCOC(=O)C1CCN(C(=O)[C@H](CCCNC(=N)N)NS(=O)(=O)c2ccc3ccccc3c2)CC1] | (S)-ethyl 1-(5-guanidino-2-(naphthalene-2-sulfonamido)pentanoyl)piperidine-4-carboxylate |
| Compound 104 | 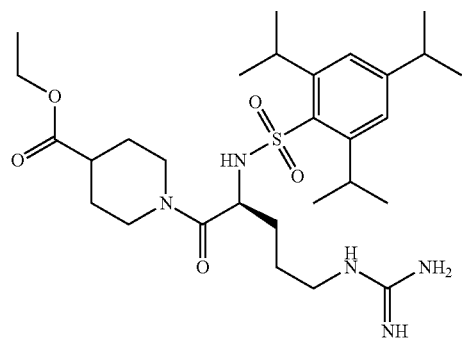 [SMILES: CCOC(=O)C1CCN(C(=O)[C@H](CCCNC(=N)N)NS(=O)(=O)c2c(C(C)C)cc(C(C)C)cc2C(C)C)CC1] | (S)-ethyl 1-(5-guanidino-2-(2,4,6-triisopropylphenylsulfonamido)pentanoyl)piperidine-4-carboxylate |

| | | |
|---|---|---|
| Compound 105 | 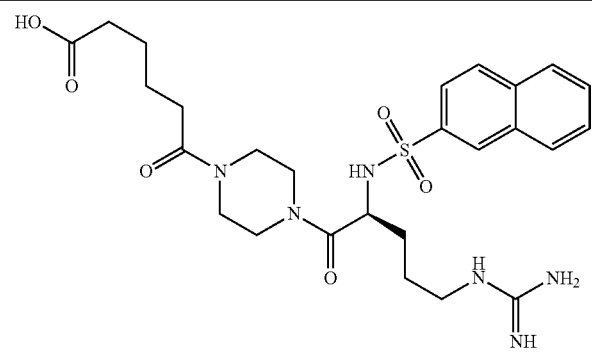 | (S)-6-(4-(5-guanidino-2-(naphthalene-2-sulfonamido)pentanoyl)piperazin-1-yl)-6-oxohexanoic acid |
| Compound 106 | 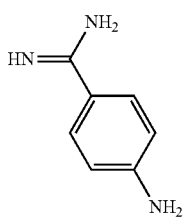 | 4-aminobenzimidamide (also 4-aminobenzamidine) |
| Compound 107 | 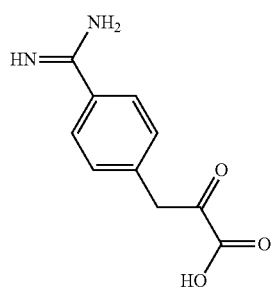 [SMILES: N=C(N)c1ccc(CC(=O)C(=O)O)cc1] | 3-(4-carbamimidoylphenyl)-2-oxopropanoic acid |
| Compound 108 | 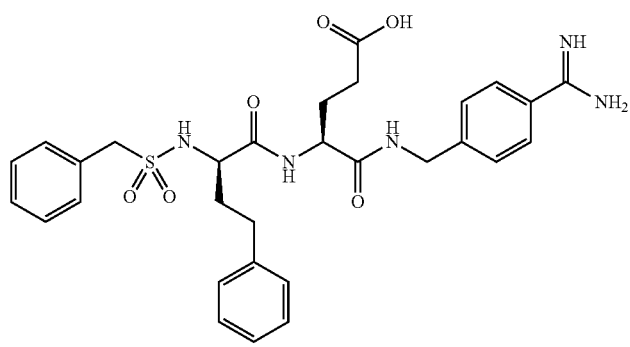 [SMILES: N=C(N)c1ccc(CNC(=O)[C@H](CCC(=O)O)NC(=O)[C@@H](CCc2ccccc2)NS(=O)(=O)Cc2ccccc2)cc1] | (S)-5-(4-carbamimidoylbenzylamino)-5-oxo-4-((R)-4-phenyl-2-(phenylmethylsulfonamido)butanamido)pentanoic acid |
| Compound 109 | 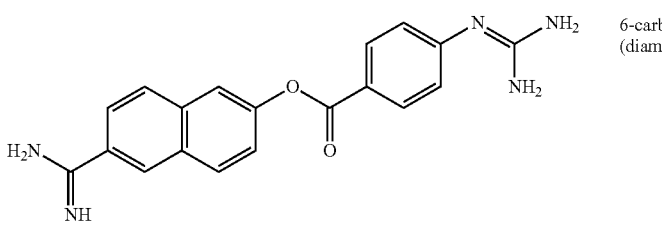 | 6-carbamimidoylnaphthalen-2-yl 4-(diaminomethyleneamino)benzoate |
| Compound 110 | 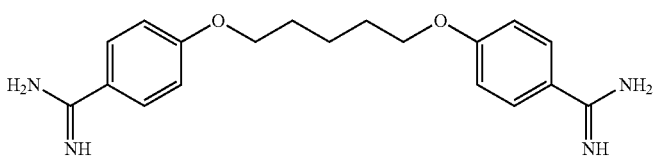 [SMILES: N=C(N)c1ccc(OCCCCCOc2ccc(C(=N)N)cc2)cc1] | 4,4'-(pentane-1,5-diylbis(oxy))dibenzimidamide |

A description of methods to prepare Compound 101, Compound 102, Compound 103, Compound 104, Compound 105, Compound 107, and Compound 108 is provided in PCT International Publication Number WO 2010/045599A1, published 22 Apr. 2010, which is hereby incorporated by reference in its entirety. Compound 106, Compound 109, and Compound 110 can be obtained commercially (Sigma-Aldrich, St. Louis, Mo., USA.).

In certain embodiments, the trypsin inhibitor is SBTI, BBSI, Compound 101, Compound 106, Compound 108, Compound 109, or Compound 110. In certain embodiments, the trypsin inhibitor is camostat.

In certain embodiments, the trypsin inhibitor is a compound of formula T-I:

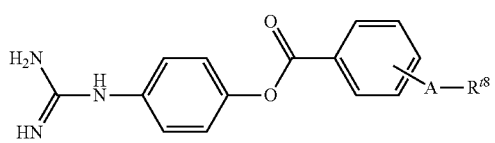
(T-I)

wherein

A represents a group of the following formula:

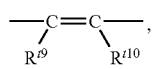

$R^{t9}$ and $R^{t10}$ each represents independently a hydrogen atom or a $C_{1-4}$ alkyl group, $R^{t8}$ represents a group selected from the following formulae:

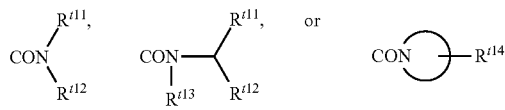

wherein $R^{t11}$, $R^{t12}$ and $R^{t13}$ each represents independently
(1) a hydrogen atom,
(2) a phenyl group,
(3) a $C_{1-4}$ alkyl group substituted by a phenyl group,
(4) a $C_{1-10}$ alkyl group,
(5) a $C_{1-10}$ alkoxyl group,
(6) a $C_{2-10}$ alkenyl group having 1 to 3 double bonds,
(7) a $C_{2-10}$ alkynyl group having 1 to 2 triple bonds,
(8) a group of formula: $R^{t15}$—C(O)XR$^{t16}$,
wherein $R^{t15}$ represents a single bond or a $C_{1-8}$ alkylene group,
X represents an oxygen atom or an NH-group, and
$R^{t16}$ represents a hydrogen atom, a $C_{1-4}$ alkyl group, a phenyl group or a $C_{1-4}$ alkyl group substituted by a phenyl group, or
(9) a $C_{3-7}$ cycloalkyl group;
the structure

represents a 4-7 membered monocyclic hetero-ring containing 1 to 2 nitrogen or oxygen atoms, $R^{t14}$ represents a hydrogen atom, a $C_{1-4}$ alkyl group substituted by a phenyl group or a group of formula: COOR$^{t17}$, wherein $R^{t17}$ represents a hydrogen atom, a $C_{1-4}$ alkyl group or a $C_{1-4}$ alkyl group substituted by a phenyl group;

provided that $R^{t11}$, $R^{t12}$ and $R^{t13}$ do not represent simultaneously hydrogen atoms;

or nontoxic salts, acid addition salts or hydrates thereof.

In certain embodiments, the trypsin inhibitor is a compound selected from the following:

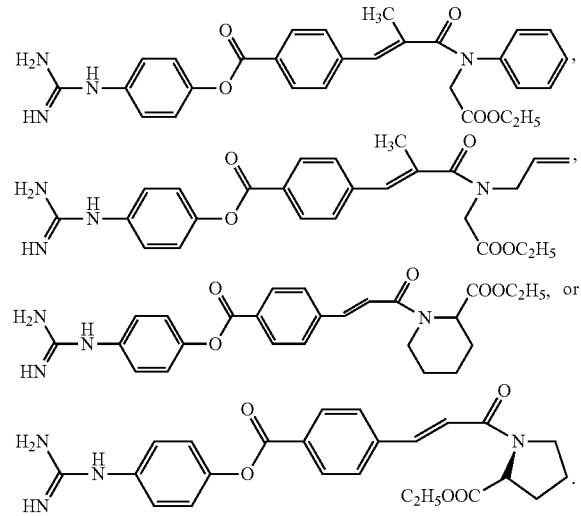

In certain embodiments, the trypsin inhibitor is a compound of formula T-II:

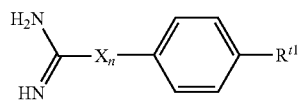
(T-II)

wherein
X is NH;
n is zero or one; and
$R^{t1}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH$_2$)$_m$—C(O)—O—(CH$_2$)$_m$—C(O)—N—R$^{n1}$R$^{n2}$, wherein each m is independently zero to 2; and $R^{n1}$ and $R^{n2}$ are independently selected from hydrogen and $C_{1-4}$ alkyl.

In certain embodiments, in formula T-II, $R^{t1}$ is guanidino or amidino.

In certain embodiments, in formula T-II, $R^{t1}$ is —(CH$_2$)$_m$—C(O)—O—(CH$_2$)$_m$—C(O)—N—R$^{n1}$R$^{n2}$, wherein m is one and $R^{n1}$ and $R^{n2}$ are methyl.

In certain embodiments, the trypsin inhibitor is a compound of formula T-III:

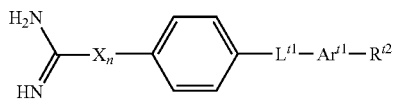
(T-III)

wherein
X is NH;
n is zero or one;
$L^{t1}$ is selected from —C(O)—O—; —O—C(O)—; —O—$(CH_2)_m$—O—; —OCH$_2$—Ar$^{t2}$—CH$_2$O—; —C(O)—NR$^{t3}$—; and —NR$^{t3}$—C(O)—;
$R^{t3}$ is selected from hydrogen, $C_{1-6}$ alkyl, and substituted $C_{1-6}$ alkyl;
Ar$^{t1}$ and Ar$^{t2}$ are independently a substituted or unsubstituted aryl group;
m is a number from 1 to 3; and
$R^{t2}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —$(CH_2)_m$—C(O)—O—$(CH_2)_m$—C(O)—N—$R^{n1}R^{n2}$, wherein each m is independently zero to 2; and $R^{n1}$ and $R^{n2}$ are independently selected from hydrogen and $C_{1-4}$ alkyl.

In certain embodiments, in formula T-III, $R^{t2}$ is guanidino or amidino.

In certain embodiments, in formula T-III, $R^{t2}$ is —$(CH_2)_m$—C(O)—O—$(CH_2)_m$—C(O)—N—$R^{n1}R^{n2}$, wherein m is one and $R^{n1}$ and $R^{n2}$ are methyl.

In certain embodiments, the trypsin inhibitor is a compound of formula T-IV:

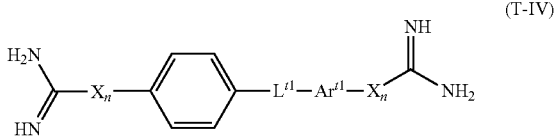

(T-IV)

wherein
each X is NH;
each n is independently zero or one;
$L^{t1}$ is selected from —C(O)—O—; —O—C(O)—; —O—$(CH_2)_m$—O—; —OCH$_2$—Ar$^{t2}$—CH$_2$O—; —C(O)—NR$^{t3}$—; and —NR$^{t3}$—C(O)—;
$R^{t3}$ is selected from hydrogen, $C_{1-6}$ alkyl, and substituted $C_{1-6}$ alkyl;
Ar$^{t1}$ and Ar$^{t2}$ are independently a substituted or unsubstituted aryl group; and
m is a number from 1 to 3.

In certain embodiments, in formula T-IV, Ar$^{t1}$ or Ar$^{t2}$ is phenyl.

In certain embodiments, in formula T-IV, Ar$^{t1}$ or Ar$^{t2}$ is naphthyl.

In certain embodiments, the trypsin inhibitor is Compound 109.

In certain embodiments, the trypsin inhibitor is

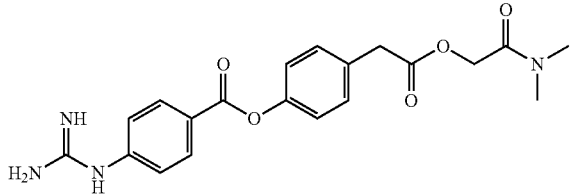 [SMILES: CN(C)C(=O)COC(=O)Cc1ccc(OC(=O)c2ccc(NC(=N)N)cc2)cc1]

In certain embodiments, the trypsin inhibitor is Compound 110 or a bis-arylamidine variant thereof; see, for example, J. D. Geratz, M. C.-F. Cheng and R. R. Tidwell (1976) J. Med. Chem. 19, 634-639.

It will be appreciated that the pharmaceutical composition according to the embodiments may further comprise one or more additional trypsin inhibitors.

It is to be appreciated that the invention also includes inhibitors of other enzymes involved in protein assimilation that can be used in combination with a prodrug disclosed herein comprising an amino acid of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine or amino acid variants thereof.

Combinations of Prodrug and Trypsin Inhibitor

As disclosed above, the present disclosure also provides pharmaceutical compositions, and their methods of use, where the pharmaceutical compositions comprise an active agent prodrug, that provides controlled release of an active agent, and a trypsin inhibitor that interacts with the trypsin that mediates the controlled release of the active agent from the prodrug so as to attenuate enzymatic cleavage of the prodrug.

The embodiments provide a pharmaceutical composition, which comprises a trypsin inhibitor and a compound of general Formulae I-XIV, or a pharmaceutically acceptable salt thereof. The embodiments provide a pharmaceutical composition, which comprises a trypsin inhibitor and a compound of general Formulae XV-XVII, or a pharmaceutically acceptable salt thereof.

The embodiments provide a pharmaceutical composition, which comprises a compound of Formulae T-I to T-IV and a compound of general Formulae I-XIV, or a pharmaceutically acceptable salt thereof. The embodiments provide a pharmaceutical composition, which comprises a compound of Formulae T-I to T-IV and a compound of general Formulae XV-XVII, or a pharmaceutically acceptable salt thereof. The embodiments provide a pharmaceutical composition, which comprises Compound 109 and a compound of general Formulae I-XIV, or a pharmaceutically acceptable salt thereof. The embodiments provide a pharmaceutical composition, which comprises Compound 109 and a compound of general Formulae XV-XVII, or a pharmaceutically acceptable salt thereof.

Certain embodiments provide for a combination of a compound of Formula I and a trypsin inhibitor, shown in the table below. Certain embodiments provide for a combination of a compound of Formula II and a trypsin inhibitor, shown in the table below. Certain embodiments provide for a combination of a compound of Formulae III-VI and a trypsin inhibitor, shown in the table below. Certain embodiments provide for a combination of a compound of Formulae VII-X and a trypsin inhibitor, shown in the table below. Certain embodiments provide for a combination of a compound of Formulae XI-XIII and a trypsin inhibitor, shown in the table below. Certain embodiments provide for a combination of a compound of Formula XIV and a trypsin inhibitor, shown in the table below. Certain embodiments provide for a combination of a compound of Formulae XV-XVII and a trypsin inhibitor, shown in the table below. Certain embodiments provide for a combination of a compound of Formula XIV and a trypsin inhibitor, shown in the table below.

| Prodrug of Formula I and Trypsin Inhibitor | Prodrug of Formula II and Trypsin Inhibitor | Prodrug of Formula III-VI and Trypsin Inhibitor | Prodrug of Formula VII-X and Trypsin Inhibitor | Prodrug of Formula XI-XIII and Trypsin Inhibitor | Prodrug of Formula XIV and Trypsin Inhibitor | Prodrug of Formula XV-XVII and Trypsin Inhibitor |
|---|---|---|---|---|---|---|
| SBTI | SBTI | SBTI | SBTI | SBTI | SBTI | SBTI |
| BBSI | BBSI | BBSI | BBSI | BBSI | BBSI | BBSI |
| Compound 101 | Compound 101 | Compound 101 | Compound 101 | Compound 101 | Compound 101 | Compound 101 |
| Compound 106 | Compound 106 | Compound 106 | Compound 106 | Compound 106 | Compound 106 | Compound 106 |
| Compound 108 | Compound 108 | Compound 108 | Compound 108 | Compound 108 | Compound 108 | Compound 108 |
| Compound 109 | Compound 109 | Compound 109 | Compound 109 | Compound 109 | Compound 109 | Compound 109 |
| Compound 110 | Compound 110 | Compound 110 | Compound 110 | Compound 110 | Compound 110 | Compound 110 |

Combinations of Active Agent Prodrugs and Other Drugs

The disclosure provides for an active agent prodrug of the embodiments and a further prodrug or drug included in a pharmaceutical composition.

For example, such a prodrug or drug would provide additional analgesia, e.g., a synergistic effect, or other benefits. Examples include opioids, opioid prodrugs, acetaminophen, non-steroidal anti-inflammatory drugs (NSAIDs) and other analgesics. In one embodiment, two or more opioid agonist prodrugs and/or drugs (e.g., a morphine prodrug or drug and an oxycodone prodrug of the embodiments), each at a sub-analgesic dose, would be combined to provide a synergistic response leading to effective analgesia with reduced side effects. In one embodiment, an opioid agonist prodrug or drug would be combined with an opioid antagonist prodrug or drug. Other examples include drugs or prodrugs that have benefits other than, or in addition to, analgesia. The embodiments provide a pharmaceutical composition, which comprises an opioid prodrug and acetaminophen and optionally comprises an enzyme inhibitor. Also included are pharmaceutically acceptable salts thereof.

In certain embodiments, the enzyme inhibitor is selected from SBTI, BBSI, Compound 101, Compound 106, Compound 108, Compound 109, and Compound 110. In certain embodiments, the enzyme inhibitor is camostat.

In certain embodiments, a pharmaceutical composition can comprise an active agent prodrug, a non-opioid drug and at least one opioid or opioid prodrug.

Pharmaceutical Compositions and Methods of Use

The present disclosure provides a composition, such as a pharmaceutical composition, which comprises a compound of Formulae I-XVII. Such a pharmaceutical composition according to the embodiments can further comprise a pharmaceutically acceptable carrier. The composition is conveniently formulated in a form suitable for oral (including buccal and sublingual) administration, for example as a tablet, capsule, thin film, powder, suspension, solution, syrup, dispersion or emulsion. The composition can contain components conventional in pharmaceutical preparations, e.g. one or more carriers, binders, lubricants, excipients (e.g., to impart controlled release characteristics), pH modifiers, sweeteners, bulking agents, coloring agents or further active agents.

Patients can be humans, and also other mammals, such as livestock, zoo animals and companion animals, such as a cat, dog or horse.

In another aspect, the embodiments provide a pharmaceutical composition as described herein for use in the treatment of pain. The pharmaceutical composition according to the embodiments is useful, for example, in the treatment of a patient suffering from, or at risk of suffering from pain. Accordingly, the present disclosure provides methods of treating or preventing pain in a subject, the methods involving administering to the subject a disclosed composition. The present disclosure provides for a disclosed composition for use in therapy or prevention or as a medicament. The present disclosure also provides the use of a disclosed composition for the manufacture of a medicament, especially for the manufacture of a medicament for the treatment or prevention of pain.

The compositions of the present disclosure can be used in the treatment or prevention of pain including, but not limited to include, acute pain, chronic pain, neuropathic pain, acute traumatic pain, arthritic pain, osteoarthritic pain, rheumatoid arthritic pain, muscular skeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, muscular skeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain.

The present disclosure provides use of a compound of Formulae I-XVII in the treatment of pain. The present disclosure provides use of a compound of Formulae I-XVII in the prevention of pain.

The present disclosure provides use of a compound of Formulae I-XVII in the manufacture of a medicament for treatment of pain. The present disclosure provides use of a compound of Formulae I-XVII in the manufacture of a medicament for prevention of pain.

In another aspect, the embodiments provide a method of treating pain in a patient in need thereof, which comprises administering to such a patient an effective amount of a pharmaceutical composition as described herein. In another aspect, the embodiments provide a method of preventing pain in a patient in need thereof, which comprises administering to such a patient an effective amount of a pharmaceutical composition as described herein.

The amount of composition disclosed herein to be administered to a patient to be effective (i.e. to provide blood levels of an active agent sufficient to be effective in the treatment or prophylaxis of pain) will depend upon the bioavailability of the particular composition, the susceptibility of the particular composition to enzyme activation in the gut, as well as other factors, such as the species, age, weight, sex, and condition of the patient, manner of administration and judgment of the prescribing physician. If the composition also comprises a trypsin inhibitor, the amount of composition disclosed herein to be administered to a patient would also depend on the amount and potency of trypsin inhibitor present in the composition. In general, the dose can be such that the active agent prodrug is in the range of from 0.01 milligrams per kilogram to 20 milligrams prodrug per kilogram (mg/kg) body weight. For example, an active agent prodrug can be administered at a dose equivalent to administering free active agent in the range of from 0.02-mg/kg to 0.5-mg/kg body weight or 0.01-mg/kg to 10-mg/kg body weight or 0.01-mg/kg to 2-mg/kg body weight. In one embodiment, the composition can be administered at a dose such that the level of the active agent achieved in the blood is in the range of from 0.5 ng/ml to 200 ng/ml. In one embodiment, the composition can be administered at a dose such that the level of the active agent achieved in the blood is in the range of from 0.5 ng/ml to 20 ng/ml. In one embodiment, the composition can be administered at a dose such that the level of the active agent achieved in the blood is in the range of from 0.5 ng/ml to 10 ng/ml.

As disclosed above, the present disclosure also provides a pharmaceutical composition that comprises an active agent prodrug of Formulae I-XVII and a trypsin inhibitor. Such an active agent prodrug comprises a promoiety comprising a trypsin-cleavable moiety that, when cleaved, facilitates release of active agent.

The present disclosure provides use of a compound of Formulae I-XVII and a trypsin inhibitor in the treatment of pain. The present disclosure provides use of a compound of Formulae I-XVII and a trypsin inhibitor in the prevention of pain.

The present disclosure provides use of a compound of Formulae I-XVII and a trypsin inhibitor in the manufacture of a medicament for treatment of pain. The present disclosure provides use of a compound of Formulae I-XVII and a trypsin inhibitor in the manufacture of a medicament for prevention of pain.

In another aspect, the embodiments provide a method of treating pain in a patient in need thereof, which comprises administering to such a patient an effective amount of a pharmaceutical composition comprising a compound of Formulae I-XVII and a trypsin inhibitor. In another aspect, the embodiments provide a method of preventing pain in a patient in need thereof, which comprises administering to such a patient an effective amount of a pharmaceutical composition comprising a compound of Formulae I-XVII and a trypsin inhibitor.

In such pharmaceutical compositions, the amount of a trypsin inhibitor to be administered to the patient to be effective (i.e. to attenuate release of an active agent when administration of a compound disclosed herein alone would lead to overexposure of the active agent) will depend upon the effective dose of the particular prodrug and the potency of the particular inhibitor, as well as other factors, such as the species, age, weight, sex and condition of the patient, manner of administration and judgment of the prescribing physician. In general, the dose of inhibitor can be in the range of from 0.05 mg to 50 mg per mg of prodrug disclosed herein. In a certain embodiment, the dose of inhibitor can be in the range of from 0.001 mg to 50 mg per mg of prodrug disclosed herein. In one embodiment, the dose of inhibitor can be in the range of from 0.01 nanomoles to 100 micromoles per micromole of prodrug disclosed herein.

Representative Embodiments of Dose Units of Prodrug and GI Enzyme Inhibitor Having a Desired Pharmacokinetic Profile The embodiments include a composition that comprises (a) an active agent prodrug of Formulae I-XVII, which comprises an active agent covalently bound to a promoiety comprising a GI enzyme-cleavable moiety, wherein cleavage of the GI enzyme-cleavable moiety by a GI enzyme mediates release of an active agent, and (b) a GI enzyme inhibitor that interacts with the GI enzyme that mediates enzymatically-controlled release of the active agent from the prodrug following ingestion of the composition. In one embodiment, the GI enzyme is trypsin, the GI enzyme-cleavable moiety is a trypsin-cleavable moiety, and the GI enzyme inhibitor is a trypsin inhibitor.

The embodiments include a dose unit comprising a composition, such as a pharmaceutical composition, comprising an active agent prodrug of Formulae I-XVII and a GI enzyme inhibitor, where the active agent prodrug of Formulae I-XVII and GI enzyme inhibitor are present in the dose unit in an amount effective to provide for a pre-selected pharmacokinetic (PK) profile following ingestion. In further embodiments, the pre-selected PK profile comprises at least one PK parameter value that is less than the PK parameter value of active agent released following ingestion of an equivalent dosage of an active agent prodrug of Formulae I-XVII in the absence of inhibitor. In further embodiments, the PK parameter value is selected from an active agent Cmax value, an active agent exposure value, and a (1/active agent Tmax) value.

In certain embodiments, the dose unit provides for a pre-selected PK profile following ingestion of at least two dose units. In related embodiments, the pre-selected PK profile of such dose units is modified relative to the PK profile following ingestion of an equivalent dosage of an active agent prodrug of Formulae I-XVII without inhibitor. In related embodiments, such a dose unit provides that ingestion of an increasing number of the dose units provides for a linear PK profile. In related embodiments, such a dose unit provides that ingestion of an increasing number of the dose units provides for a nonlinear PK profile. In related embodiments, the PK parameter value of the PK profile of such a dose unit is selected from an active agent Cmax value, a (1/active agent Tmax) value, and an active agent exposure value.

The embodiments include methods for treating a patient comprising administering any of the compositions, such as pharmaceutical compositions, comprising an active agent prodrug of Formulae I-XVII and a GI enzyme inhibitor or dose units described herein to a patient in need thereof. The embodiments include methods to reduce side effects of a therapy comprising administering any of such compositions, e.g., pharmaceutical compositions, or dose units described herein, to a patient in need thereof. The embodiments include methods of improving patient compliance with a therapy prescribed by a clinician comprising directing administration of any of such compositions, e.g., pharmaceutical compositions, or dose units described herein, to a patient in need thereof. Such embodiments can provide for improved patient compliance with a prescribed therapy as compared to patient compliance with a prescribed therapy using drug and/or using prodrug without inhibitor as compared to prodrug with inhibitor.

The embodiments include methods of reducing risk of unintended overdose of an active agent comprising directing administration of any of such compositions, e.g., pharmaceutical compositions, or dose units described herein, to a patient in need of treatment.

The embodiments include methods of making a dose unit comprising combining an active agent prodrug of Formulae I-XVII and a GI enzyme inhibitor in a dose unit, wherein the active agent prodrug of Formulae I-XVII and GI enzyme inhibitor are present in the dose unit in an amount effective to attenuate release of active agent from the active agent prodrug of Formulae I-XV.

The embodiments include methods of deterring misuse or abuse of multiple dose units of an active agent prodrug of Formulae I-XVII comprising combining an active agent prodrug of Formulae I-XVII and a GI enzyme inhibitor in a dose unit, wherein the active agent prodrug of Formulae I-XVII and GI enzyme inhibitor are present in the dose unit in an amount effective to attenuate release of an active agent from the active agent prodrug of Formulae I-XVII such that ingestion of multiples of dose units by a patient does not provide a proportional release of the active agent. In further embodiments, release of drug is decreased compared to release of drug by an equivalent dosage of prodrug in the absence of inhibitor.

One embodiment is a method for identifying a GI enzyme inhibitor and prodrug of Formulae I-XVII suitable for formulation in a dose unit. Such a method can be conducted as, for example, an in vitro assay, an in vivo assay, or an ex vivo assay. In one embodiment, the GI enzyme inhibitor is a trypsin inhibitor.

The embodiments include methods for identifying a GI enzyme inhibitor and prodrug of Formulae I-XVII suitable for formulation in a dose unit comprising combining a prodrug of Formulae I-XVII, a GI enzyme inhibitor, and a GI enzyme in a reaction mixture, and detecting prodrug conversion, wherein a decrease in prodrug conversion in the presence of the GI enzyme inhibitor as compared to prodrug conversion in the absence of the GI enzyme inhibitor indicates the GI enzyme inhibitor and prodrug of Formulae I-XVII are suitable for formulation in a dose unit.

The embodiments include methods for identifying a GI enzyme inhibitor and prodrug of Formulae I-XVII suitable for formulation in a dose unit comprising administering to an animal a GI enzyme inhibitor and prodrug of Formulae I-XVII and detecting prodrug conversion, wherein a decrease in active agent conversion in the presence of the GI enzyme inhibitor as compared to active agent conversion in the absence of the GI enzyme inhibitor indicates the GI enzyme inhibitor and prodrug of Formulae I-XVII are suitable for formulation in a dose unit. In certain embodiments, administering comprises administering to the animal increasing doses of inhibitor co-dosed with a selected fixed dose of prodrug. Detecting prodrug conversion can facilitate identification of a dose of inhibitor and a dose of prodrug that provides for a pre-selected pharmacokinetic (PK) profile. Such methods can be conducted as, for example, an in vivo assay or an ex vivo assay.

The embodiments include methods for identifying a GI enzyme inhibitor and prodrug of Formulae I-XVII suitable for formulation in a dose unit comprising administering to an animal tissue a GI enzyme inhibitor and prodrug of Formulae I-XVII and detecting prodrug conversion, wherein a decrease in prodrug conversion in the presence of the GI enzyme inhibitor as compared to prodrug conversion in the absence of the GI enzyme inhibitor indicates the GI enzyme inhibitor and prodrug of Formulae I-XVII are suitable for formulation in a dose unit.

Dose Units of Prodrug and Inhibitor Having a Desired Pharmacokinetic Profile

The present disclosure provides dose units of prodrug and inhibitor that can provide for a desired pharmacokinetic (PK) profile. Dose units can provide a modified PK profile compared to a reference PK profile as disclosed herein. It will be appreciated that a modified PK profile can provide for a modified pharmacodynamic (PD) profile. Ingestion of multiples of such a dose unit can also provide a desired PK profile.

Unless specifically stated otherwise, "dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

As used herein, a "PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile".) A PK profile is characterized by PK parameters.

As used herein, a "PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

For purposes of describing the features of dose units of the present disclosure, "PK parameter values" that define a PK profile include drug Cmax (e.g., active agent Cmax), total drug exposure (e.g., area under the curve) (e.g., active agent exposure) and 1/(drug Tmax) (such that a decreased 1/Tmax is indicative of a delay in Tmax relative to a reference Tmax) (e.g., 1/active agent Tmax). Thus a decrease in a PK parameter value relative to a reference PK parameter value can indicate, for example, a decrease in drug Cmax, a decrease in drug exposure, and/or a delayed Tmax.

Dose units of the present disclosure can be adapted to provide for a modified PK profile, e.g., a PK profile that is different from that achieved from dosing a given dose of prodrug in the absence of inhibitor (i.e., without inhibitor). For example, dose units can provide for at least one of decreased drug Cmax, delayed drug Tmax and/or decreased drug exposure compared to ingestion of a dose of prodrug in the same amount but in the absence of inhibitor. Such a modification is due to the inclusion of an inhibitor in the dose unit.

As used herein, "a pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax), and side effects.

FIG. 1 is a schematic illustrating an example of the effect of increasing inhibitor concentrations upon the PK parameter drug Cmax for a fixed dose of prodrug. At low concentrations of inhibitor, there may be no detectable effect on drug release, as illustrated by the plateau portion of the plot of drug Cmax (Y axis) versus inhibitor concentration (X axis). As inhibitor concentration increases, a concentration is reached at which drug release from prodrug is attenuated, causing a decrease in, or suppression of, drug Cmax. Thus, the effect of inhibitor upon a prodrug PK parameter for a dose unit of the present disclosure can range from undetectable, to moderate, to complete inhibition (i.e., no detectable drug release).

A dose unit can be adapted to provide for a desired PK profile (e.g., a concentration-time PK profile) following ingestion of a single dose. A dose unit can be adapted to provide for a desired PK profile (e.g., a concentration-dose PK profile) following ingestion of multiple dose units (e.g., at least 2, at least 3, at least 4 or more dose units).

Dose Units Providing Modified PK Profiles

A combination of a prodrug and an inhibitor in a dose unit can provide a desired (or "pre-selected") PK profile (e.g., a concentration-time PK profile) following ingestion of a single dose. The PK profile of such a dose unit can be characterized by one or more of a pre-selected drug Cmax, a pre-selected drug Tmax or a pre-selected drug exposure. The PK profile of the dose unit can be modified compared to a PK profile achieved from the equivalent dosage of prodrug in the absence of inhibitor (i.e., a dose that is the same as the dose unit except that it lacks inhibitor).

A modified PK profile can have a decreased PK parameter value relative to a reference PK parameter value (e.g., a PK parameter value of a PK profile following ingestion of a dosage of prodrug that is equivalent to a dose unit except without inhibitor). For example, a dose unit can provide for a decreased drug Cmax, decreased drug exposure, and/or delayed drug Tmax.

Figure 2:
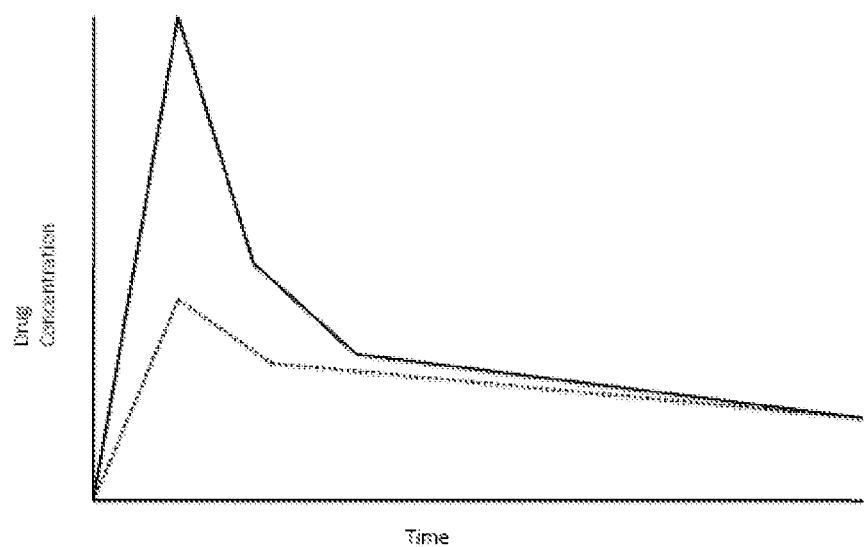
FIG. 2 provides schematics of drug concentration in plasma (Y axis) over time (X axis). Panel A is a schematic of a pharmacokinetic (PK) profile following ingestion of prodrug with a GI enzyme inhibitor (dashed line) where the drug Cmax is modified relative to that of prodrug without inhibitor (solid line). Panel B is a schematic of a PK profile following ingestion of prodrug with inhibitor (dashed line) where drug Cmax and drug Tmax are modified relative to that of prodrug without inhibitor (solid line). Panel C is a schematic of a PK profile following ingestion of prodrug with inhibitor (dashed line) where drug Tmax is modified relative to that of prodrug without inhibitor (solid line).
Figure 2:
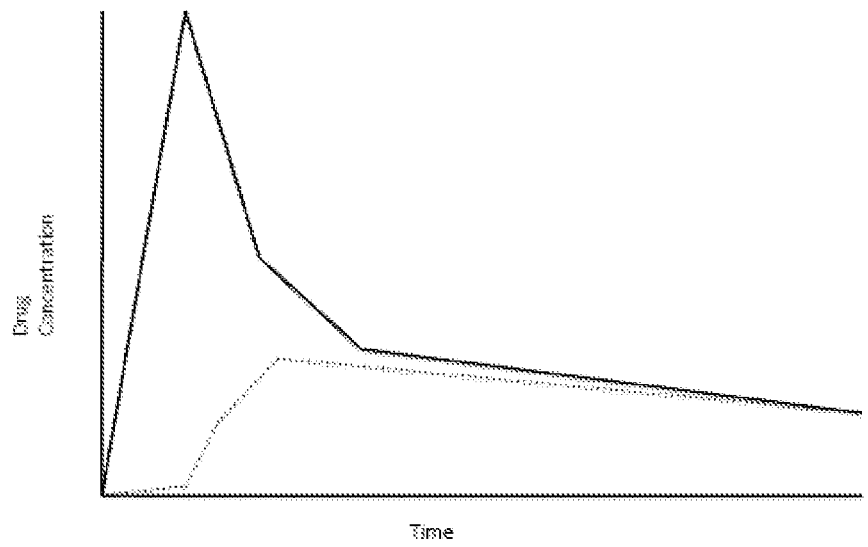
Figure 2:
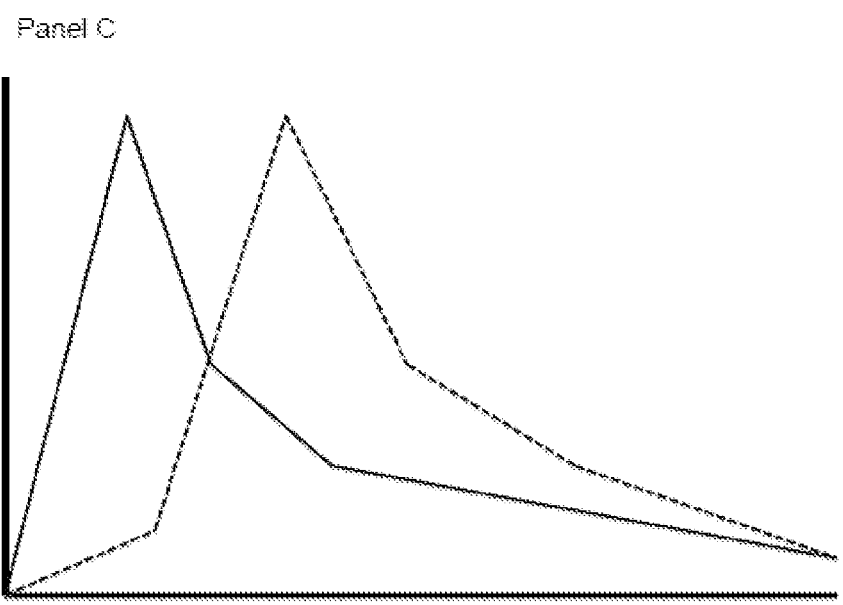

FIG. 2 presents schematic graphs showing examples of modified concentration-time PK profiles of a single dose unit. Panel A is a schematic of drug concentration in blood or plasma (Y axis) following a period of time (X axis) after ingestion of prodrug in the absence or presence of inhibitor. The solid, top line in Panel A provides an example of drug concentration following ingestion of prodrug without inhibitor. The dashed, lower line in Panel A represents drug concentration following ingestion of the same dose of prodrug with inhibitor. Ingestion of inhibitor with prodrug provides for a decreased drug Cmax relative to the drug Cmax that results from ingestion of the same amount of prodrug in the absence of inhibitor. Panel A also illustrates that the total drug exposure following ingestion of prodrug with inhibitor is also decreased relative to ingestion of the same amount of prodrug without inhibitor.

Panel B of FIG. 2 provides another example of a dose unit having a modified concentration-time PK profile. As in Panel A, the solid top line represents drug concentration over time in blood or plasma following ingestion of prodrug without inhibitor, while the dashed lower line represents drug concentration following ingestion of the same amount of prodrug with inhibitor. In this example, the dose unit provides a PK profile having a decreased drug Cmax, decreased drug exposure, and a delayed drug Tmax (i.e., decreased (1/drug Tmax) relative to ingestion of the same dose of prodrug without inhibitor.

Panel C of FIG. 2 provides another example of a dose unit having a modified concentration-time PK profile. As in Panel A, the solid line represents drug concentration over time in blood or plasma following ingestion of prodrug without inhibitor, while the dashed line represents drug concentration following ingestion of the same amount of prodrug with inhibitor. In this example, the dose unit provides a PK profile having a delayed drug Tmax (i.e., decreased (1/drug Tmax) relative to ingestion of the same dose of prodrug without inhibitor.

Dose units that provide for a modified PK profile (e.g., a decreased drug Cmax and/or delayed drug Tmax as compared to, a PK profile of drug or a PK profile of prodrug without inhibitor), find use in tailoring of drug dose according to a patient's needs (e.g., through selection of a particular dose unit and/or selection of a dosage regimen), reduction of side effects, and/or improvement in patient compliance (as compared to side effects or patient compliance associated with drug or with prodrug without inhibitor). As used herein, "patient compliance" refers to whether a patient follows the direction of a clinician (e.g., a physician) including ingestion of a dose that is neither significantly above nor significantly below that prescribed. Such dose units also reduce the risk of misuse, abuse or overdose by a patient as compared to such risk(s) associated with drug or prodrug without inhibitor. For example, dose units with a decreased drug Cmax provide less reward for ingestion than does a dose of the same amount of drug, and/or the same amount of prodrug without inhibitor.

Dose Units Providing Modified PK Profiles Upon Ingestion of Multiple Dose Units

A dose unit of the present disclosure can be adapted to provide for a desired PK profile (e.g., a concentration-time PK profile or concentration-dose PK profile) following ingestion of multiples of a dose unit (e.g., at least 2, at least 3, at least 4, or more dose units). A concentration-dose PK profile refers to the relationship between a selected PK parameter and a number of single dose units ingested. Such a profile can be dose proportional, linear (a linear PK profile) or nonlinear (a nonlinear PK profile). A modified concentration-dose PK profile can be provided by adjusting the relative amounts of prodrug and inhibitor contained in a single dose unit and/or by using a different prodrug and/or inhibitor.

Figure 3:
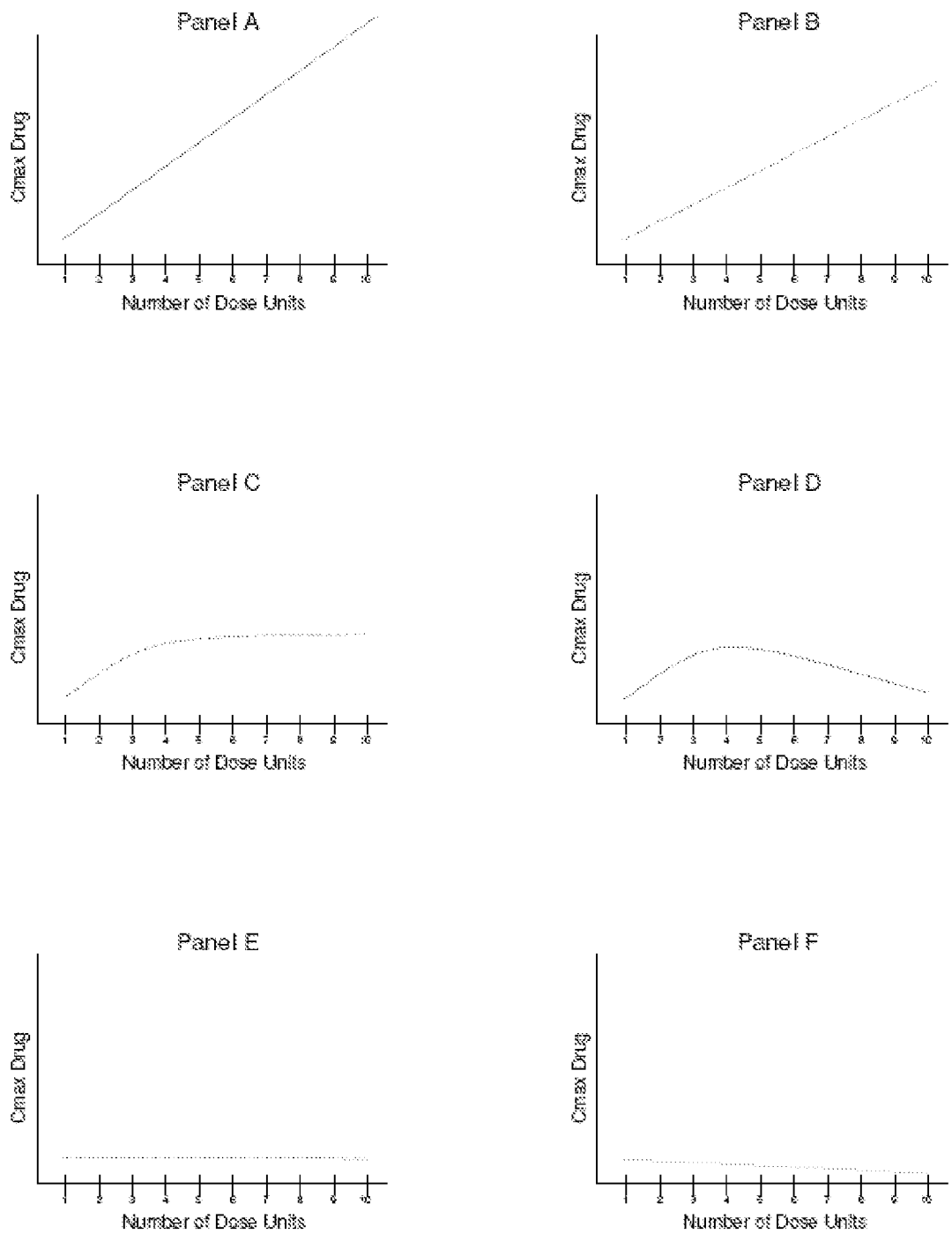
FIG. 3 provides schematics representing differential concentration-dose PK profiles that can result from the dosing of multiples of a dose unit (X axis) of the present disclosure. Different PK profiles (as exemplified herein for a representative PK parameter, drug Cmax (Y axis)) can be provided by adjusting the relative amount of prodrug and GI enzyme inhibitor contained in a single dose unit or by using a different prodrug or inhibitor in the dose unit.

FIG. 3 provides schematics of examples of concentration-dose PK profiles (exemplified by drug Cmax, Y axis) that can be provided by ingestion of multiples of a dose unit (X axis) of the present disclosure. Each profile can be compared to a concentration-dose PK profile provided by increasing doses of drug alone, where the amount of drug in the blood or plasma from one dose represents a therapeutically effective amount equivalent to the amount of drug released into the blood or plasma by one dose unit of the disclosure. Such a "drug alone" PK profile is typically dose proportional, having a forty-five degree angle positive linear slope. It is also to be appreciated that a concentration-dose PK profile resulting from ingestion of multiples of a dose unit of the disclosure can also be compared to other references, such as a concentration-dose PK profile provided by ingestion of an increasing number of doses of prodrug without inhibitor wherein the amount of drug released into the blood or plasma by a single dose of prodrug in the absence of inhibitor represents a therapeutically effective amount equivalent to the amount of drug released into the blood or plasma by one dose unit of the disclosure.

As illustrated by the relationship between prodrug and inhibitor concentration in FIG. 2, a dose unit can include inhibitor in an amount that does not detectably affect drug release following ingestion. Ingestion of multiples of such a dose unit can provide a concentration-dose PK profile such that the relationship between number of dose units ingested and PK parameter value is linear with a positive slope, which is similar to, for example, a dose proportional PK profile of increasing amounts of prodrug alone. Panel A of FIG. 3 depicts such a profile. Dose units that provide a concentration-dose PK profile having such an undetectable change in drug Cmax in vivo compared to the profile of prodrug alone can find use in thwarting enzyme conversion of prodrug from a dose unit that has sufficient inhibitor to reduce or prevent in vitro cleavage of the enzyme-cleavable prodrug by its respective enzyme.

Panel B in FIG. 3 represents a concentration-dose PK profile such that the relationship between the number of dose units ingested and a PK parameter value is linear with positive slope, where the profile exhibits a reduced slope relative to panel A. Such a dose unit provides a profile having a decreased PK parameter value (e.g., drug Cmax) relative to a reference PK parameter value exhibiting dose proportionality.

Concentration-dose PK profiles following ingestion of multiples of a dose unit can be non-linear. Panel C in FIG. 3 represents an example of a non-linear, biphasic concentration-dose PK profile. In this example, the biphasic concentration-dose PK profile contains a first phase over which the concentration-dose PK profile has a positive rise, and then a second phase over which the relationship between number of dose units ingested and a PK parameter value (e.g., drug Cmax) is relatively flat (substantially linear with zero slope). For such a dose unit, for example, drug Cmax can be increased for a selected number of dose units (e.g., 2, 3, or 4 dose units). However, ingestion of additional dose units does not provide for a significant increase in drug Cmax.

Panel D in FIG. 3 represents another example of a non-linear, biphasic concentration-dose PK profile. In this example, the biphasic concentration-dose PK profile is characterized by a first phase over which the concentration-dose PK profile has a positive rise and a second phase over which the relationship between number of dose units ingested and a PK parameter value (e.g., drug Cmax) declines. Dose units that provide this concentration-dose PK profile provide for an increase in drug Cmax for a selected number of ingested dose units (e.g., 2, 3, or 4 dose units). However, ingestion of further additional dose units does not provide for a significant increase in drug Cmax and instead provides for decreased drug Cmax.

Panel E in FIG. 3 represents a concentration-dose PK profile in which the relationship between the number of dose units ingested and a PK parameter (e.g., drug Cmax) is linear with zero slope. Such dose units do not provide for a significant increase or decrease in drug Cmax with ingestion of multiples of dose units.

Panel F in FIG. 3 represents a concentration-dose PK profile in which the relationship between number of dose units ingested and a PK parameter value (e.g., drug Cmax) is linear with a negative slope. Thus drug Cmax decreases as the number of dose units ingested increases.

Dose units that provide for concentration-dose PK profiles when multiples of a dose unit are ingested find use in tailoring of a dosage regimen to provide a therapeutic level of released drug while reducing the risk of overdose, misuse, or abuse. Such reduction in risk can be compared to a reference, e.g., to administration of drug alone or prodrug alone. In one embodiment, risk is reduced compared to administration of a drug or prodrug that provides a proportional concentration-dose PK profile. A dose unit that provides for a concentration-dose PK profile can reduce the risk of patient overdose through inadvertent ingestion of dose units above a prescribed dosage. Such a dose unit can reduce the risk of patient misuse (e.g., through self-medication). Such a dose unit can discourage abuse through deliberate ingestion of multiple dose units. For example, a dose unit that provides for a biphasic concentration-dose PK profile can allow for an increase in drug release for a limited number of dose units ingested, after which an increase in drug release with ingestion of more dose units is not realized. In another example, a dose unit that provides for a concentration-dose PK profile of zero slope can allow for retention of a similar drug release profile regardless of the number of dose units ingested.

Ingestion of multiples of a dose unit can provide for adjustment of a PK parameter value relative to that of ingestion of multiples of the same dose (either as drug alone or as a prodrug) in the absence of inhibitor such that, for example, ingestion of a selected number (e.g., 2, 3, 4 or more) of a single dose unit provides for a decrease in a PK parameter value compared to ingestion of the same number of doses in the absence of inhibitor.

Pharmaceutical compositions include those having an inhibitor to provide for protection of a therapeutic compound from degradation in the GI tract. Inhibitor can be combined with a drug (i.e., not a prodrug) to provide for protection of the drug from degradation in the GI system. In this example, the composition of inhibitor and drug provide for a modified PK profile by increasing a PK parameter. Inhibitor can also be combined with a prodrug that is susceptible to degradation by a GI enzyme and has a site of action outside the GI tract. In this composition, the inhibitor protects ingested prodrug in the GI tract prior to its distribution outside the GI tract and cleavage at a desired site of action.

Methods Used to Define Relative Amounts of Prodrug and Inhibitor in a Dose Unit

Dose units that provide for a desired PK profile, such as a desired concentration-time PK profile and/or a desired concentration-dose PK profile, can be made by combining a prodrug and an inhibitor in a dose unit in relative amounts effective to provide for release of drug that provides for a desired drug PK profile following ingestion by a patient.

Prodrugs can be selected as suitable for use in a dose unit by determining the GI enzyme-mediated drug release competency of the prodrug. This can be accomplished in vitro, in vivo or ex vivo.

In vitro assays can be conducted by combining a prodrug with a GI enzyme (e.g., trypsin) in a reaction mixture. The GI enzyme can be provided in the reaction mixture in an amount sufficient to catalyze cleavage of the prodrug. Assays are conducted under suitable conditions, and optionally may be under conditions that mimic those found in a GI tract of a subject, e.g., human. "Prodrug conversion" refers to release of drug from prodrug. Prodrug conversion can be assessed by detecting a level of a product of prodrug conversion (e.g., released drug) and/or by detecting a level of prodrug that is maintained in the presence of the GI enzyme. Prodrug conversion can also be assessed by detecting the rate at which a product of prodrug conversion occurs or the rate at which prodrug disappears. An increase in released drug, or a decrease in prodrug, indicate prodrug conversion has occurred. Prodrugs that exhibit an acceptable level of prodrug conversion in the presence of the GI enzyme within an acceptable period of time are suitable for use in a dose unit in combination with an inhibitor of the GI enzyme that is shown to mediate prodrug conversion.

In vivo assays can assess the suitability of a prodrug for use in a dose unit by administration of the prodrug to an animal (e.g., a human or non-human animal, e.g., rat, dog, pig, etc.). Such administration can be enteral (e.g., oral administration). Prodrug conversion can be detected by, for example, detecting a product of prodrug conversion (e.g., released drug or a metabolite of released drug) or detecting prodrug in blood or plasma of the animal at a desired time point(s) following administration.

Ex vivo assays, such as a gut loop or inverted gut loop assay, can assess the suitability of a prodrug for use in a dose unit by, for example, administration of the prodrug to a ligated section of the intestine of an animal. Prodrug conversion can be detected by, for example, detecting a product of prodrug conversion (e.g., released drug or a metabolite of released drug) or detecting prodrug in the ligated gut loop of the animal at a desired time point(s) following administration.

Inhibitors are generally selected based on, for example, activity in interacting with the GI enzyme(s) that mediate release of drug from a prodrug with which the inhibitor is to be co-dosed. Such assays can be conducted in the presence of enzyme either with or without prodrug. Inhibitors can also be selected according to properties such as half-life in the GI system, potency, avidity, affinity, molecular size and/or enzyme inhibition profile (e.g., steepness of inhibition curve in an enzyme activity assay, inhibition initiation rate). Inhibitors for use in prodrug-inhibitor combinations can be selected through use of in vitro, in vivo and/or ex vivo assays.

One embodiment is a method for identifying a prodrug and a GI enzyme inhibitor suitable for formulation in a dose unit wherein the method comprises combining a prodrug (e.g., an active agent prodrug), a GI enzyme inhibitor (e.g., a trypsin inhibitor), and a GI enzyme (e.g., trypsin) in a reaction mixture and detecting prodrug conversion. Such a combination is tested for an interaction between the prodrug, inhibitor and enzyme, i.e., tested to determine how the inhibitor will interact with the enzyme that mediates enzymatically-controlled release of the drug from the prodrug. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit. Such a method can be an in vitro assay.

One embodiment is a method for identifying a prodrug and a GI enzyme inhibitor suitable for formulation in a dose unit wherein the method comprises administering to an animal a prodrug and a GI enzyme inhibitor and detecting prodrug conversion. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit. Such a method can be an in vivo assay; for example, the prodrug and GI enzyme inhibitor can be administered orally. Such a method can also be an ex vivo assay; for example, the prodrug and GI enzyme inhibitor can be administered orally or to a tissue, such as an intestine, that is at least temporarily exposed. Detection can occur in the blood or plasma or respective tissue. As used herein, tissue refers to the tissue itself and can also refer to contents within the tissue.

One embodiment is a method for identifying a prodrug and a GI enzyme inhibitor suitable for formulation in a dose unit wherein the method comprises administering a prodrug and a gastrointestinal (GI) enzyme inhibitor to an animal tissue that has removed from an animal and detecting prodrug conversion. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit.

In vitro assays can be conducted by combining a prodrug, an inhibitor and a GI enzyme in a reaction mixture. The GI enzyme can be provided in the reaction mixture in an amount sufficient to catalyze cleavage of the prodrug, and assays conducted under suitable conditions, optionally under conditions that mimic those found in a GI tract of a subject, e.g., human. Prodrug conversion can be assessed by detecting a level of a product of prodrug conversion (e.g., released drug) and/or by detecting a level of prodrug maintained in the presence of the GI enzyme. Prodrug conversion can also be assessed by detecting the rate at which a product of prodrug conversion occurs or the rate at which prodrug disappears. Prodrug conversion that is modified in the presence of inhibitor as compared to a level of prodrug conversion in the absence of inhibitor indicates the inhibitor is suitable for attenuation of prodrug conversion and for use in a dose unit. Reaction mixtures having a fixed amount of prodrug and increasing amounts of inhibitor, or a fixed amount of inhibitor and increasing amounts of prodrug, can be used to identify relative amounts of prodrug and inhibitor which provide for a desired modification of prodrug conversion.

In vivo assays can assess combinations of prodrugs and inhibitors by co-dosing of prodrug and inhibitor to an animal. Such co-dosing can be enteral. "Co-dosing" refers to administration of prodrug and inhibitor as separate doses or a combined dose (i.e., in the same formulation). Prodrug conversion can be detected by, for example, detecting a product of prodrug conversion (e.g., released drug or drug metabolite) or detecting prodrug in blood or plasma of the animal at a desired time point(s) following administration. Combinations of prodrug and inhibitor can be identified that provide for a prodrug conversion level that yields a desired PK profile as compared to, for example, prodrug without inhibitor.

Combinations of relative amounts of prodrug and inhibitor that provide for a desired PK profile can be identified by dosing animals with a fixed amount of prodrug and increasing amounts of inhibitor, or with a fixed amount of inhibitor and increasing amounts of prodrug. One or more PK parameters can then be assessed, e.g., drug Cmax, drug Tmax, and drug exposure. Relative amounts of prodrug and inhibitor that provide for a desired PK profile are identified as amounts of prodrug and inhibitor for use in a dose unit. The PK profile of the prodrug and inhibitor combination can be, for example, characterized by a decreased PK parameter value relative to prodrug without inhibitor. A decrease in the PK parameter value of an inhibitor-to-prodrug combination (e.g., a decrease in drug Cmax, a decrease in 1/drug Tmax (i.e., a delay in drug Tmax) or a decrease in drug exposure) relative to a corresponding PK parameter value following administration of prodrug without inhibitor can be indicative of an inhibitor-to-prodrug combination that can provide a desired PK profile. Assays can be conducted with different relative amounts of inhibitor and prodrug.

In vivo assays can be used to identify combinations of prodrug and inhibitor that provide for dose units that provide for a desired concentration-dose PK profile following ingestion of multiples of the dose unit (e.g., at least 2, at least 3, at least 4 or more). Ex vivo assays can be conducted by direct administration of prodrug and inhibitor into a tissue and/or its contents of an animal, such as the intestine, including by introduction by injection into the lumen of a ligated intestine (e.g., a gut loop, or intestinal loop, assay, or an inverted gut assay). An ex vivo assay can also be conducted by excising a tissue and/or its contents from an animal and introducing prodrug and inhibitor into such tissues and/or contents.

For example, a dose of prodrug that is desired for a single dose unit is selected (e.g., an amount that provides an efficacious plasma drug level). A multiple of single dose units for which a relationship between that multiple and a PK parameter to be tested is then selected. For example, if a concentration-dose PK profile is to be designed for ingestion of 2, 3, 4, 5, 6, 7, 8, 9 or 10 dose units, then the amount of prodrug equivalent to ingestion of that same number of dose units is determined (referred to as the "high dose"). The multiple of dose units can be selected based on the number of ingested pills at which drug Cmax is modified relative to ingestion of the single dose unit. If, for example, the profile is to provide for abuse deterrence, then a multiple of 10 can be selected, for example. A variety of different inhibitors (e.g., from a panel of inhibitors) can be tested using different relative amounts of inhibitor and prodrug. Assays can be used to identify suitable combination(s) of inhibitor and prodrug to obtain a single dose unit that is therapeutically effective, wherein such a combination, when ingested as a multiple of dose units, provides a modified PK parameter compared to ingestion of the same multiple of drug or prodrug alone (wherein a single dose of either drug or prodrug alone releases into blood or plasma the same amount of drug as is released by a single dose unit).

Increasing amounts of inhibitor are then co-dosed to animals with the high dose of prodrug. The dose level of inhibitor that provides a desired drug Cmax following ingestion of the high dose of prodrug is identified and the resultant inhibitor-to-prodrug ratio determined.

Prodrug and inhibitor are then co-dosed in amounts equivalent to the inhibitor-to-prodrug ratio that provided the desired result at the high dose of prodrug. The PK parameter value of interest (e.g., drug Cmax) is then assessed. If a desired PK parameter value results following ingestion of the single dose unit equivalent, then single dose units that provide for a desired concentration-dose PK profile are identified. For example, where a zero dose linear profile is desired, the drug Cmax following ingestion of a single dose unit does not increase significantly following ingestion of a multiple number of the single dose units.

Methods for Manufacturing, Formulating, and Packaging Dose Units

Dose units of the present disclosure can be made using manufacturing methods available in the art and can be of a variety of forms suitable for enteral (including oral, buccal and sublingual) administration, for example as a tablet, capsule, thin film, powder, suspension, solution, syrup, dispersion or emulsion. The dose unit can contain components conventional in pharmaceutical preparations, e.g. one or more carriers, binders, lubricants, excipients (e.g., to impart controlled release characteristics), pH modifiers, flavoring agents (e.g., sweeteners), bulking agents, coloring agents or further active agents. Dose units of the present disclosure can include can include an enteric coating or other component(s) to facilitate protection from stomach acid, where desired.

Dose units can be of any suitable size or shape. The dose unit can be of any shape suitable for enteral administration, e.g., ellipsoid, lenticular, circular, rectangular, cylindrical, and the like.

Dose units provided as dry dose units can have a total weight of from about 1 microgram to about 1 gram, and can be from about 5 micrograms to 1.5 grams, from about 50 micrograms to 1 gram, from about 100 micrograms to 1 gram, from 50 micrograms to 750 milligrams, and may be from about 1 microgram to 2 grams.

Dose units can comprise components in any relative amounts. For example, dose units can be from about 0.1% to 99% by weight of active ingredients (i.e., prodrug and inhibitor) per total weight of dose unit (0.1% to 99% total combined weight of prodrug and inhibitor per total weight of single dose unit). In some embodiments, dose units can be from 10% to 50%, from 20% to 40%, or about 30% by weight of active ingredients per total weight dose unit.

Dose units can be provided in a variety of different forms and optionally provided in a manner suitable for storage. For example, dose units can be disposed within a container suitable for containing a pharmaceutical composition. The container can be, for example, a bottle (e.g., with a closure device, such as a cap), a blister pack (e.g., which can provide for enclosure of one or more dose units per blister), a vial, flexible packaging (e.g., sealed Mylar or plastic bags), an ampule (for single dose units in solution), a dropper, thin film, a tube and the like.

Containers can include a cap (e.g., screw cap) that is removably connected to the container over an opening through which the dose units disposed within the container can be accessed.

Containers can include a seal which can serve as a tamper-evident and/or tamper-resistant element, which seal is disrupted upon access to a dose unit disposed within the container. Such seal elements can be, for example, a frangible element that is broken or otherwise modified upon access to a dose unit disposed within the container. Examples of such frangible seal elements include a seal positioned over a container opening such that access to a dose unit within the container requires disruption of the seal (e.g., by peeling and/or piercing the seal). Examples of frangible seal elements include a frangible ring disposed around a container opening and in connection with a cap such that the ring is broken upon opening of the cap to access the dose units in the container.

Dry and liquid dose units can be placed in a container (e.g., bottle or package, e.g., a flexible bag) of a size and configuration adapted to maintain stability of dose units over a period during which the dose units are dispensed into a prescription. For example, containers can be sized and configured to contain 10, 20, 30, 40, 50, 60, 70, 80, 90, 100 or more single dry or liquid dose units. The containers can be sealed or resealable. The containers can packaged in a carton (e.g., for shipment from a manufacturer to a pharmacy or other dispensary). Such cartons can be boxes, tubes, or of other configuration, and may be made of any material (e.g., cardboard, plastic, and the like). The packaging system and/or containers disposed therein can have one or more affixed labels (e.g., to provide information such as lot number, dose unit type, manufacturer, and the like).

The container can include a moisture barrier and/or light barrier, e.g., to facilitate maintenance of stability of the active ingredients in the dose units contained therein. Where the dose unit is a dry dose unit, the container can include a desiccant pack which is disposed within the container. The container can be adapted to contain a single dose unit or multiples of a dose unit. The container can include a dispensing control mechanism, such as a lock out mechanism that facilitates maintenance of dosing regimen.

The dose units can be provided in solid or semi-solid form, and can be a dry dose unit. "Dry dose unit" refers to a dose unit that is in other than in a completely liquid form. Examples of dry dose units include, for example, tablets, capsules (e.g., solid capsules, capsules containing liquid), thin film, microparticles, granules, powder and the like. Dose units can be provided as liquid dose units, where the dose units can be provided as single or multiple doses of a formulation containing prodrug and inhibitor in liquid form. Single doses of a dry or liquid dose unit can be disposed within a sealed container, and sealed containers optionally provided in a packaging system, e.g., to provide for a prescribed number of doses, to provide for shipment of dose units, and the like.

Dose units can be formulated such that the prodrug and inhibitor are present in the same carrier, e.g., solubilized or suspended within the same matrix. Alternatively, dose units can be composed of two or more portions, where the prodrug and inhibitor can be provided in the same or different portions, and can be provided in adjacent or non-adjacent portions.

Dose units can be provided in a container in which they are disposed, and may be provided as part of a packaging system (optionally with instructions for use). For example, dose units containing different amounts of prodrug can be provided in separate containers, which containers can be disposed within a larger container (e.g., to facilitate protection of dose units for shipment). For example, one or more dose units as described herein can be provided in separate containers, where dose units of different composition are provided in separate containers, and the separate containers disposed within package for dispensing.

In another example, dose units can be provided in a double-chambered dispenser where a first chamber contains a prodrug formulation and a second chamber contains an inhibitor formulation. The dispenser can be adapted to provide for mixing of a prodrug formulation and an inhibitor formulation prior to ingestion. For example, the two chambers of the dispenser can be separated by a removable wall (e.g., frangible wall) that is broken or removed prior to administration to allow mixing of the formulations of the two chambers. The first and second chambers can terminate into a dispensing outlet, optionally through a common chamber. The formulations can be provided in dry or liquid form, or a combination thereof. For example, the formulation in the first chamber can be liquid and the formulation in the second chamber can be dry, both can be dry, or both can be liquid.

Dose units that provide for controlled release of prodrug, of inhibitor, or of both prodrug and inhibitor are contemplated by the present disclosure, where "controlled release" refers to release of one or both of prodrug and inhibitor from the dose unit over a selected period of time and/or in a pre-selected manner.

Methods of Use of Dose Units

Dose units are advantageous because they find use in methods to reduce side effects and/or improve tolerability of drugs to patients in need thereof by, for example, limiting a PK parameter as disclosed herein. The present disclosure thus provides methods to reduce side effects by administering a dose unit of the present disclosure to a patient in need so as to provide for a reduction of side effects as compared to those associated with administration of drug and/or as compared to administration of prodrug without inhibitor. The present disclosure also provides methods to improve tolerability of drugs by administering a dose unit of the present disclosure to a patient in need so as to provide for improvement in tolerability as compared to administration of drug and/or as compared to administration of prodrug without inhibitor.

Dose units find use in methods for increasing patient compliance of a patient with a therapy prescribed by a clinician, where such methods involve directing administration of a dose unit described herein to a patient in need of therapy so as to provide for increased patient compliance as compared to a therapy involving administration of drug and/or as compared to administrations of prodrug without inhibitor. Such methods can help increase the likelihood that a clinician-specified therapy occurs as prescribed.

Dose units can provide for enhanced patient compliance and clinician control. For example, by limiting a PK parameter (e.g., such as drug Cmax or drug exposure) when multiples (e.g., two or more, three or more, or four or more) dose units are ingested, a patient requiring a higher dose of drug must seek the assistance of a clinician. The dose units can provide for control of the degree to which a patient can readily "self-medicate", and further can provide for the patient to adjust dose to a dose within a permissible range. Dose units can provide for reduced side effects, by for example, providing for delivery of drug at an efficacious dose but with a modified PK profile over a period of treatment, e.g., as defined by a decreased PK parameter (e.g., decreased drug Cmax, decreased drug exposure).

Dose units find use in methods to reduce the risk of unintended overdose of drug that can follow ingestion of multiple doses taken at the same time or over a short period of time. Such methods of the present disclosure can provide for reduction of risk of unintended overdose as compared to risk of unintended overdose of drug and/or as compared to risk of unintended overdose of prodrug without inhibitor. Such methods involve directing administration of a dosage described herein to a patient in need of drug released by conversion of the prodrug. Such methods can help avoid unintended overdosing due to intentional or unintentional misuse of the dose unit.

The present disclosure provides methods to reduce misuse and abuse of a drug, as well as to reduce risk of overdose, that can accompany ingestion of multiples of doses of a drug, e.g., ingested at the same time. Such methods generally involve combining in a dose unit a prodrug and an inhibitor of a GI enzyme that mediates release of drug from the prodrug, where the inhibitor is present in the dose unit in an amount effective to attenuate release of drug from the prodrug, e.g., following ingestion of multiples of dose units by a patient. Such methods provide for a modified concentration-dose PK profile while providing therapeutically effective levels from a single dose unit, as directed by the prescribing clinician. Such methods can provide for, for example, reduction of risks that can accompany misuse and/or abuse of a prodrug, particularly where conversion of the prodrug provides for release of a narcotic or other drug of abuse (e.g., active agent). For example, when the prodrug provides for release of a drug of abuse, dose units can provide for reduction of reward that can follow ingestion of multiples of dose units of a drug of abuse.

Dose units can provide clinicians with enhanced flexibility in prescribing drug. For example, a clinician can prescribe a dosage regimen involving different dose strengths, which can involve two or more different dose units of prodrug and inhibitor having different relative amounts of prodrug, different amounts of inhibitor, or different amounts of both prodrug and inhibitor. Such different strength dose units can provide for delivery of drug according to different PK parameters (e.g., drug exposure, drug Cmax, and the like as described herein). For example, a first dose unit can provide for delivery of a first dose of drug following ingestion, and a second dose unit can provide for delivery of a second dose of drug following ingestion. The first and second prodrug doses of the dose units can be different strengths, e.g., the second dose can be greater than the first dose. A clinician can thus prescribe a collection of two or more, or three or more dose units of different strengths, which can be accompanied by instructions to facilitate a degree of self-medication, e.g., to increase delivery of an active agent drug according to a patient's needs to treat pain.

Thwarting Tampering by Trypsin Mediated Release of Active Agent from Prodrugs

The disclosure provides for a composition comprising a compound disclosed herein and a trypsin inhibitor that reduces drug abuse potential. A trypsin inhibitor can thwart the ability of a user to apply trypsin to effect the release of an active agent from the active agent prodrug in vitro. For example, if an abuser attempts to incubate trypsin with a composition of the embodiments that includes an active agent prodrug and a trypsin inhibitor, the trypsin inhibitor can reduce the action of the added trypsin, thereby thwarting attempts to release the active agent for purposes of abuse.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Celsius, and pressure is at or near atmospheric. Standard abbreviations may be used.

Synthesis of Ketone-Modified Opioid Prodrugs

Example 1

Synthesis of oxycodone 6-(N-methyl-N-(2-amino) ethylcarbamate (Compound KC-19)

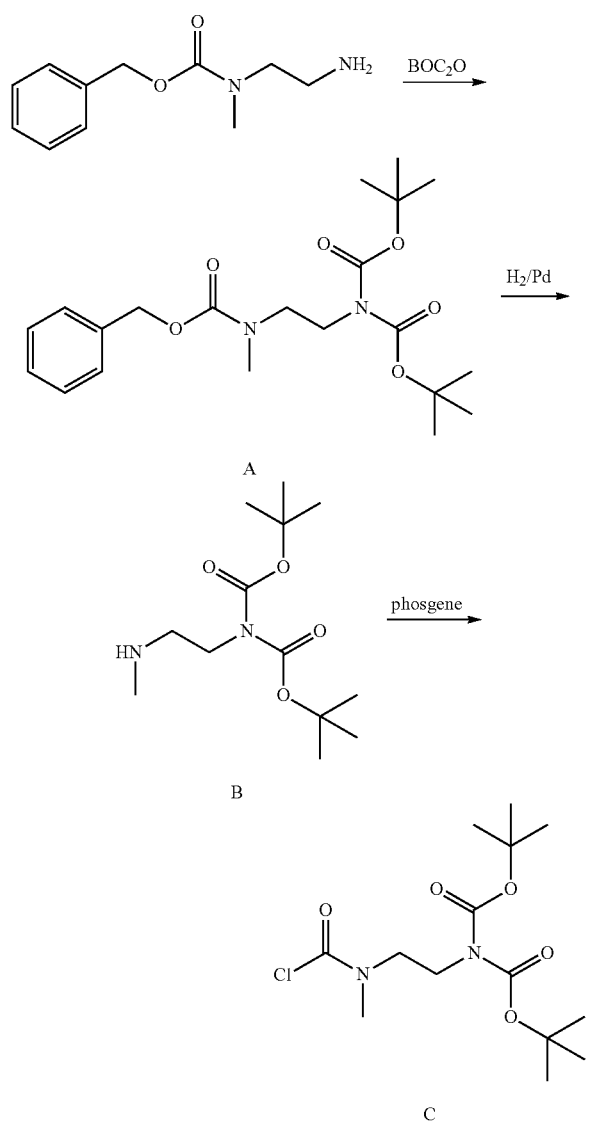

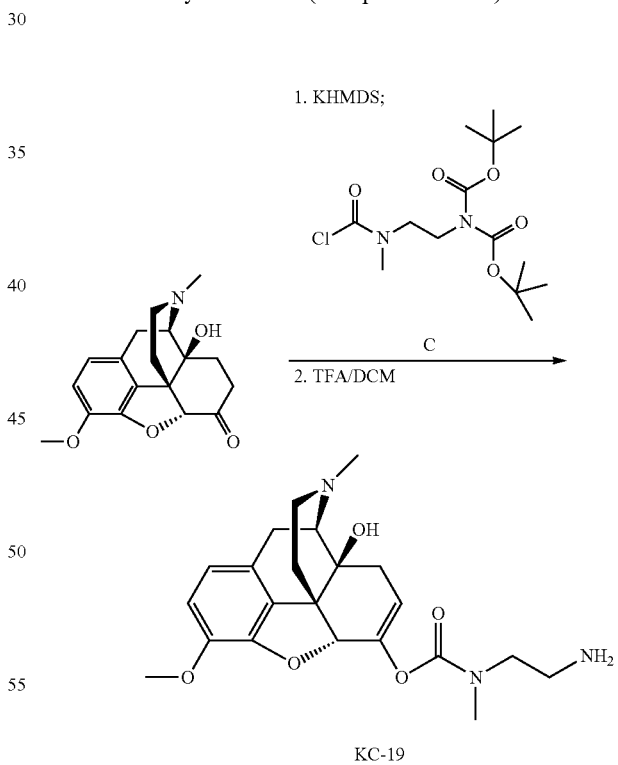

Preparation of Compound A 2-(Aminoethyl)-methyl-carbamic acid benzyl ester (2.0 g, 9.6 mmol) was dissolved in dichloroethene (DCE) (20 mL) at room temperature. Triethyl amine (NEt$_3$) (1.40 mL, 11.5 mmol) was added, followed by di-tert-butyl dicarbonate (BOC$_2$O) (10.5 g, 48 mmol) and dimethylaminopyridine (DMAP) (120 mg). The reaction mixture was stirred at room temperature under nitrogen (N$_2$) for 2 h and then heated at 60° C. for 16 h. The reaction mixture was then concentrated. The residue was purified by silica gel chromatography, using 4/1 hexanes/EtOAc, to give Compound A in 86% yield (3.4 g, 8.3 mmol). MS: (m/z) calc: 408.2, observed (M+Na$^+$) 431.9.

Preparation of Compound B

Compound A (1.3 g, 3.18 mmol) was dissolved in methanol/EtOAc (10 mL/3 mL respectively). The mixture was degassed and saturated with N$_2$. Palladium on carbon (Pd/C) (330 mg, 5% on carbon) was added. The mixture was shaken in a Parr hydrogenator flask (50 psi H$_2$) for 4 h. The mixture was then filtered through a celite pad, and the filtrate was concentrated to give Compound B (1.08 g, yield exceeded quantitative). Compound B was used without further purification.

Preparation of Compound C

Compound B (500 mg, 1.82 mmol) and NEt$_3$ (0.4 mL, 2.74 mmol) were mixed together in dichloromethane (4 mL). The mixture was added to a pre-chilled 0° C. solution of phosgene (5.5 mL, 0.5 M in toluene). The reaction mixture was stirred at 0° C. for 1 h, followed by dilution with ether (20 mL) and filtration through filter paper. The filtrate was concentrated and passed through a short silica gel column (10 cm×3 cm), and eluted with 3/1 hexanes/EtOAc. The fractions were concentrated to give N,N-Bis(tert-butyl) N'-2-(chlorocarbonyl (methyl)amino)ethylcarbamate (Compound C) as a colorless solid in quantitative yield (615 mg, 1.82 mmol). MS: (m/z) calc: 336.1, observed (M+Na$^+$) 359.8.

Synthesis of Oxycodone 6-(N-methyl-N-(2-amino) ethylcarbamate (Compound KC-19)

Oxycodone free base (6.5 g, 20.6 mmol) was dissolved in dry, degassed tetrahydrofuran (120 mL), and the mixture was cooled to −10° C. using a dry ice/acetone bath. Potassium bis(trimethylsilyl)amide (KHMDS) (103.0 mL, 51.6 mmol, 0.5 M in toluene) was added via cannula. The mixture was stirred under N$_2$ at below −5° C. for 30 min. N,N-Bis(tert-butyl) N'-2-(chlorocarbonyl(methyl)amino)ethylcarbamate (8.0 g, 23.7 mmol), (Compound C) in THF (30 mL) was then added via cannula over 15 min. The mixture was stirred at −5° C. for 30 min. Another portion of carbamoyl chloride (4.0 g, 11.9 mmol) in THF (10 mL) was added. The reaction was stirred at room temperature for 2 h. Sodium bicarbonate (10 mL, sat. aq.) was added. The mixture was concentrated under vacuum to half of its initial volume. EtOAc (50 mL) was added, and layers were separated. The organic phase was further washed with water (3×20 mL) and brine (40 mL), and then was concentrated. The residue was purified by silica gel chromatography, using DCM/MeOH (gradient 100/1 to 100/15) to afford a white foam in 55% yield (7.0 g, 13.4 mmol). This material was dissolved in a 1:1 mixture of DCM/trifluoroacetic acid (TFA) (20 mL/20 mL) at room temperature and stirred for 1 h. The solution was then concentrated under vacuum to afford a TFA salt of oxycodone 6-(N-methyl-N-(2-amino)ethylcarbamate (Compound KC-19) as a thick oil (7.3 g, 11.4 mmol, 99% purity). MS: (m/z) calc: 415.2, observed (M+H$^+$) 416.5.

Example 2

Synthesis of N-1-[2-(oxycodone-6-enol-carbonyl-methyl-amino)-ethylamine]-L-arginine-malonate (Compound KC-3) [also named: N-{(S)-4-guanidino-1-[2-(methyl-[(5R,9R,13S,14S)-4,5a-epoxy-6,7-didehydro-14-hydroxy-3-methoxy-17-methylmorphinan-6-oxy]carbonyl-amino)-ethylcarbamoyl]-butyl}-malonate]

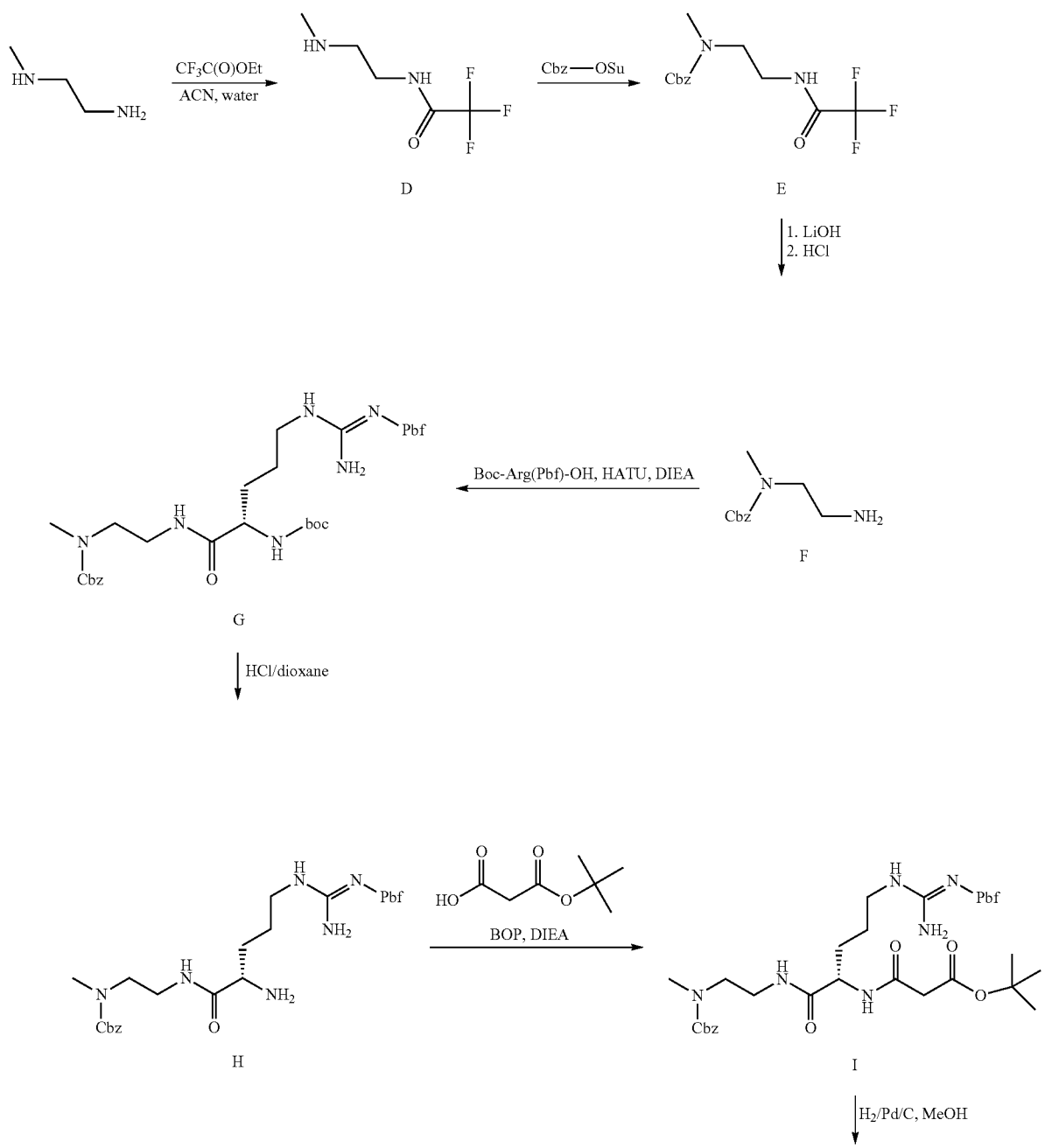

-continued

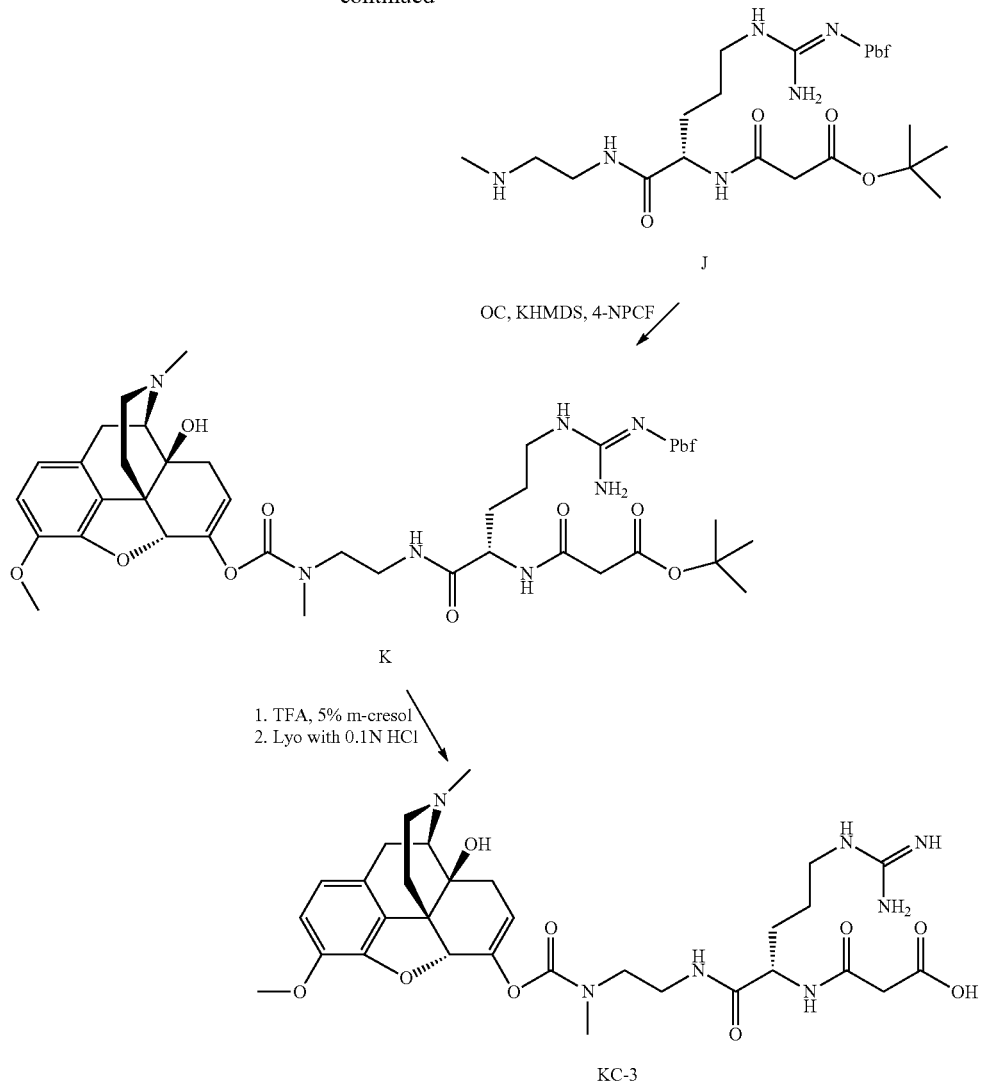

Preparation of Compound D

A solution of N-methylethylenediamine (27.0 g, 364 mmol) and ethyl trifluoroacetate (96.6 mL, 812 mmol) in a mixture of ACN (350 mL) and water (7.8 mL, 436 mmol) was refluxed with stirring overnight. Solvents were evaporated under vacuum. The residue was re-evaporated with i-PrOH (3×100 mL), followed by heat-cool crystallization from DCM (500 mL). Formed crystals were filtered, washed with DCM and dried under vacuum to provide Compound D (88.3 g, 85%) as white solid powder.

Preparation of Compound E

A solution of Compound D (88.2 g, 311 mmol) and DIEA (54.1 mL, 311 mmol) in THF (350 mL) was cooled in an ice bath, followed by the addition of a solution of N-(benzyloxycarbonyl)succinimide (76.6 g, 307 mmol) in THF (150 mL) dropwise over the period of 20 min. The temperature of the reaction mixture was raised to ambient temperature and stirring was continued for an additional 30 min. Solvents were then evaporated and the resulting residue was dissolved in EtOAc (600 mL). The organic layer was extracted with 5% aq. NaHCO$_3$ (2×150 mL) and brine (150 mL). The organic layer was evaporated to provide Compound E as yellowish oil. LC-MS [M+H] 305.1 ($C_{13}H_{15}F_3N_2O_3$+H, calc: 305.3). Compound E was used directly in the next reaction without purification as a MeOH solution.

Preparation of Compound F

To a solution of Compound E (~311 mmol) in MeOH (1.2 L) was added a solution of LiOH (14.9 g, 622 mmol) in water (120 mL). The reaction mixture was stirred at ambient temperature for 3 h. Solvents were evaporated to 75% of the initial volume followed by dilution with water (400 mL). The solution was extracted with EtOAc (2×300 mL). The organic layer was washed with brine (200 mL), dried over MgSO$_4$ and evaporated under vacuum. The residue was dissolved in ether (300 mL) and treated with 2 N HCl/ether (200 mL). Formed precipitate was filtrated, washed with ether and dried under vacuum to provide the hydrochloric salt of Compound F (67.8 g, 89%) as a white solid. LC-MS [M+H] 209.0 ($C_{11}H_{16}N_2O_2$+H, calc: 209.3). Compound F was used directly in the next reaction without purification as a DMF solution.

Preparation of Compound G

A solution of Boc-Arg(Pbf)-OH (16.0 g, ~30.4 mmol), Compound F hydrochloride (8.2 g, 33.4 mmol), and DIEA (16.9 mL, 97.2 mmol) in DMF (150 mL) was cooled in an ice bath followed by the addition of a solution of HATU (13.8 g, 36.4 mmol) dropwise over 20 min. The temperature of the reaction mixture was raised to ambient temperature, and stirring was continued for an additional 1 h. The reaction mixture was diluted with EtOAc (1 L) and extracted with water (3×200 mL) and brine (200 mL). The organic layer was dried over MgSO$_4$ and evaporated to provide Compound G (24.4 g, yield exceeded quantitative) as a yellowish oil. LC-MS [M+H] 717.4 ($C_{35}H_{52}N_6O_8S$+H, calc: 717.9). Compound G was used directly in the next reaction without purification as a dioxane solution.

Preparation of Compound H

Compound G (24.4 g, ~30.4 mmol) was dissolved in dioxane (150 mL) and treated with 4 N HCl/dioxane (150 mL, 600 mmol) at ambient temperature for 1 h. The solvent was then evaporated. The residue was suspended in i-PrOH (100 mL), and the mixture was evaporated (procedure was repeated twice). The residue was then dried under vacuum to provide Compound H (21.1 g, yield exceeded quantitative) as a yellowish solid. LC-MS [M+H] 617.5 ($C_{30}H_{44}N_6O_6S$+H, calc: 617.8). Compound H was used directly in the next reaction without purification as a DMF solution.

Preparation of Compound I

A solution of Compound H (21.1 g, ~30.4 mmol), mono-tert-butyl malonate (5.9 mL, 36.7 mmol), BOP (16.2 g, 36.7 mmol) and DIEA (14.9 mL, 83.5 mmol) in DMF (100 mL) was maintained at ambient temperature for 1 h. The reaction mixture was diluted with EtOAc (1 L) and extracted with water (500 mL), 5% aq. NaHCO$_3$ (500 mL), water (3×500 mL) and brine (500 mL). The organic layer was dried over MgSO$_4$, filtered, and then evaporated to provide Compound I (24.5 g, 97%) as a yellowish amorphous solid. LC-MS [M+H] 759.6 ($C_{37}H_{54}N_6O_9S$+H, calc: 759.9). Compound I was used without further purification.

Preparation of Compound J

Compound I (12.3 g, 16.7 mmol) was dissolved in methanol (100 mL) followed by the addition of a Pd/C (5% wt, 2.0 g) suspension in water (2 mL). The reaction mixture was subjected to hydrogenation (Parr apparatus, 70 psi H$_2$) at ambient temperature for 1 h. The catalyst was then filtered and washed with methanol. The filtrate was evaporated under vacuum to provide Compound J (10.0 g, 99%) as a colorless amorphous solid. LC-MS [M+H] 625.5 ($C_{29}H_{48}N_6O_7S$+H, calc: 625.8). Compound J was used without further purification.

Preparation of Oxycodone Free Base

Oxycodone hydrochloride (10.0 g, 28.5 mmol) was dissolved in chloroform (150 mL) and washed with 5% aq. NaHCO$_3$ (50 mL). The organic layer was dried over MgSO$_4$ and evaporated. The residue was dried under vacuum overnight to provide oxycodone free base (8.3 g, 93%) as a white solid.

Preparation of Compound K

A solution of oxycodone free base (6.6 g, 21.0 mmol) in THF (400 mL) was cooled to −20° C., followed by addition of a 0.5 M solution of KHMDS in toluene (46.3 mL, 23.1 mmol). The obtained solution was then added to a solution of 4-nitro-phenyl chloroformate (4.3 g, 21.0 mmol) in THF (100 mL) dropwise over the period of 20 min at −20° C. The reaction was maintained at −20° C. for an additional 1 h, followed by addition of a solution of Compound J (10.0 g, 16.1 mmol) in THF (200 mL) at −20° C. The reaction mixture was allowed to warm to ambient temperature and stirred overnight. Solvents were evaporated under vacuum. The resulting residue was dissolved in EtOAc (20 mL) and precipitated with ether (1 L). The formed precipitate was filtrated, washed with ether and dried under vacuum to provide Compound K (13.6 g, 87%) as an off-white solid. LC-MS [M+H] 966.9 ($C_{48}H_{67}N_7O_{12}S$+H, calc: 966.2).

Synthesis of N-1-[2-(oxycodone-6-enol-carbonyl-methyl-amino)-ethylamine]-L-arginine-malonate (Compound KC-3)

Compound K (13.6 g, 14.1 mmol) was dissolved in a mixture of 5% m-cresol/TFA (100 mL). The reaction mixture was maintained at ambient temperature for 1 h, followed by dilution with ethyl ether (1 L). The formed precipitate was filtered, washed with ether and hexane, and dried under vacuum to provide a TFA salt of Compound KC-3 (11.4 g, 81%) as an off-white solid. LC-MS [M+H] 658.6 ($C_{31}H_{43}N_7O_9$+H, calc: 658.7).

The TFA salt of crude Compound KC-3 (11.4 g, 11.4 mmol) was dissolved in water (50 mL). The obtained solution was subjected to HPLC purification. [Nanosyn-Pack YMC-GEL-ODS A (100-10) C-18 column (75×500 mm); flow rate: 250 mL/min; injection volume 50 mL; mobile phase A: 100% water, 0.1% TFA; mobile phase B: 100% ACN, 0.1% TFA; isocratic elution at 0% B in 4 min, gradient elution from 0% to 10% B in 20 min, isocratic elution at 10% B in 30 min, gradient elution from 10% B to 30% B in 41 min; detection at 254 nm]. Fractions containing Compound KC-3 were combined and concentrated under vacuum. The TFA counterion of the latter was replaced with an HCl counterion via lyophilization using 0.1N HCl to provide an HCl salt of Compound KC-3 (4.2 g, 41% yield) as a white solid. LC-MS [M+H] 658.6 ($C_{31}H_{43}N_7O_9$+H, calc: 658.7).

Example 3

Synthesis of N-(oxycodone-6-enol-carbonyl)piperidine-2-methylamine (Compound KC-11) and N-(oxycodone-6-enol-carbonyl)piperidine-2-methylamine-L-arginine-L-alanine-acetate (Compound KC-13)

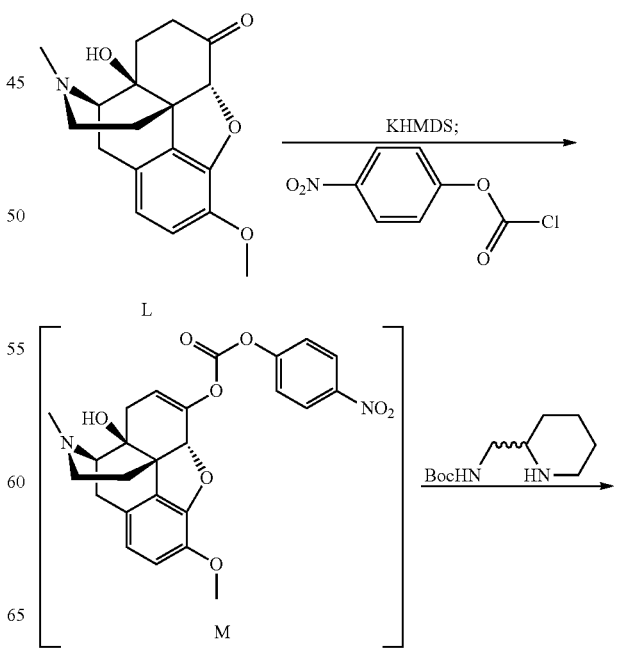

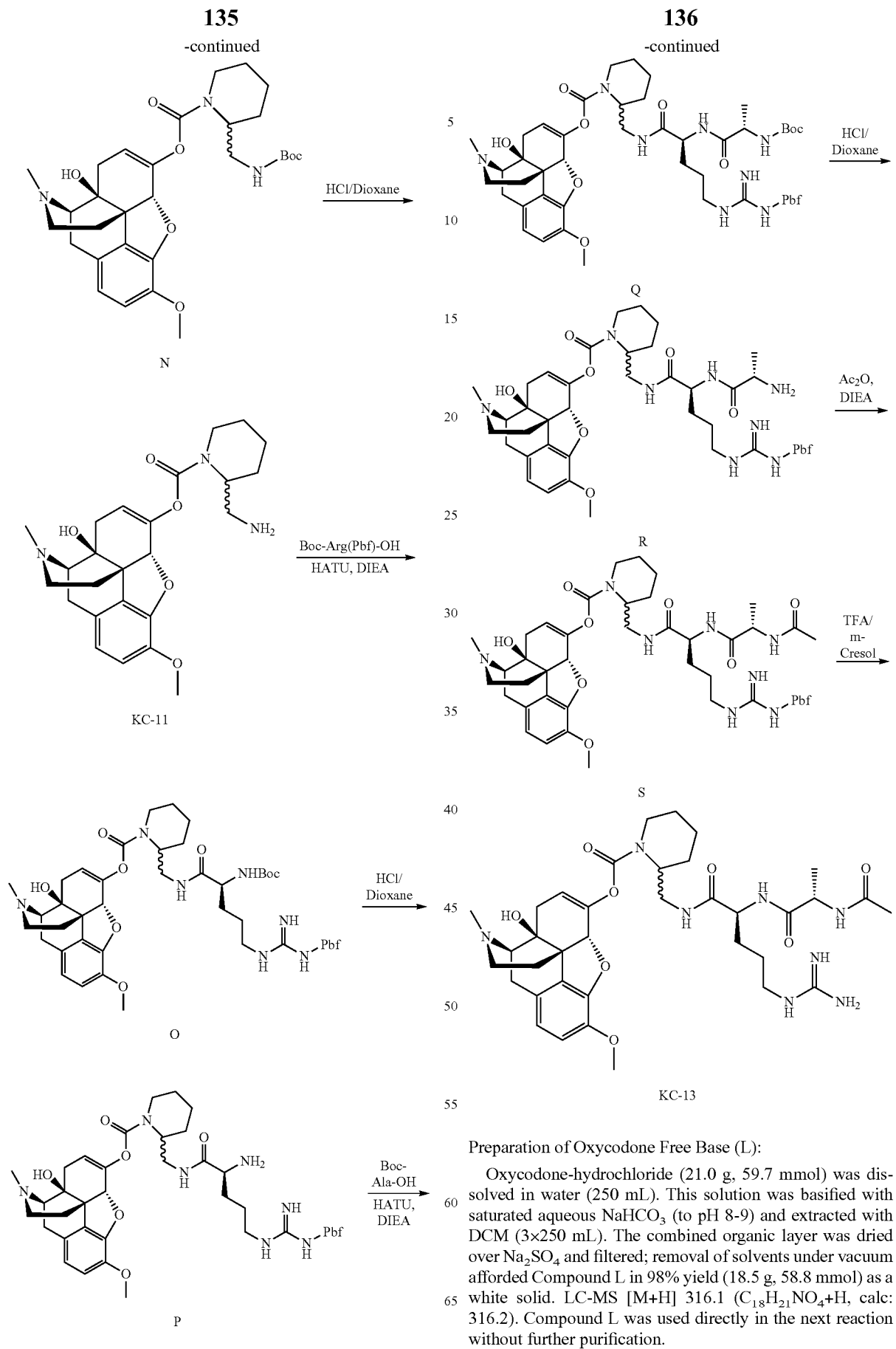

Preparation of Oxycodone Free Base (L):

Oxycodone-hydrochloride (21.0 g, 59.7 mmol) was dissolved in water (250 mL). This solution was basified with saturated aqueous $NaHCO_3$ (to pH 8-9) and extracted with DCM (3×250 mL). The combined organic layer was dried over $Na_2SO_4$ and filtered; removal of solvents under vacuum afforded Compound L in 98% yield (18.5 g, 58.8 mmol) as a white solid. LC-MS [M+H] 316.1 ($C_{18}H_{21}NO_4$+H, calc: 316.2). Compound L was used directly in the next reaction without further purification.

Preparation of Compound N

To a solution of Compound L (14.71 g, 46.7 mmol) in THF (250 mL) at −60° C. was added 0.5 M KHMDS solution in THF (103 mL) dropwise. After stirring at −60° C. for 30 min, the reaction mixture was added to a solution of 4-nitrophenyl chloroformate at −60° C. (9.41 g, 46.7 mmol) in THF (200 mL). This reaction mixture was then stirred for 30 min at −60° C., followed by addition of piperidine-2-yl-methylcarbamic acid tert-butyl ester, also referred to herein as (R,S)-piperidine-2-yl-methylcarbamic acid tert-butyl ester, (5.0 g, 23.3 mmol) in portions. The reaction was allowed to warm to ambient temperature and then stirred for 18 h. The reaction was then concentrated under vacuum, and the residue diluted with EtOAc (500 mL). The mixture was then washed with water (2×250 mL) and brine (250 mL). The organic layer was separated, dried over $Na_2SO_4$, and filtered. Removal of solvents under vacuum afforded crude Compound N. Crude Compound N was purified by flash chromatography using 100% EtOAc. Removal of solvent under vacuum afforded Compound N in 50% yield (6.5 g, 11.7 mmol) as a white solid. LC-MS [M+H] 556.1 ($C_{30}H_{41}N_3O_7$+H, calc: 555.3).

Preparation of N-(oxycodone-6-enol-carbonyl)piperidine-2-methylamine) (KG-11)

A solution of Compound N (6.5 g, 11.7 mmol) in 1,4-dioxane (100 mL) was treated with hydrogen chloride (4.0M solution in 1,4-dioxane, 100 mL). After 1 h, most of the 1,4-dioxane was removed under vacuum to ~20 mL remaining. To this solution was added $Et_2O$ (~750 mL). The product was then precipitated as an HCl salt. The precipitate was filtered, washed with ether and dried under vacuum to afford Compound KC-11 in 97% yield (5.96 g, 11.3 mmol) as a white solid. LC-MS [M+H] 456.3 ($C_{25}H_{33}N_3O_5$+H, calc: 456.2). Compound KC-11 was used directly in the next reaction without further purification.

Preparation of Compound O

To a solution of Boc-Arg(Pbf)-OH (5.94 g, 11.3 mmol), Compound KC-11 (5.95 g, 11.3 mmol) and DIEA (8.24 mL, 47.4 mmol) in DMF (100 mL) at ~0° C. was added HATU (4.28 g, 11.3 mmol) in portions over 10 min. The temperature of the reaction mixture was raised to ambient temperature and stirring was continued for an additional 1 h. DMF was removed under vacuum, and the reaction mixture was diluted with EtOAc (300 mL), washed with water (3×150 mL) and brine (150 mL). The organic layer was separated, dried over $Na_2SO_4$, and filtered. Removal of solvents under vacuum afforded crude Compound O. This compound was purified by silica gel chromatography using $CHCl_3$ and 0% to 20% MeOH. Removal of solvents under vacuum afforded Compound O in 23% yield (2.5 g, 2.6 mmol) as a foamy solid. LC-MS [M+H] 964.8 ($C_{49}H_{69}N_7O_{11}S$+H, calc: 964.5).

Preparation of Compound P

A solution of Compound O (2.5 g, 2.6 mmol) in 1,4-dioxane (50 mL) was treated with hydrogen chloride (4.0 M solution in 1,4-dioxane, 50 mL). After 1 h, most of the 1,4-dioxane was removed under vacuum until ~10 mL remained. To this solution was added $Et_2O$ (~500 mL). The product precipitated as an HCl salt. The precipitate was filtered off, washed with ether, and dried under vacuum to afford Compound P in 52% yield (1.25 g, 1.33 mmol) as a white solid. LC-MS [M+H] 864.6 ($C_{44}H_{61}N_7O_9S$+H, calc: 863.4). Compound P was used directly in the next reaction without further purification.

Preparation of Compound Q

To a solution of Boc-Ala-OH (0.13 g, 0.66 mmol), Compound P (0.62 g, 0.66 mmol), and DIEA (0.48 mL, 2.77 mmol) in DMF (10 mL) at 5° C., was added HATU (0.25 g, 0.66 mmol) in portions over 5 min. The temperature of the reaction mixture was raised to ambient temperature, and stiffing was continued for an additional 1 h. DMF was removed under vacuum. Next the reaction mixture was diluted with EtOAc (100 mL), and washed with water (3×50 mL) and brine (50 mL). The organic layer was separated, dried over $Na_2SO_4$, and filtered. Removal of solvents under vacuum afforded crude Compound Q, yield exceeded quantitative, (0.69 g, 0.66 mmol) as an off-white solid. LC-MS [M+H] 1035.6 ($C_{52}H_{74}N_8O_{12}S$+H, calc: 1035.5). Compound Q was used directly in the next reaction without further purification.

Preparation of Compound R

A solution of Compound Q (0.69 g, 0.66 mmol) in 1,4-dioxane (10 mL) was treated with hydrogen chloride (4.0 M solution in 1,4-dioxane, 10 mL). After 1 h, most of the 1,4-dioxane was removed under vacuum until ~2 mL remained. To this solution was added $Et_2O$ (~100 mL). The product precipitated as an HCl salt. The precipitate was washed with ether and dried under vacuum to afford crude Compound R, yield exceeded quantitative, (0.67 g, 0.66 mmol) as an off-white solid. LC-MS [M+H] 935.8 ($C_{47}H_{66}N_8O_{10}S$+H, calc: 935.5). Compound R was used directly in the next reaction without further purification.

Preparation of Compound S

To a solution of Compound R (0.67 g, 0.66 mmol) and DIEA (0.37 mL, 2.1 mmol) in $CHCl_3$ (50 mL) and cooled to ~0° C., was added acetic anhydride ($Ac_2O$) (0.07 mL, 0.7 mmol). The reaction mixture was stirred at ambient temperature for 30 min. The reaction mixture was diluted with $CHCl_3$ (50 mL), and washed with water (2×100 mL) and brine (50 mL). The organic layer was separated, dried over $Na_2SO_4$, and filtered. Removal of solvents under vacuum afforded the crude Compound S, yield exceeded quantitative, (0.65 g, 0.66 mmol) as an off-white solid. LC-MS [M+H] 977.4 ($C_{49}H_{68}N_8O_{11}S$+H, calc: 977.5). Compound S was used directly in the next reaction without further purification.

Preparation of N-(oxycodone-6-enol-carbonyl)piperidine-2-methylamine-L-arginine-L-alanine-acetate (Compound KC-13)

Compound S (0.65 g, 0.66 mmol) was treated with 5% m-cresol in TFA (15 mL) for 1 h. The product was precipitated via addition of $Et_2O$ (100 mL). The precipitate was washed with $Et_2O$ (2×100 mL) and dried under vacuum to afford crude Compound KC-13. This product was dissolved in water (15 mL), and the solution was subjected to HPLC purification. [Nanosyn-Pack Microsorb (100-10) C-18 column (50×300 mm); flow rate: 100 mL/min; injection volume 15 mL; mobile phase A: 100% water, 0.1% TFA; mobile phase B: 100% ACN, 0.1% TFA; isocratic elution at 0% B in 5 min, gradient elution from 0% to 20% B in 20 min, isocratic elution at 20% B in 20 min, gradient elution from 20% B to 45% B in 40 min; detection at 254 nm]. Fractions containing the desired compound were combined and concentrated under vacuum. The residue was dissolved in ACN (~2 mL) and 0.1 N HCl (~8 mL), and lyophilized overnight to provide the hydrochloric salt of Compound KC-13 in 90% yield (0.65 g, 0.59 mmol, 93.1% purity) as a white solid. LC-MS [M+H] 725.8 ($C_{36}H_{52}N_8O_8$+H, calc: 725.4).

Example 4

Synthesis of N-(oxycodone-6-enol-carbonyl)pyrrolidine-2-methylamine (Compound KC-9)

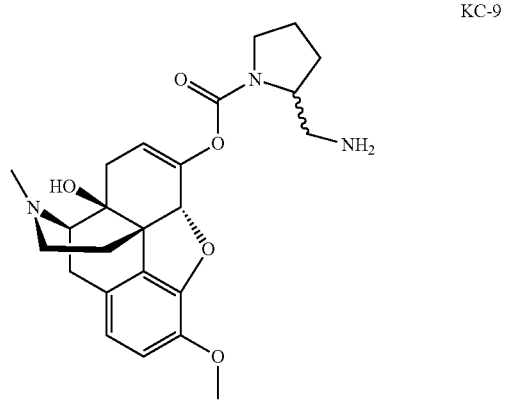

KC-9

Compound KC-9 was prepared following the method described in Example 3 to prepare N-(oxycodone-6-enol-carbonyl)piperidine-2-methylamine (Compound KC-11), but using pyrrolidine-2-yl-methylcarbamic acid tert-butyl ester instead of piperidine-2-yl-methylcarbamic acid tert-butyl ester. LC-MS [M+H] 442.1 ($C_{24}H_{31}N_3O_5$+H, calc: 442.3).

Example 5

Synthesis of N-(oxycodone-6-enol-carbonyl)pyrrolidine-2-methylamine-L-arginine-malonate (Compound KC-10)

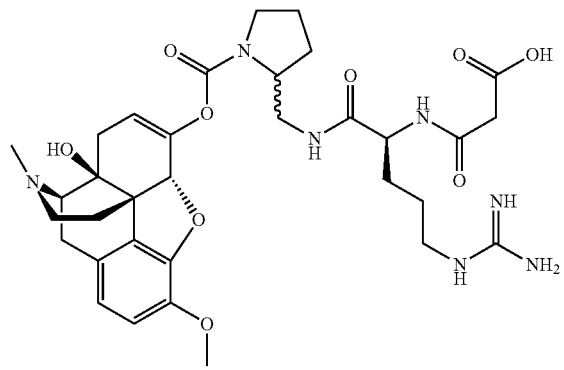

KC-10

Compound KC-10 was prepared following the method described in Example 3 to prepare N-(oxycodone-6-enol-carbonyl)piperidine-2-methylamine-L-arginine-L-alanine-acetate (Compound KC-13), but using pyrrolidine-2-yl-methylcarbamic acid tert-butyl ester instead of piperidine-2-yl-methylcarbamic acid tert-butyl ester, and using mono-tert-butyl malonate instead of Boc-Ala-OH. LC-MS [M+H] 684.4 ($C_{33}H_{45}N_7O_9$+H, calc: 684.4).

Example 6

Synthesis of N-(oxycodone-6-enol-carbonyl)piperidine-2-methylamine-L-arginine-malonate (Compound KC-12)

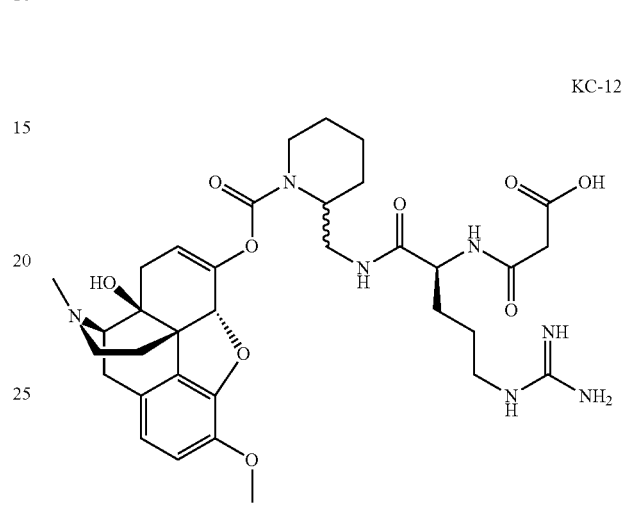

KC-12

Compound KC-12 was prepared following the method described in Example 3 to prepare N-(oxycodone-6-enol-carbonyl)piperidine-2-methylamine-L-arginine-L-alanine-acetate (Compound KC-13), but using mono-tert-butyl malonate instead of Boc-Ala-OH. LC-MS [M+H] 698.4 ($C_{35}H_{47}N_7O_9$+H, calc: 698.7).

Example 7

Synthesis of N-(oxycodone-6-enol-carbonyl)piperidine-2-methylamine-L-arginine-glycine-acetate (Compound KC-14)

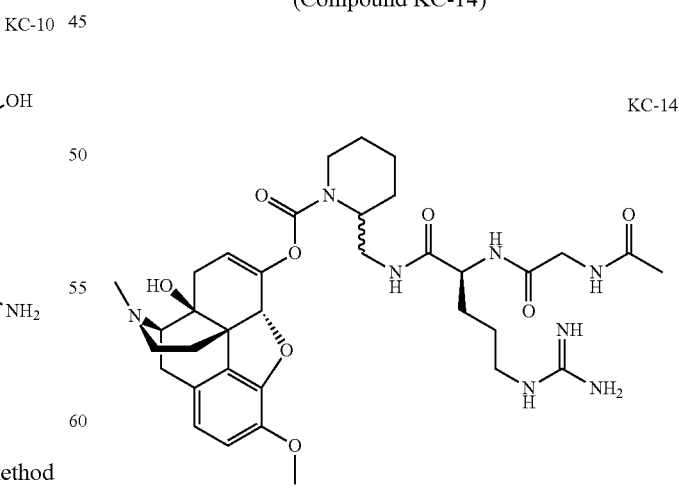

KC-14

Compound KC-14 was prepared following the method described in Example 3 to prepare N-(oxycodone-6-enol-carbonyl)piperidine-2-methylamine-L-arginine-L-alanineacetate (Compound KC-13), but using Boc-Gly-OH instead of Boc-Ala-OH. LC-MS [M+H] 711.3 ($C_{35}H_{50}N_8O_8$+H, calc: 711.4).

of Boc-Ala-OH, and using mono-tert-butyl malonate instead of acetic anhydride. LC-MS [M+H] 755.4 ($C_{36}H_{50}N_8O_{10}$+H, calc: 755.4).

Example 8

Synthesis of N-(oxycodone-6-enol-carbonyl)piperidine-2-methylamine-L-arginine-L-alanine-malonate (Compound KC-15)

Example 10

Synthesis of N-(oxycodone-6-enol-carbonyl)-R-(piperidine-2-methylamine)-L-arginine-glycine-malonate (Compound KC-17)

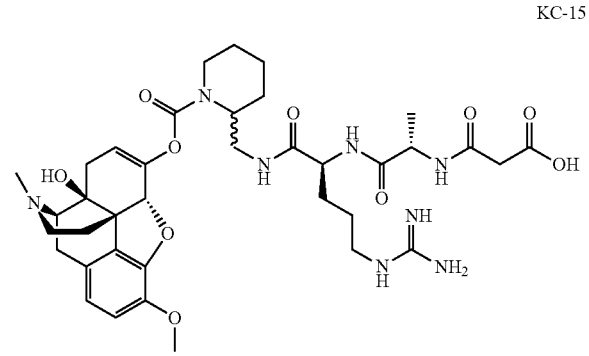

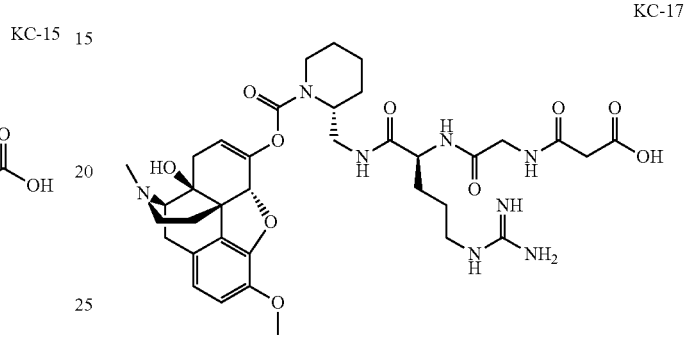

Compound KC-15 was prepared following the method described in Example 3 to prepare N-(oxycodone-6-enol-carbonyl)piperidine-2-methylamine-L-arginine-L-alanine-acetate (Compound KC-13), but using mono-tert-butyl malonate instead of acetic anhydride. LC-MS [M+H] 769.6 ($C_{37}H_{52}N_8O_{10}$+H, calc: 769.4).

Compound KC-17 was prepared following the method described in Example 3 to prepare N-(oxycodone-6-enol-carbonyl)piperidine-2-methylamine-L-arginine-L-alanine-acetate (Compound KC-13), but using (R)-piperidine-2-yl-methylcarbamic acid tert-butyl ester instead of (R,S)-piperidine-2-yl-methylcarbamic acid tert-butyl ester, using Boc-Gly-OH instead of Boc-Ala-OH, and using mono-tert-butyl malonate instead of acetic anhydride. LC-MS [M+H] 755.5 ($C_{36}H_{50}N_8O_{10}$+H, calc: 755.4).

Example 9

Synthesis of N-(oxycodone-6-enol-carbonyl)piperidine-2-methylamine-L-arginine-glycine-malonate (Compound KC-16)

Example 11

Synthesis of N-(oxycodone-6-enol-carbonyl)-R-(piperidine-2-methylamine) (Compound KC-18)

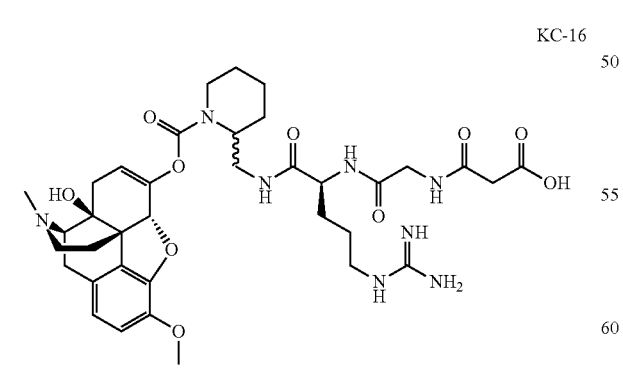

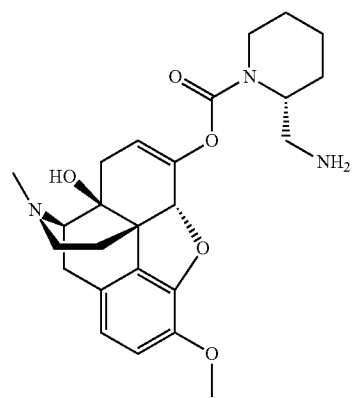

Compound KC-16 was prepared following the method described in Example 3 to prepare N-(oxycodone-6-enol-carbonyl)piperidine-2-methylamine-L-arginine-L-alanine-acetate (Compound KC-13), but using Boc-Gly-OH instead Compound KC-18 was prepared following the method described in Example 3 to prepare N-(oxycodone-6-enol-carbonyl)piperidine-2-methylamine (Compound KC-11), but using (R)-piperidine-2-yl-methylcarbamic acid tert-butyl ester instead of (R,S)-piperidine-2-yl-methylcarbamic acid tert-butyl ester. LC-MS [M+H] 456.2 ($C_{25}H_{33}N_3O_8$+H, calc: 456.3).

Example 12

Synthesis of N-(hydrocodone-6-enol-carbonyl)-R-(piperidine-2-methylamine)-L-arginine-glycine-malonate (Compound KC-31)

Compound KC-31 was prepared following the method described in Example 10 to prepare N-(oxycodone-6-enol-carbonyl)-R-(piperidine-2-methylamine)-L-arginine-glycine-malonate (Compound KC-17), except hydrocodone was used instead of oxycodone. LC-MS [M+H] 739.6 ($C_{36}H_{50}N_8O_9$+H calc: 739.9).

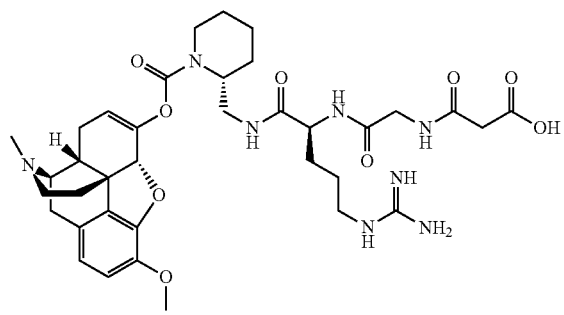

KC-31

Example 13

Synthesis of N-(Tapentadol-carbonyl)piperidine-2-methylamine-L-arginine-malonate (Compound TP-5)

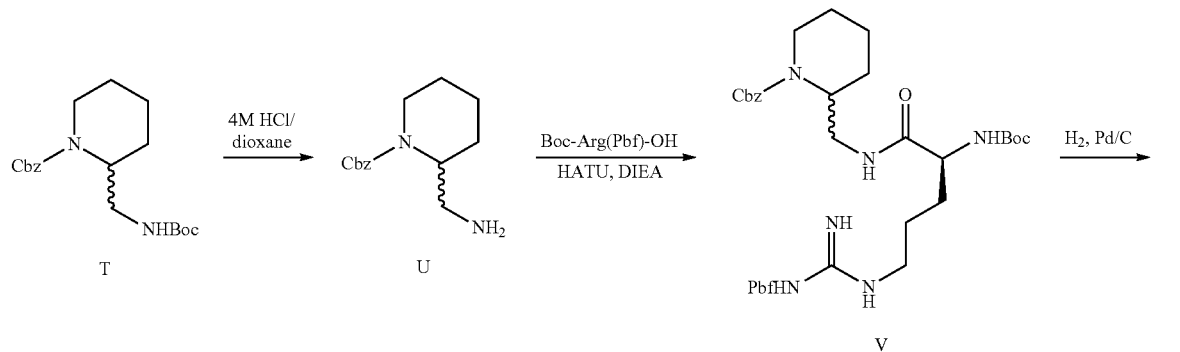

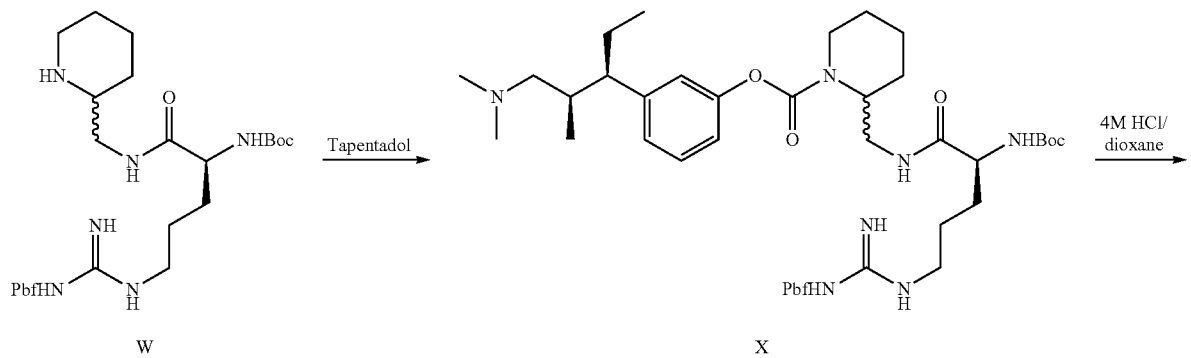

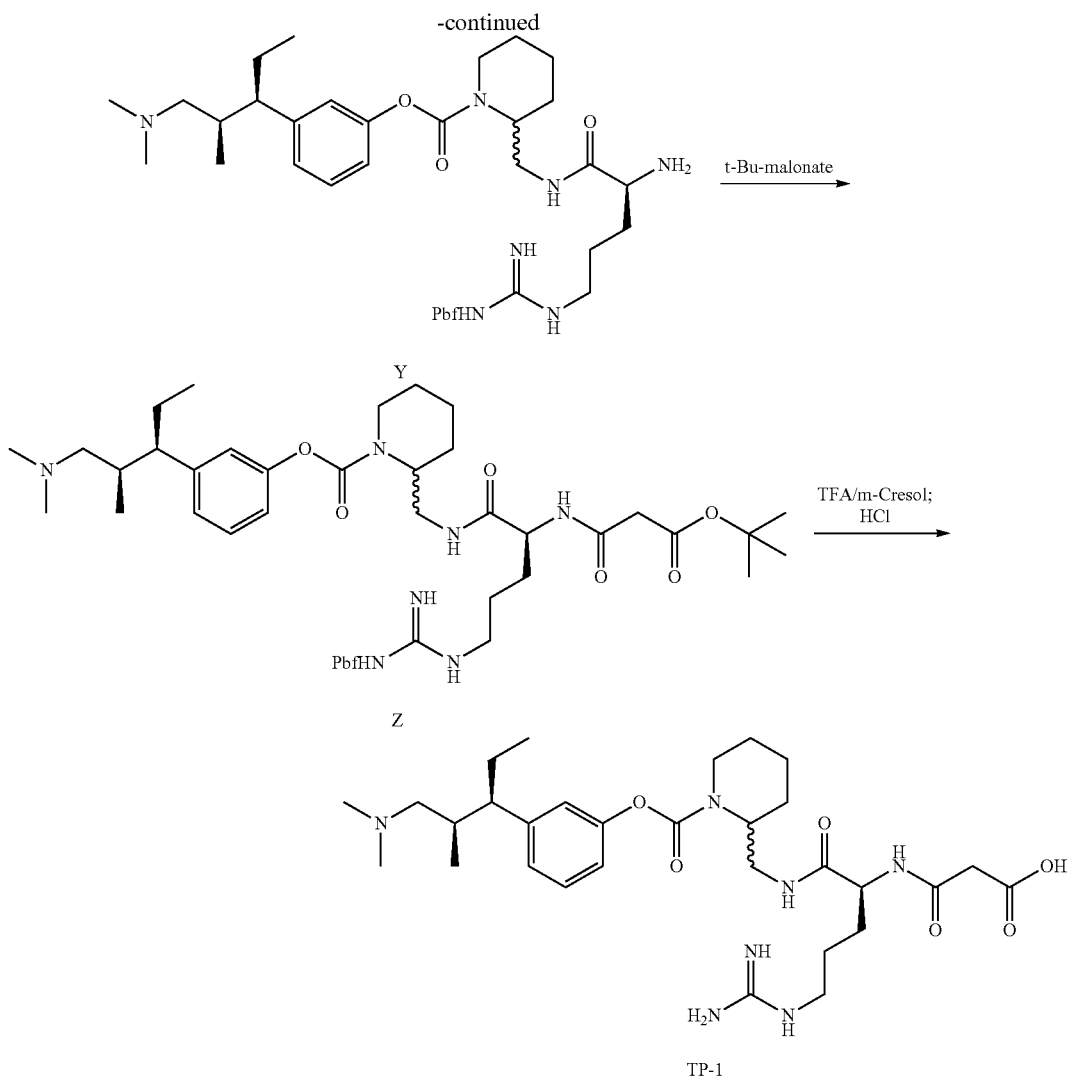

Preparation of Compound U

A solution of 2-(tert-butoxycarbonylamino-methyl)-piperidine-1-carboxylic acid benzyl ester (Compound T) (3.0 g, 8.61 mmol) was treated with HCl (4.0 M solution in 1,4-dioxane, 20 mL) for 1 h. The solvents were removed under vacuum until a volume of ~10 mL remained, after which $Et_2O$ (500 mL) was added. The precipitate was filtered off and washed with $Et_2O$ (2×100 mL) and dried to afford crude Compound U in a quantitative yield (2.87 g, 8.61 mmol) as a white solid. LC-MS [M+H] 249.3 ($C_{19}H_{28}N_2O_4$+H, calc: 249.3). Compound U was used directly in the next reaction without further purification.

Preparation of Compound V

A solution of Boc-Arg(Pbf)-OH (4.54 g, 8.61 mmol), Compound U (2.87 g, 8.61 mmol), and DIEA (3.9 mL, 22.4 mmol) in DMF (100 mL) was cooled to 0° C. (in an ice bath); HATU (3.5 g, 8.61 mmol) was added in portions over 15 min. The reaction mixture was raised to ambient temperature, and stirring was continued for an additional 2 h. DMF was then removed under vacuum, and the residue was diluted with EtOAc (500 mL) and extracted with water (3×100 mL) and brine (100 mL). The organic layer was dried over $Na_2SO_4$ and filtered. The removal of the solvents under vacuum yielded the crude Compound V which was purified by flash chromatography using $CHCl_3$ and MeOH to afford Compound V in 45% yield (2.9 g, 3.83 mmol) as a foamy solid. LC-MS [M+H] 757.6 ($C_{38}H_{56}N_6O_8S$+H, calc: 757.4).

Preparation of Compound W

A solution of Compound V (2.7 g, 3.57 mmol) in MeOH (100 mL) was treated with palladium (5 wt. % on activated carbon, 0.6 g) and subjected to hydrogenation at 70 psi for 1 h. The reaction mixture was filtered using a Celite pad. The removal of MeOH afforded Compound W in 99% yield (2.19 g, 3.51 mmol) as a foamy solid. LC-MS [M+H] 623.6 ($C_{30}H_{50}N_6O_6S$+H, calc: 623.4). Compound W was used directly in the next reaction without further purification.

Preparation of Compound X

To a solution of tapentadol hydrochloride (0.5 g, 1.94 mmol) and DIEA (0.34 mL, 1.94 mmol) in $CHCl_3$ (15 mL) was added 4-nitrophenyl chloroformate (0.38 g, 1.89 mmol), and the reaction mixture was sonicated for 30 min. To this reaction mixture was added Compound W (1.18 g, 1.89 mmol) in DMF (5 mL) at 5° C. The resultant reaction mixture was warmed to ambient temperature, and then allowed to stir for 2 h. The solvents were then removed under vacuum, and the residue was diluted with EtOAc (100 mL), and washed with water (2×50 mL) and brine (25 mL). The organic layer was dried over $Na_2SO_4$ and filtered; the removal of the solvents under vacuum afforded Compound X in quantitative yield (1.7 g, 1.94 mmol) as an oil. LC-MS [M+H] 870.8 ($C_{45}H_{71}N_7O_8S$+H, calc: 870.5). Compound X was used directly in the next reaction without further purification.

Preparation of Compound Y

A solution of Compound X (1.7 g, 1.94 mmol) in 1,4-dioxane (10 mL) was treated with HCl (4.0 M solution in 1,4-dioxane, 10 mL) for 30 min. The solvents were then removed until a volume of ~5 mL was reached, after which $Et_2O$ was added (250 mL). The resulting precipitate was filtered off, washed with $Et_2O$ (2×75 mL), and dried to afford crude Compound Y. The crude compound was dissolved in water (15 mL), and the solution was subjected to HPLC purification. [Nanosyn-Pack Microsorb (100-10) C-18 column (50×300 mm); flow rate: 100 mL/min; injection volume 15 mL; mobile phase A: 100% water, 0.1% TFA; mobile phase B: 100% ACN, 0.1% TFA; isocratic elution at 0% B in 5 min, gradient elution from 0% to 30% B in 30 min, isocratic elution at 30% B in 20 min, gradient elution from 30% B to 50% B in 40 min; detection at 254 nm]. Fractions containing the desired product were combined and concentrated under vacuum. The residue was dissolved in MeCN (~2 mL) and 0.1 N HCl (~8 mL) and lyophilized overnight to provide Compound Y in 53% yield (0.84 g, 1.00 mmol) as a foamy solid. LC-MS [M+H] 770.4 ($C_{40}H_{63}N_7O_6S$+H, calc: 770.5).

Preparation of Compound Z

To a solution of Compound Y (0.75 g, 0.89 mmol), mono-tert-Butyl Malonate (0.13 mL, 1.08 mmol), and DIEA (0.46 mL, 2.7 mmol) in DMF (15 mL) at 5° C. was added BOP (0.39 g, 1.08 mmol) in portions. The reaction mixture was stirred at ambient temperature for 1 h. DMF was removed under vacuum, and the residue was diluted with EtOAc (100 mL), and washed with water (2×50 mL) and brine (25 mL). The organic layer was dried over $Na_2SO_4$ and filtered; the removal of the solvents afforded Compound Z in quantitative yield (1.2 g, 0.89 mmol) as an oil. LC-MS [M+H] 912.8 ($C_{47}H_{73}N_7O_9S$+H, calc: 912.5). Compound Z was used directly in the next reaction without further purification.

Preparation of N-(Tapentadol-carbonyl)piperidine-2-methylamine-L-arginine-malonate (Compound TP-5)

A solution of Compound Z (1.2 g, 0.89 mmol) in TFA (10 mL) was treated with 5% m-cresol for 1 h. The product was precipitated via addition of $Et_2O$ (100 mL). The precipitate was washed with $Et_2O$ (2×100 mL) and dried under vacuum. The resultant product was dissolved in water (15 mL), and the solution was subjected to HPLC purification. [Nanosyn-Pack Microsorb (100-10) C-18 column (50×300 mm); flow rate: 100 mL/min; injection volume 15 mL; mobile phase A: 100% water, 0.1% TFA; mobile phase B: 100% ACN, 0.1% TFA; gradient elution from 0% to 20% B in 30 min, isocratic elution at 20% B in 30 min, gradient elution from 20% B to 45% B in 35 min; detection at 254 nm]. Fractions containing the desired product were combined and concentrated under vacuum. The residue was dissolved in MeCN (~2 mL) and 0.1 N HCl (~8 mL) and lyophilized overnight to provide Compound TP-5 in 88% yield (0.56 g, 0.79 mmol, 95.0% purity) as a foamy solid. LC-MS [M+H] 604.5 ($C_{30}H_{49}N_7O_6$+H, calc: 604.4).

Example 14

Synthesis of N-(hydrocodone-6-enol-carbonyl)-R-(piperidine-2-methylamine)-L-arginine-L-alanine-malonate (Compound KC-35)

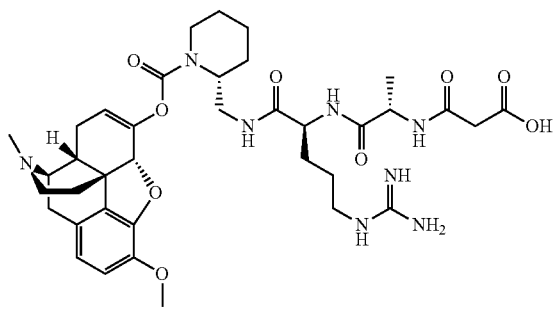

KC-35

Compound KC-35 was prepared following the method described in Example 10 to prepare N-(oxycodone-6-enol-carbonyl)-R-(piperidine-2-methylamine)-L-arginine-glycine-malonate (Compound KC-17), except using Boc-Ala-OH instead of Boc-Gly-OH and using hydrocodone instead of oxycodone. LC-MS [M+H] 753.7 ($C_{37}H_{52}N_8O_9$+H calc: 753.9).

Example 15

Synthesis of N-(hydrocodone-6-enol-carbonyl)-R-(piperidine-2-methylamine)-L-arginine-glycine-acetate (Compound KC-36)

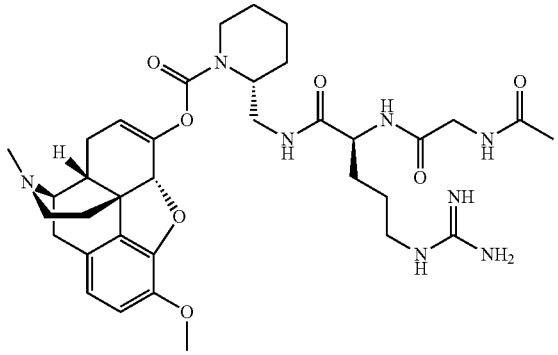

KC-36

Compound KC-36 was prepared following the method described in Example 10 to prepare N-(oxycodone-6-enol-carbonyl)-R-(piperidine-2-methylamine)-L-arginine-glycine-malonate (Compound KC-17), except using acetic anhydride instead of mono-tert-butyl malonate and using hydrocodone instead of oxycodone. LC-MS [M+H] 695.8 ($C_{35}H_{50}N_8O_7$+H calc: 695.8).

Example 16

Synthesis of N-(hydrocodone-6-enol-carbonyl)-R-(piperidine-2-methylamine)-L-arginine-L-alanine-acetate (Compound KC-37)

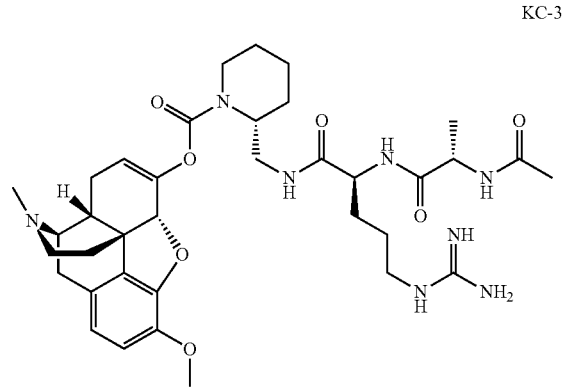

KC-37

Compound KC-37 was prepared following the method described in Example 10 to prepare N-(oxycodone-6-enol-carbonyl)-R-(piperidine-2-methylamine)-L-arginine-glycine-malonate (Compound KC-17), except using acetic anhydride instead of mono-tert-butyl malonate, using Boc-Ala-OH instead of Boc-Gly-OH and using hydrocodone instead of oxycodone. LC-MS [M+H] 695.8 ($C_{36}H_{52}N_8O_7$+H calc: 695.8).

Example 17

Synthesis of N-(hydrocodone-6-enol-carbonyl)-R-(piperidine-2-methylamine)-L-arginine-acetate (Compound KC-38)

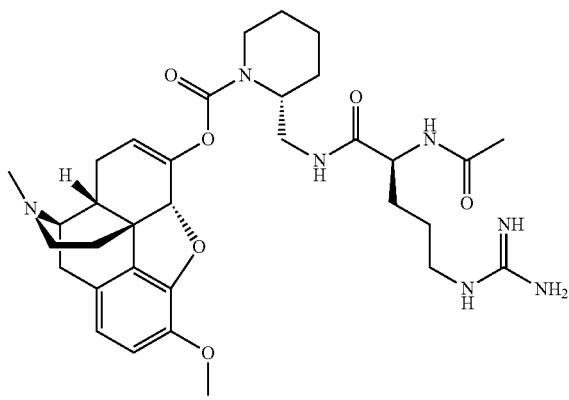

KC-38

Compound KC-38 was prepared following the method described in Example 10 to prepare N-(oxycodone-6-enol-carbonyl)-R-(piperidine-2-methylamine)-L-arginine-glycine-malonate (Compound KC-17), except not employing Boc-Gly-OH, using acetic anhydride instead of mono-tert-butyl malonate, and using hydrocodone instead of oxycodone. LC-MS [M+H] 638.5 ($C_{33}H_{47}N_7O_6$+H calc: 638.7).

Example 18

Synthesis of N-(hydrocodone-6-enol-carbonyl)-R-(piperidine-2-methylamine)-L-arginine-malonate (Compound KC-39)

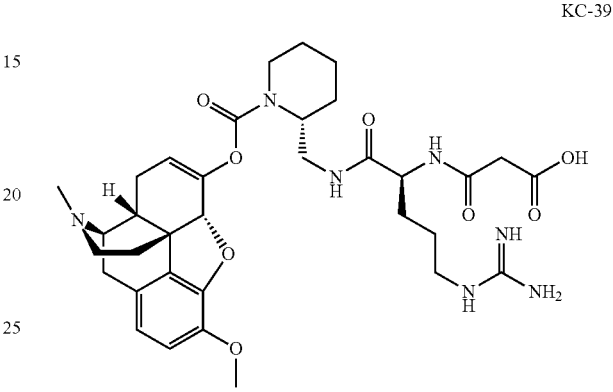

KC-39

Compound KC-39 was prepared following the method described in Example 10 to prepare N-(oxycodone-6-enol-carbonyl)-R-(piperidine-2-methylamine)-L-arginine-glycine-malonate (Compound KC-17), except not employing Boc-Gly-OH and using hydrocodone instead of oxycodone. LC-MS [M+H] 682.7 ($C_{34}H_{47}N_7O_8$+H calc: 682.8).

Example 19

Synthesis of N-(hydrocodone-6-enol-carbonyl)-N-[ethyl-(2-methylamino)piperazine-4-carboxylate]-L-arginine-glycine-acetate (Compound KC-42)

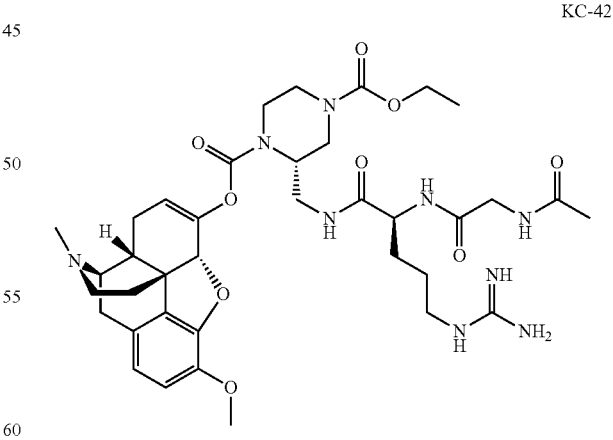

KC-42

Compound KC-42 was prepared following the method described in Example 10 to prepare N-(oxycodone-6-enol-carbonyl)-R-(piperidine-2-methylamine)-L-arginine-glycine-malonate (Compound KC-17), except employing ethyl 3-((tert-butoxycarbonylamino)methyl)piperazine-1-carboxylate (compound CC, see Example 20 for synthesis)

instead of piperidine-2-yl-methylcarbamic acid tert-butyl ester, using acetic anhydride instead of mono-tert-butyl malonate, and using hydrocodone instead of oxycodone. LC-MS [M+H] 768.7 ($C_{37}H_{53}N_9O_9$+H calc: 768.9).

Example 20

Synthesis of Ethyl 3-((tert-butoxycarbonylamino)methyl)piperazine-1-carboxylate (Compound CC)

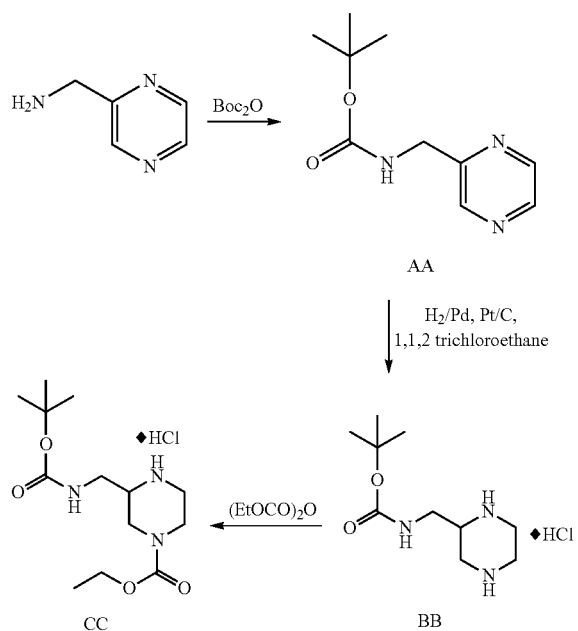

Synthesis of pyrazin-2-ylmethyl-carbamic acid tert-butyl ester (Compound AA)

To a solution of 2-aminomethyl-pyrazine (5.0 g, 45.87 mmol) in isopropanol (50 ml) was added di-tert-butyl-pyrocarbonate (12.0 g, 55.84 mmol); the mixture was stirred at ambient temperature for 2 h. Next, the solvent was evaporated and the residue was dissolved in DCM (30 ml), and subjected to silica gel purification (chloroform/methanol gradient 0→30% in 100 min.). Fractions containing desired product were combined and evaporated. Residue was dried under vacuum to provide Compound AA in quantitative yield (10.22 g, 99% purity) as amorphous solid. LC-MS: (m/z) observed (M+H$^+$) 210.5 ($C_{10}H_{15}N_3O_2$+H calc: 210.3).

Synthesis of piperazin-2-ylmethyl-carbamic acid tert-butyl ester (Compound BB)

Compound AA (10.22 g, 45.87 mmol) was dissolved in methanol (350 ml) followed by the addition of 1,1,2-trichloroethane (9.39 ml, 100.91 mmol), a suspension of palladium on activated carbon (10 wt. %, 488 mg) and platinum on activated carbon (10 wt. %, 897 mg) in water (20 ml). The mixture was subjected to hydrogen (70 psi) on a Parr apparatus at ambient temperature for 3 h. The reaction mixture was then filtered through the pad of celite and the filtrate was separated and evaporated. The residue was re-dissolved in isopropanol and re-evaporated. The resulting solid was dried under vacuum at ambient temperature overnight to provide the hydrochloric salt of Compound BB in quantitative yield (14.05 g, 99% purity) as off-white solid. LC-MS: (m/z) observed (M+H$^+$) 216.5 ($C_{10}H_{21}N_3O_2$+H calc: 216.3). The desired product was used directly without further purification.

Synthesis of Ethyl 3-((tert-butoxycarbonylamino)methyl)piperazine-1-carboxylate (Compound CC)

To a solution of Compound BB (7.00 g, 22.79 mmol) in EtOH (abs., 200 ml) was added diethyl pyrocarbonate (3.35 ml, 22.79 mmol) portionwise (330 μl×10) over 5 min. The reaction was monitored via LC-MS until complete consumption of the starting material. Upon completion, the formed precipitate was filtered and discarded. The filtrate was evaporated until dryness and was then dried under vacuum to provide hydrochloric salt of Compound CC in 94% yield (6.75 g, 99% purity) as an off-white solid. LC-MS: (m/z) observed (M+H$^+$) 288.2 ($C_{13}H_{25}N_3O_4$+H calc: 288.4).

Example 21

Synthesis of N-(hydrocodone-6-enol-carbonyl)-N-[ethyl-(2-methylamino)piperazine-4-carboxylate]-L-arginine-acetate (Compound KC-43)

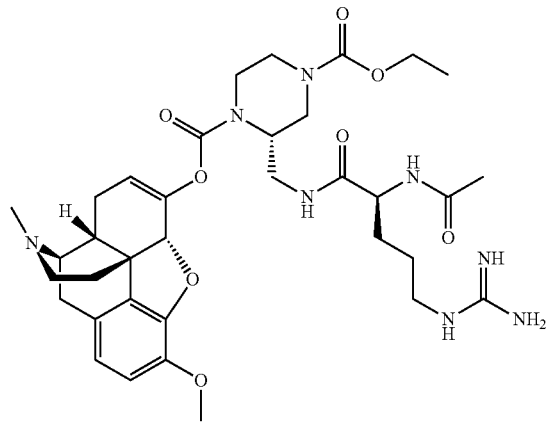

KC-43

Compound KC-43 was prepared following the method described in Example 10 to prepare N-(oxycodone-6-enol-carbonyl)-R-(piperidine-2-methylamine)-L-arginine-glycine-malonate (Compound KC-17), except using ethyl 3-((tert-butoxycarbonylamino)methyl)piperazine-1-carboxylate (Compound CC, see Example 20 for synthesis) instead of piperidine-2-yl-methylcarbamic acid tert-butyl ester, not employing Boc-Gly-OH, using acetic anhydride instead of mono-tert-butyl malonate, and using hydrocodone instead of oxycodone. LC-MS [M+H] 711.7 ($C_{35}H_{50}N_8O_8$+H calc: 711.8).

Example 22

Synthesis of N-(hydrocodone-6-enol-carbonyl)-N-[ethyl-(2-methylamino)piperazine-4-carboxylate]-L-arginine-malonate (Compound KC-44)

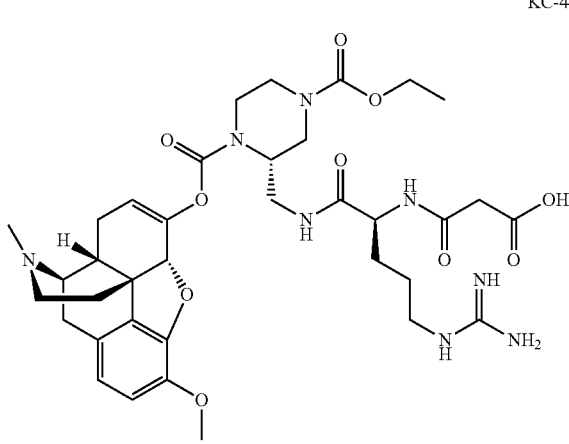

KC-44

Compound KC-44 was prepared following the method described in Example 10 to prepare N-(oxycodone-6-enol-carbonyl)-R-(piperidine-2-methylamine)-L-arginine-glycine-malonate (Compound KC-17), except using ethyl 3-((tert-butoxycarbonylamino)methyl)piperazine-1-carboxylate (compound CC, see Example 20 for synthesis) instead of piperidine-2-yl-methylcarbamic acid tert-butyl ester, not employing Boc-Gly-OH, and using hydrocodone instead of oxycodone. LC-MS [M+H] 755.5 ($C_{36}H_{50}N_8O_{10}$+H calc: 755.8).

Example 23

Synthesis of N-(hydrocodone-6-enol-carbonyl)-N-[ethyl-(2-methylamino)piperazine-4-carboxylate]-L-arginine-glycine-malonate (Compound KC-45)

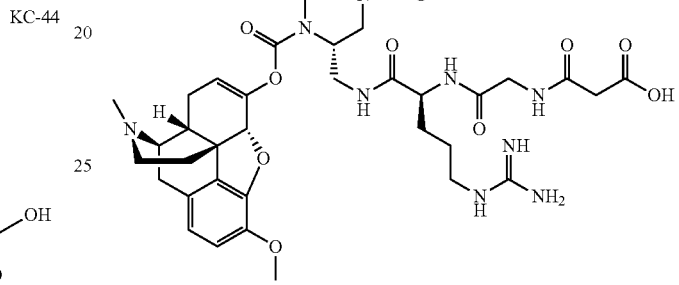

KC-45

Compound KC-45 was prepared following the method described in Example 10 to prepare N-(oxycodone-6-enol-carbonyl)-R-(piperidine-2-methylamine)-L-arginine-glycine-malonate (Compound KC-17), except using ethyl 3-((tert-butoxycarbonylamino)methyl)piperazine-1-carboxylate (compound CC, see Example 20 for synthesis) instead of piperidine-2-yl-methylcarbamic acid tert-butyl ester and using hydrocodone instead of oxycodone. LC-MS [M+H] 812.8 ($C_{38}H_{53}N_9O_{11}$+H calc: 812.9).

Example 24

Synthesis of N-(hydrocodone-6-enol-carbonyl)-(2-methylamino)piperidine-4-carboxylate]-L-arginine-glycine-acetate (Compound KC-40)

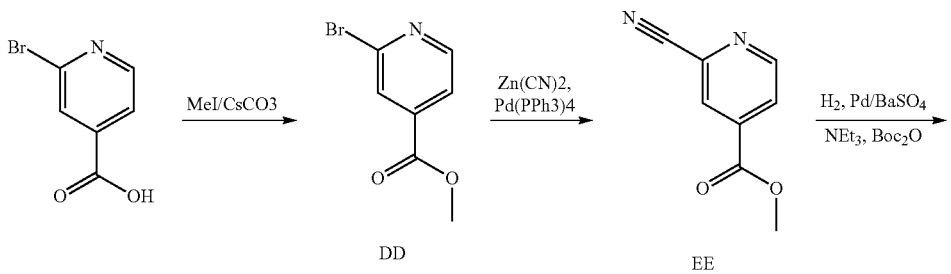

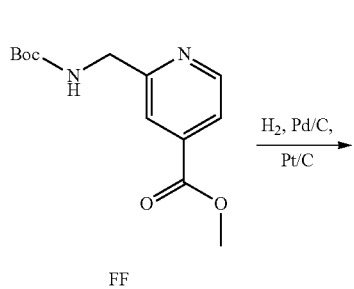
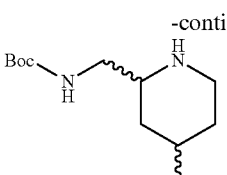
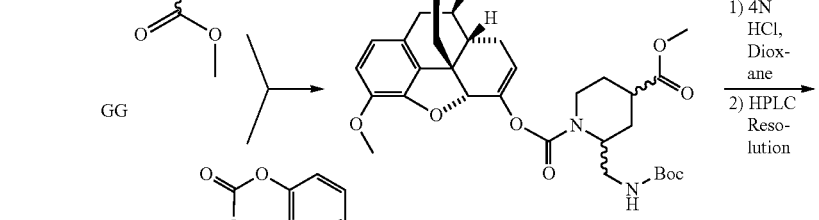
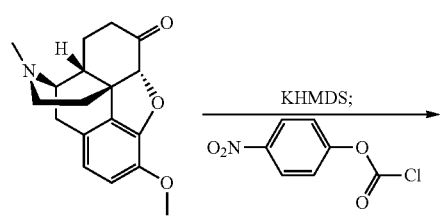
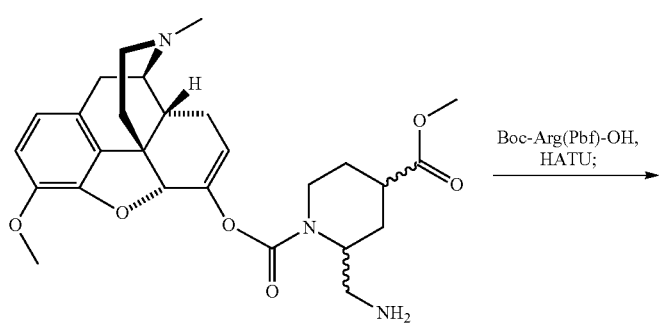
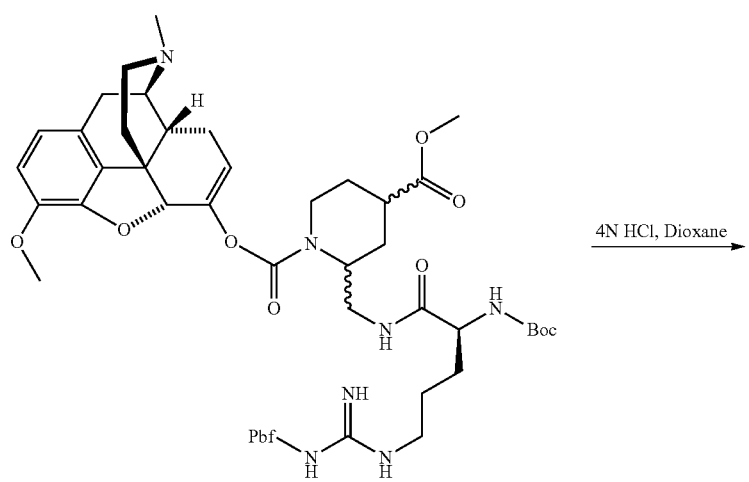

-continued
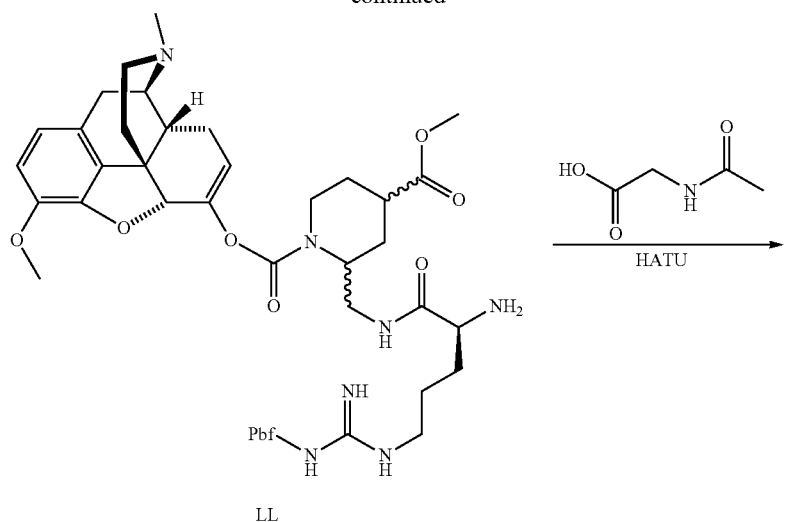
LL
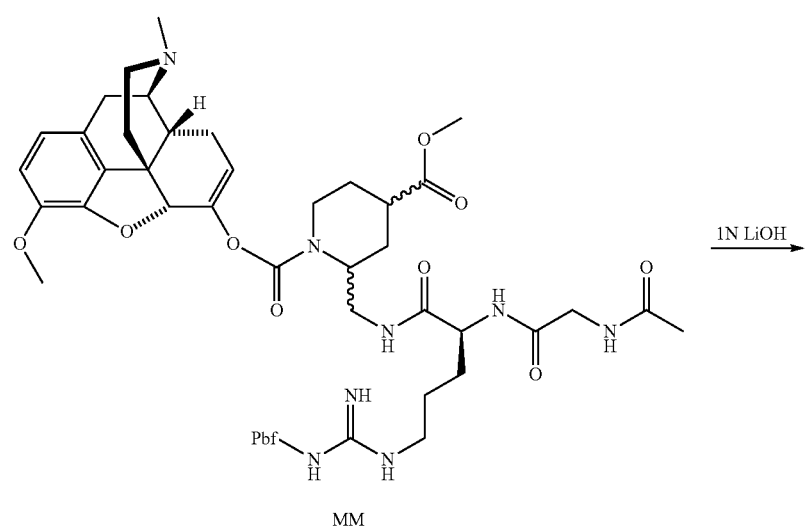
MM
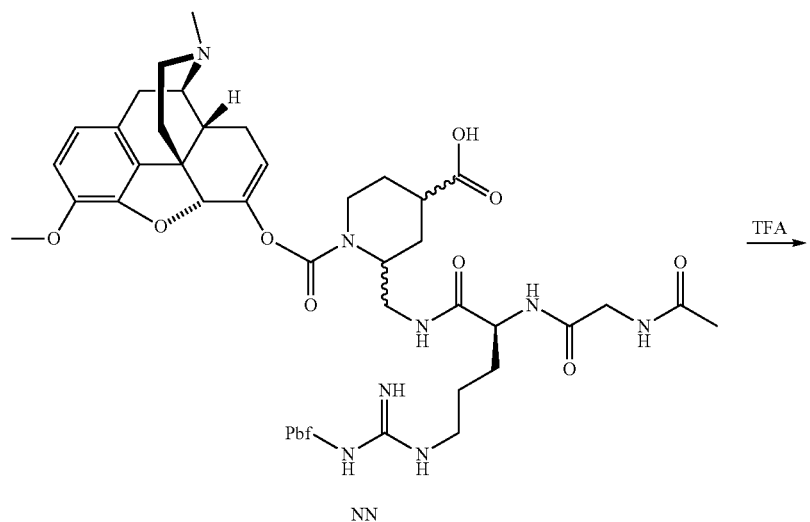
NN

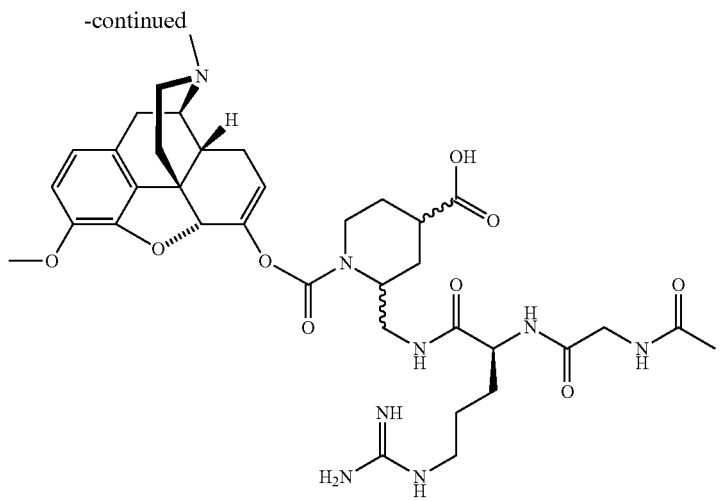

KC-40

Preparation of Compound DD

2-Bromo isonicotinic acid (20.2 g, 100 mmol) was dissolved in DMF (500 mL) at ambient temperature. $Cs_2CO_3$ (32.6 g, 100 mmol) was added in one portion, followed by MeI (6.3 mL, 100 mmol). The mixture was stirred at ambient temperature for 15 h, followed by the addition of water (500 mL). The mixture was extracted with EtOAc (500 mL). The organic layer was washed with water (500 mL), brine (500 mL) and then dried over $Na_2SO_4$. The organic layer was then filtrated and concentrated to give compound DD as a white solid in 80% yield (17.4 g, 80.5 mmol). LC-MS: [M+H] 217.0 ($C_7H_6BrNO_2$+H, calc: 216.1). Compound DD was used directly without further purification.

Preparation of Compound EE

Compound DD (17.4 g, 80.5 mmol) was dissolved in DMF (160 mL), followed by the addition of $Zn(CN)_2$ (5.7 g, 48.53 mmol) in one portion. The mixture was degassed using nitrogen and then $Pd(PPh_3)_4$ (4.7 g) was added. The mixture was degassed again and then heated in an oil bath (120° C.). After 2.5 h, the reaction was cooled to ambient temperature and water (200 mL) was added. The mixture was stirred for 30 min and then filtered through a frit. The solid collected was washed with water (2×100 mL) and then dried under vacuum to give compound EE in 84% yield (11.0 g, 67.9 mmol). LC-MS: [M+H] 163.2 ($C_8H_6N_2O_2$+H, calc: 162.1). Compound EE was used directly without further purification.

Preparation of Compound FF

Compound EE (20.0 g, 123.4 mmol) was dissolved in IPA (500 mL). $Boc_2O$ (37.7 g, 172.8 mmol), Pd/5% on barium sulfate (6.0 g) and $NEt_3$ (35 mL, 246.9 mmol) were added to the reaction mixture. The mixture was hydrogenated at 55 psi for 4 h on a Parr hydrogenator. The mixture was then filtered through a celite pad and then the celite pad was washed with MeOH (3×80 mL). The combined filtrate was then concentrated and the residue was partitioned between EtOAc (300 mL) and water (100 mL). The organic layer was washed with 10% citric acid (50 mL) and brine (50 mL), followed by drying over $Na_2SO_4$. Next the mixture was filtered and concentrated to afford compound FF in 86% yield (28.0 g, 106.8 mmol). LC-MS: [M+H] 267.4 ($C_{13}H_{18}N_2O_4$+H, calc: 266.5). Compound FF was used directly without further purification.

Preparation of Compound GG

To a solution of compound FF (1.50 g, 5.64 mmol) in MeOH (25 mL) was carefully added, under nitrogen, 10% Pd/C (250 mg), 10% Pt/C (200 mg) and 1,1,2-trichloroethane (630 mL, 6.8 mmol, 1.2 eq). The reaction mixture was stirred at 65 psi overnight. Upon completion, the reaction mixture was filtered through a Celite-padded glass frit and washed with MeOH (3×20 mL). The filtrate was concentrated under vacuum to the volume ~10 mL and diethyl ether (100 mL) was added. The resulting fine white precipitate was filtered, washed with ether (2×50 mL) and dried under high vacuum. The resulting HCl salt was dissolved with sonication in water (30 mL) and aqueous 1 N NaOH solution (10 mL) was added. The reaction mixture was extracted with DCM (3×25 mL). The organic phase was dried over anhydrous $Na_2SO_4$, filtered, the solvent was evaporated under vacuum and the oily product was dried under high vacuum overnight. This afforded Compound GG (1.08 g, 72.5%). LC-MS: [M+H] 267.2 ($C_{13}H_{18}N_2O_4$+H, calc: 267.1). Retention time [Chromolith SpeedRod RP-18e C18 column (4.6×50 mm); flow rate: 1.5 mL/min; mobile phase A: 0.1% TFA/water; mobile phase B 0.1% TFA/ACN; gradient elution from 5% B to 100% B over 9.6 min): 2.79 min.

Preparation of Compound HH

A solution of hydrocodone-free base (1.90 g, 6.35 mmol) in THF (50 mL) was cooled to −78° C. and then 0.5 M toluene solution of KHMDS (12.7 mL, 6.35 mmol) was added dropwise over 5 min under nitrogen. The reaction mixture was stirred for 30 min, and then added to a solution of 4-nitrophenyl chloroformate (1.35 g, 6.35 mmol) in THF (25 mL) dropwise over 5 min under nitrogen and cooling with dry ice/acetone. Upon completion, 2 M HCl in diethyl ether (25 mL) and ether (100 mL) was added dropwise to the reaction mixture to produce a fine white precipitate. The precipitate was filtered on a glass frit and washed with ether (3×50 mL). The solid was dried under high vacuum overnight, then dissolved in 5% aq $KH_2PO_4$ solution (200 mL) and extracted with DCM (2×50 mL). The organic phase was dried over $Na_2SO_4$ (anh.), filtered, and the solvent was concentrated under vacuum to the volume ~10 mL. To the mixture was added 2 M solution of HCl in diethyl ether (20 mL) and ether (100 mL). The resulting fine white precipitate was filtered off, washed with ether (2×50 mL) and dried under high vacuum to afford compound HH in 66.1% yield (2.1 g, 4.20 mmol). LC-MS [M+H]: 465.3 ($C_{25}H_{24}N_2O_7$+H, calc: 464.2). Retention time [Chromolith SpeedRod RP-18e C18 column (4.6×50 mm); flow rate: 1.5 mL/min; mobile phase A: 0.1% TFA/water;

mobile phase B 0.1% TFA/ACN; gradient elution from 5% B to 100% B over 9.6 min, detection 254 nm]: 4.94 min.

Preparation of Compound II

Compound GG (6.0 g, 22.0 mmol) and compound HH (12.5 g, 24.0 mmol) were dissolved in DMF (40 mL) and DIEA (15.3 mL, 88 mmol) was added. The reaction mixture was stirred at 40° C. for approximately 4 h, until all the starting amine GG was consumed. Upon reaction completion, the DMF was evaporated and the resulting oily product was dissolved in DCM (700 mL). The mixture was then washed with 5% sodium phosphate (2×700 mL), 0.1 N aq. HCl (500 mL) and brine (750 mL). The organic phase was dried over $Na_2SO_4$ (anhydrous), filtered and the solvent was evaporated. The oily product was dried in high vacuum overnight to afford compound II in 91.2% yield. (12.2 g, 20.1) LC-MS: [M+H] 578.6 ($C_{32}H_{43}N_3O_8$+H, calc: 578.7). Retention time [Chromolith SpeedRod RP-18e C18 column (4.6×50 mm); flow rate: 1.5 mL/min; mobile phase A: 0.1% TFA/water; mobile phase B 0.1% TFA/ACN; gradient elution from 5% B to 100% B over 9.6 min, detection 254 nm): as 4 isomers, 5.90 min ($A_1$), 5.94 min ($A_2$), 6.47 min (B), 6.58 min (C).

Preparation of Compound JJ (Major Isomers)

A solution of compound II (12.2 g, 21.2 mmol) in DCM (100 mL) was treated with 4 M solution of hydrogen chloride in 1,4-dioxane (50 mL). After 1 h, solvent was removed under vacuum until about ~50 mL remained. Diethyl ether (~500 mL) was added to the reaction mixture, which produced a fine white precipitate. The precipitate was filtered off, washed with ether (3×150 mL) and dried under vacuum to give the HCl salt of compound JJ as a fine white solid. The solid was dissolved in water (70 mL) and acetic acid (10 mL) and the solution was subjected to HPLC purification, 5 runs: [Nanosyn-Pack Microsorb (100-10) C-18 column (50×300 mm); flow rate: 100 mL/min; injection volume: 4×5 mL; mobile phase A: 100% water, 0.1% TFA; mobile phase B: 100% acetonitrile, 0.1% TFA; gradient elution from 5% to 30% B in 60 min; detection at UV 254 nm. Fractions containing the major isomers were combined and concentrated under vacuum. The resulting oily residue was co-evaporated with isopropanol (3×100 mL). The oily product was treated with 2 M HCl in ether (20 mL) and ether (400 mL) to produce a fine white precipitate. The precipitate was filtered off, washed with ether (2×50 mL) and dried under high vacuum to afford the two major isomer of compound JJ in 69.2% yield (8.1 g, 14.7 mmol). LC-MS, [M+H] 498.4 ($C_{27}H_{35}N_3O_6$+H, calc: 498.6). Retention time [Chromolith SpeedRod RP-18e C18 column (4.6×50 mm); flow rate: 1.5 mL/min; mobile phase A: 0.1% TFA/water; mobile phase B 0.1% TFA/ACN; gradient elution from 5% B to 100% B over 9.6 min, detection 254 nm]: as 2 isomers: 2.81 min (major-1), 2.96 min (major-2).

Preparation of Compound KK (Major Isomers)

To a solution of Boc-Arg(Pbf)-OH (18.96 g, 36.0 mmol), Compound JJ (19.6 g, 34.3 mmol) and HATU (13.3 g, 37.7 mmol) in DMF (200 mL) at 5° C. was added DIEA (24.0 mL, 137 mmol) dropwise over 5 min. The temperature of the reaction mixture was raised to ambient temperature and stirring was continued for an additional hour. Upon reaction completion, DMF was removed under vacuum and the reaction mixture was then diluted with DCM (300 mL), washed with 2% aq. $H_2SO_4$ (500 mL), then with 5% sodium phosphate (500 mL) and brine (750 mL). The organic phase was dried over $Na_2SO_4$ (anh.), filtered, and the solvent was evaporated under vacuum. The oily product was dried under high vacuum overnight to afford compound KK as a foamy solid in 97.2% yield. (34.2 g, 33.3 mmol) LC-MS: [M+H] 1007.1 ($C_{51}H_{71}N_7O_{12}$S+H, calc: 1007.2). Retention time [Chromolith SpeedRod RP-18e C18 column (4.6×50 mm); flow rate: 1.5 mL/min; mobile phase A: 0.1% TFA/water; mobile phase B 0.1% TFA/ACN; gradient elution from 5% B to 100% B over 9.6 min, detection 254 nm): 5.43 min.

Preparation of Compound LL (Major Isomers)

To a solution of compound KK (34.3 g, 34.0 mmol) in DCM (100 mL) was added 4.0 M solution of hydrogen chloride in 1,4-dioxane (150 mL). After 1 h, the solvent was evaporated under vacuum to about 50 mL and to the reaction mixture was added diethyl ether (500 mL) to produce a fine white precipitate. The precipitate was filtered off, washed with ether (3×150 mL) and dried under vacuum to give the HCl salt of compound LL in 82.7% yield (23.9 g, 28.1 mmol) as a fine white solid. LC-MS, [M+H] 906.6 ($C_{46}H_{63}N_7O_{10}$S+H, calc: 906.1). Retention time [Chromolith SpeedRod RP-18e C18 column (4.6×50 mm); flow rate: 1.5 mL/min; mobile phase A: 0.1% TFA/water; mobile phase B 0.1% TFA/ACN; gradient elution from 5% B to 100% B over 9.6 min, detection 254 nm]: 4.46 min.

Preparation of Compound MM (Major Isomers)

To a solution of HO-Gly-NAc (3.0 g, 25.5 mmol), Compound LL (23.4 g, 24.3 mmol, 1 eq) and HATU (9.7 g, 25.5 mmol) in DMF (100 mL) at 5° C. was added DIEA (17 mL, 100 mmol) dropwise over 5 min. The temperature of the reaction mixture was raised to ambient temperature and stirring was continued for an additional hour. Upon reaction completion, DMF was removed in high vacuum, and the reaction mixture was diluted with DCM (300 mL), washed with 2% aq. $H_2SO_4$ (500 mL), then with 5% sodium phosphate (500 mL) and brine (750 mL). The organic phase was dried over $Na_2SO_4$ (anh.), filtered and the solvent was evaporated. The oily product was dried under high vacuum overnight to afford compound MM in 93.8% yield (22.9 g, 23.9 mmol) as a yellow oil. LC-MS: [M+H] 1005.7 ($C_{50}H_{68}N_8O_{12}$S+H, calc: 1005.2). Retention time [Chromolith SpeedRod RP-18e C18 column (4.6×50 mm); flow rate: 1.5 mL/min; mobile phase A: 0.1% TFA/water; mobile phase B 0.1% TFA/ACN; gradient elution from 5% B to 100% B over 9.6 min, detection 254 nm): 4.75 min.

Preparation of Compound NN (Major Isomers)

To a solution of Compound MM (22.8 g, 22.9 mmol) in methanol (120 mL) at 5° C. was added aqueous solution of LiOH (1.6 g, 70 mmol) in water (50 mL). The temperature of the reaction mixture was raised to ambient temperature and stirring was continued for an additional 2 h. Upon the reaction completion, the reaction mixture was neutralized with acetic acid to pH ~4.0 and the methanol was evaporated under vacuum. The resulted solution was subjected to prep HPLC purification. [Nanosyn-Pack Microsorb (100-10) C-18 column (50×300 mm); flow rate: 100 mL/min; injection volume: 4×5 mL; mobile phase A: 100% water, 0.1% TFA; mobile phase B: 100% acetonitrile, 0.1% TFA; gradient elution from 5% to 30% B in 20 min; isocratic 30% B in 15 min, 30% to 65% in 25 min; detection at UV 254 nm. Fractions containing the pure product were combined and concentrated under vacuum. The resulting oily residue was co-evaporated with toluene (3×100 mL). The oily product was dried under high vacuum to give compound NN in 54.9% yield (12.4 g, 12.6 mmol). LC-MS, [M+H] 991.7 ($C_{49}H_{66}N_8O_{12}$S+H, calc: 991.5). Retention time [Chromolith SpeedRod RP-18e C18 column (4.6×50 mm); flow rate: 1.5 mL/min; mobile phase A: 0.1% TFA/water; mobile phase B 0.1% TFA/ACN; gradient elution from 5% B to 100% B over 9.6 min, detection 254 nm]: 4.59 min.

Preparation of N-(hydrocodone-6-enol-carbonyl)-[(2-methylamino)piperidine-4-carboxylate]-L-arginine-glycine-acetate (Compound KC-40, major isomers)

Compound NN (7.9 g, 7.9 mmol) was dissolved in TFA (50 mL) and was stirred for 1 h. Next the TFA was evaporated under vacuum and the resulting oily residue was dissolved in acetic acid/DCM (10 mL/10 mL) and treated with 2 M HCl/ether. The formed white precipitate was filtered off and washed with ether (2×50 mL). The solid was dissolved in water (60 mL) and subjected to prep HPLC purification. [Nanosyn-Pack Microsorb (100-10) C-18 column (50×300 mm); flow rate: 100 mL/min; injection volume: 4×5 mL; mobile phase A: 100% water, 0.1% TFA; mobile phase B: 100% acetonitrile, 0.1% TFA; gradient elution from 5% to 30% B in 60 min; detection at UV 210 nm. Fractions containing the desired product were combined and concentrated under vacuum. The resulting oily residue was co-evaporated with toluene (3×100 mL). The oily product was dried under high vacuum to give a solid. The resulting solid was dissolved in 0.1 M HCl (50 mL) and lyophilized to give Compound KC-40 in 61.9% yield (3.2 g, 4.9 mmol). LC-MS, [M+H] 739.7 ($C_{36}H_{50}N_8O_9$+H, calc: 739.4). Retention time [Chromolith SpeedRod RP-18e C18 column (4.6×50 mm); flow rate: 1.5 mL/min; mobile phase A: 0.1% TFA/water; mobile phase B 0.1% TFA/ACN; gradient elution from 5% B to 100% B over 9.6 min, detection 210 nm]: 3.11 min.

Example 25

N-(hydrocodone-6-enol-carbonyl)-[(2-methylamino)piperidine-3-carboxylate]-L-arginine-glycine-acetate (Compound KC-32)

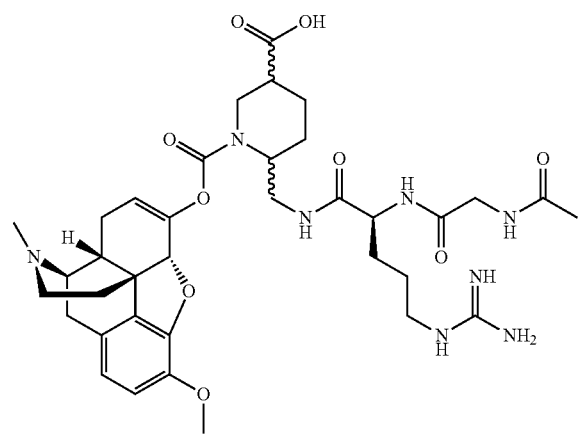

KC-32

Compound KC-32 was prepared following the method described in Example 24 to prepare N-(hydrocodone-6-enol-carbonyl)-(2-methylamino)piperidine-3-carboxylate]-L-arginine-glycine-acetate (Compound KC-40), except using methyl 6-bromonicotinate instead of methyl 2-bromoisomicothinate. LC-MS [M+H] 739.9 ($C_{36}H_{50}N_8O_9$+H calc: 739.8).

Example 26

N-(hydrocodone-6-enol-carbonyl)-[(2-methylamino)-methyl piperidine-4-carboxylate]-L-arginine-glycine-acetate (Compound KC-41)

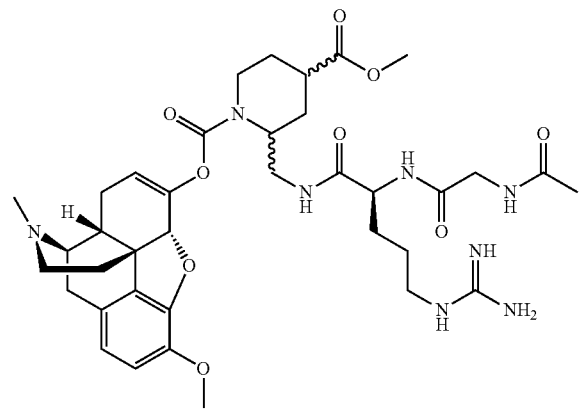

KC-41

Compound KC-41 was prepared following the method described in Example 24 to prepare N-(hydrocodone-6-enol-carbonyl)-(2-methylamino)piperidine-3-carboxylate]-L-arginine-glycine-acetate (Compound KC-40), except not employing LiOH (for methyl ester hydrolysis). LC-MS [M+H] 753.7 ($C_{37}H_{52}N_8O_9$+H calc: 753.9).

Example 27

N-(hydrocodone-6-enol-carbonyl)-[(2-methylamino)-N,N-dimethyl piperidine-4-carboxamide]-L-arginine-glycine-acetate (Compound KC-46)

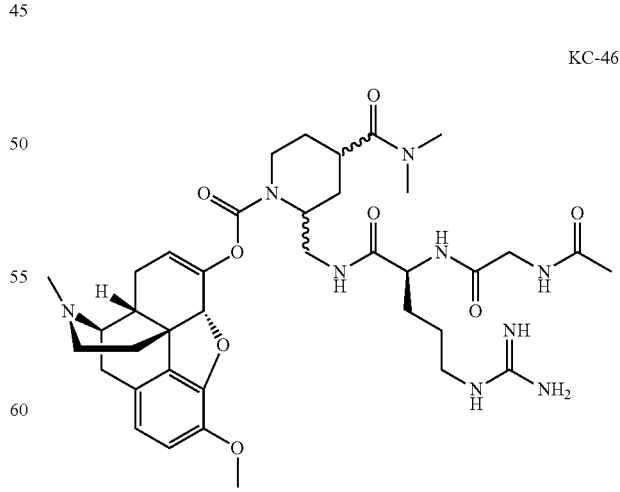

KC-46

Compound KC-46 was prepared following the method described in Example 24 to prepare N-(hydrocodone-6-enol-carbonyl)-(2-methylamino)piperidine-3-carboxylate]-L- arginine-glycine-acetate (Compound KC-40), except conducting a amide bond coupling of KC-40 with dimethyl amine using standard HATU coupling procedures (see synthesis of Compound O for a representative example). LC-MS [M+H] 766.6 ($C_{38}H_{55}N_9O_8$+H calc: 766.9).

Example 28

N-(hydrocodone-6-enol-carbonyl)-[(2-methylamino)-piperidine-4-carboxylate]-L-arginine-glycine-malonate (Compound KC-47)

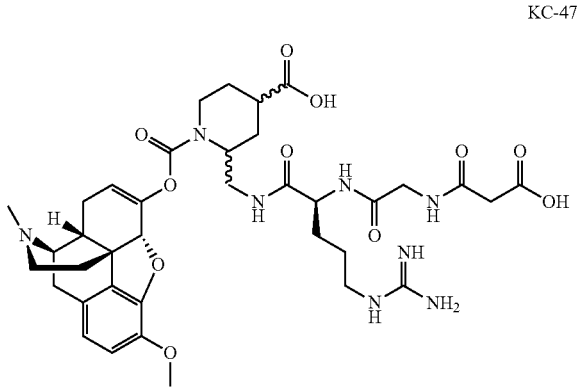

Compound KC-47 was prepared following the method described in Example 24 to prepare N-(hydrocodone-6-enol-carbonyl)-(2-methylamino)piperidine-3-carboxylate]-L-arginine-glycine-acetate (Compound KC-40), except employing Boc-Gly-OH instead of NAc-Gly-OH, followed by Boc removal and coupling with mono-tert-butyl malonate (See synthetic procedures for the synthesis of compound KC-13 for representative examples of these synthetic transformations) LC-MS [M+H] 783.7 ($C_{37}H_{50}N_8O_{11}$+H calc: 783.8).

Example 29

N-(hydrocodone-6-enol-carbonyl)-[(2-methylamino)-piperidine-4-carboxylate]-L-arginine-malonate (Compound KC-48)

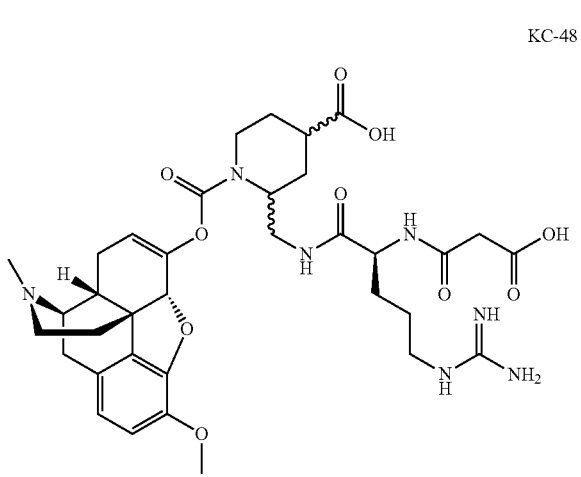

Compound KC-48 was prepared following the method described in Example 24 to prepare N-(hydrocodone-6-enol-carbonyl)-(2-methylamino)piperidine-3-carboxylate]-L-arginine-glycine-acetate (Compound KC-40), except employing mono-tert-butyl malonate instead of NAc-Gly-OH. LC-MS [M+H] 726.7 ($C_{35}H_{47}N_7O_{10}$+H calc: 726.8).

Example 30

N-(hydrocodone-6-enol-carbonyl)-[(2-methylamino)-piperidine-4-carboxylate]-L-arginine-acetate (Compound KC-49)

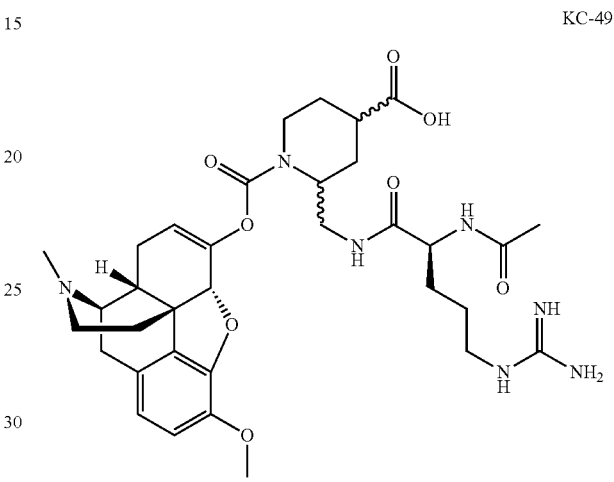

Compound KC-49 was prepared following the method described in Example 24 to prepare N-(hydrocodone-6-enol-carbonyl)-(2-methylamino)piperidine-3-carboxylate]-L-arginine-glycine-acetate (Compound KC-40), except employing acetic anhydride instead of NAc-Gly-OH (see preparation of Compound S for representative synthetic example of the use of acetic anhydride). LC-MS [M+H] 682.6 ($C_{37}H_{47}N_7O_8$+H calc: 682.8).

Example 31

N-(hydrocodone-6-enol-carbonyl)-[(2-methylamino)-piperidine-4-carboxylate]-L-lysine-glycine-acetate (Compound KC-50)

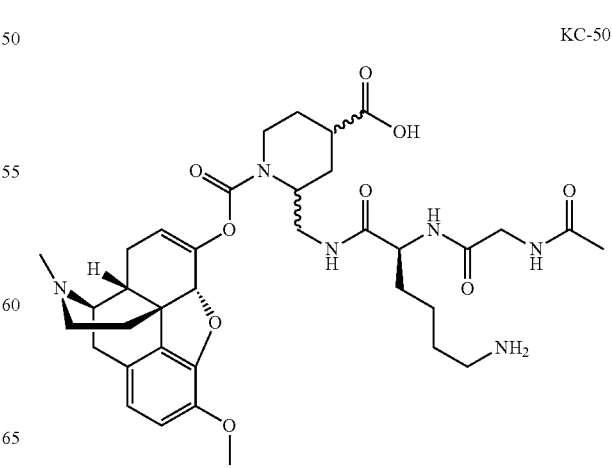

Compound KC-50 was prepared following the method described in Example 24 to prepare N-(hydrocodone-6-enol-carbonyl)-(2-methylamino)piperidine-3-carboxylate]-L-arginine-glycine-acetate (Compound KC-40), except employing Fmoc-Lys(Boc)-OH instead of Boc-Arg(Pbf)-OH (see Greene and Wuts for examples of Fmoc removal). LC-MS [M+H] 711.7 ($C_{36}H_{50}N_6O_9$+H calc: 711.8).

Example 32

N-(hydrocodone-6-enol-carbonyl)-[(2-methylamino)-piperidine-4-carboxylate]-L-lysine-acetate (Compound KC-51)

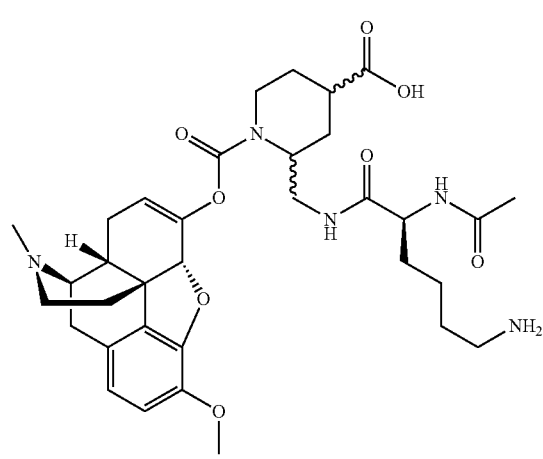

KC-51

Compound KC-51 was prepared following the method described in Example 24 to prepare N-(hydrocodone-6-enol-carbonyl)-(2-methylamino)piperidine-3-carboxylate]-L-arginine-glycine-acetate (Compound KC-40), except employing Fmoc-Lys(Boc)-OH instead of Boc-Arg(Pbf)-OH (see Greene and Wuts for examples of Fmoc and also see Compound S for representative synthetic example of the use of acetic anhydride). LC-MS [M+H] 711.7 ($C_{34}H_{47}N_5O_8$+H calc: 711.8).

Example 33

N-(hydrocodone-6-enol-carbonyl)-[(2-methylamino)-piperidine-4-carboxylate]-L-lysine-malonate (Compound KC-52)

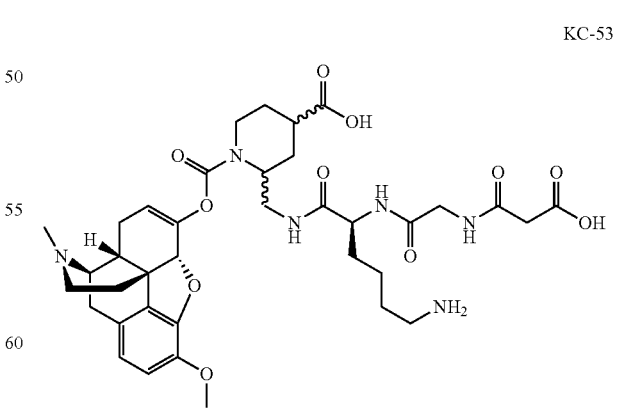

KC-52

Compound KC-52 was prepared following the method described in Example 24 to prepare N-(hydrocodone-6-enol-carbonyl)-(2-methylamino)piperidine-3-carboxylate]-L-arginine-glycine-acetate (Compound KC-40), except employing Fmoc-Lys(Boc)-OH instead of Boc-Arg(Pbf)-OH (see Greene and Wuts for examples of Fmoc removal) and employing mono-tert-butyl malonate instead of NAc-Gly-OH. LC-MS [M+H] 698.5 ($C_{35}H_{47}N_5O_{10}$+H calc: 698.8).

Example 34

N-(hydrocodone-6-enol-carbonyl)-[(2-methylamino)-piperidine-4-carboxylate]-L-lysine-glycine-malonate (Compound KC-53)

KC-53

Compound KC-53 was prepared following the method described in Example 24 to prepare N-(hydrocodone-6-enol-carbonyl)-(2-methylamino)piperidine-3-carboxylate]-L- arginine-glycine-acetate (Compound KC-40), except employing Fmoc-Lys(Boc)-OH instead of Boc-Arg(Pbf)-OH (see Greene and Wuts for examples of Fmoc removal), Boc-Gly-OH instead of NAc-Gly-OH, followed by Boc removal and coupling with mono-tert-butyl malonate (See synthetic procedures for the synthesis of compound KC-13 for representative examples of these synthetic transformations). LC-MS [M+H] 755.5 ($C_{37}H_{50}N_6O_{11}$+H calc: 755.8.8).

Example 35

N-(oxycodone-6-enol-carbonyl)-[(2-methylamino)-piperidine-4-carboxylate]-L-arginine-glycine-acetate (Compound KC-55)

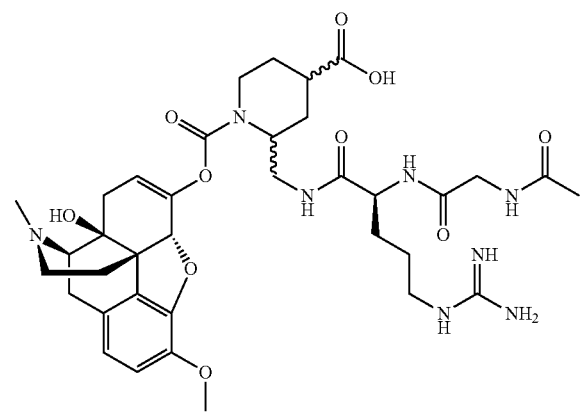

Compound KC-55 was prepared following the method described in Example 24 to prepare N-(hydrocodone-6-enol-carbonyl)-(2-methylamino)piperidine-3-carboxylate]-L-arginine-glycine-acetate (Compound KC-40), except employing oxycodone instead of hydrocodone. LC-MS [M+H] 755.6 ($C_{36}H_{50}N_8O_{10}$+H calc: 755.8).

Example 36

Pharmacokinetics Following PO Administration of Ketone-Modified Opioid Prodrugs to Rats This Example demonstrates the release of opioid into plasma when ketone-modified opioid prodrugs of the embodiments were administered orally (PO) to rats.

Saline solutions of Compound KC-9, Compound KC-11, Compound KC-12, Compound KC-13, Compound KC-14, Compound KC-15, Compound KC-16, Compound KC-17 (each of which can be prepared as described in the examples herein) or oxycodone were dosed as indicated in Table 1 via oral gavage into jugular vein-cannulated male Sprague Dawley rats (4 per group, except for the Compound KC-16 group which consisted of 3 rats) that had been fasted for 16-18 h prior to oral dosing. At specified time points, blood samples were drawn, harvested for plasma via centrifugation at 5,400 rpm at 4° C. for 5 min, and 100 microliters (A) plasma transferred from each sample into a fresh tube containing 2 μl of 50% formic acid. The tubes were vortexed for 5-10 seconds, immediately placed in dry ice, and then stored in a −80° C. freezer until analysis by HPLC/MS.

Figure 4:
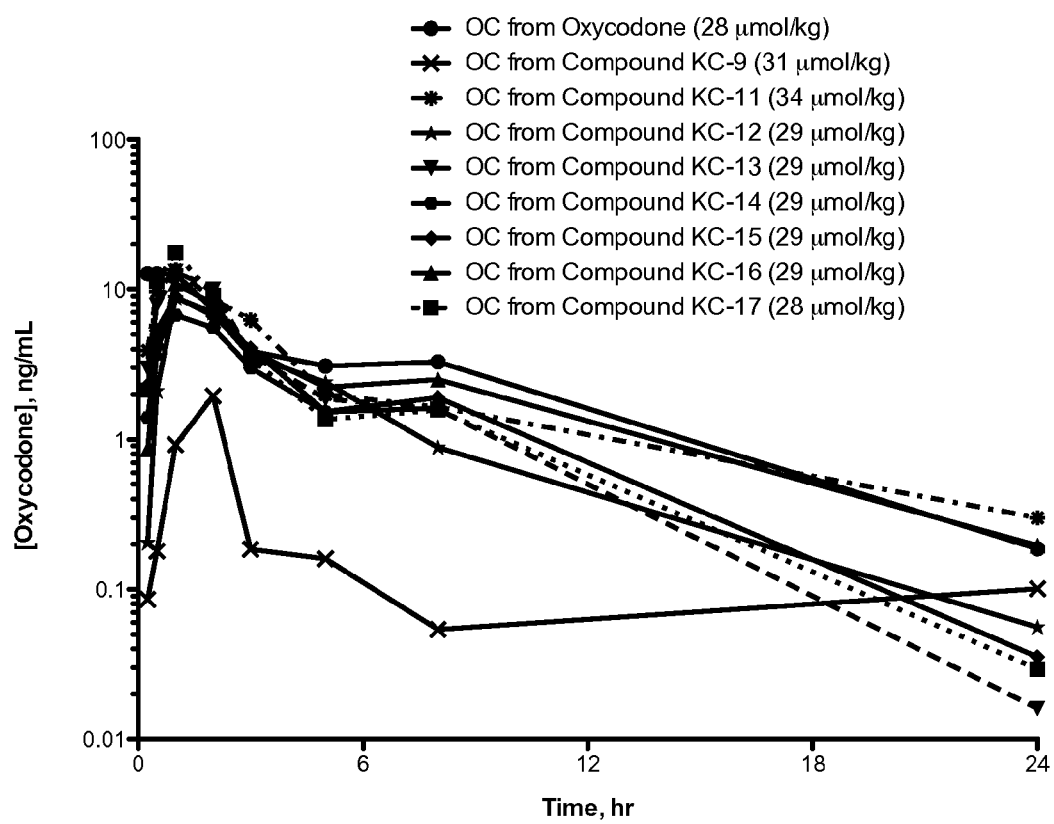
FIG. 4 compares mean plasma concentrations over time of oxycodone release following PO administration to rats of several ketone-modified active agent prodrugs of the embodiments.

Table 1 and FIG. 4 provide oxycodone exposure results for rats administered the indicated compounds. Results in Table 1 are reported, for each group of rats, as (a) maximum plasma concentration value (Cmax) of oxycodone (OC) (average±standard deviation), (b) time after administration of compound to reach maximum oxycodone concentration value (Tmax) (average±standard deviation) and (c) area under the curve value (AUC) from 0 to 24 h (average±standard deviation).

TABLE 1

Cmax, Tmax and AUC values of oxycodone in rat plasma

| Compound | Dose, mg/kg | Dose μmol/kg | OC Cmax ± sd, ng/mL | Tmax ± sd, h | AUC ± sd, ng * h/mL |
|---|---|---|---|---|---|
| KC-9 | 16 | 31 | 2.35 ± 2.3* | 1.50 ± 0.58 | 4.63 ± 3.1 |
| KC-11 | 18 | 34 | 13.6 ± 3.0* | 1.00 ± 0.0 | 57.0 ± 9.0 |
| KC-12 | 22 | 29 | 9.99 ± 6.3* | 1.25 ± 0.50 | 31.4 ± 13 |
| KC-13 | 23 | 29 | 13.5 ± 3.5^ | 1.50 ± 0.58 | 40.6 ± 17 |
| KC-14 | 23 | 29 | 7.06 ± 2.2* | 1.25 ± 0.50 | 23.3 ± 4.9 |
| KC-15 | 24 | 29 | 9.02 ± 2.5* | 1.50 ± 1.0 | 31.8 ± 9.2 |
| KC-16 | 24 | 29 | 12.4 ± 4.2* | 1.67 ± 0.58 | 54.7 ± 6.1 |
| KC-17 | 23 | 28 | 17.7 ± 3.8^ | 1.00 ± 0.0 | 42.2 ± 9.7 |
| Oxycodone | 10 | 28 | 14.7 ± 6.5# | 0.625 ± 0.43 | 71.2 ± 5.3 |

Lower limit of quantitation was 0.0250 ng/mL
^Lower limit of quantitation was 0.0500 ng/mL
*Lower limit of quantitation was 0.100 ng/mL FIG. 4 compares mean plasma concentrations over time of oxycodone release following PO administration of oxycodone prodrugs of the embodiments to rats.

The results in Table 1 and FIG. 4 indicate that oral administration of each of the tested prodrugs to rats leads to release of oxycodone. Compound KC-11, Compound KC-12, Compound KC-13, Compound KC-14, Compound KC-15, Compound KC-16, and Compound KC-17 effect release of significantly more oxycodone than does Compound KC-9.

Example 37

Pharmacokinetics of Ketone-Modified Opioid Prodrugs Following PO Administration to Dogs This Example demonstrates the release of oxycodone into plasma when ketone-modified oxycodone prodrugs of the embodiments were administered orally (PO) to dogs. This Example also compares such release to that of Compound KC-3, an oxycodone prodrug that, unlike the prodrugs of these embodiments, lacks a heterocyclic ring in its cyclizable spacer leaving group. Also compared are oxycodone plasma levels in dogs administered oxycodone or OxyContin® tablets.

Purebred male young adult/adult beagles were fasted overnight. Solutions in water of Compound KC-3, Compound KC-12, Compound KC-13, Compound KC-14, Compound KC-15, Compound KC-16, Compound KC-17 (each of which can be prepared as described in the examples herein) or 2 mg/kg oxycodone (Johnson Matthey Pharmaceutical Materials, West Deptford, N.J., USA) were administered via oral gavage to the dogs (4 per group), as indicated in Table 2. One additional group of 4 dogs was administered one 20-mg Oxy-Contin® (oxycodone HCl) Controlled-Release C-II Tablet (NDC 59011-420-10, Purdue Pharma, Stamford, Conn., USA). The tablet dose was followed by approximately 5 mL of water to facilitate swallowing. The doses were selected to provide approximately equimole amounts. Blood was collected from each animal via a jugular vein at various times over a 24-h period, centrifuged, and 0.8 mL plasma transferred to a fresh tube containing 8 μL formic acid; samples were vortexed, then immediately placed in dry ice, and stored in a −80° C. freezer until analysis by HPLC/MS.

Figure 5A:
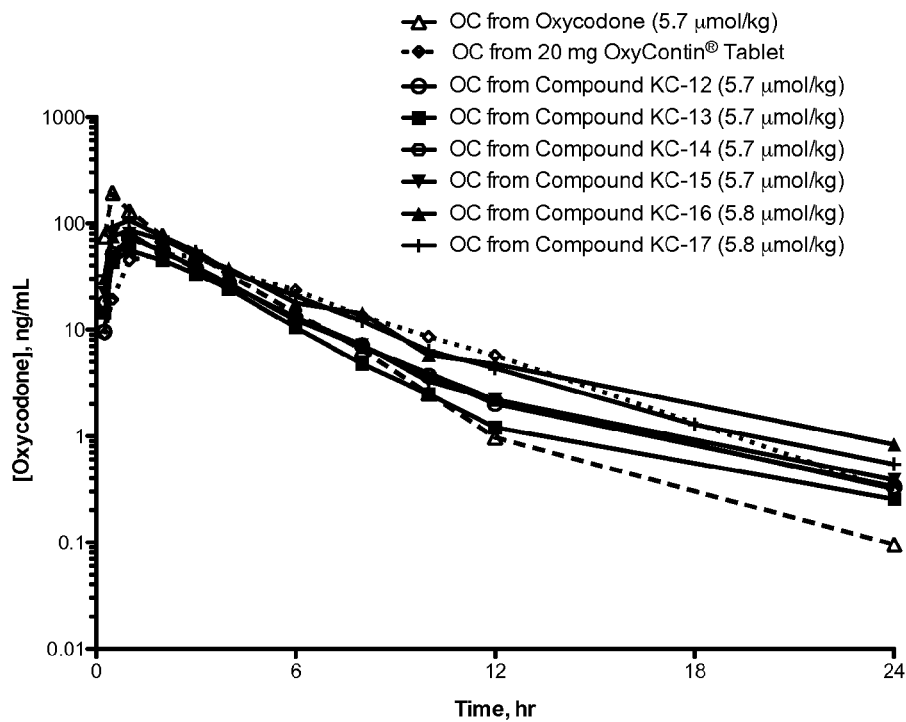
FIG. 5A compares mean plasma concentrations over time of oxycodone release following PO administration to dogs of several ketone-modified active agent prodrugs of the embodiments.
Figure 5B:
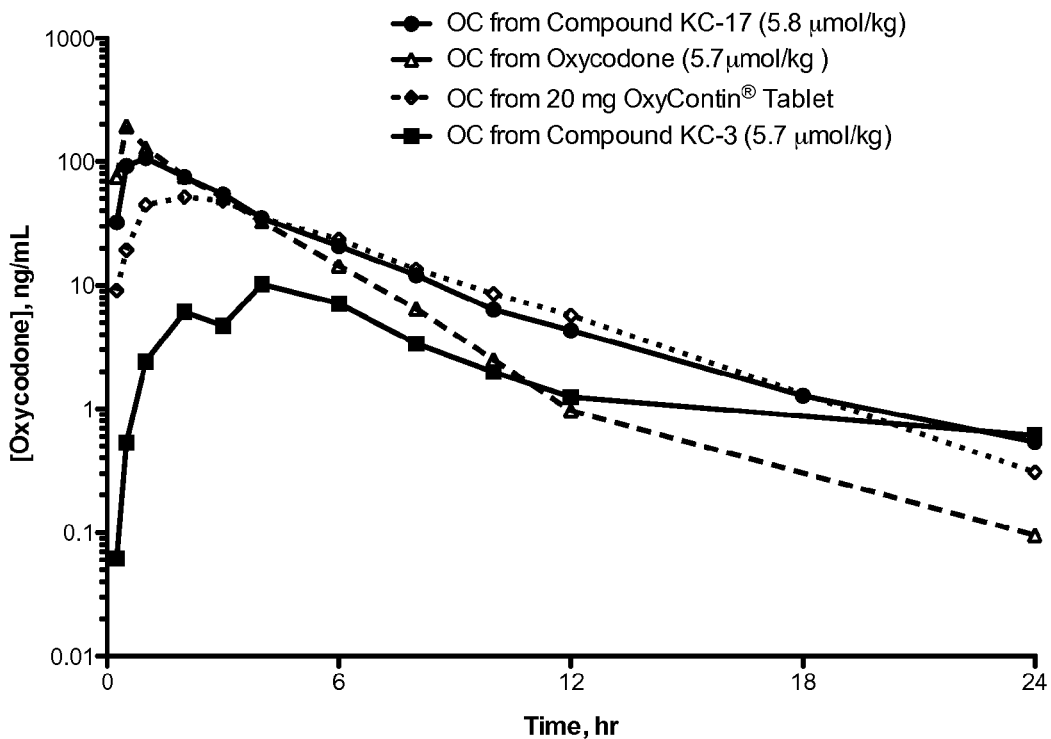
FIG. 5B compares mean plasma concentrations over time of oxycodone release following PO administration to dogs of ketone-modified active agent prodrug Compound KC-17 of the embodiments, oxycodone prodrug Compound KC-3, OxyContin® tablets, or oxycodone HCl.

Table 2, FIG. 5A and FIG. 5B provide oxycodone exposure results for dogs administered the indicated compounds. The oxycodone Cmax, Tmax and AUC values in Table 2 are reported, for each group of four dogs, as described in Example 36.

TABLE 2

Cmax, Tmax and AUC values of oxycodone in dog plasma

| Compound | Dose, mg/kg | Dose, μmol/kg | OC Cmax ± sd, ng/mL | Tmax ± sd, h | AUC ± sd (ng × h)/mL |
|---|---|---|---|---|---|
| KC-3 | 4.15 | 5.7 | 10.2 ± 3.3# | 4.00 ± 0.00 | 65.6 ± 22 |
| KC-12 | 4.38 | 5.7 | 75.0 ± 9.3^ | 0.875 ± 0.25 | 272 ± 43 |
| KC-13 | 4.53 | 5.7 | 57.4 ± 8.5^ | 0.875 ± 0.25 | 221 ± 30 |
| KC-14 | 4.46 | 5.7 | 74.7 ± 6.2# | 1.00 ± 0.0 | 275 ± 25 |
| KC-15 | 4.78 | 5.7 | 93.7 ± 8.1* | 0.625 ± 0.25 | 292 ± 25 |
| KC-16 | 4.78 | 5.8 | 95.3 ± 10* | 1.13 ± 0.63 | 391 ± 46 |
| KC-17 | 4.78 | 5.8 | 120 ± 38^ | 0.750 ± 0.29 | 421 ± 62 |
| Oxycodone | 2 | 5.7 | 193 ± 69# | 0.500 ± 0.0 | 418 ± 54 |
| OxyContin ® | 20 mg tablet | | 64.7 ± 8.8# | 2.75 ± 0.96 | 329 ± 160 |

Lower limit of quantitation was 0.0250 ng/mL
^Lower limit of quantitation was 0.0500 ng/mL
*Lower limit of quantitation was 0.100 ng/mL FIG. 5A compares mean plasma concentrations over time of oxycodone following PO administration of Compound KC-12, Compound KC-13, Compound KC-14, Compound KC-15, Compound KC-16, Compound KC-17, OxyContin® tablets or oxycodone to dogs. FIG. 5B compares mean plasma concentrations over time of oxycodone following PO administration of Compound KC-17, Compound KC-3, OxyContin® tablets or oxycodone to dogs.

The results in Table 2, FIG. 5A, and FIG. 5B indicate that prodrug compounds of the embodiments administered orally to dogs effect efficient release of oxycodone into dog plasma. The results also demonstrate that compounds of the embodiments effect higher oxycodone Cmax values and faster oxycodone Tmax values in dog plasma than does Compound KC-3, an oxycodone prodrug with an ethylene diamine cyclizable spacer leaving group.

Example 38

Pharmacokinetics of Ketone-Modified Opioid Prodrugs Following PO Administration of Increasing Amounts of Such Prodrugs to Rats This Example demonstrates the release of opioid into plasma when ketone-modified opioid prodrugs of the embodiments were administered orally (PO) to rats.

Saline solutions of Compound KC-12 or Compound KC-17 (each of which can be prepared as described in the examples herein) were dosed as indicated in Table 3 via oral gavage into jugular vein-cannulated male Sprague Dawley rats (4 per group) that had been fasted for 16-18 h prior to oral dosing. At specified time points, blood samples were collected, treated, and analyzed in a manner similar to that described in Example 36.

TABLE 3

Dosing of Compound KC-12 and Compound KC-17 PO to rats.

| Compound | Dose, mg/kg | Dose, μmol/kg |
|---|---|---|
| Compound KC-12 | 5 | 6.5 |
| Compound KC-12 | 22 | 29 |
| Compound KC-17 | 5 | 6.0 |
| Compound KC-17 | 23 | 28 |
| Compound KC-17 | 50 | 60 |

Figure 6A:
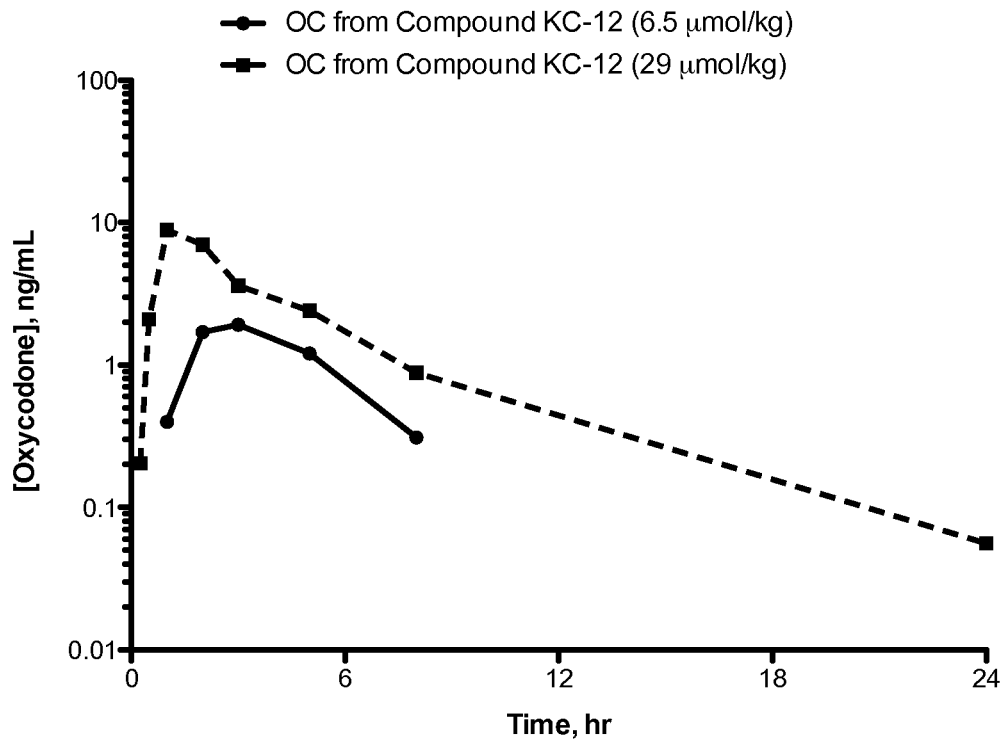
FIG. 6A compares mean plasma concentrations over time of oxycodone release following PO administration to rats of increasing doses of ketone-modified active agent prodrug Compound KC-12.

FIG. 6A compares mean plasma concentrations over time of oxycodone release following PO administration of increasing doses of Compound KC-12 to rats.

Figure 6B:
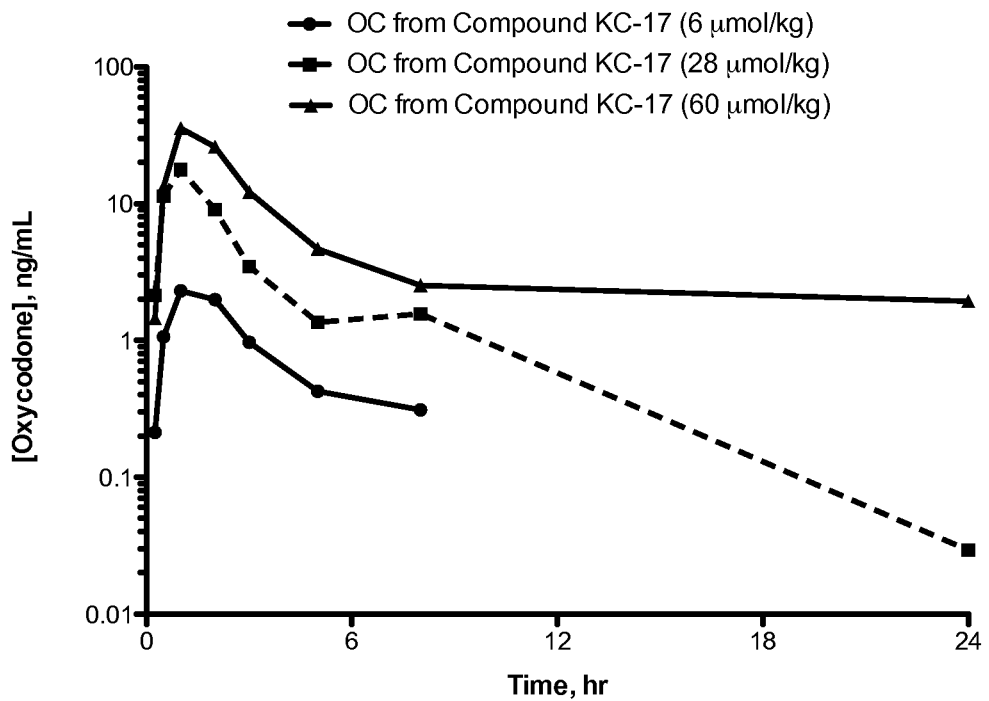
FIG. 6B compares mean plasma concentrations over time of oxycodone release following PO administration to rats of increasing doses of ketone-modified active agent prodrug Compound KC-17.

FIG. 6B compares mean plasma concentrations over time of oxycodone release following PO administration of increasing doses of Compound KC-17 to rats.

The results in Table 3, FIG. 6A, and FIG. 6B indicate that plasma concentrations of oxycodone increase proportionally with dose of prodrugs of the embodiments administered to rats.

Example 39

In Vitro Trypsin-Mediated Prodrug Cleavage and Spacer Leaving Group Cyclization Rate of Ketone-Modified Opioid Prodrugs This Example assesses the ability of trypsin to cleave ketone-modified opioid prodrugs of the embodiments. This Example also assesses the rates of cyclization and release of oxycodone by compounds that lack the trypsin-cleavable moiety but retain oxycodone attached to the respective cyclizable spacer leaving group.

Compound KC-10, Compound KC-12, Compound KC-13, Compound KC-14, Compound KC-15, Compound KC-16, and Compound KC-17 (each of which can be prepared as described in the examples herein) were each incubated with trypsin from bovine pancreas (Catalog No. T8003, Type I, ~10,000 BAEE units/mg protein, Sigma-Aldrich, St. Louis, Mo., USA). Specifically, the reactions included 0.761 mM of the respective prodrug, 22.5 mM calcium chloride, 40 to 172 mM Tris pH 8 and 0.25% DMSO with trypsin preparations of varying activities. The reactions were conducted at 37° C. for 24 h. Samples were collected at specified time points, transferred into 0.5% formic acid in acetonitrile to stop trypsin activity, and stored at less than −70° C. until analysis by LC-MS/MS.

Clock cyclization release rates were measured by following the rate of disappearance of Compound KC-9, Compound KC-11, and Compound KC-18 (2.18 mM initial concentration) in a 50 mM pH 7.4 phosphate buffer at 20° C.

Table 4 indicates the results of exposure of the tested prodrugs to trypsin. The results are expressed as half-life of prodrug when exposed to trypsin (i.e., Prodrug trypsin half-life) in hours, and rate of oxycodone formation in μmmoles per hour per BAEE unit (μmmol/h/BAEE U) trypsin. Table 4 also indicates the cyclization rate of the cyclizable spacer leaving group of Compound KC-9, Compound KC-11, and Compound KC-18. The results are expressed as half-life of compound disappearance. For Compound KC-11, a diastereomer, two peaks (A and B) were analyzed.

TABLE 4

In vitro trypsin cleavage of prodrugs, and cyclization rates of respective cyclizable spacer leaving groups

| Prodrug | Prodrug trypsin half-life, h* | OC formation rate, μmol/h/BAEE U | Compound | half-life, h |
|---|---|---|---|---|
| KC-10 | 0.1502 ± 0.0051 | 0.00274 ± 0.000270 | KC-9 | 714.4 ± 3.76 |
| KC-12 | 0.1583 ± 0.00019 | 0.231 ± 0.0097 | KC-11 peak A | 1.30 ± 0.038 |
|  |  |  | KC-11 peak B | 0.876 ± 0.012 |
| KC-13 | 0.000763 ± 0.0000085 | 47.1 ± 5.72 | KC-11 peak A | 1.30 ± 0.038 |
|  |  |  | KC-11 peak B | 0.876 ± 0.012 |
| KC-14 | 0.008572 ± 0.000033 | 5.48 ± 0.1 | KC-11 peak A | 1.30 ± 0.038 |
|  |  |  | KC-11 peak B | 0.876 ± 0.012 |
| KC-15 | 0.002876 ± 0.00019 | 22.3 ± 0.8 | KC-11 peak A | 1.30 ± 0.038 |
|  |  |  | KC-11 peak B | 0.876 ± 0.012 |
| KC-16 | 0.0395 ± 0.0027 | 1.46 ± 0.093 | KC-11 peak A | 1.30 ± 0.038 |
|  |  |  | KC-11 peak B | 0.876 ± 0.012 |
| KC-17 | 0.0441 ± 0.00195 | 1.23 ± 0.011 | KC-18 | 0.875 ± 0.016 |

*Adjusted to 4815 BAEE U trypsin/mL

The results in Table 4 indicate that prodrugs of the embodiments can be cleaved by trypsin, and that the respective spacer leaving groups can cyclize in a relatively rapid rate.

Example 40

Oral Administration of Ketone-Modified Opioid Prodrugs Co-Dosed with a Trypsin Inhibitor to Rats This Example demonstrates the ability of a trypsin inhibitor to affect the ability of ketone-modified opioid prodrugs of the embodiments to release opioid into plasma when such ketone-modified opioid prodrugs were co-administered with such a trypsin inhibitor orally to rats.

Saline solutions of prodrug Compound KC-12 or prodrug Compound KC-17 (each of which can be prepared as described in the examples herein) were co-dosed with increasing concentrations of Compound 109 (Catalog No. 3081, Tocris Bioscience, Ellisville, Mo., USA or Catalog No. WS38665, Waterstone Technology, Carmel, 1N, USA) as indicated in Table 5A and Table 5B respectively, to rats, using a method similar to that described in Example 36. Sampling and analysis procedures were also similar to those described in Example 36.

Figure 7A:
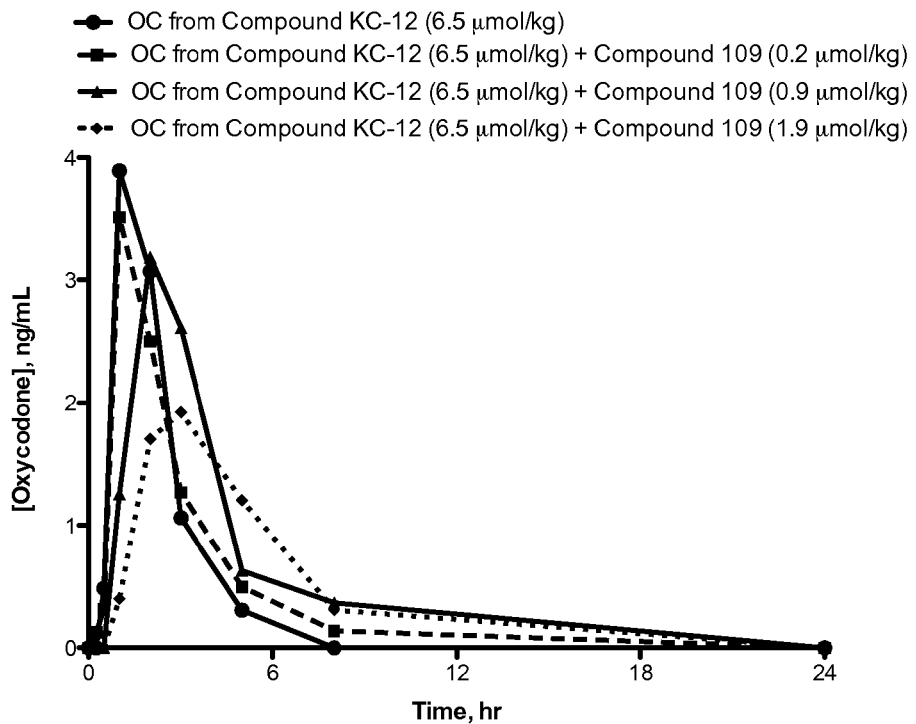
FIG. 7A compares mean plasma concentrations over time of oxycodone release following PO administration to rats of ketone-modified active agent prodrug Compound KC-12 co-dosed with increasing amounts of trypsin inhibitor Compound 109.

Table 5A and FIG. 7A provide oxycodone exposure results for rats administered 5 mg/kg (6.5 μmol/kg) of Compound KC-12 co-dosed with increasing amounts of trypsin inhibitor Compound 109. The oxycodone Cmax, Tmax, and AUC values in Table 5A are reported, for each group of four rats, as described in Example 36.

TABLE 5A

Cmax, Tmax and AUC values of oxycodone in rat plasma

| KC-12 Dose, mg/kg | KC-12 Dose, μmol/kg | Compound 109 Dose, mg/kg | Compound 109 Dose, μmol/kg | OC Cmax ± sd, ng/mL | Tmax ± sd, h | AUC ± sd, ng * h/mL |
|---|---|---|---|---|---|---|
| 5 | 6.5 | 0 | 0 | 4.67 ± 1.7 | 1.25 ± 0.50 | 7.32 ± 0.97 |
| 5 | 6.5 | 0.1 | 0.2 | 3.86 ± 1.7 | 1.50 ± 0.58 | 7.82 ± 1.6 |
| 5 | 6.5 | 0.5 | 0.9 | 3.71 ± 1.9 | 2.50 ± 0.58 | 9.60 ± 5.0 |
| 5 | 6.5 | 1.0 | 1.9 | 2.30 ± 0.48 | 2.50 ± 0.58 | 7.57 ± 1.5 |

Lower limit of quantitation was 0.500 ng/mL

Figure 7B:
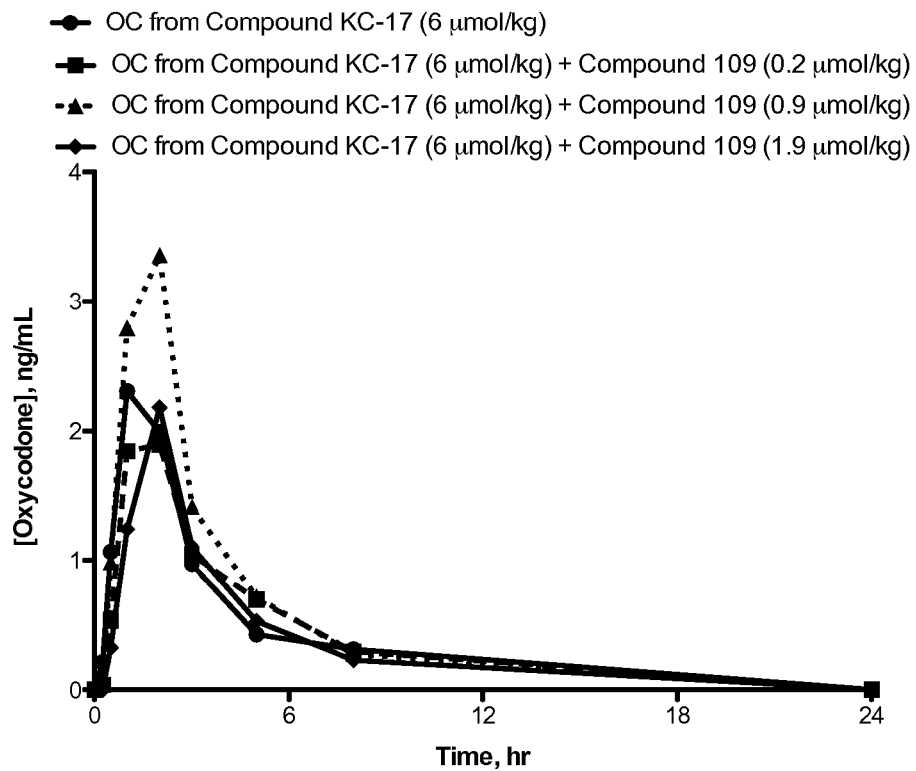
FIG. 7B and FIG. 7C compare mean plasma concentrations over time of oxycodone release following PO administration to rats of two doses of ketone-modified active agent prodrug Compound KC-17, each co-dosed with increasing amounts of trypsin inhibitor Compound 109.
Figure 7C:
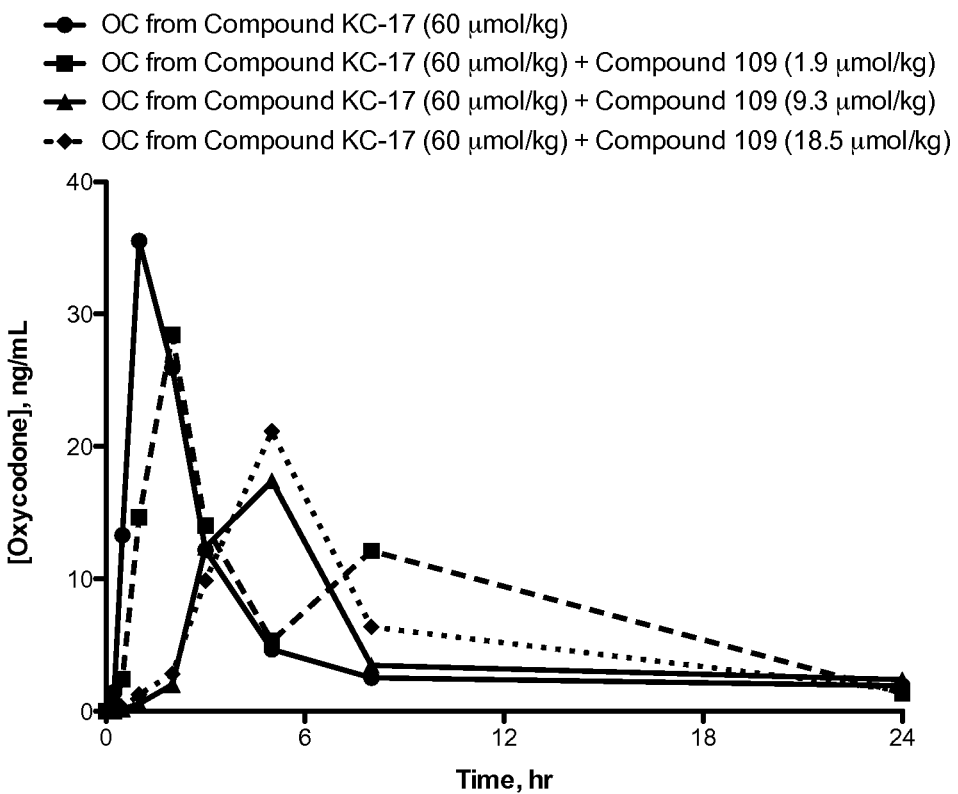

Table 5B, FIG. 7B and FIG. 7C provide oxycodone exposure results for rats administered 5 mg/kg (6 μmol/kg) or 50 mg/kg (60 μmol/kg) doses of Compound KC-17, each co-dosed with increasing amounts of trypsin inhibitor Compound 109. The oxycodone Cmax, Tmax, and AUC values in Table 5B are reported, for each group of four rats, as described in Example 36.

TABLE 5B

Cmax, Tmax and AUC values of oxycodone in rat plasma

| KC-17 Dose, mg/kg | KC-17 Dose, μmol/kg | Compound 109 Dose, mg/kg | Compound 109 Dose, μmol/kg | OC Cmax ± sd, ng/mL | Tmax ± sd, h | AUC ± sd, ng * h/mL |
|---|---|---|---|---|---|---|
| 5 | 6 | 0 | 0 | 2.35 ± 0.33^ | 1.25 ± 0.50 | 7.16 ± 1.6 |
| 5 | 6 | 0.1 | 0.2 | 2.03 ± 0.85^ | 1.50 ± 0.58 | 6.99 ± 2.8 |

TABLE 5B-continued

Cmax, Tmax and AUC values of oxycodone in rat plasma

| KC-17 Dose, mg/kg | KC-17 Dose, μmol/kg | Compound 109 Dose, mg/kg | Compound 109 Dose, μmol/kg | OC Cmax ± sd, ng/mL | Tmax ± sd, h | AUC ± sd, ng * h/mL |
|---|---|---|---|---|---|---|
| 5 | 6 | 0.5 | 0.9 | 3.85 ± 1.1^ | 1.75 ± 0.50 | 10.2 ± 2.0 |
| 5 | 6 | 1.0 | 1.9 | 2.18 ± 0.38^ | 2.00 ± 0.0 | 6.36 ± 1.3 |
| 50 | 60 | 0 | 0 | 40.1 ± 10* | 1.25 ± 0.50 | 127 ± 15 |
| 50 | 60 | 1 | 1.9 | 32.4 ± 11* | 3.50 ± 3.0 | 201 ± 190 |
| 50 | 60 | 5 | 9.3 | 21.0 ± 9.0* | 4.50 ± 1.0 | 117 ± 25 |
| 50 | 60 | 10 | 18.5 | 23.2 ± 3.0* | 4.50 ± 1.0 | 145 ± 54 |

^Lower limit of quantitation was 0.100 ng/mL
*Lower limit of quantitation was 0.500 ng/mL FIG. 7A compares mean plasma concentrations over time of oxycodone release following PO administration of 5 mg/kg (6.5 μmol/kg) of prodrug Compound KC-12 with increasing amounts of co-dosed trypsin inhibitor Compound 109 to rats.

FIG. 7B and FIG. 7C compare the mean plasma concentrations over time of oxycodone release following PO administration of 5 mg/kg (6 μmol/kg) and of 50 mg/kg (60 μmol/kg) dose of prodrug Compound KC-17 with increasing amounts of co-dosed trypsin inhibitor Compound 109 to rats.

The results in Table 5A, Table 5B, FIG. 7A, FIG. 7B and FIG. 7C indicate Compound 109's ability to attenuate release of oxycodone by prodrugs of the embodiments.

Example 41

Effect of Trypsin Inhibition on In Vitro Trypsin-Mediated Release of Opioid from a Phenolic Opioid Prodrug This Example demonstrates the ability of trypsin to cleave a phenolic opioid prodrug of the embodiments. This Example further demonstrates the effect of a trypsin inhibitor of the embodiments on such in vitro trypsin-mediated release.

Tapentadol prodrug Compound TP-5 (which can be prepared as described in the Examples herein) was incubated with trypsin from bovine pancreas (Catalog No. T8003, Type I, ~10,000 BAEE units/mg protein, Sigma-Aldrich), in the absence or presence of Compound 109 (Catalog No. 3081, Tocris Bioscience or Catalog No. WS38665, Waterstone Technology), as shown in Table 6. When Compound 109 was part of the reaction mixture, Compound TP-5 was added 5 min after the other incubation components. Other reaction, incubation, sample treatment and analysis procedures were similar to those described in Example 39.

Table 6 indicates the results of exposure of Compound TP-5 to trypsin in the absence or presence of trypsin inhibitor. The results are expressed as half-life of prodrug when exposed to trypsin (i.e., Prodrug trypsin half-life) in hours and rate of tapentadol (TP) formation in μmol/h/BAEE U trypsin.

TABLE 6

In vitro trypsin conversion of Compound TP-5 to tapentadol and inhibition thereof by Compound 109

| Compound | Compound 109, μM | Pro-drug trypsin half-life, h* Average ± sd | Rate of TP formation, μmol/h/BAEE U Average ± sd |
|---|---|---|---|
| TP-5 | 0 | 0.0665 ± 0.000004 | 0.684 ± 0.036 |
| TP-5 | 8 | 1.04 ± 0.00061 | 0.1043 ± 0.0049 |

*Adjusted to 4815 BAEE U/mL trypsin

The results in Table 6 indicate that trypsin can effect release of tapentadol from a phenolic opioid prodrug of the embodiments, and that a trypsin inhibitor of the embodiments can attenuate such release.

Example 42

Oral Administration of a Phenolic Opioid Prodrug Co-Dosed with a Trypsin Inhibitor to Rats This Example demonstrates the ability of a trypsin inhibitor of the embodiments to affect the ability of a phenolic opioid prodrug of the embodiments to release such opioid into plasma when such prodrug is administered orally to rats.

Saline solutions of tapentadol prodrug Compound TP-5 (which can be prepared as described in the examples herein) were administered to rats either without or with trypsin inhibitor Compound 109 as indicated in Table 7. Dosing, blood sampling and analysis procedures were similar to those described in Example 40.

Figure 8:
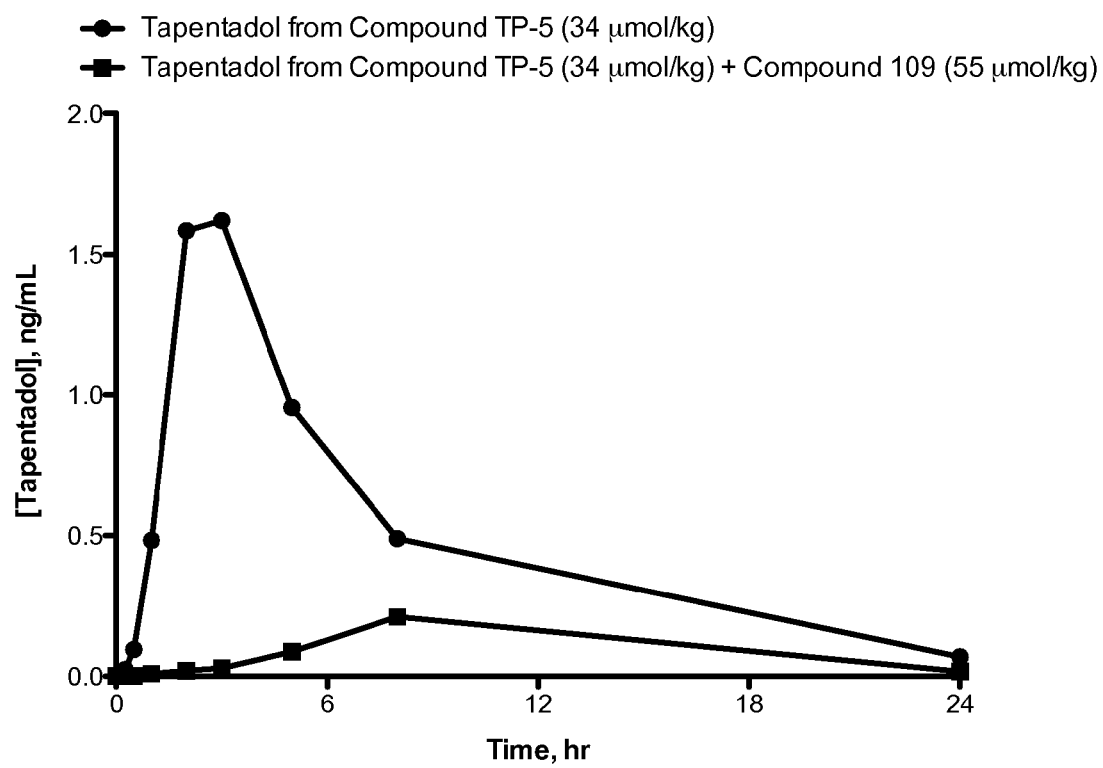
FIG. 8 compares mean plasma concentrations over time of tapentadol release following PO administration to rats of phenolic active agent prodrug Compound TP-5 in the absence or presence of a co-dose of trypsin inhibitor Compound 109.

Table 7 and FIG. 8 provide tapentadol exposure results for rats administered Compound TP-5 in the absence or presence of trypsin inhibitor Compound 109. The tapentadol Cmax, Tmax, and AUC values in Table 7 are reported for each group of four rats, as described in Example 36.

TABLE 7

Cmax, Tmax and AUC values of tapentadol in rat plasma

| Dosing mg/kg [µmol/kg] | Compound 109 Dose, mg/kg | Compound 109 Dose, µmol/kg | TP Cmax ± sd, ng/mL | Tmax ± sd, h | AUC ± sd (ng × h)/mL |
|---|---|---|---|---|---|
| TP-5 23 [34] | 0 | 0 | 1.90 ± 0.35 | 2.50 ± 0.58 | 12.0 ± 1.30 |
| TP-5 23 [34] | 30 | 55 | 0.211 ± 0.074 | 8.00 ± 0.0 | 1.64 ± 1.50 |

Lower limit of quantitation was 0.0250 ng/mL

FIG. 8 compares mean plasma concentrations over time of tapentadol release following PO administration of prodrug Compound TP-5 to rats, with or without a co-dose of trypsin inhibitor.

The results in Table 7 and FIG. 8 indicate that trypsin inhibitor Compound 109 attenuates prodrug Compound TP-5's ability to release tapentadol in rats.

Example 43

Pharmacokinetics of a Ketone-Modified Opioid Prodrug Following PO Administration of Increasing Doses of Such a Prodrug to Rats This Example demonstrates the release of opioid into plasma when increasing doses of a ketone-modified opioid prodrug of the embodiments were administered orally (PO) to rats.

Increasing doses of Compound KC-31 (which can be prepared as described in the examples herein) in sterile water or hydrocodone in sterile water were dosed as indicated in Table 8 via oral gavage into jugular vein-cannulated male Sprague Dawley rats (4 per group) that had been fasted for 16-18 h prior to oral dosing. At specified time points, blood samples were collected, treated, and analyzed in a manner similar to that described in Example 36.

Figure 9:
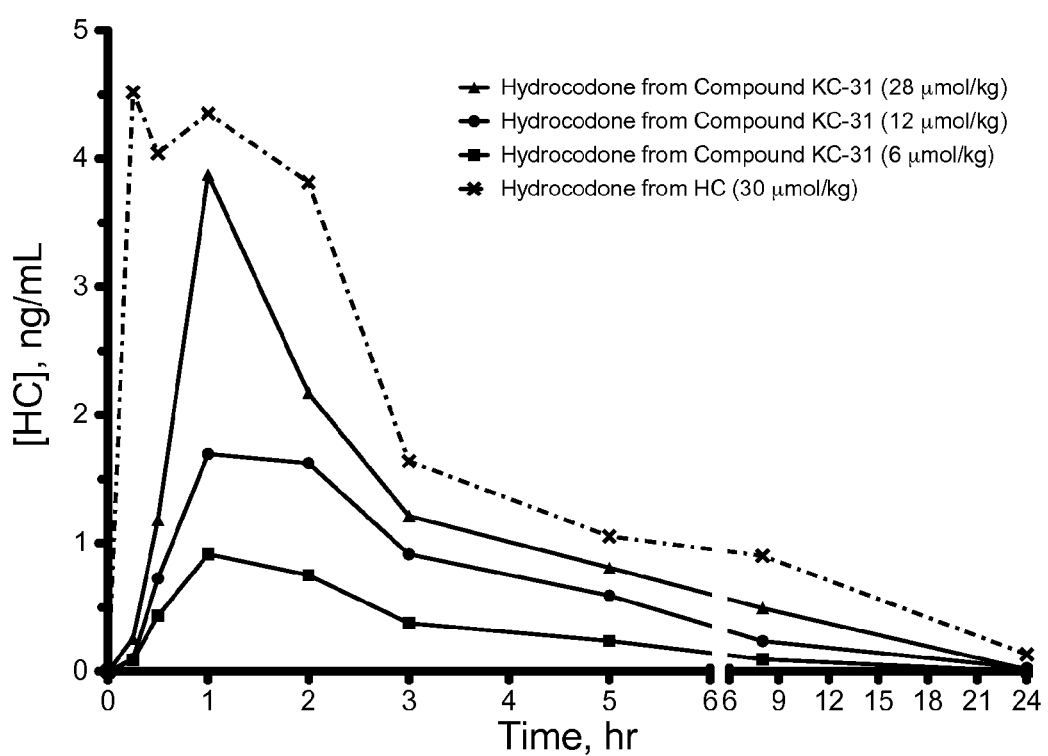
FIG. 9 compares mean plasma concentrations over time of hydrocodone release following PO administration to rats of increasing doses of ketone-modified active agent prodrug Compound KC-31.

Table 8 and FIG. 9 provide hydrocodone exposure results for rats administered Compound KC-31 or hydrocodone. Results in Table 8 are reported, for each group of rats, as (a) maximum plasma concentration value (Cmax) of hydrocodone (HC) (average±standard deviation) and (b) time after administration of compound to reach maximum hydrocodone concentration value (Tmax) (average±standard deviation).

TABLE 8

Cmax, Tmax and AUC values of hydrocodone in rat plasma

| Compound | Dose, mg/kg | Dose µmol/kg | HC Cmax ± sd, ng/mL | Tmax ± sd, h |
|---|---|---|---|---|
| KC-31 | 5 | 6 | 1.03 ± 0.083 | 1.25 ± 0.50 |
| KC-31 | 10 | 12 | 1.77 ± 0.63 | 1.75 ± 0.50 |
| KC-31 | 23 | 28 | 3.87 ± 1.7 | 1.00 ± 0.0 |
| Hydrocodone | 10 | 30 | 5.49 ± 1.7 | 1.06 ± 0.72 |

Lower limit of quantitation was 0.0500 ng/mL

FIG. 9 compares mean plasma concentrations over time of hydrocodone release following PO administration of increasing doses of Compound KC-31 to rats.

The results in Table 8 and FIG. 9 indicate that plasma concentrations of hydrocodone increase proportionally with dose of a prodrug of the embodiments administered to rats.

Example 44

In Vitro Trypsin-Mediated Prodrug Cleavage of Ketone-Modified Opioid Prodrugs

This Example assesses the ability of trypsin to cleave ketone-modified opioid prodrugs of the embodiments.

Compound KC-31, Compound KC-32, Compound KC-35, Compound KC-36, Compound KC-37, Compound KC-38, Compound KC-39, and Compound KC-40 (each of which can be prepared as described in the examples herein) were each incubated with trypsin, and samples were collected and analyzed as described in Example 39.

Table 9 indicates the results of exposure of the tested prodrugs to trypsin. The results are expressed as half-life of prodrug when exposed to trypsin (i.e., Prodrug trypsin half-life) in hours, and rate of hydrocodone formation in µmmoles per hour per BAEE unit (µmmol/h/BAEE U) trypsin.

TABLE 9

In vitro trypsin cleavage of prodrugs

| Prodrug | Prodrug trypsin half-life, h* | HC formation rate, µmol/h/ BAEE U |
|---|---|---|
| Compound KC-31 | 0.065 ± 0.00 | ☐ |
| Compound KC-32 | 0.15 ± 0.00 | ☐ |
| Compound KC-35 | 0.008 ± 0.00 | ☐ |
| Compound KC-36 | 0.018 ± 0.00 | 0.004 ± 0.00 |
| Compound KC-37 | 0.00 ± 0.00 | 0.004 ± 0.00 |
| Compound KC-38 | 0.12 ± 0.01 | 0.001 ± 0.00 |
| Compound KC-39 | 0.398 ± 0.00 | 0.00 ± 0.00 |
| Compound KC-40 | 0.010 ± 0.00 | 0.003 ± 0.00 |

*Adjusted to 4815 BAEE U trypsin/mL
☐ not analyzed

The results in Table 9 indicate that prodrugs of the embodiments can be cleaved by trypsin.

Example 45

Pharmacokinetics Following PO Administration of Ketone-Modified Opioid Prodrugs to Rats This Example demonstrates the release of opioid into plasma when ketone-modified opioid prodrugs of the embodiments were administered orally (PO) to rats.

Aqueous solutions of Compound KC-32, Compound KC-35, Compound KC-36, Compound KC-37, Compound KC-38, Compound KC-39, Compound KC-40, Compound KC-47 and Compound KC-50 (each of which can be prepared as described in the examples herein) or hydrocodone (Johnson Matthey, London, UK) were dosed as indicated in Table 10 to rats, using a method similar to that described in Example 36. Sampling and analysis procedures were also similar to those described in Example 36.

Table 10 provides hydrocodone exposure (i.e., due to hydrocodone release from prodrug) results for rats administered the indicated compounds. Results in Table 10 are reported, for each group of rats, as (a) maximum plasma concentration value (Cmax) of hydrocodone (HC) (average±standard deviation) and (b) time after administration of compound to reach maximum hydrocodone concentration value (Tmax) (average±standard deviation).

TABLE 10

Cmax and Tmax of hydrocodone in rat plasma

| Compound | Dose, mg/kg | Dose μmol/kg | HC Cmax ± sd, ng/mL | Tmax ± sd, h |
|---|---|---|---|---|
| KC-32 | 23 | 28 | 1.50 ± 0.81^ | 3.75 ± 2.9 |
| KC-35 | 20 | 24 | 2.70 ± 0.46^ | 1.00 ± 0.00 |
| KC-36 | 21 | 27 | 5.43 ± 1.4* | 0.958 ± 0.085 |
| KC-37 | 22 | 28 | 5.61 ± 2.7* | 1.17 ± 0.56 |
| KC-38 | 20 | 28 | 5.83 ± 1.6* | 1.00 ± 0.00 |
| KC-39 | 21 | 28 | 6.40 ± 3.7* | 1.75 ± 0.50 |
| KC-40 | 23 | 28 | 5.86 ± 1.8* | 0.417 ± 0.096 |
| KC-47 | 24 | 28 | 4.24 ± 0.82^ | 0.584 ± 0.096 |
| KC-50 | 22 | 28 | 4.65 ± 0.85^ | 0.500 ± 0.00 |
| hydrocodone | 10 | 30 | 5.49 ± 1.7^ | 1.06 ± 0.72 |

Figure 10:
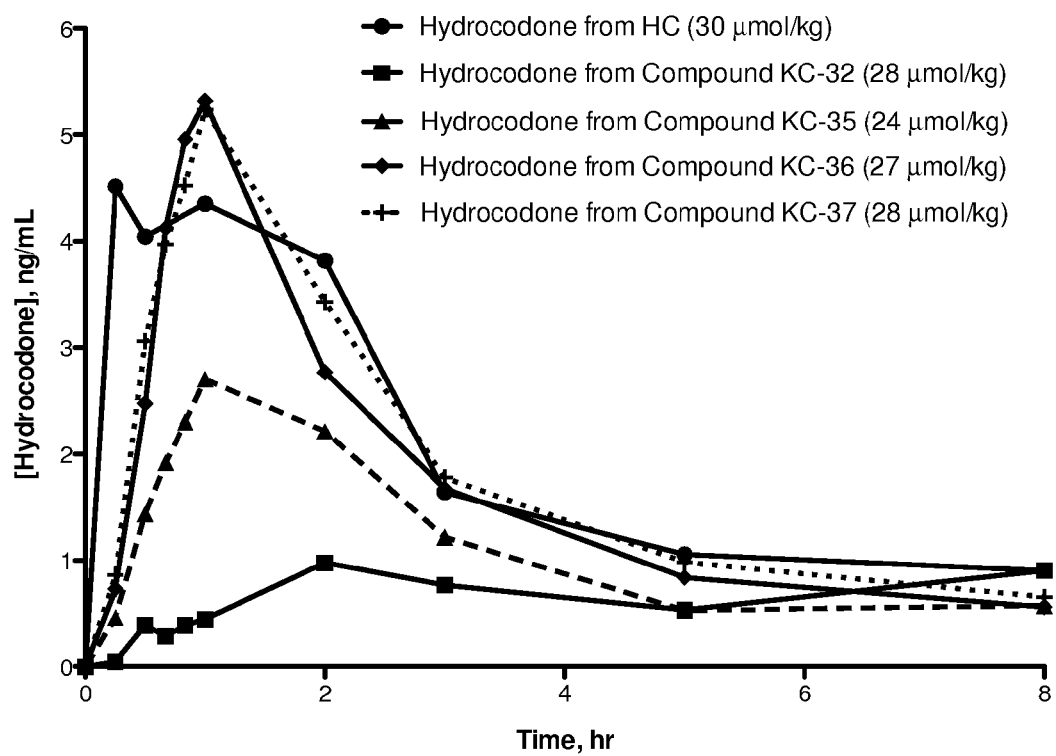
FIG. 10 compares mean plasma concentrations over time of hydrocodone release following PO administration to rats of hydrocodone and PO administration to rats of hydrocodone prodrugs Compound KC-32, Compound KC-35, Compound KC-36, and Compound KC-37.
Figure 11:
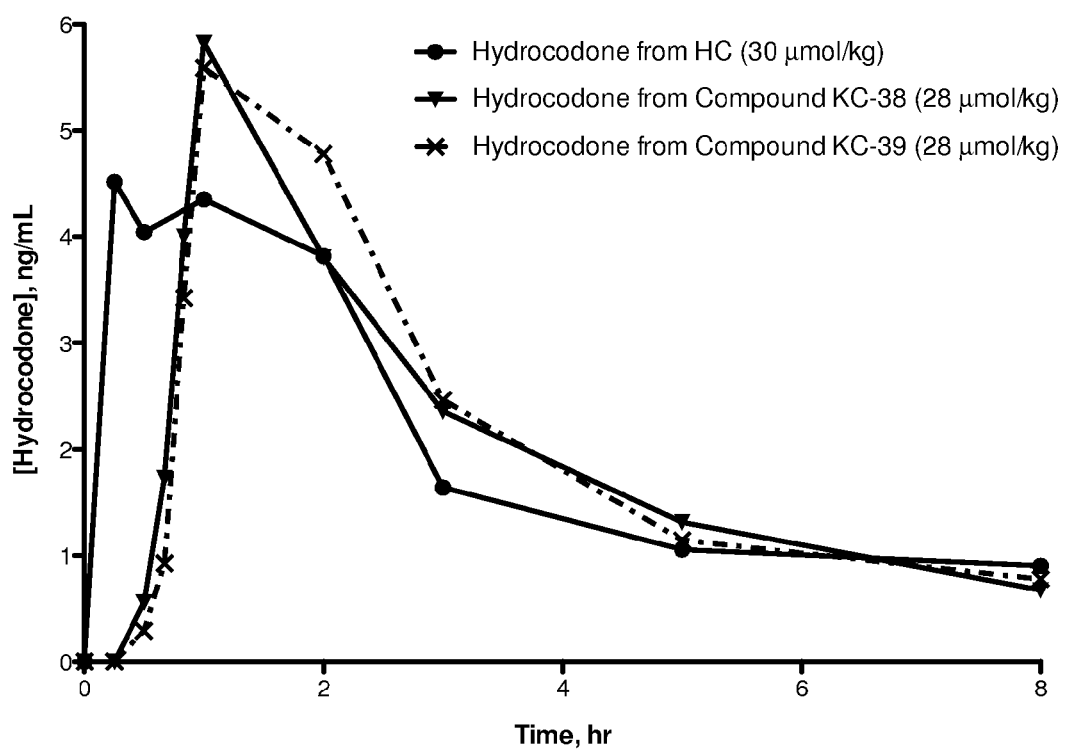
FIG. 11 compares mean plasma concentrations over time of hydrocodone release following PO administration to rats of hydrocodone and PO administration to rats of hydrocodone prodrugs Compound KC-38 and Compound KC-39.
Figure 12:
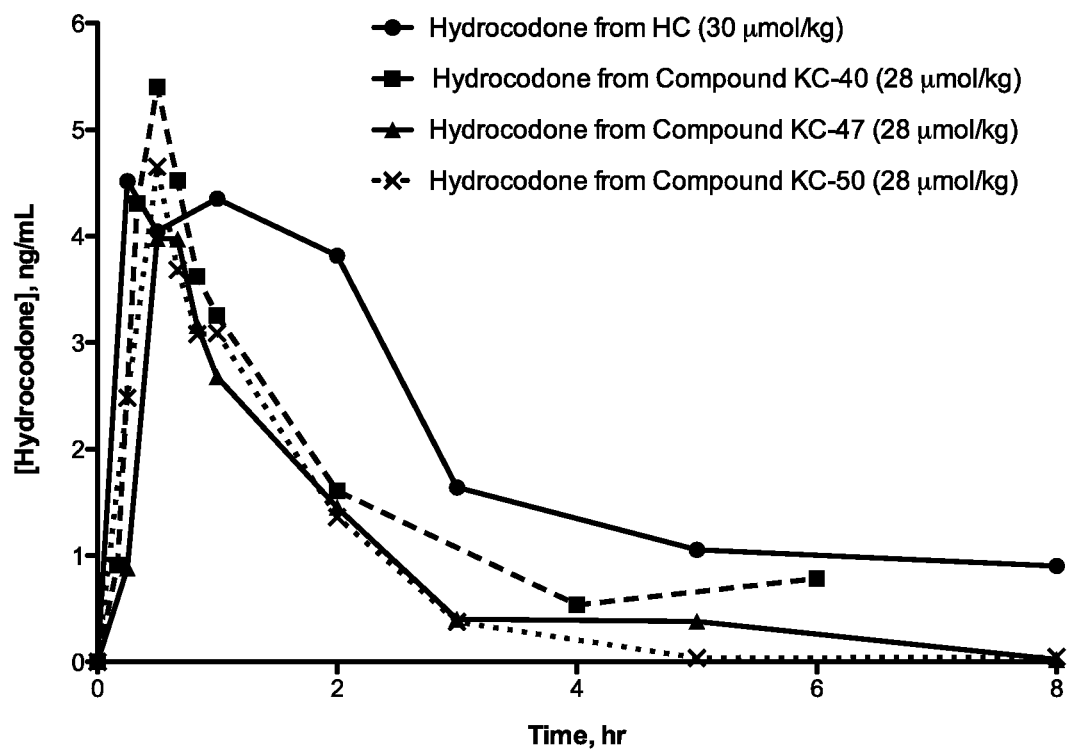
FIG. 12 compares mean plasma concentrations over time of hydrocodone release following PO administration to rats of hydrocodone and PO administration to rats of hydrocodone prodrugs Compound KC-40, Compound KC-47, and Compound KC-50.

^Lower limit of quantitation was 0.0500 ng/mL
*Lower limit of quantitation was 0.100 ng/mL FIG. 10, FIG. 11, and FIG. 12 compare mean plasma concentrations over time of hydrocodone release following PO administration of hydrocodone prodrugs of the embodiments to rats.

The results in Table 10, FIG. 10, FIG. 11 and FIG. 12 indicate that oral administration to rats of each of the tested prodrugs leads to release of hydrocodone.

Example 46

Oral Administration of Ketone-Modified Opioid Prodrugs Co-Dosed with a Trypsin Inhibitor to Rats This Example demonstrates the ability of a trypsin inhibitor to affect the ability of ketone-modified opioid prodrugs of the embodiments to release opioid into plasma when such ketone-modified opioid prodrugs were co-administered with such trypsin inhibitor orally to rats.

Aqueous solutions of prodrug Compound KC-40 or prodrug Compound KC-50 (each of which can be prepared as described in the examples herein) were co-dosed with increasing concentrations of Compound 109 (Catalog No. 3081, Tocris Bioscience, Ellisville, Mo., USA or Catalog No. WS38665, Waterstone Technology, Carmel, 1N, USA) as indicated in Table 11A and Table 11B respectively, or hydrocodone to rats, using a method similar to that described in Example 36. Sampling and analysis procedures were also similar to those described in Example 36.

Table 11A provides hydrocodone exposure results for rats administered hydrocodone or 5 mg/kg (6 μmol/kg) or 50 mg/kg (62 μmol/kg) doses of Compound KC-40 co-dosed with increasing amounts of trypsin inhibitor Compound 109. The hydrocodone Cmax and Tmax values in Table 11A are reported, for each group of three or four rats, as indicated in Table 11A, and as described in Example 36.

TABLE 11A

Cmax and Tmax of hydrocodone in rat plasma

| KC-40 Dose, mg/kg | KC-40 Dose, μmol/kg | Compound 109 Dose, mg/kg | Compound 109 Dose, μmol/kg | HC Cmax ± sd, ng/mL | Tmax ± sd, h |
|---|---|---|---|---|---|
| 5 | 6 | 0 | 0 | 1.08 ± 0.17^ | 1.00 ± 0.68 |
| 5 | 6 | 0.1 | 0.2 | 1.09 ± 0.27^ | 0.500 ± 0.00 |
| 5 | 6 | 0.25 | 0.44 | 1.19 ± 0.29^ | 0.708 ± 0.25 |
| 5 | 6 | 0.5 | 0.9 | 0.892 ± 0.16^ | 1.09 ± 0.63 |
| 5 | 6 | 1.0 | 1.7 | 0.987 ± 0.55^ | 1.00 ± 0.68 |
| 50 | 62 | 1 | 1.7 | 5.97 ± 1.4* | 2.00 ± 0.00 |
| 50 | 62 | 2.5☐ | 4.4 | 7.37 ± 2.3* | 2.33 ± 0.58 |
| 50 | 62 | 5 | 9.0 | 4.98 ± 2.0* | 2.50 ± 0.58 |
| 50 | 62 | 10 | 17.4 | 5.43 ± 4.1* | 4.00 ± 1.2 |
| Hydrocodone values in Table 10 adjusted to provide expected values at a 21.7 mg/kg (62 μmol/kg) dose | | | | 11.9 ± n/a^ | 1.06 ± n/a |

Figure 13A:
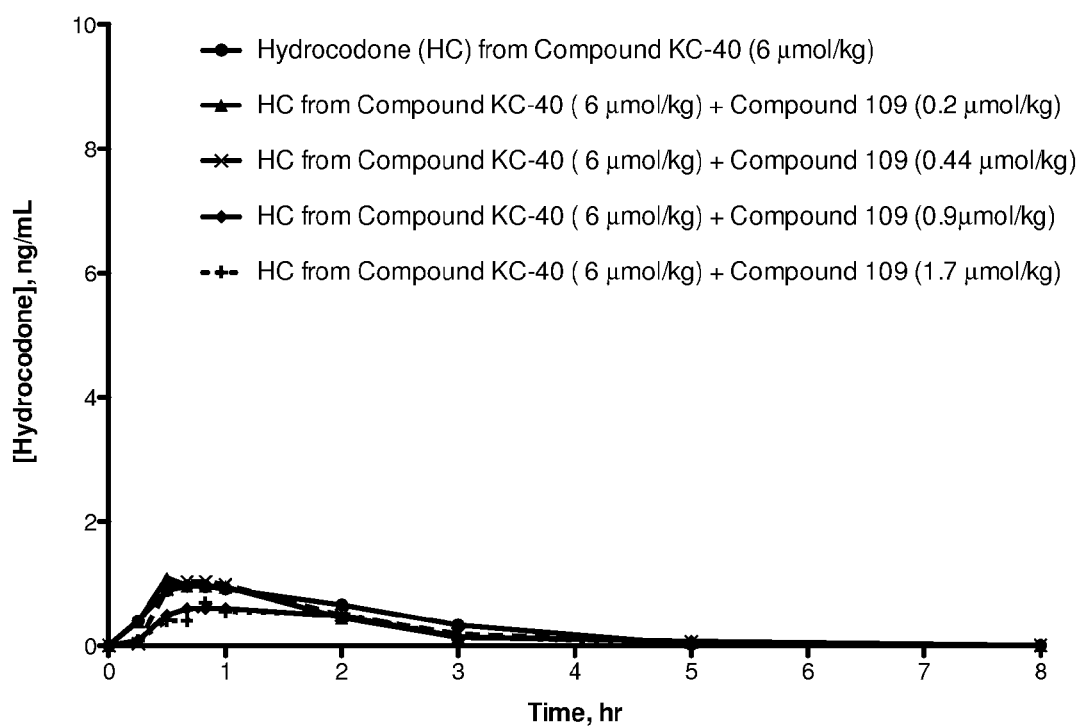
FIG. 13A compares mean plasma concentrations over time of hydrocodone release following PO administration to rats of prodrug Compound KC-40 with increasing amounts of co-dosed trypsin inhibitor Compound 109.
Figure 13B:
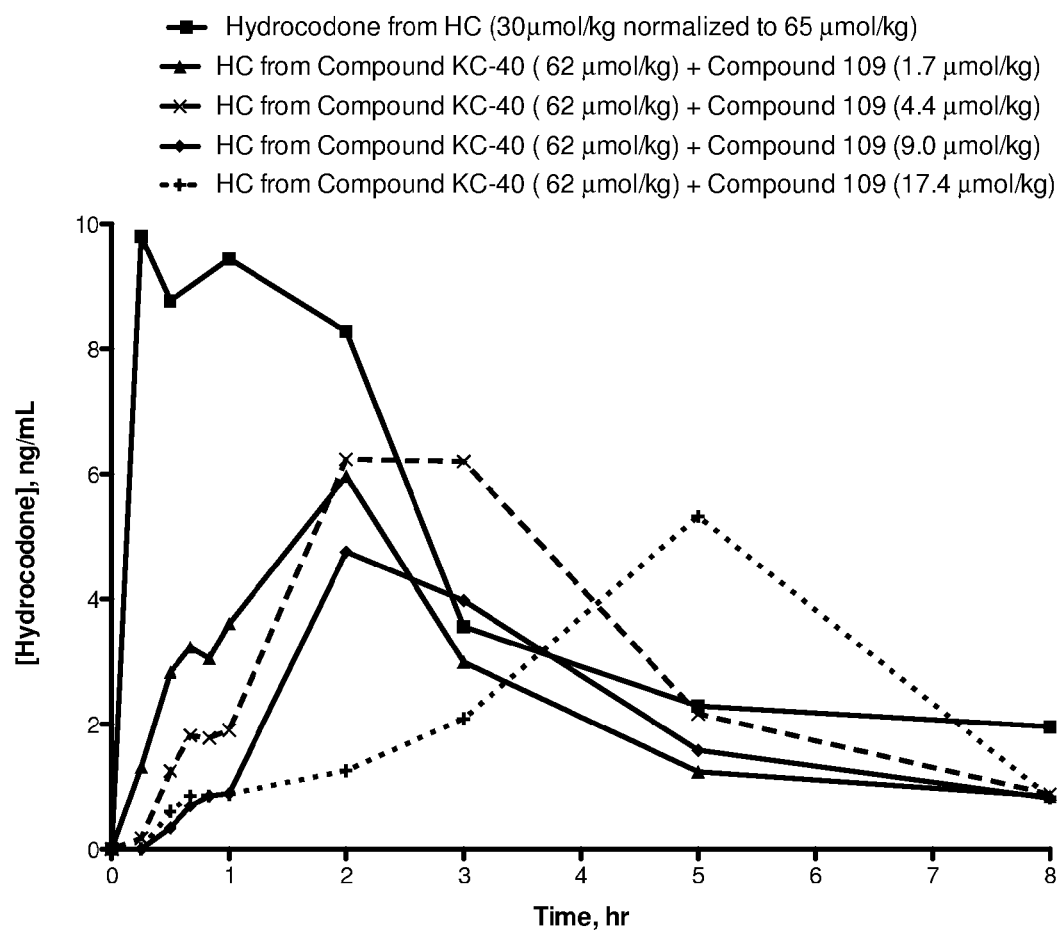
FIG. 13B compares mean plasma concentrations over time of hydrocodone release following PO administration to rats of prodrug Compound KC-40 with increasing amounts of co-dosed trypsin inhibitor Compound 109 to hydrocodone values expected from a normalized hydrocodone dose.

^Lower limit of quantitation was 0.0500 ng/mL
*Lower limit of quantitation was 0.500 ng/mL
☐3 rats dosed FIG. 13A compares mean plasma concentrations over time of hydrocodone release following PO administration to rats of a 5 mg/kg (6 μmol/kg) dose of prodrug Compound KC-40 with increasing amounts of co-dosed trypsin inhibitor Compound 109. FIG. 13B compares mean plasma concentrations over time of hydrocodone release following PO administration to rats of a 50 mg/kg (62 μmol/kg) dose of prodrug Compound KC-40 with increasing amounts of co-dosed trypsin inhibitor Compound 109 to hydrocodone values expected from a 21.7 mg/kg (62 μmol/kg) hydrocodone dose, based on the plasma concentrations of hydrocodone release following PO administration to rats of 10 mg/kg hydrocodone.

Table 11B provides hydrocodone exposure results for rats administered hydrocodone or 5 mg/kg (6 μmol/kg) or 50 mg/kg (64 μmol/kg) doses of Compound KC-50 each co-dosed with increasing amounts of trypsin inhibitor Compound 109. The hydrocodone Cmax and Tmax values in Table 11B are reported, for each group of four rats, as described in Example 36.

TABLE 11B

Cmax and Tmax of hydrocodone in rat plasma

| KC-50 Dose, mg/kg | KC-50 Dose, μmol/kg | Compound 109 Dose, mg/kg | Compound 109 Dose, μmol/kg | HC Cmax ± sd, ng/mL | Tmax ± sd, h |
|---|---|---|---|---|---|
| 5 | 6 | 0 | 0 | 1.45 ± 0.21 | 0.542 ± 0.084 |
| 5 | 6 | 0.1 | 0.2 | 1.18 ± 0.16 | 0.500 ± 0.00 |
| 5 | 6 | 0.25 | 0.44 | 1.12 ± 0.27 | 0.667 ± 0.14 |
| 5 | 6 | 0.5 | 0.9 | 1.19 ± 0.44 | 1.00 ± 0.68 |
| 5 | 6 | 1.0 | 1.7 | 0.807 ± 37 | 1.75 ± 0.50 |
| 50 | 64 | 1 | 1.7 | 5.28 ± 3.0 | 1.75 ± 0.50 |
| 50 | 64 | 2.5 | 4.4 | 4.49 ± 0.22 | 1.42 ± 0.69 |
| 50 | 64 | 5 | 9.0 | 5.11 ± 1.5 | 3.00 ± 1.2 |
| Hydrocodone values in Table 10 adjusted to provide expected values at a 62 μmol/kg (21.7 mg/kg) dose | | | | 12.4 ± n/a | 1.06 ± n/a |

Lower limit of quantitation was 0.0500 ng/mL

Figure 13C:
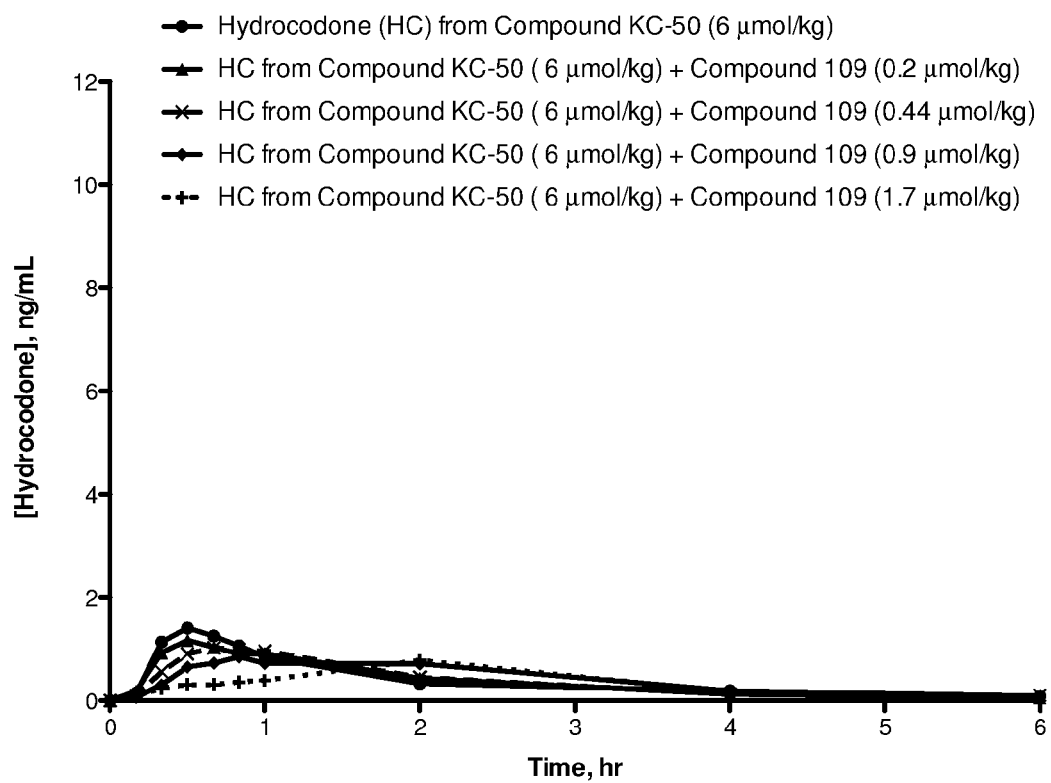
FIG. 13C compares the mean plasma concentrations over time of hydrocodone release following PO administration to rats of prodrug Compound KC-50 with increasing amounts of co-dosed trypsin inhibitor Compound 109.
Figure 13D:
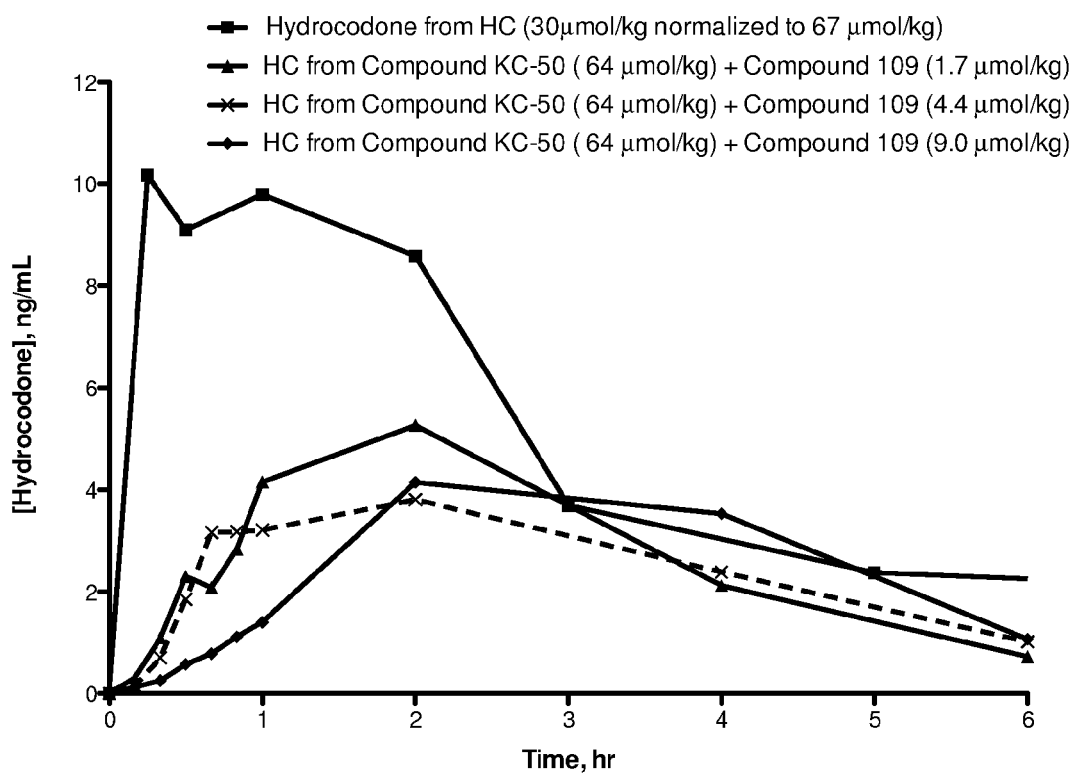
FIG. 13D compares mean plasma concentrations over time of hydrocodone release following PO administration to rats of prodrug Compound KC-50 with increasing amounts of co-dosed trypsin inhibitor Compound 109 to hydrocodone values expected from a normalized hydrocodone dose.

FIG. 13C compares the mean plasma concentrations over time of hydrocodone release following PO administration to rats of a 5 mg/kg (6 μmol/kg) dose of prodrug Compound KC-50 with increasing amounts of co-dosed trypsin inhibitor Compound 109. FIG. 13D compares mean plasma concentrations over time of hydrocodone release following PO administration to rats of a 50 mg/kg (62 μmol/kg) dose of prodrug Compound KC-50 with increasing amounts of co-dosed trypsin inhibitor Compound 109 to hydrocodone values expected from a 21.7 mg/kg (62 μmol/kg) hydrocodone dose, based on the plasma concentrations of hydrocodone release following PO administration to rats of 10 mg/kg hydrocodone.

The results in Table 11A, Table 11B, FIG. 13A, FIG. 13B, FIG. 13C and FIG. 13D indicate Compound 109's ability to attenuate release of hydrocodone by prodrugs of the embodiments.

Example 47

Pharmacokinetics of Ketone-Modified Opioid Prodrugs Following PO Administration to Dogs and Effects of Co-Administration of a Trypsin Inhibitor This Example demonstrates the release of hydrocodone into plasma when ketone-modified hydrocodone prodrugs of the embodiments were administered orally (PO) to dogs.

This Example also demonstrates the release of hydrocodone into plasma when an increasing number of dose units of a ketone-modified hydrocodone prodrug and a trypsin inhibitor were administered PO to dogs.

Purebred male young adult/adult beagles were fasted overnight. Aqueous solutions of either Compound KC-40 or Compound 50 (each of which can be prepared as described in the examples herein) as indicated in Table 12 and Table 13, respectively, or 0.17 mg/kg hydrocodone were administered via oral gavage to the dogs (4 per group). The study also included (a) dogs that were dosed with an increasing number of dose units of Compound KC-40 and Compound 109 as indicated in Table 12 and (b) dogs that were co-dosed with Compound KC-50 and increasing doses of Compound 109, as indicated in Table 13.

Blood was collected from each animal via a jugular vein at various times over a 24-h period, centrifuged, and 0.8 mL plasma transferred to a fresh tube containing 8 μL formic acid; samples were vortexed, then immediately placed in dry ice, and stored in a −80° C. freezer until analysis by HPLC/MS.

Table 12 provides hydrocodone (HC) exposure results for dogs administered either hydrocodone or increasing doses of prodrug Compound KC-40. Table 12 also provides hydrocodone (HC) exposure results when an increasing number of dose units of prodrug Compound KC-40 and trypsin inhibitor Compound 109 (i.e., 1, 4 or 10 dose units) were administered PO to dogs. The hydrocodone Cmax and Tmax values in Table 12 are reported, for each group of four dogs, as described in Example 36.

TABLE 12

Cmax and Tmax of hydrocodone in dog plasma

| Compound | Dose, mg/kg | Dose, μmol/kg | Compound 109 Dose mg/kg | Compound 109 Dose μmol/kg | HC Cmax ± sd, ng/mL | Tmax ± sd, h |
|---|---|---|---|---|---|---|
| KC-40 | 0.1 | 0.1 | n/a | n/a | 4.12 ± 1.2* | 0.417 ± 0.096 |
| KC-40 | 0.4 | 0.5 | n/a | n/a | 13.2 ± 2.7* | 0.625 ± 0.14 |
| KC-40 | 1.6 | 2.0 | n/a | n/a | 66.5 ± 8.1* | 0.458 ± 0.084 |
| KC-40 | 0.4 | 0.5 | 0.08 | 0.14 | 12.9 ± 4.8^ | 0.938 ± 0.13 |
| KC-40 | 1.6 | 2.0 | 0.32 | 0.56 | 23.3 ± 12* | 2.50 ± 0.58 |
| KC-40 | 4 | 4.9 | 0.8 | 1.4 | 13.2 ± 7.6# | 5.00 ± 2.6 |
| hydrocodone | 0.17 | 0.5 | n/a | n/a | 14.0 ± 4.3^ | 0.417 ± 0.096 |
| hydrocodone | 0.17 | Values adjusted to expected value for a 2 μmol/kg dose (4 dose equivalents) | | | 56.0 ± n/a^ | 0.417 ± n/a |
| hydrocodone | 0.17 | Values adjusted to expected value for a 5 μmol/kg dose (10 dose equiv) | | | 140 ± n/a^ | 0.417 ± n/a |

Lower limit of quantitation was 0.0250 ng/mL
^Lower limit of quantitation was 0.0500 ng/mL
*Lower limit of quantitation was 0.100 ng/mL Table 13 provides hydrocodone (HC) exposure results for dogs administered either hydrocodone or increasing amounts of prodrug Compound KC-50 and exposure results when Compound KC-50 was co-dosed with increasing amounts of trypsin inhibitor Compound 109. The hydrocodone Cmax and Tmax values in Table 13 are reported, for each group of four dogs, as described in Example 36.

TABLE 13

Cmax and Tmax of hydrocodone in dog plasma

| Compound | Dose, mg/kg | Dose, μmol/kg | Compound 109 Dose mg/kg | Compound 109 Dose μmol/kg | HC Cmax ± sd, ng/mL | Tmax ± sd, h |
|---|---|---|---|---|---|---|
| KC-50 | 0.1 | 0.1 | n/a | n/a | 3.74 ± 1.3* | 0.625 ± 0.025 |
| KC-50 | 0.4 | 0.5 | n/a | n/a | 9.69 ± 3.8§ | 0.604 ± 0.33 |
| KC-50 | 1.6 | 2 | n/a | n/a | 55.9 ± 18* | 0.563 ± 0.13 |
| KC-50 | 0.4 | 0.5 | 0.08 | 0.14 | 8.26 ± 5.4* | 1.75 ± 0.50 |
| KC-50 | 0.4 | 0.5 | 0.16 | 0.28 | 8.63 ± 1.1* | 1.75 ± 0.50 |
| KC-50 | 4 | 5 | 0.08 | 0.14 | 70.2 ± 30# | 2.25 ± 0.50 |
| KC-50 | 4 | 5 | 0.4 | 0.7 | 47.8 ± 23# | 4.25 ± 2.1 |
| hydrocodone | 0.17 | 0.5 | n/a | n/a | 14.0 ± 4.3^ | 0.417 ± 0.096 |
| hydrocodone | 0.17 | Values adjusted to expected value for a 5 μmol/kg dose (10 dose equiv) | | | 140 ± n/a^ | 0.417 ± n/a |

Figure 14A:
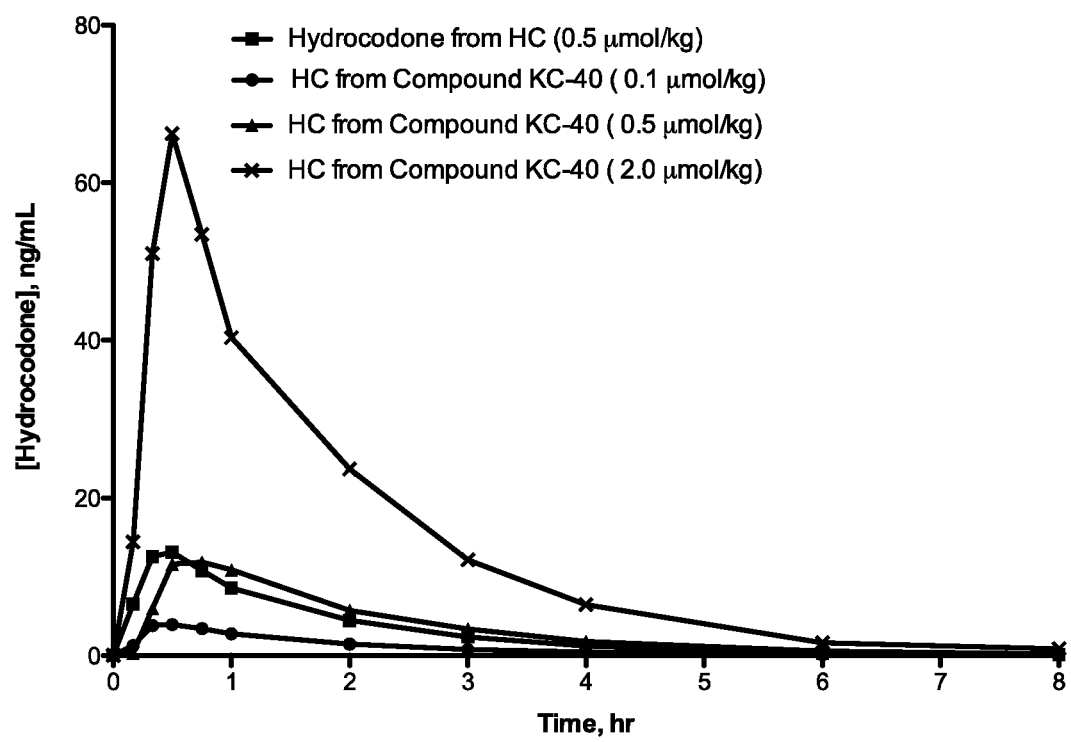
FIG. 14A compares mean plasma concentrations over time of hydrocodone following PO administration to dogs of hydrocodone and PO administration to dogs of increasing amounts of prodrug Compound KC-40.
Figure 14B:
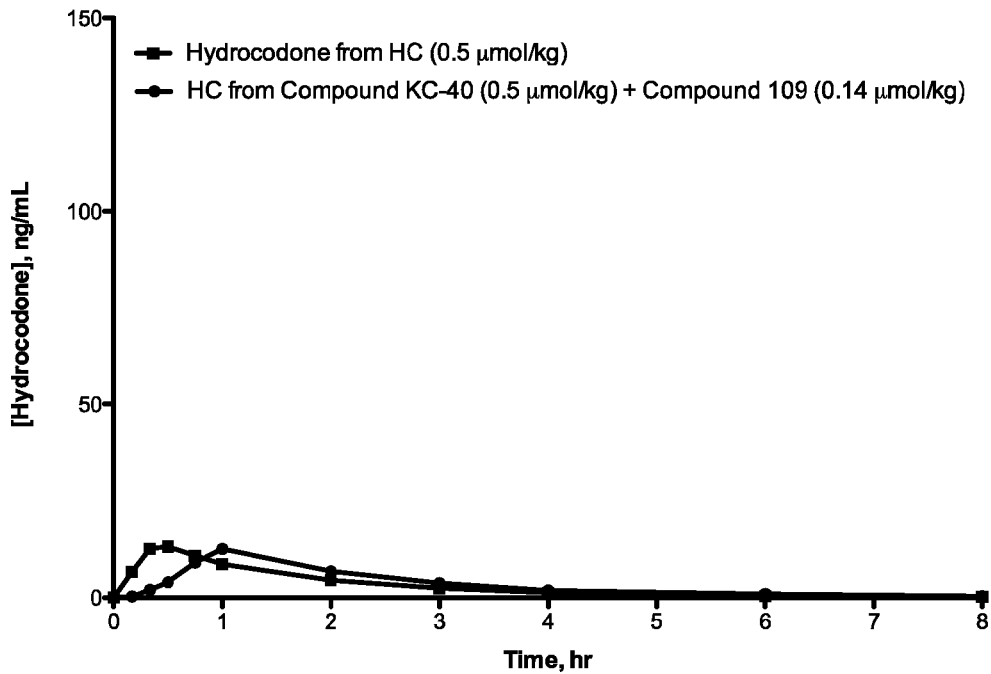
FIG. 14B, FIGS. 14C and 14D each compares mean plasma concentrations over time of hydrocodone following PO administration to dogs of, respectively, 1, 4 or 10 dose units comprising prodrug Compound KC-40 and trypsin inhibitor Compound 109 to plasma concentrations of hydrocodone following PO administered to dogs of 1 dose equivalent of hydrocodone or predicted concentrations for 4 or 10 dose equivalents of hydrocodone, respectively.
Figure 14C:
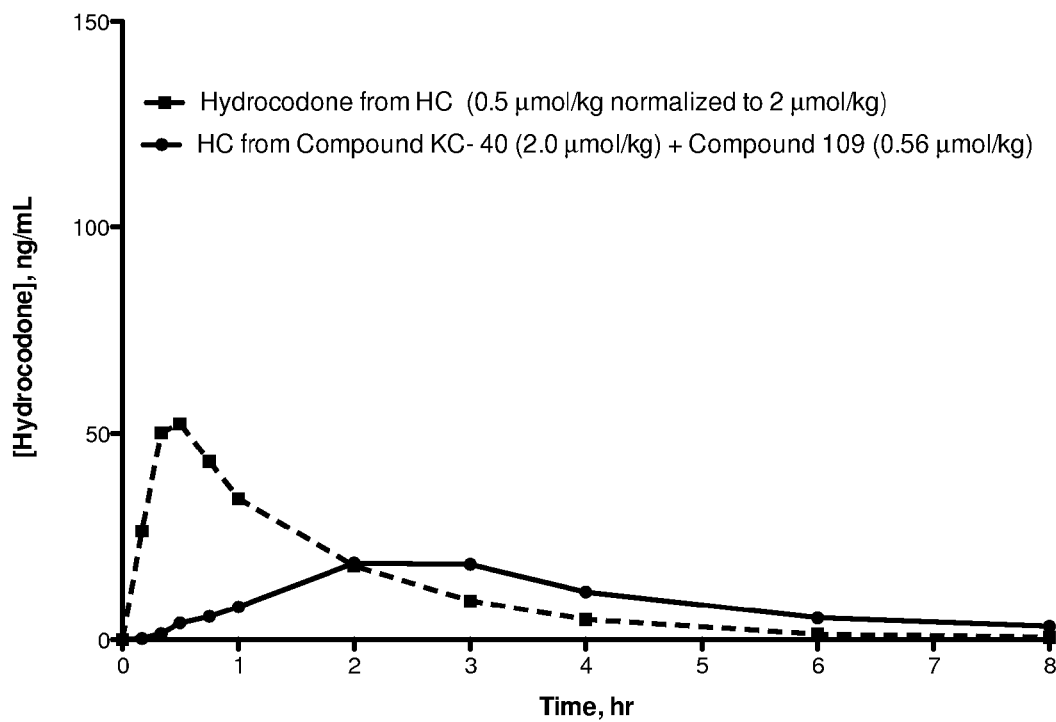
Figure 14D:
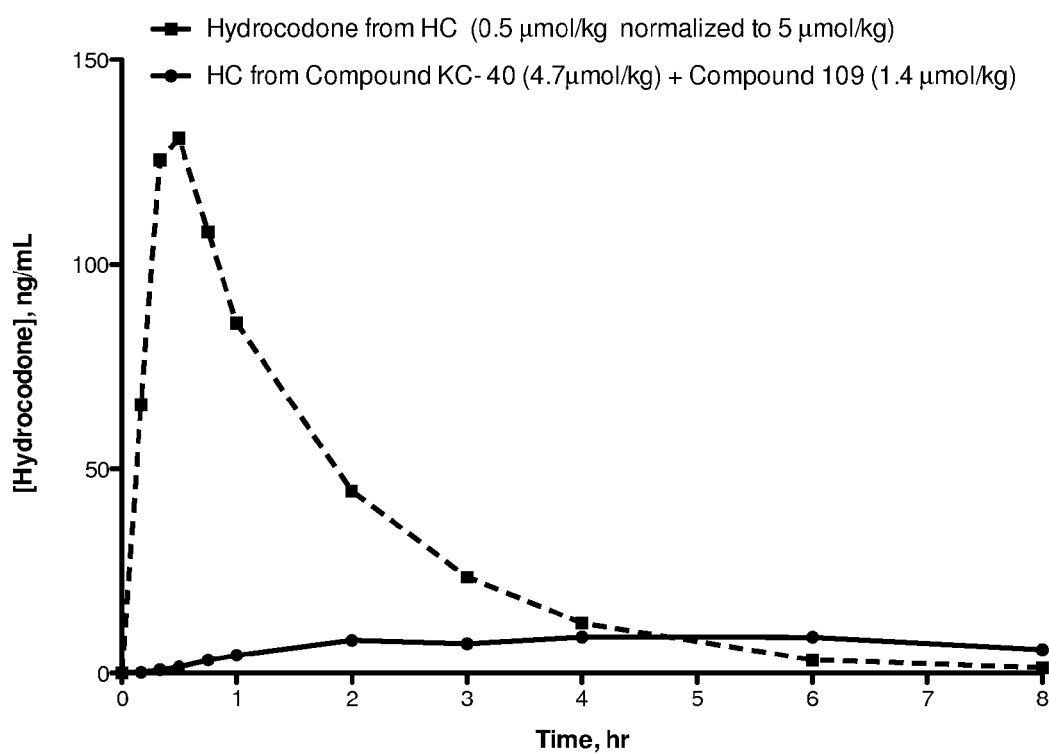

§Lower limit of quantitation was 0.0125 ng/mL
Lower limit of quantitation was 0.0250 ng/mL
^Lower limit of quantitation was 0.0500 ng/mL
*Lower limit of quantitation was 0.100 ng/mL FIG. 14A compares mean plasma concentrations over time of hydrocodone following PO administration to dogs of hydrocodone or of increasing amounts of Compound KC-40. FIG. 14B, FIGS. 14C and 14D each compares mean plasma concentrations over time of hydrocodone following PO administration to dogs of, respectively, 1, 4 and 10 dose units comprising prodrug Compound KC-40 and trypsin inhibitor Compound 109 to plasma concentrations of hydrocodone following PO administered to dogs of 1 dose equivalent of hydrocodone or predicted concentrations for 4 or 10 dose equivalents of hydrocodone, respectively.

Figure 15A:
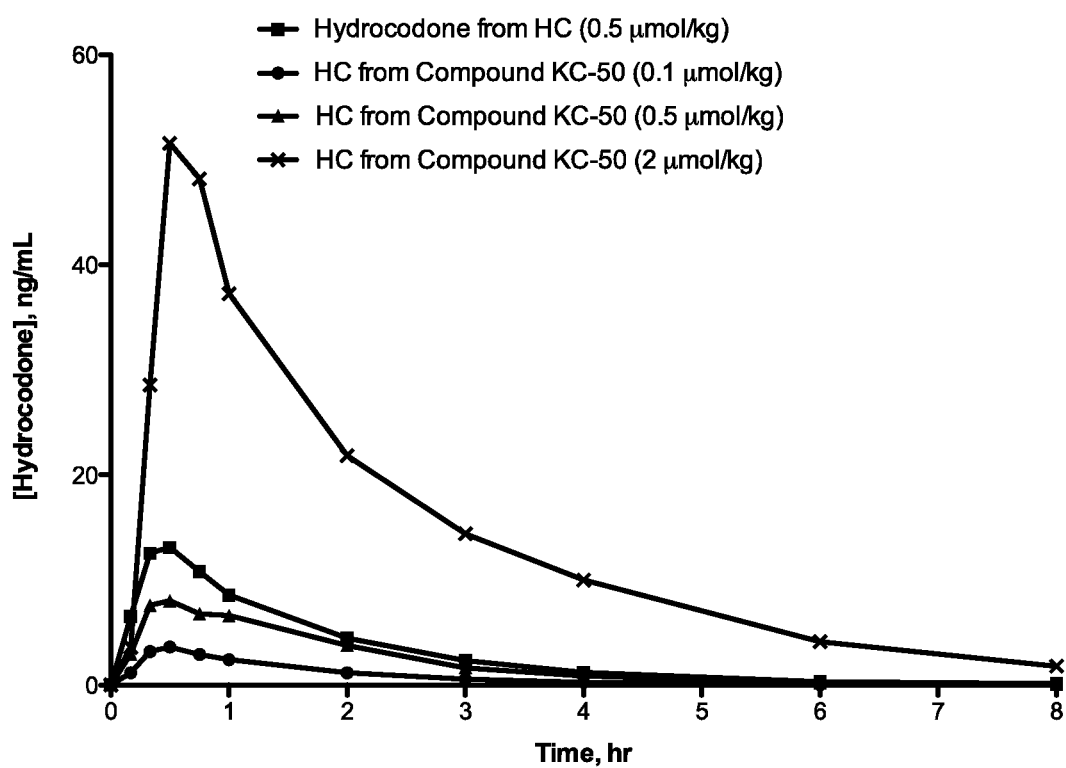
FIG. 15A compares mean plasma concentrations over time of hydrocodone following PO administration to dogs of hydrocodone and PO administration to dogs of increasing amounts of prodrug Compound KC-50.
Figure 15B:
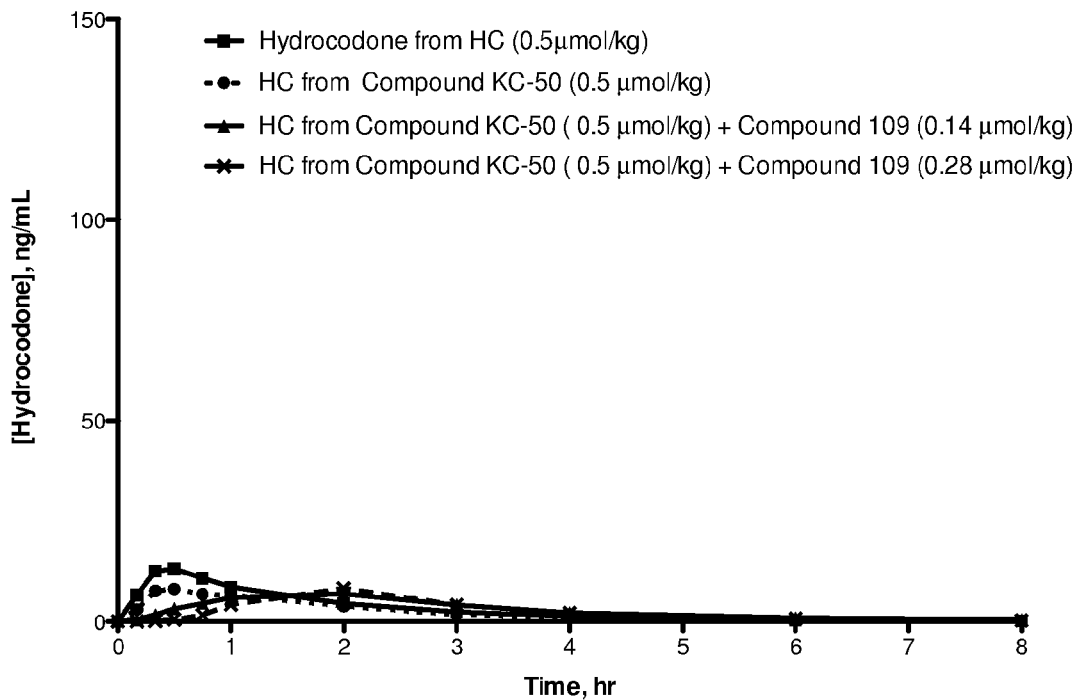
FIG. 15B and FIG. 15C compare mean plasma concentrations over time of hydrocodone following PO administration to dogs of hydrocodone to plasma concentrations over time of hydrocodone following PO administration to dogs of the indicated doses of prodrug Compound KC-50 with or without trypsin inhibitor Compound 109.
Figure 15C:
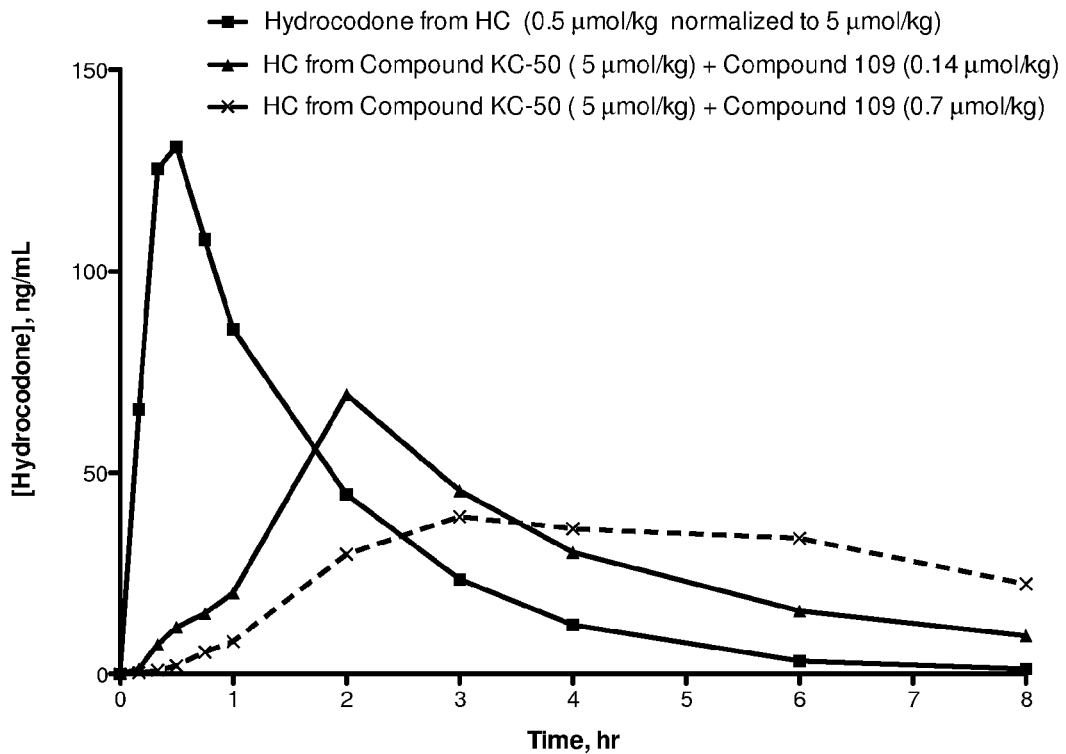

FIG. 15A compares mean plasma concentrations over time of hydrocodone following PO administration of hydrocodone or of increasing amounts of Compound KC-50 to dogs. FIG. 15B and FIG. 15C compare mean plasma concentrations over time of hydrocodone following PO administration to dogs of hydrocodone to plasma concentrations over time of hydrocodone following PO administration to dogs of the indicated doses of Compound KC-50 with or without trypsin inhibitor Compound 109.

The results in Table 12, Table 13, FIG. 14A-D and FIG. 15A-C indicate that prodrug compounds of the embodiments administered orally to dogs effect efficient release of hydrocodone into dog plasma. The results also demonstrate that release of hydrocodone can be attenuated (a) with an increasing number of dose units comprising prodrug and trypsin inhibitor compared to administration of an equivalent dosage of drug alone as well as (b) with a co-dose of prodrug and increasing amounts of trypsin inhibitor compared to administration of an equivalent dosage of drug alone.

Example 48

Pharmacokinetics Following PO Administration of Ketone-Modified Opioid Prodrugs to Rats This Example demonstrates the release of opioid into plasma when a ketone-modified opioid prodrug Compound KC-55 of the embodiments was administered orally (PO) to rats.

Aqueous solutions of Compound KC-55 (which can be prepared as described in the examples herein) or saline solutions of oxycodone were dosed as indicated in Table 14 via oral gavage into jugular vein-cannulated male Sprague Dawley rats (4 per group) that had been fasted for 16-18 h prior to oral dosing. At specified time points, blood samples were drawn and harvested using a method similar to that described in Example 36. Sampling and analysis procedures were also similar to those described in Example 36.

Table 14 provides oxycodone exposure results for rats administered oxycodone or Compound KC-55. Results in Table 14 are reported, for each group of rats, as (a) maximum plasma concentration value (Cmax) of oxycodone (OC) (average±standard deviation), and (b) time after administration of compound to reach maximum oxycodone concentration value (Tmax) (average±standard deviation)

TABLE 14

Cmax, Tmax and AUC values of oxycodone in rat plasma

| Compound | Dose, mg/kg | Dose μmol/kg | OC Cmax ± sd, ng/mL | Tmax ± sd, h |
|---|---|---|---|---|
| KC-55 | 5 | 6 | 2.73 ± 1.4# | 0.542 ± 0.21 |
| KC-55 | 23.5 | 28 | 15.9 ± 2.3* | 0.500 ± 0.00 |
| Oxycodone | 10 | 28 | 14.7 ± 6.5^ | 0.625 ± 0.43 |

Figure 16:
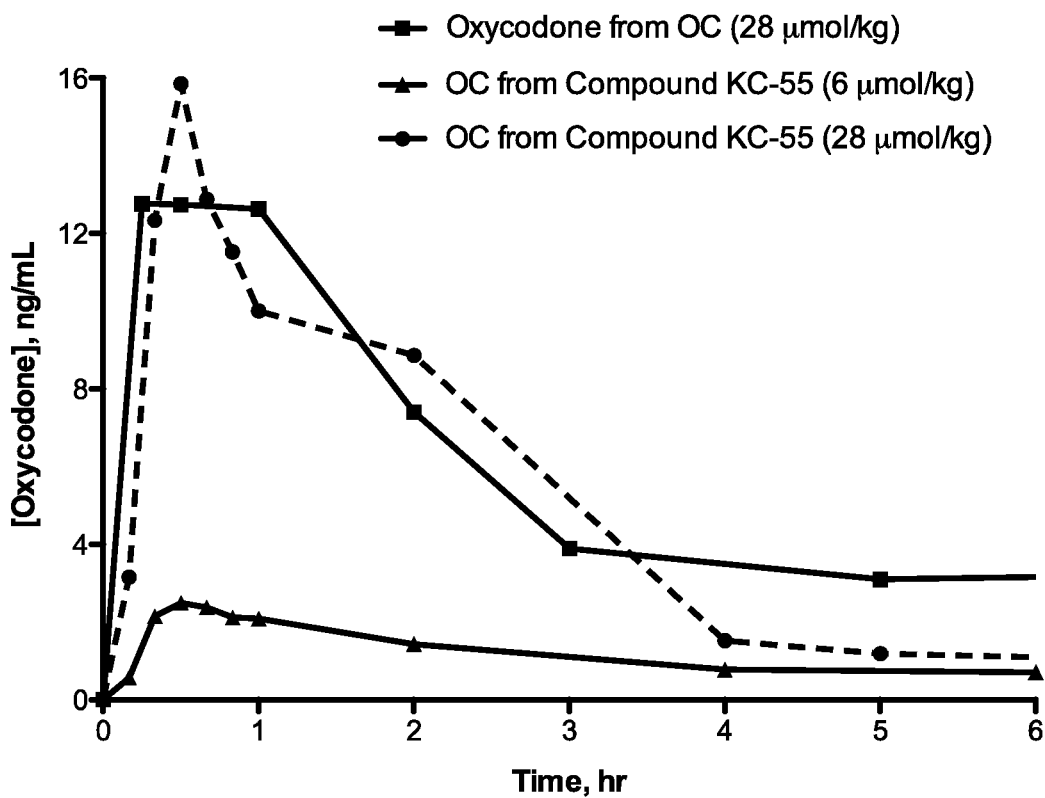
FIG. 16 compares mean plasma concentrations over time of oxycodone release following PO administration to rats of oxycodone prodrug Compound KC-55 or oxycodone.

^Lower limit of quantitation was 0.0250 ng/mL
*Lower limit of quantitation was 0.0500 ng/mL
Lower limit of quantitation was 0.500 ng/mL FIG. 16 compares mean plasma concentrations over time of oxycodone release following PO administration to rats of oxycodone prodrug Compound KC-55 or oxycodone.

The results in Table 14 and FIG. 16 indicate that oral administration of Compound KC-55 to rats leads to release of oxycodone.

Example 49

Oral Administration of Ketone-Modified Opioid Prodrug Compound KC-55 Co-Dosed with a Trypsin Inhibitor to Rats This Example demonstrates the ability of a trypsin inhibitor to affect the ability of ketone-modified opioid prodrug Compound KC-55 to release opioid into plasma when the prodrug is co-administered with such a trypsin inhibitor orally to rats.

Aqueous solutions of prodrug Compound KC-55 (which can be prepared as described in the examples herein), aqueous solutions of an increasing number of dose units comprising Compound KC-55 and Compound 109 (Catalog No. 3081, Tocris Bioscience, Ellisville, Mo., USA or Catalog No. WS38665, Waterstone Technology, Carmel, 1N, USA), or saline solution of oxycodone were administered orally to rats, as indicated in Table 15, using a method similar to that described in Example 36. Sampling and analysis procedures were also similar to those described in Example 36.

Table 15 provides oxycodone exposure results for rats administered oxycodone, Compound KC-55, or a single dose unit or 6 dose units comprising Compound KC-55 and trypsin inhibitor Compound 109. The oxycodone Cmax and Tmax values, in Table 15 are reported, for each group of four rats, as described in Example 36.

TABLE 15

| Cmax and Tmax of oxycodone in rat plasma | | | | | |
|---|---|---|---|---|---|
| KC-55 Dose, mg/kg | KC-55 Dose, µmol/kg | Compound 109 Dose, mg/kg | Compound 109 Dose, µmol/kg | OC Cmax ± sd, ng/mL | Tmax ± sd, h |
| 5 | 6 | 0 | 0 | 2.73 ± 1.4 | 0.542 ± 0.21 |
| 5 | 6 | 0.5 | 0.9 | 3.59 ± 2.0 | 0.583 ± 0.17 |
| 30 | 36 | 3 | 5 | 9.96 ± 3.4 | 0.875 ± 0.16 |
| Oxycodone values in Table 14 adjusted to provide expected values at a 36 µmol/kg dose | | | | 18.8 ± n/a | 0.625 ± n/a |

Lower limit of quantitation was 0.500 ng/mL

Figure 17A:
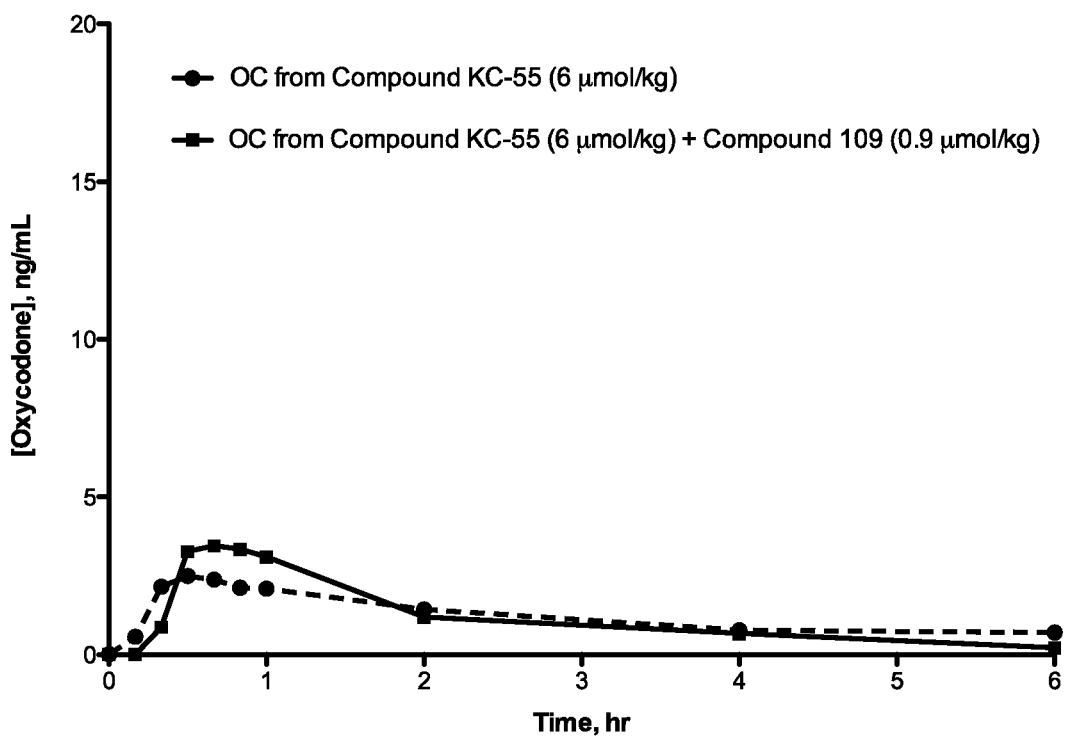
FIG. 17A provides oxycodone exposure results for rats orally administered prodrug Compound KC-55 alone or co-dosed with trypsin inhibitor Compound 109.

FIG. 17A provides oxycodone exposure results for rats orally administered a 5 mg/kg (6 µmol/kg) dose of Compound KC-55 alone or co-dosed with 0.5 mg/kg (0.9 µmol/kg) of trypsin inhibitor Compound 109.

Figure 17B:
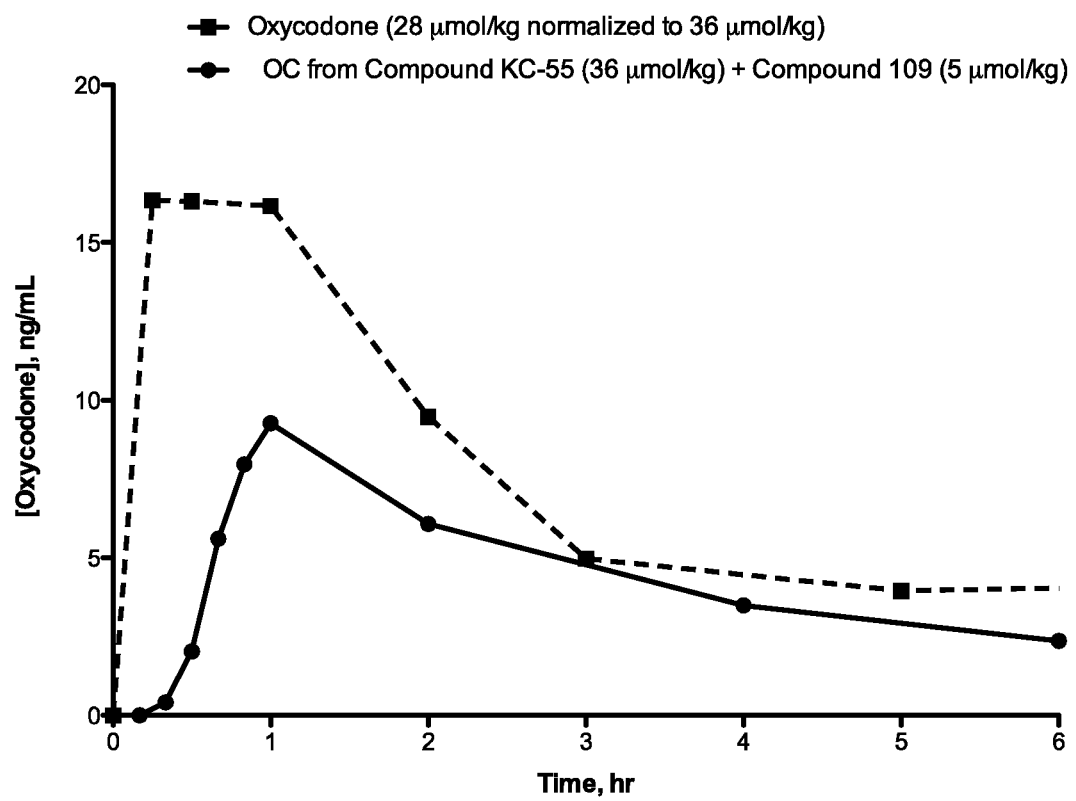
FIG. 17B provides oxycodone exposure results for rats orally administered prodrug Compound KC-55 alone or co-dosed with trypsin inhibitor Compound 109.

FIG. 17B provides oxycodone exposure results for rats orally administered a 30 mg/kg (36 µmol/kg) dose of Compound KC-55 alone or co-dosed with 3 mg/kg (5 µmol/kg) of trypsin inhibitor Compound 109.

The results in Table 15 and the Figures demonstrate that release of oxycodone can be attenuated with an increasing number of dose units comprising prodrug and trypsin inhibitor compared to administration of an equivalent dosage of drug alone.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of formula I:

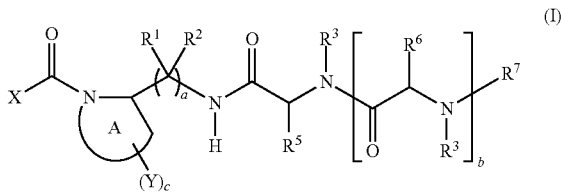

(I)

wherein
X is selected from a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; a phenolic active agent, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; and an amide-containing active agent, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to the amide-containing active agent through the oxygen of the amide group, wherein the amide group is converted to an amide enol or an imine tautomer;
the A ring is a heterocyclic 5 to 12-membered ring;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or
$R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;
a is an integer from one to 8;
provided that when a is one, the A ring is a heterocyclic 6 to 12-membered ring; and when the A ring is a heterocyclic 5-membered ring, then a is an integer from 2 to 8;
each $R^3$ is independently hydrogen, alkyl, substituted alkyl, aryl or substituted aryl;
$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
b is a number from zero to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

2. The compound of claim 1, wherein

X represents a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

3. The compound of claim 1, wherein

X represents a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

4. The compound of claim 1, wherein

X represents a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;
each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or
$R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;
a is an integer from one to 8;
provided that when a is one, the A ring is a heterocyclic 6 to 12-membered ring; and when the A ring is a heterocyclic 5-membered ring, then a is an integer from 2 to 8;
each $R^3$ is independently hydrogen, alkyl, substituted alkyl, aryl or substituted aryl;
$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;
each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;
b is a number from zero to 100;
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

5. The compound of claim 1, wherein the compound is of formula VIIa:

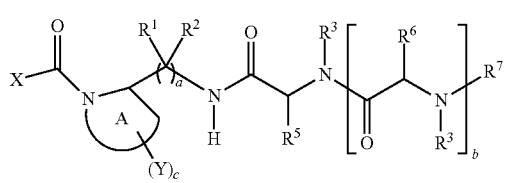

(VIIa)

wherein
X represents a phenolic active agent, wherein the hydrogen atom of the phenolic hydroxyl group is replaced by a covalent bond to —C(O)—N[(A ring)-$Y_c$]-(C$R^1R^2$)$_a$—NH—C(O)—CH($R^5$)—N($R^3$)—[C(O)—CH($R^6$)—N($R^3$)]$_b$—$R^7$;
the A ring is a heterocyclic 5 to 12-membered ring;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or
$R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;
a is an integer from one to 8;
provided that when a is one, the A ring is a heterocyclic 6 to 12-membered ring; and when the A ring is a heterocyclic 5-membered ring, then a is an integer from 2 to 8;
each $R^3$ is independently hydrogen, alkyl, substituted alkyl, aryl or substituted aryl;
$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
b is a number from zero to 100;
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

6. The compound of claim 1, wherein the compound is of formula IXa:

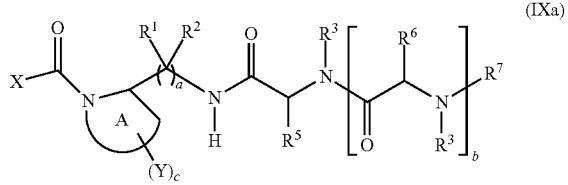

(IXa)

wherein
X represents a phenolic active agent, wherein the hydrogen atom of the phenolic hydroxyl group is replaced by a covalent bond to —C(O)—N[(A ring)-$Y_c$]-(C$R^1R^2$)$_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

7. The compound of claim 1, wherein the compound is of formula Xa:

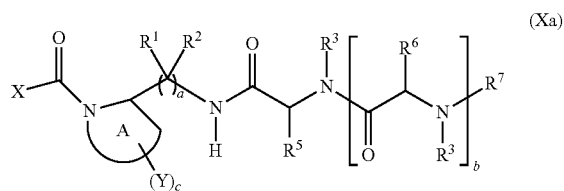

wherein

X represents a phenolic active agent, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

8. The compound of claim 1, wherein the compound is of formula XIa:

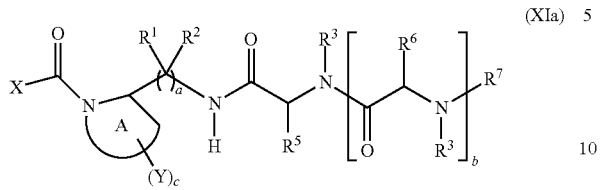

(XIa)

wherein
X represents an amide-containing active agent, wherein —C(O)—N[(A ring)-Y$_c$]-(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing opioid through the oxygen of the amide group, wherein the amide group is converted to an amide enol or an imine tautomer;
the A ring is a heterocyclic 5 to 12-membered ring;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or
R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;
a is an integer from one to 8;
provided that when a is one, the A ring is a heterocyclic 6 to 12-membered ring; and when the A ring is a heterocyclic 5-membered ring, then a is an integer from 2 to 8;
each R$^3$ is independently hydrogen, alkyl, substituted alkyl, aryl or substituted aryl;
R$^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
b is a number from zero to 100;

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

9. The compound of claim 1, wherein the compound is of formula XIIa:

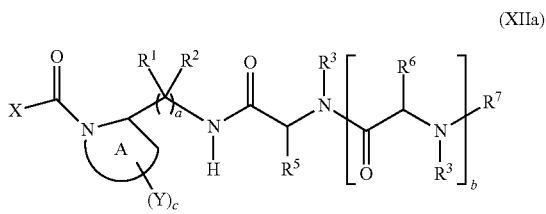

(XIIa)

wherein
X represents an amide-containing active agent, wherein —C(O)—N[(A ring)-Y$_c$]-(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing opioid through the oxygen of the amide group, wherein the amide group is converted to an amide enol or an imine tautomer;
the A ring is a heterocyclic 5 to 12-membered ring;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or
R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;
a is an integer from one to 8;
provided that when a is one, the A ring is a heterocyclic 6 to 12-membered ring; and
when the A ring is a heterocyclic 5-membered ring, then a is an integer from 2 to 8;
each R$^3$ is independently hydrogen, alkyl, substituted alkyl, aryl or substituted aryl;
R$^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

10. The compound of claim 1, wherein the compound is of formula XIIIa:

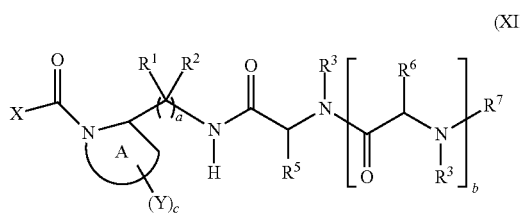

(XIIIa)

wherein

X represents an amide-containing active agent, wherein —C(O)—N[(A ring)-$Y_c$]-$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

11. The compound of claim 1, wherein the compound is of formula XIV:

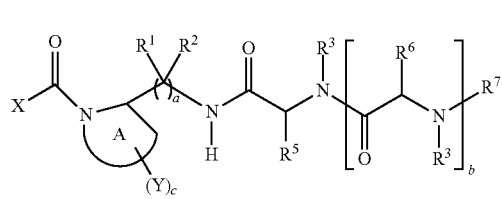

(XIV)

wherein

X represents acetaminophen, wherein the hydrogen atom of the phenolic hydroxyl group of acetaminophen is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; or wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to acetaminophen through the oxygen of the amide group of acetaminophen, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R¹ and R² together with the carbon to which they are attached can form a cycloalkyl or substituted cycloalkyl group, or two R¹ or R² groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R³ is independently hydrogen, alkyl, substituted alkyl, aryl or substituted aryl;

R⁵ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100;

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

12. The compound of claim 1, wherein the compound is of formula XVa:

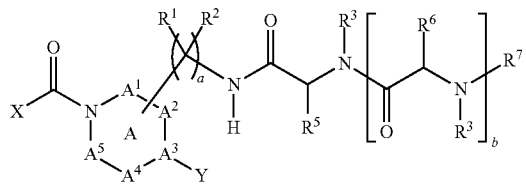

(XVa)

wherein

X is selected from a ketone-containing active agent, wherein the hydrogen atom of the corresponding hydroxyl group of the enolic tautomer of the ketone is replaced by a covalent bond to —C(O)—N[(A ring)-Y]-(CR¹R²)ₐ—NH—C(O)—CH(R⁵)—N(R³)—[C(O)—CH(R⁶)—N(R³)]ᵦ—R⁷; a phenolic active agent, wherein the hydrogen atom of the phenolic hydroxyl group is replaced by a covalent bond to —C(O)—N[(A ring)-Y]-(CR¹R²)ₐ—NH—C(O)—CH(R⁵)—N(R³)—[C(O)—CH(R⁶)—N(R³)]ᵦ—R⁷; and an amide-containing active agent, wherein —C(O)—N[(A ring)-Y]-(CR¹R²)ₐ—NH—C(O)—CH(R⁵)—N(R³)—[C(O)—CH(R⁶)—N(R³)]ᵦ—R⁷ is connected to the amide-containing opioid through the oxygen of the amide group, wherein the amide group is converted to an amide enol or an imine tautomer;

A¹, A², A⁴, and A⁵ are independently selected from carbon, nitrogen, oxygen, and sulfur;

A³ is carbon or nitrogen;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R¹ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R² is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R¹ and R² together with the carbon to which they are attached can form a cycloalkyl or substituted cycloalkyl group, or two R¹ or R² groups on adjacent carbon atoms, together with the carbon atoms to which they are attached, can form a cycloalkyl or substituted cycloalkyl group;

a is an integer from one to 8;

each R³ is independently hydrogen, alkyl, substituted alkyl, aryl or substituted aryl;

R⁵ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

13. The compound of claim 1, wherein the compound is of formula XVa:

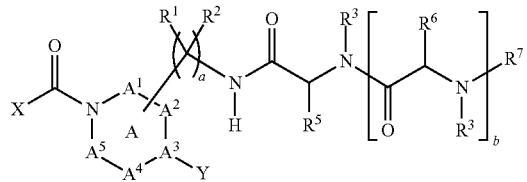

(XVa)

wherein

X is selected from a ketone-containing active agent, wherein the hydrogen atom of the corresponding hydroxyl group of the enolic tautomer of the ketone is replaced by a covalent bond to —C(O)—N[(A ring)-Y]-(CR¹R²)ₐ—NH—C(O)—CH(R⁵)—N(R³)—[C(O)—CH(R⁶)—N(R³)]ᵦ—R⁷; a phenolic active agent, wherein the hydrogen atom of the phenolic hydroxyl group is replaced by a covalent bond to —C(O)—N[(A ring)-Y]-(CR¹R²)ₐ—NH—C(O)—CH(R⁵)—N(R³)—[C(O)—CH(R⁶)—N(R³)]ᵦ—R⁷; and an amide-containing active agent, wherein —C(O)—N[(A ring)-Y]-

$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

$A^1$, $A^2$, $A^4$, and $A^5$ are independently selected from carbon, nitrogen, oxygen, and sulfur;

$A^3$ is carbon or nitrogen;

Y is selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

each $R^3$ is independently hydrogen, alkyl, substituted alkyl, aryl or substituted aryl;

$R^5$ is a side chain of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homoarginine, homolysine, ornithine, arginine mimic, arginine homologue, arginine truncate, arginine with varying oxidation states, lysine mimic, lysine homologue, lysine truncate, and lysine with varying oxidation states;

each $R^6$ is a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

b is a number from zero to 100;

$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

14. The compound of claim 1, wherein the compound is of formula XVa:

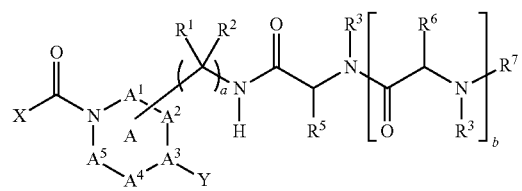

wherein

X is selected from a ketone-containing active agent, wherein the hydrogen atom of the corresponding hydroxyl group of the enolic tautomer of the ketone is replaced by a covalent bond to —C(O)—N[(A ring)-Y]-$(CR^1R^2)_a$—NH—C(O)—CH($R^5$)—N($R^3$)—[C(O)—CH($R^6$)—N($R^3$)]$_b$—$R^7$; a phenolic active agent, wherein the hydrogen atom of the phenolic hydroxyl group is replaced by a covalent bond to —C(O)—N[(A ring)-Y]-$(CR^1R^2)_a$—NH—C(O)—CH($R^5$)—N($R^3$)—[C(O)—CH($R^6$)—N($R^3$)]$_b$—$R^7$; and an amide-containing active agent, wherein —C(O)—N[(A ring)-Y]-$(CR^1R^2)_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer;

$A^1$, $A^2$, $A^4$, and $A^5$ are independently selected from carbon, nitrogen, oxygen, and sulfur;

$A^3$ is carbon or nitrogen;

Y is selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

each $R^3$ is independently hydrogen, alkyl, substituted alkyl, aryl or substituted aryl;

$R^5$ represents a side chain of an amino acid, a side chain of an amino acid variant, a derivative of a side chain of an amino acid, or a derivative of a side chain of an amino acid variant that effects —C(O)—CH($R^5$)—N($R^3$)— to be a GI enzyme-cleavable moiety;

each $R^6$ represents a side chain of an amino acid independently selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;
b is a number from zero to 100;
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

15. The compound claim 12, wherein $A^1$, $A^2$, $A^4$, and $A^5$ are carbon.

16. The compound of claim 12, wherein $A^3$ is carbon.

17. The compound of claim 12, wherein $A^3$ is nitrogen.

18. A composition comprising
a compound of claim 1; and
a pharmaceutically acceptable carrier.

19. A method of treating or preventing pain in a patient in need thereof, which comprises administering an effective amount of a compound of claim 1.

20. A composition comprising
a trypsin inhibitor;
a compound of claim 1; and
a pharmaceutically acceptable carrier.

21. A method for reducing drug abuse potential of a composition containing an active agent prodrug, the method comprising: combining a compound of claim 1 with a trypsin inhibitor, wherein the trypsin inhibitor reduces the ability of a user to release the active agent from the active agent prodrug by addition of trypsin.

22. A method of treating or preventing pain in a patient in need thereof, which comprises administering an effective amount of a composition of claim 20.

23. A composition comprising:
an active agent prodrug comprising an active agent covalently bound to a promoiety comprising a GI enzyme-cleavable moiety, wherein cleavage of the GI enzyme-cleavable moiety by a GI enzyme mediates release of the active agent; wherein the active agent prodrug is of formula I:

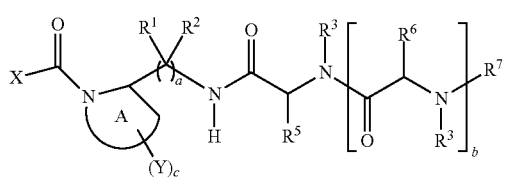

(I)

wherein
X is selected from a ketone-containing active agent, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; a phenolic active agent, wherein the hydrogen atom of the phenolic hydroxyl group is replaced by a covalent bond to —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$; and an amide-containing active agent, wherein —C(O)—N[(A ring)-$Y_c$]—$(CR^1R^2)_a$—NH—C(O)—CH($R^5$)—N($R^3$)—[C(O)—CH($R^6$)—N($R^3$)]$_b$—$R^7$ is connected to the amide-containing active agent through the oxygen of the amide group, wherein the amide group is converted to an amide enol or an imine tautomer;
the A ring is a heterocyclic 5 to 12-membered ring;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or
$R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;
a is an integer from one to 8;
provided that when a is one, the A ring is a heterocyclic 6 to 12-membered ring; and when the A ring is a heterocyclic 5-membered ring, then a is an integer from 2 to 8;
each $R^3$ is independently hydrogen, alkyl, substituted alkyl, aryl or substituted aryl;
$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
b is a number from zero to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl; or a salt, hydrate or solvate thereof; and
a GI enzyme inhibitor that interacts with the GI enzyme that mediates enzymatically-controlled release of the active agent from the active agent prodrug following ingestion of the composition.

24. A dose unit comprising the composition of claim 23, wherein
the active agent prodrug and the inhibitor are present in the dose unit in an amount effective to provide for a preselected pharmacokinetic (PK) profile following ingestion.

25. The dose unit of claim 24, wherein the dose unit provides for a pre-selected PK profile following ingestion of at least two dose units.

26. A method to treat a patient comprising administering a composition of claim 23.

27. A method of making a dose unit, the method comprising:
    combining in a dose unit:
        an active agent prodrug comprising an active agent covalently bound to a promoiety cleavable by a GI enzyme, wherein cleavage of the promoiety by the GI enzyme mediates release of the active agent from the active agent prodrug;
        wherein the active agent prodrug is of formula I:

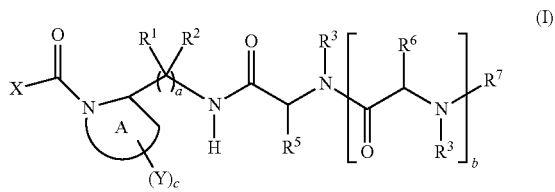

wherein
    X is selected from a ketone-containing active agent, wherein the hydrogen atom of the corresponding hydroxyl group of the enolic tautomer of the ketone is replaced by a covalent bond to —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$; a phenolic active agent, wherein the hydrogen atom of the phenolic hydroxyl group is replaced by a covalent bond to —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$; and an amide-containing active agent, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;
    the A ring is a heterocyclic 5 to 12-membered ring;
    each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
    c is a number from zero to 3;
    each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
    each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or
    R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;
    a is an integer from one to 8;
    provided that when a is one, the A ring is a heterocyclic 6 to 12-membered ring;
    and when the A ring is a heterocyclic 5-membered ring, then a is an integer from 2 to 8;
    each R$^3$ is independently hydrogen, alkyl, substituted alkyl, aryl or substituted aryl;
    R$^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
    each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;
    b is a number from zero to 100; and
    R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl; or a salt, hydrate or solvate thereof; and
    a GI enzyme inhibitor that interacts with the GI enzyme that mediates enzymatically-controlled release of the active agent from the active agent prodrug;
    wherein the active agent prodrug and the GI enzyme inhibitor are present in the dose unit in an amount effective to attenuate release of the active agent from the active agent prodrug such that ingestion of multiples of dose units by a patient does not provide a proportional release of active agent.

28. A method for identifying an active agent prodrug and a GI enzyme inhibitor suitable for formulation in a dose unit, the method comprising:
    combining an active agent prodrug, a GI enzyme inhibitor, and a GI enzyme in a reaction mixture, wherein the active agent prodrug comprises an active agent covalently bound to a promoiety comprising a GI enzyme-cleavable moiety, wherein cleavage of the GI enzyme-cleavable moiety by the GI enzyme mediates release of the active agent; or
    administering to an animal an active agent prodrug and a GI enzyme inhibitor, wherein the active agent prodrug comprises an active agent covalently bound to a promoiety comprising a GI enzyme-cleavable moiety, wherein cleavage of the GI enzyme-cleavable moiety by the GI enzyme mediates release of the active agent; or
    administering to an animal tissue an active agent prodrug and a GI enzyme inhibitor, wherein the active agent prodrug comprises an active agent covalently bound to a promoiety comprising a GI enzyme-cleavable moiety, wherein cleavage of the GI enzyme-cleavable moiety by the GI enzyme mediates release of the active agent;
    wherein the active agent prodrug is of formula I:

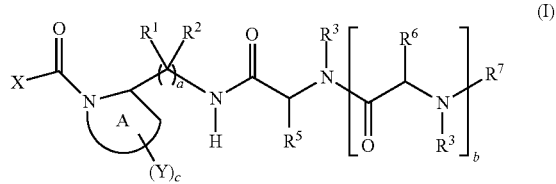

wherein

X is selected from a ketone-containing active agent, wherein the hydrogen atom of the corresponding hydroxyl group of the enolic tautomer of the ketone is replaced by a covalent bond to —C(O)—N[(A ring)-Y$_c$]—(CR$^1$R$^2$)$_a$—NH—C(O)—CH(R$^5$)—N(R$^5$)—N(R$^3$)—[C(O)—CH(R$^6$)—N(R$^3$)]$_b$—R$^7$; a phenolic active agent, wherein the hydrogen atom of the phenolic hydroxyl group is replaced by a covalent bond to —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$; and an amide-containing active agent, wherein —C(O)—N[(A ring)-Y$_c$]—(CR$^1$R$^2$)$_a$—NH—C(O)—CH(R$^5$)—N(R$^3$)—[C(O)—CH(R$^6$)—N(R$^3$)]$_b$—R$^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each R$^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each R$^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or R$^1$ and R$^2$ together with the carbon to which they are attached can form a cycloalkyl or substituted cycloalkyl group, or two R$^1$ or R$^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each R$^3$ is independently hydrogen, alkyl, substituted alkyl, aryl or substituted aryl;

R$^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl; or a salt, hydrate or solvate thereof; and detecting active agent prodrug conversion, wherein a decrease in active agent prodrug conversion in the presence of the GI enzyme inhibitor as compared to active agent prodrug conversion in the absence of the GI enzyme inhibitor indicates the active agent prodrug and the GI enzyme inhibitor are suitable for formulation in a dose unit.

29. A method to treat a patient comprising administering a dose unit of claim 24 to a patient.

* * * * *